(12) United States Patent
Yannone et al.

(10) Patent No.: US 11,015,181 B2
(45) Date of Patent: *May 25, 2021

(54) NUCLEIC ACIDS USEFUL FOR INTEGRATING INTO AND GENE EXPRESSION IN HYPERTHERMOPHILIC ACIDOPHILIC ARCHAEA

(71) Applicant: The Regents of the University of California, Oakland, CA (US)

(72) Inventors: Steven M. Yannone, Concord, CA (US); Adam Barnebey, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/105,930

(22) Filed: Aug. 20, 2018

(65) Prior Publication Data

US 2018/0355336 A1 Dec. 13, 2018

Related U.S. Application Data

(63) Continuation of application No. 14/646,673, filed as application No. PCT/US2013/071328 on Nov. 21, 2013, now Pat. No. 10,066,223.

(60) Provisional application No. 61/729,268, filed on Nov. 21, 2012.

(51) Int. Cl.
*C12N 15/74* (2006.01)
*C12N 9/42* (2006.01)

(52) U.S. Cl.
CPC ........... *C12N 9/2437* (2013.01); *C12N 15/74* (2013.01)

(58) Field of Classification Search
None
See application file for complete search history.

(56) References Cited

U.S. PATENT DOCUMENTS

| 8,580,543 | B2 | 11/2013 | Burk et al. |
| 2007/0134201 | A1 | 6/2007 | Schleper |
| 2010/0209986 | A1 | 8/2010 | Liao et al. |

FOREIGN PATENT DOCUMENTS

| KR | 20080055552 A | 6/2008 |
| WO | 2012/064195 A2 | 5/2012 |

OTHER PUBLICATIONS

Albers et al., "Conditions for gene disruption by homologous recombination of exogenous DNA into the *Sulfolobus solfataricus* genome," Archaea, 2:145-149 (2007).
Albers, et al., "Production of Recombinant and Tagged Proteins in the Hyperthermophilic Archaeon *Sulfolobus solfataricus*," Applied And Environmental Microbiology, 72(1):102-111 (Jan. 2006).
Barthelme, et al., "Structural Organization of Essential Iron-Sulfur Clusters in the Evolutionarily Highly Conserved ATP-binding Cassette Protein ABCE1," Journal of Biological Chemistry, 282(19):14598-14607 (2007).
Bouabe et al., Nucleic Acids Research, 2008, 36(5):1-9.
GenBank Accession No. AE006641 (Apr. 24, 2001).
Extended European Search Report from European Patent Application No. 13856207.9, dated Jun. 30, 2016.
Peng, "An upstream activation element exerting differential transcriptional activation on an archaeal promoter," Molecular Microbiology, 74(4) pp. 928-939 (2009).
Ghosh, et al., "Archaeal flagellar ATPase motor shows ATP-dependent hexameric assembly and activity stimulation by specific lipid binding," Biochem. J., 437:43-52 (2011).
Jonuscheit, et al., "A reporter gene system for the hyperthermophilic archaeon *Sulfolobus solfataricus* based on a selectable and integrative shuttle vector," Molecular Microbiology, 48(5):1241-1252 (2003).
Peng, "Evidence for the horizontal transfer of an integrase gene from a fusellovirus to a pRN-like plasmid within a single strain of Sulfolobus and the implications for plasmid survival," Microbiology, 154:383-391 (2008).
Pisani, et al., "Thermostable Beta-galactosidase from the archaebacterium *Sulfolobus solfataricus* Purificationa nd properties," Eur. J. Biochem., 187:321-328 (1990).
Stedman, et al., "Genetic Requirements for the Function of the Archaeal Virus SSV1 in Sulfolobus solfataricus: Construction and Testing of Viral Shuttle Vectors," Genetics, 152: 1397-1405 (Aug. 1999).
The International Search Report and Written Opinion from PCT/US2013/071328, dated Feb. 27, 2014.

*Primary Examiner* — Nicole Kinsey White
(74) *Attorney, Agent, or Firm* — Kilpatrick Townsend & Stockton LLP

(57) ABSTRACT

The present invention provides for a novel recombinant or isolated nucleic acid useful for integrating or being maintained in an Archaea or acidophilic hyperthermophilic eubacteria. The nucleic acid encodes a nucleotide sequence that is capable of stably integrating into the chromosome of a host cell, or being maintained as an extrachromosomal element in a host cell, that is an Archea, and a nucleotide sequence of interest. The present invention also provides for an Archaea host cell comprising the nucleic acid stably integrated into the chromosome or maintained episomally in the host cell, and a method of expressing the nucleotide sequence of interest in the host cell and/or directing glycosylation, multimerization, and/or membrane association or integration.

15 Claims, 10 Drawing Sheets
Specification includes a Sequence Listing.

NUCLEIC ACIDS USEFUL FOR INTEGRATING INTO AND GENE EXPRESSION IN HYPERTHERMOPHILIC ACIDOPHILIC ARCHAEA

CROSS REFERENCE TO RELATED APPLICATIONS

This application is a continuation of U.S. application Ser. No. 14/646,673, filed May 21, 2015, U.S. Pat. No. 10,066, 223; which is a U.S. national stage entry of international Application No. PCT/US2013/071328, filed Nov. 21, 2013, which claims the benefit of U.S. Provisional Patent Application Ser. No. 61/729,268, filed Nov. 21, 2012, which applications are herein incorporated by reference in their entirety.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

REFERENCE TO SUBMISSION OF A SEQUENCE LISTING

This application includes a Sequence Listing as a text file named "077429_1099099_SEQLIST" created Aug. 20, 2018 and containing 159,470 bytes. The material contained in this text file is incorporated by reference in its entirety for all purposes.

FIELD OF THE INVENTION

The present invention is in the field of molecular biology and enzymology for extremophiles.

BACKGROUND OF THE INVENTION

Advances in molecular biology for extremophiles have long held promise to provide a broad range of stable enzymes and novel biochemistry for industrial and bioenergy applications. Recombinant expression of hyperthermophilic proteins in *Escherichia coli* has had many successes but also proven limiting (1). Often recombinant proteins expressed in non-native organisms lack appropriate post translational modifications, binding partners, and/or fail to fold correctly, all of which can result in inactive enzymes. Broadly applicable recombinant DNA technologies for archaea have been slow to develop in part due to the highly diverse biology and environments of this domain of life (2). Many *Sulfolobus* vectors have been developed but only narrowly applied due to a number of technical challenges (reviewed in (3)). Recent advances with archaeal genetics in *Pyrococcus, Sulfolobus* and other extremophiles have reinvigorated interest in the promise of extremophilic enzymes for industrial application (4-11).

The hyperthermophilic/acidophilic microbe *Sulfolobus solfataricus* that thrives at 80° C. and a pH of 2-3 in volcanic springs across the globe and is among the most well studied archaeal hyperthermophiles (12). Many natural viral pathogens of *Sulfolobus* have been used for a number of years to advance the development of viral shuttle vectors for this extremophile (11, 13-16). However, the large sizes of these vectors (~20 kb), among other technical difficulties, have made rapid and efficient cloning impractical to date (17).

SUMMARY OF THE INVENTION

The present invention provides for a novel recombinant or isolated nucleic acid useful for integrating into an Archaea or acidophilic hyperthermophilic eubacteria. The nucleic acid is capable of introducing a nucleic acid of interest into the Archaea. The nucleic acid encodes a nucleotide sequence that is capable of stably integrating into the chromosome of a host cell that is an Archea, and a nucleotide sequence of interest.

The present invention provides for the nucleic acid of the present invention comprising a single or multiple cloning site instead of, or in addition to, the nucleotide sequence of interest. In some embodiments, the multiple cloning site comprises two or more tandem restriction sequences or the destination sequences required for in vitro recombinational targeting of desired nucleotide sequences into the destination vectors into which one skilled in the art can introduce a nucleotide sequence of interest into the nucleic acid sequence of the shuttle vector. In some embodiments, the nucleic acid comprises a sequence to directed target integration via one or more enzymatic processes.

The present invention provides for an Archaea host cell, such as a *Sulfolobus* species, comprising the nucleic acid stably integrated into the chromosome of the host cell. The present invention provides for a host cell comprising the nucleic acid as a stably maintained in the host cell, wherein the host cell can be a non-Archaea or non-*Sulfolobus* species. One can culture the host cell in order to amplify the nucleic acid and isolate it from the host cell.

The present invention provides for a method of constructing a host cell of the present invention, comprising: (a) introducing a nucleic acid of the present invention into an Archaea host cell, and (b) integrating the nucleic acid into a chromosome of the host cell to produce the host cell of the present invention or maintaining the nucleic acid in the host cell as an extrachromosomal element.

The present invention provides for a method of expressing a peptide or protein or RNA of interest in an Archaea, comprising: (a) optionally constructing a nucleic acid of the present invention, (b) optionally introducing the nucleic acid into an Archaea host cell, (c) optionally integrating the nucleic acid into a chromosome of the host cell to produce a host cell of the present invention, (d) culturing the host cell in a suitable medium such that a peptide or protein or RNA of interest encoded in the nucleic acid is expressed, (e) optionally directing the protein of interest into a pathway for glycosylation and/or other post-translational modification that impacts functionality, and (f) optionally isolating the peptide or protein or RNA from the host cell.

The present invention provides for a method of expressing a peptide or protein or RNA of interest in an Archaea, comprising: (a) optionally introducing a nucleic acid of the present invention into an Archaea host cell, (b) optionally integrating the nucleic acid into a chromosome of the host cell, (c) culturing the host cell in a medium such that a peptide or protein of interest encoded in the nucleic acid is expressed, (d) optionally directing the peptide, protein, or protein domains determined to encode activity of interest for secretion by the microbe into the medium, (e) optionally secreting the peptide or protein of interest, or domain(s) thereof, or part thereof, comprising an amino acid sequence having an activity of interest into the medium, and (f) optionally isolating the peptide or protein of interest, or domain(s) thereof, or part thereof, or RNA from the host cell or medium; wherein the peptide or protein of interest is a thermophilic enzyme, or enzymatically active fragment thereof, capable of catalyzing an enzymatic reaction. In some embodiments, the enzymatic reaction is an enzymatic degradation or catabolic reaction. In some embodiments, the medium comprises a biomass, such as pretreated biomass.

In some embodiments, the protein of interest is an enzyme, such as a cellulase or protease. In some embodiments, the enzyme is stable, or able to retain substantial enzymatic activity, under or in the presence of (1) a high temperature, such as at a temperature equal to or more than about 70° C., 75° C., 80° C., 85° C., or 90° C., (2) an acidic condition, such as at a pH equal to or less than about 4.0, 3.5, 3.0, 2.5, or 2.0, and/or, (3) detergent, such as equal to or more than 0.5% SDS, 1% SDS, 2% SDS, 4% SDS, 5% SDS, or 10% SDS.

The present invention provides an isolated or recombinant protease having an amino acid sequence shown in any one of SEQ ID NOs:25-35.

The present invention includes a rapid and effective means to screen for and produce industrial-scale quantities of acid/temperature stable enzymes. The time required for recombinant protein expression and purification has been reduced from months/years to days/weeks. The present invention is useful for targeting recombinant proteins for secretion into the media. In some embodiments, this advance precludes the need for engineering microbes to not consume the sugar produced during cellulosic degradation as the degradation of cellulose can be physically and/or temporally separated from microbial growth. The means to express multiple enzymes simultaneously on polycistronic vectors are developed which allow for the production of designer cocktails and microbes for specific feedstocks and processes. The present invention can be for the production of acid/heat-stable enzymes and multi-subunit enzymes. The present invention can be for the production of microbes designed to express multiple enzymes simultaneously.

The present invention has one or more of the following applications. The ability to manipulate the biology of microbes that thrive in the hot sulfuric acid permits commercial products and processes for cellulosic biomass saccharification. The merger of acid/heat pre-treatments with microbe growth, enzyme production and/or saccharification of lignocellulosic biomass. The technologies described here can be applied to accomplish: (1) production of enzymes that are active at lower pH and higher temperatures than currently available, (2) the ability to grow microbes that produce enzymes in pretreatment conditions, thereby greatly diminishing or eliminating enzyme production costs, (3) reduce the needed heat input for pretreatments by executing pretreatments in-line with enzyme production at 80° C. in dilute sulfuric acid, (4) to bring to market active enzymes evolved in the highly divergent Archaeal clade of life that have yet to be exploited for industrial or energy applications, (5) produce Archaeal hyper-stable enzymes with the archaea-appropriate post-translational modifications (including, but not limited to, glycosylation) and targeted localization to membranes, intracellular and extracellular compartments to facilitate solubility, stability and activity, unlike current approaches using fungi and bacteria microbial platforms, and (6) production of engineered strains of hyperthermophilic acidophilic microbes that thrive at 80° C. in dilute sulfuric acid (pH 1-4) and produce, modify, and secrete one or more enzymes into the surrounding media for industrial and energy applications.

The present invention can be used to produce one or more of the following: (a) hyper-stable enzyme mixes for industrial processes requiring extremes in pH, temperature, and stability in detergents (b) designer microbial strains that produce, modify, and secrete mixtures of enzymes for on-site enzyme production and industrial application, (c) degraded cellulosic material that is primarily monomeric sugars for biofuel and microbe-based production of other commodities, (d) production of integral and membrane associated thermal and acid stable enzymes and the related immobilized enzyme forms in membranes and membrane rafts, and (e) hybrid pretreatment and saccharification process for lignocellulosic breakdown into useful industrial commodities, including sugar. An inventive aspect of the peptide or protein is that it is stable in a detergent, or mixture thereof, such as Triton X-100, sodium doceyl sulfate, or the like.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
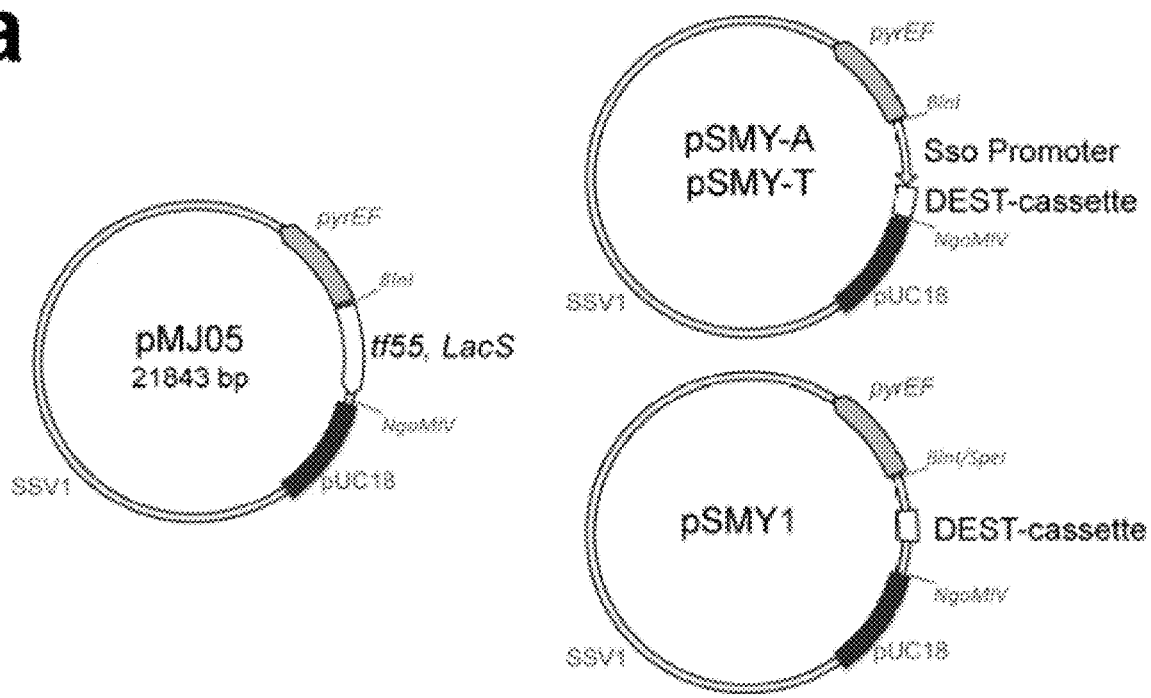
FIG. 1 shows shuttle vectors suitable for propagation in *E. coli* and gene transfer to *Sulfolobus* and the rapid (10-day) cloning process: (Panel a) The parent shuttle vector (pMJ05) and the derivative vectors used for propagation in *E. coli* and high-throughput cloning, expression, and localization targeting of genes encoding acid/heat stable proteins, RNA's and protein domains in *Sulfolobus* species. (Panel b) A schematic diagram of the rapid PCR-based strategy for introducing genes into *Sulfolobus*.
Figure 1:
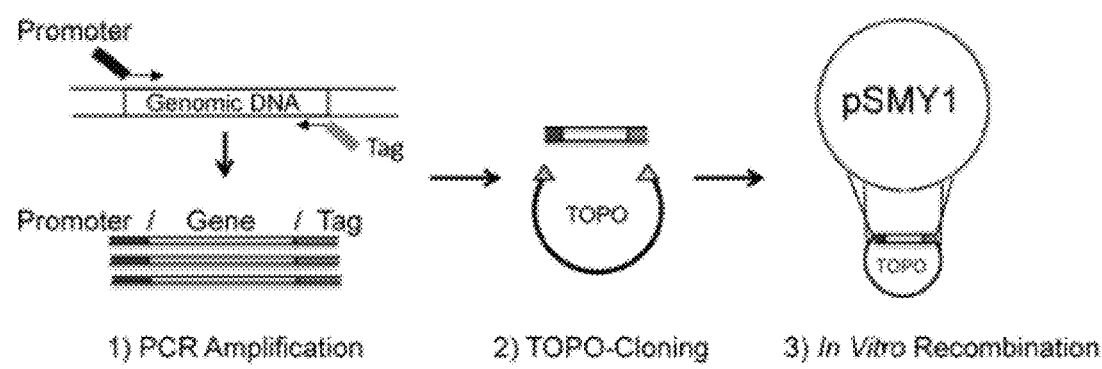

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

In some embodiments, the Archaea is a hyperthermophilic Archaea. In some embodiments, the Archaea is an acidophilic Archaea. A hyperthermophilic organism is an organism capable of growth or is viable at a temperature equal to or more than about 70° C., 75° C., 80° C., 85° C., or 90° C. An acidophilic organism is an organism capable of growth or is viable at a pH equal to or less than about 4.0, 3.5, 3.0, 2.5, or 2.0. In some embodiments, a hyperthermophilic organism is an organism capable of growth or is viable at a temperature equal to 80° C. In some embodiments, an acidophilic organism is an organism capable of growth or is viable at a pH within the range of from about 2.0 to about 3.0.

In some embodiments, the Archaea is a hyperthermophilic acidophilic Archaea. In some embodiments, the Archaea is of the kingdom Crenarchaeota. In some embodiments, the Archaea is of the phylum Crenarchaeota. In some embodiments, the Archaea is of the class Thermoprotei. In some embodiments, the Archaea is of the order Sulfolobales. In some embodiments, the Archaea is of the family Sulfolobaceae. In some embodiments, the Archaea is of the genus *Sulfolobus*.

In some embodiments, the nucleic acid encodes a nucleotide sequence that is capable of stably integrating into the chromosome of a host cell that is a *Sulfolobus* species, and a nucleotide sequence of interest. Suitable nucleotide sequences that are capable of stably integration into the chromosome of a host cell that is a *Sulfolobus* species include, but are not limited to, CGCCGCGGCCGGGATTTGAACCCGGGT-CACGGGCTCGAGAGGCCCGCAT (SEQ ID NO: 1), TGCCGCGGCCGGGATTT-GAACCCGGGTCAgGGGCTCGAGAGGCCCGCAT (SEQ ID No:2), GGGGCGCGGACT-GAGGCTCCGCTGGCGAAGGCCTGCACGGTTCA (SEQ ID No:3), GGGGGCGGACT-GAGGCTCCGCTGGCGAAGGCCTGCACGGGTTCA (SEQ ID NO:4), and TCCGCTGGCGAAGGCCTGCACGGGTTCA (SEQ ID NO:5). In some embodiments, the nucleotide sequence that is capable of stably integrating into the chromosome of a host cell that is a *Sulfolobus* species comprises a nucleotide sequence selected from the group consisting of:
GCCGCGGCCGGGATTTGAACCCGGGT-CASGGGCTCGAGAGGCCCGCAT (SEQ ID NO:6), YGCCGCGGCCGGGATTTGAACCCGGGT-CASGGGCTCGAGAGGCCCGCAT (SEQ ID NO:7), TCCGCTGGCGAAGGCCTGCACGGGTTCA (SEQ ID NO:8), and GGGSGCGGACT-GAGGCTCCGCTGGCGAAGGCCTGCACGGGTTCA (SEQ ID NO:9), wherein is C or and S is C or G.

In some embodiments, the integration of the nucleic acid into the chromosome requires a recombinase or integrase, or a functional variant thereof.

In some embodiments, the nucleotide sequence that is capable of stably integrating into the chromosome is the integration sequence of a virus. In some embodiments, the virus is a Fusellovirus capable of infecting *Sulfolobus* species, such as any *Sulfolobus* spindle-shaped virus, such as SSV1, SSV2, SSV3, SSVL1, SSVK1, and SSVRH (see Ceballos et al., "Differential virus host-ranges of the *Fuselloviridae* of hyperthermophilic Archaea: implications for evolution in extreme environments", Front Microbiol. 3:295, 2012, which is hereby incorporated by reference). Fusellovirus is a genus of dsDNA virus that infects the species of the clade Archaea. The *Fuselloviridae* are ubiquitous in high-temperature (≥about 70° C.), acidic (pH ≤about 4) hot springs around the world. They possess a lipid membrane and a protective inner capsid in the form of a core. Exemplary nucleotide sequences include, but are not limited to, sequences for SSV1 (Accession: NC_001338.1 GI: 9625519), SSV2 (Accession: NC_005265.1 GI: 38639801), SSV4 (Accession: NC_009986.1 GI: 160688416), SSV5 (Accession: NC_011217.1 GI: 198449227), SSVK1 (Accession: NC_005361.1 GI: 42495057), and SSVRH (Accession: NC_005360.1 GI: 42494927) which are publicly available.

In some embodiments, the host cell is a hyperthermophilic acidophilic Archaea. In some embodiments, the host cell is *Sulfolobus solfataricus, Sulfolobus islandicus, Sulfolobus acidocaldarius, Sulfolobus tokodaii, Metallosphaera yellowstonensis, Metallosphaera sedula*, or *Acidianus brierleyi*.

In some embodiments, the nucleotide sequence of interest encodes a peptide or protein or RNA, of which expression in the host cell is desired, or a DNA sequence that binds a protein in the host cell. In some embodiments, the peptide, protein or RNA is heterologous to the host cell. The nucleic acid can further comprise promoters, activator sites, repressor sites, and the like, operably linked to the nucleotide sequence of interest such that the peptide or protein or RNA can be expressed in the host cell. In some embodiments, the promoters, activator sites, repressor sites, and the like can be either native or heterologous to the host cell. Depending on the promoters, activator sites, repressor sites, and the like, the expression of the peptide or protein or RNA is constitutive, modulated, or regulated as desired. Suitable promoters, activator sites, and repressor sites, include, but are limited to, those responsive to the presence of carbohydrates or otherwise regulated in response to small molecules, temperature, or other cellular stimuli. A suitable example is the AraS promoter, which is responsive to the sugar arabinose, and the Tf55 promoter which is responsive to heat shock. In some embodiments, the promoter comprises the nucleotide sequence of a Mini Promoters, such as "a" promoter, ATGTTAAACAAGTTAGGTATACTATTTATAAAATAGT TAGGTCATAAAAG TACCCGAGAA T (SEQ ID NO:13), and "t" promoter, GCTGAGAGAA AAATTTTTATATAAGCGATACTAATGTTCTCACG-GAACGGTGTTGTGAGGT (SEQ ID NO:14).

In some embodiments, the protein or peptide, in order to be correctly folded in order to be biologically or biochemically active, i.e., possess a biological activity, such as an enzymatic activity, has to be expressed, synthesized and/or folded at a temperature equal to or more than about 70° C., 75° C., 80° C., 85° C., or 90° C. In some embodiments, the protein or peptide, in order to possess a biological activity, has to be glycosylated during or after expression, synthesis and/or folding. In some embodiments, the protein or peptide is or must be directed to the membrane, intra- or extracellular compartment for function and solubility. Where the protein or peptide has to be glysosylated, the host cell has the native or transformed means to glycosylate the protein or peptide.

In some embodiments, the promoter is operably linked to an open reading frame (ORF). In some embodiments, the ORF comprises a nucleotide sequence at the 5' end of the ORF an export or membrane localization peptide signal. In some embodiments, the export peptide signal comprises an amino acid sequence encoded by a XPO, SP, Seq1, Seq2, Seq3, Seq4, or Seq5 nucleotide sequence. The amino acid sequence of Seq4 is MKLIEMLKEITQVPGISGY-EERVREKIIEW (SEQ ID NO:22). The amino acid sequence of Seq5 is MVDWELMKKIIESPGVSGYEHL-GIRDLVVD (SEQ ID NO:23).

The XPO sequence comprises the following nucleotide sequence: ATGACTCTCCAAATTCAGTT-TAAAAAGTACGAGCTACCTCCATTACCCTACAAGA TAGATGCATTAGAACCGTATATAAGTAAAGA-TATAATTGATGTACATTATAACGG ACATCATAAA (SEQ ID NO:15). The SP sequence comprises the following nucleotide sequence:

ATGAATAAGCTGATTCCTATAT-
TTGTCGTGGTAATAATTGTACTAGGCATAATTG
TGTCTATAGAATTTGGAAAG (SEQ ID NO:16). The Seq1 sequence comprises the following nucleotide sequence:
ATGAATAAATTATATATTGTGCTTCCGGTAATTGT-
GATAATAGCCATTGGCGTTA TGGGGGGAATCATT-
TACTTGCATCAACAGTCTCTCAGC (SEQ ID NO:17). The Seq2 sequence comprises the following nucleotide sequence:
ATGAATAAAACCCTCGGTCTAATCCTAACCTCTGT-
ATTCCTACTATCCACTTTAGG CATAATAACTGGAT-
TTGTAATACCAACACAAGCT (SEQ ID NO:18). The Seq3 sequence comprises the following nucleotide sequence:
TTGGTTGTGAAAAAAACATTCGTTTTATCTACCTT-
GATATTAATTTCAGTTGTAGC GTTAGTGAGTA-
CAGCAGTTTATACATCTGGT (SEQ ID NO:19). The Seq4 sequence comprises the following nucleotide sequence:
ATGAAGCTAATTGAAATGCTAAAGGAGATAACC-
CAAGTCCCAGGGATTTCAGGG TATGAG-
GAAAGAGTTAGAGAGAAAATTATTGAATGG (SEQ ID NO:20). The Seq5 sequence comprises the following nucleotide sequence:
ATGGTAGATTGGGAACTAAT-
GAAAAAAATAATAGAATCTCCAGGAGTTTCTGGG
TATGAACACCTGGGAATTAGAGACCTTGTGGTA-
GAT (SEQ ID NO:21).

In some embodiments, the nucleic acid further comprises one or more control sequences which permit stable maintenance of the nucleic acid as a vector in a non-*Sulfolobus* host cell. In some embodiments, the control sequence is a sequence comprising an origin of replication (ori) functional in *Escherichia coli* cells. Such control sequences are capable of facilitating DNA replication in heterologous host organisms. Such control sequences can be found in plasmids such as pUC18, pBR322, pACYC184, or the like.

Exemplary vectors that are capable of stably integrating into the *Sulfolobus* chromosome include, but are not limited to, pSMY-T, pSMY1, and pSMY-A.

The nucleotide sequence of pSMY-T is:

(SEQ ID NO: 10)
TCATTTTTTCCTAAAAATTGCTCCTTTACATTTCATCACCTTATCCTCGA

TAATCTTATTTATAGTTCTTAATGCTGTTAATGGATTCCCTGCATTATAA

ATACTTCTTCCAATGATTTCATAATCCGCTCCAGCACATACTGCATCGCC

ATAACTTCCACCTTGACTACCCATACCCGGAGAGACTATGGTCATTTTTT

CGAAGTCTCTCCTATACTGCGTTATATGATCTAATTTAGTCCCTCCAACT

ACTATTCCTTTTGGGCTTATCTCTCTTATAACGTTTTTAATATAGTCTGC

GAATAACGTACTCCATCCTTCATGTGACATTACGGCAACTAAGTATAAAT

TTTTAGAGTTTGCATCAAGATATCTTTTTAATTCATCTAGAGATCCCTTA

ACGCCTATAAAGGAATGTGCTATGAACGAGTTGGCGAAAGATAATCTTTC

AACTATGCTTTTCATTATGTATCCGATATCTGCAAGCTTAAAATCAACAA

TAATTTCCTCCACGTCTAAACCAATTAAGAGCTCTCTAGTTTTATCCACT

CCTAGATCTAAAACTAAAGGTAAACCAACTTTTATCCCATATAACTCATT

TTCCATCTCTTTAAGAACTTGATATGAGAGAGGTTTATCCATTGCTAATA

TTACTCTACTTTTCAACATTCTTCACCAAATAATCTAGAATTGACTTCTT

TTCATTATCCTTAAGTTTATCACTCTTCAACAATTCATCTAGAATTTCTG

AAATTTTAAATAGAGAGTGTAATTTGACTCCTAGTTTTTCCAATCTTTGT

GAAGCCCCTTCTTGTCTATCTATGATTACTAGTGCGTCTGAAACTTTACC

TCCACCGTTAAGAATCTCCAATGTTGCTTTCTCTATGGATACTCCTGTAG

TTGCAACGTCATCTACTAACAATACTCTTTTTCCTTTTACATCGAGTTCT

AATGTACGATTAGTTCCATGACCTTTCTTTTCTATTCTAATATATCCCAT

AGGCTCTTTAAGGTTACAAGCTATGAATGCCGATAAGGGAACTCCTCCAG

TGGCTATTCCTACTATTATATCATGGGGTATATCTTTTGCTTTCTTTATA

GCTTGATTAACTATATCGTAAAATTCTGGATAATTTGGTAAAGGTCTTAA

GTCTAAGTAATATGGACTAACCTTACCTGATGTTAAAACGAAACTTCCTA

TTAATAATAATTTCCTTTCGAGTAAGACTTCTGCGAAATTCATACGTAGA

GACTCTGCGAAAAGAATTTAAATATACTTCTATCATAACCAGTTATAAG

GGCTTTGTGAGATTAAGACACGTAGTTTCGTCGCTTGACTTGACCAGAGA

TGACTACTTTAGAATATTCGAACTTGCAGACAAGTTCTATGATGTAAAAA

AACTAAATTATCTATCAGGGAAAGTAGTTTCATTAGCATTCTTTGAGCCA

AGTACTAGAACTGCTCAAAGCTTTCATACTGCAGCAATAAAATTAGGTGC

TGATGTGATAGGATTTGCATCCGAGGAGTCTACTTCGATAGCAAAAGGTG

AAAATTTGGCTGATACCATTAGGATGCTAAACAACTATTCAAACTGTATT

GTAATGAGACATAAGTTTGATGGGGCAGCATTATTCCctaggccGTGATT

TCGTAATATTGTAAGTTAAATTTAGCGTAGATTTTGTTTATTATATTTTT

TAGAATTTCACGAATAAAGCTTAAGTAAGAGGGATAAGCGAATAAGATCT

TGTCTTTATATACTATTATCTTTCTCGGATAAAGCTCTCTTTTAATTCTC

TTGGTTATCTCATCTTTACTGCATATTTCACATAATCTTCTTCCTCCTAC

TACGTTTATGGCATTTCTTTTGTTACATCTTTCGCACATCATATTAGAGG

AGAATGGATTTCCTATTTATTTAAAAAATTACTTCTCGGTTTAGCTGAGA

GAAAAATTTTTATATAAGCGATACTAATGTTCTCACGGAACGGTGTTGTG

AGGTACTAGTCCAGTGTGGTGGAATTCTGCAGATATCAACAAGTTTGTAC

AAAAAAGCTGAACGAGAAACGTAAAATGATATAAATATCAATATATTAAA

TTAGATTTTGCATAAAAAACAGACTACATAATACTGTAAAACACAACATA

TCCAGTCACTATGGCGGCCGCATTAGGCACCCCAGGCTTTACACTTTATG

CTTCCGGCTCGTATAATGTGTGGATTTTGAGTTAGGATCCGTCGAGATTT

TCAGGAGCTAAGGAAGCTAAAATGGAGAAAAAAATCACTGGATATACCAC

CGTTGATATATCCCAATGGCATCGTAAAGAACATTTTGAGGCATTTCAGT

CAGTTGCTCAATGTACCTATAACCAGACCGTTCAGCTGGATATTACGGCC

TTTTTAAAGACCGTAAAGAAAAATAAGCACAAGTTTTATCCGGCCTTTAT

TCACATTCTTGCCCGCCTGATGAATGCTCATCCGGAATTCCGTATGGCAA

TGAAAGACGGTGAGCTGGTGATATGGGATAGTGTTCACCCTTGTTACACC

GTTTTCCATGAGCAAACTGAAACGTTTTCATCGCTCTGGAGTGAATACCA

CGACGATTTCCGGCAGTTTCTACACATATATTCGCAAGATGTGGCGTGTT

ACGGTGAAAACCTGGCCTATTTCCCTAAAGGGTTTATTGAGAATATGTTT

```
TTCGTCTCAGCCAATCCCTGGGTGAGTTTCACCAGTTTTGATTTAAACGT
GGCCAATATGGACAACTTCTTCGCCCCGTTTTCACCATGGGCAAATATT
ATACGCAAGGCGACAAGGTGCTGATGCCGCTGGCGATTCAGGTTCATCAT
GCCGTTTGTGATGGCTTTCCATGTCGGCAGAATGCTTAATGAATTACAAC
AGTACTGCGATGAGTGGCAGGGCGGGGCGTAAAGATCTGGATCCGGCTTA
CTAAAAGCCAGATAACAGTATGCGTATTTGCGCGCTGATTTTTGCGGTAT
AAGAATATATACTGATATGTATACCCGAAGTATGTCAAAAAGAGGTATGC
TATGAAGCAGCGTATTACAGTGACAGTTGACAGCGACAGCTATCAGTTGC
TCAAGGCATATATGATGTCAATATCTCCGGTCTGGTAAGCACAACCATGC
AGAATGAAGCCCGTCGTCTGCGTGCCGAACGCTGGAAAGCGGAAAATCAG
GAAGGGATGGCTGAGGTCGCCCGGTTTATTGAAATGAACGGCTCTTTTGC
TGACGAGAACAGGGGCTGGTGAAATGCAGTTTAAGGTTTACACCTATAAA
AGAGAGAGCCGTTATCGTCTGTTTGTGGATGTACAGAGTGATATTATTGA
CACGCCCGGGCGACGGATGGTGATCCCCCTGGCCAGTGCACGTCTGCTGT
CAGATAAAGTCTCCCGTGAACTTTACCCGGTGGTGCATATCGGGGATGAA
AGCTGGCGCATGATGACCACCGATATGGCCAGTGTGCCGGTCTCCGTTAT
CGGGGAAGAAGTGGCTGATCTCAGCCACCGCGAAAATGACATCAAAAACG
CCATTAACCTGATGTTCTGGGGAATATAAATGTCAGGCTCCCTTATACAC
AGCCAGTCTGCAGGTCGACCATAGTGACTGGATATGTTGTGTTTTACAGT
ATTATGTAGTCTGTTTTTTATGCAAAATCTAATTTAATATATTGATATTT
ATATCATTTTACGTTTCTCGTTCAGCTTTCTTGTACAAAGTGGTTGATAT
CCAGCACAGTGGCgCCGGCCGCCACCGCGGTGGAGCTCGAATTCGTAATC
ATGTCATAGCTGTTTCCTGTGTGAAATTGTTATCCGCTCACAATTCCACA
CAACATACGAGCCGGAAGCATAAAGTGTAAAGCCTGGGGTGCCTAATGAG
TGAGCTAACTCACATTAATTGCGTTGCGCTCACTGCCCGCTTTCCAGTCG
GGAAACCTGTCGTGCCAGCTGCATTAATGAATCGGCCAACGCGCGGGGAG
AGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCG
GTAATACGGTTATCCACAGAATCAGGGGATAACGCAGGAAAGAACATGTG
AGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGC
TCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCG
GTAACTATCGTCTTGAGTCCAACCCGGTAAGACACGACTTATCGCCACTG
GCAGCAGCCACTGGTAACAGGATTAGCAGAGCGAGGTATGTAGGCGGTGC
TACAGAGTTCTTGAAGTGGTGGCCTAACTACGGCTACACTAGAAGGACA
TATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATC
CTTTGATCTTTTCTACGGGGTCTGACGCTCAGTGGAACGAAAACTCACGT
TAAGGGATTTTGGTCATGAGATTATCAAAAAGGATCTTCACCTAGATCCT
TTTAAATTAAAAATGAAGTTTTAAATCAATCTAAAGTATATATGAGTAAA
CTTGGTCTGACAGTTACCAATGCTTAATCAGTGAGGCACCTATCTCAGCG
ATCTGTCTATTTCGTTCATCCATAGTTGCCTGACTCCCCGTCGTGTAGAT
AACTACGATACGGGAGGGCTTACCATCTGGCCCCAGTGCTGCAATGATAC
CGCGAGACCCACGCTCACCGGCTCCAGATTTATCAGCAATAAACCAGCCA
GCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTA
ATAGTTTGCGCAACGTTGTTGCCATTGCTACAGGCATCGTGGTGTCACGC
TCGTCGTTTGGTATGGCTTCATTCAGCTCCGGTTCCCAACGATCAAGGCG
AGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTT
ATGGCAGCACTGCATAATTCTCTTACTGTCATGCCATCCGTAAGATGCTT
TTCTGTGACTGGTGAGTACTCAACCAAGTCATTCTGAGAATAGTGTATGC
GGCGACCGAGTTGCTCTTGCCCGGCGTCAATACGGGATAATACCGCGCCA
CATAGCAGAACTTTAAAAGTGCTCATCATTGGAAAACGTTCTTCGGGGCG
AAAACTCTCAAGGATCTTACCGCTGTTGAGATCCAGTTCGATGTAACCCA
CTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGC
GACACGGAAATGTTGAATACTCATACTCTTCCTTTTTCAATATTATTGAA
GCATTTATCAGGGTTATTGTCTCATGAGCGGATACATATTTGAATGTATT
TAGAAAAATAAACAAATAGGGGTTCCGCGCACATTTCCCCGAAAAGTGCC
ACCTGACGTCTAAGAAACCATTATTATCATGACATTAACCTATAAAAATA
GGCGTATCACGAGGCCCTTTCGTCTCGCGCGTTTCGGTGATGACGGTGAA
AACCTCTGACACATGCAGCTCCCGGAGACGGTCACAGCTTGTCTGTAAGC
GGATGCCGGGAGCAGACAAGCCCGTCAGGGCGCGTCAGCGGGTGTTGGCG
GGTGTCGGGGCTGGCTTAACTATGCGGCATCAGAGCAGATTGTACTGAGA
GTGCACCATATGCGGTGTGAAATACCGCACAGATGCGTAAGGAGAAAATA
CCGCATCAGGCGCCATTCGCCATTCAGGCTGCGCAACTGTTGGGAAGGGC
GATCGGTGCGGGCCTCTTCGCTATTACGCCAGCTGGCGAAAGGGGGATGT
GCTGCAAGGCGATTAAGTTGGGTAACGCCAGGGTTTTCCCAGTCACGACG
TTGTAAAACGACGGCCAGTGCCAAGCTTGCATGCCTGCAGAGTCTCATAT
GTTTCCTCACTTATTGAAATGTTAAGCCTTTTGACTATCCTATCTTTCCT
CTTCTCTATCATTTAGGTCACCTTGTTTATTGTTATTTGAAATACGTATC
CGTCTTCGTCACATCGAAGTATAAATTTTGTATCCATTATTAGCATATTCT
ACGTCAAAGTTCCCACAACAATAATTCGGGTCTTCGGACTCGTTATAGAC
TTTGCTCCAACCATCTTTTTTGTAGTGCCTCTTCTAAGTAGTCTACTCTGA
TGAAGCCTTCATCATATTCGTTCAGTACCCTAAAGCTTATACTATCAATG
```

```
CCTAATACGTCTAATAGCTTCAACAGATCGAATATAGGAACTTGCACCAT
CATTTCAGCTCACCTTAATGAGCTGATATAATTCCGCTTCTATCTTTTGA
ACTTGGAAGTATGCCTTGCCTAGCTTTTGCTTATCCATATTGCCCGTTAT
TCTATCAATCTTAATCTCGTGGATTAATGATAATAGCTCTCTGACATCCT
CATCAAGCATTTCAAATAATTCTTTCTCTAAGACTTCTTTACTCATTGTT
TTTCACCTTAGCAAACTCATCTAACGTTGTTTGTCTCAGTTCTCTTTTCT
TTATCAAATAAAATTCCGAATGTCCCTTCTTATTGTTATTACTGTACTTC
ATGTCAGTTCACTGCTTTGCCTTTATAAATCCTTGATCCGTTTGCTCAAA
ATTTGCGGGCTGGGCATCAAATATCTTAGCTATATTGTCTTGTGTTTGCT
CTTGTTTTTGTTCTTCTTTCTGCTCTTGCTTAATCCATTTGAACGTTGTC
TTTCTGTTTTTGTATTGTACTTCACACTCGTCTGGATGTCTTTCGCAAAT
AGCTTTCAATGCTCTCTGTATGTTATACGCACTCGGGACTGAAATCTCAA
ATTGAGCTAGTATATCCTCTAACGTTAATTCACCTTTCTTTTCAAGAATT
TTATACATTATTTCCGCCATCTTGTATGAATTTAGAGTTTGTGCCATATT
CCCATCCCACTCTATCTATACTCTATGTATAAATTAGTATTTAAGTCTTA
CTCTATCTATACTCTATCTATCTCTCTATATACACAGTGTTTGGGTAACT
GGCAAAATTCTGTCTGACTGCTGTCTGACAAGAGTTTACTCTATCTCTCT
ATATCTATATACACAAACAGAGTTAGTCGACTCTGTGTATCTTATGTATC
TTATACAAAAAATATGGGATGTGCAAAATCTGAGCTACTAATACTGCTTG
AATATATAGATAGAGTGTAAGGACTACGAGAGTTGTAAAAGAATAATA
GTAGAGCTAGAAGAGAGAGTGAAGAAAATAGCTTTCGTAGAAGCAATAAA
TGATTTGTTCTAAACTACTTTTTTCTCTATCTCTATATCTATATATAT
ACATAACTAAAACTAAAAGAATAAACAAAAAACTAACAAAATCAACTCAC
CATTATACAAACTCAGAAAAACTATTTTTTTGTTATACTCTTACCCCATA
TATATATAGATATATAGATAGAGAGAGATAGAGTATAGTAGGGCATTTAA
GATTTTAGAAGTTCTTCAATGCGTCTTCTGATTGCATCTGCAACAAACTC
TTGTCTGCTTATATATCCGCCCTTGCCTGACGCTATTAGTTCATCTATTT
GTTTTGCTAATTCGATTGGAATCGAAACGGTCACATATTCTTTTTTGACT
GATTTCCTCGGCATACGCTATCTATACTATATTAATATGATAATATTAAA
TGATTCACGATATATAGATAGAGTATAGATAGAGTAAAGTTTAAATACTT
ATATAGATAGAGTATAGATAGAGGGTTCAAAAAATGGTTTCACCCCAAAC
CCGAAAAGAAGAAGAGTTATTAGAAAAACAAAATTCAGTTTTTTATTTGT
TAACTTTAGGAAGGAAACCGTATGGTTCATATTTGCATATAAAAATTGAA
CTAGACGAAGATGAAAAATTAGAGAAGGAAATCTATGCGGATAACATTAA
GCTAGAGAATGAATTAAGACAACTGAAGAGGTTGTATGAAGTATATCAGA
GCGTAGAGATTGACGATGCTCAGAAAGCAATACAGAAGGAAGCATTACTG
ACGATAGCGAAAATACTAAGTGTTTTTGACTTCTGAGGAGGCTGAGGGGC
AATGAAGGCTGAGGAAACAATCGTGGAACAGATTCAGGACATAATTCAAA
AACTTCGCTATTATACAGGAAGATCAAATAGACATTTCAAGATGATTAGA
AACTATTATGAGGAGTGTATAATAATAGTAGACGCTGAGGAGTTTATACA
AGAAAATAACACTCTAAGCATTACTGTATATTCTGAGGATCTTATATATT
ATACTGTTGATATCCCGCTGAATTTCATTAAACATGTATTCGTATCCGCT
TCGATTGATCAGCTCAATGATCAGCTTCAGCTAAAATATAATGAGGGTCT
GATTAGAGTTTCTCTTACTTTGAACGATGACTTATGTGAGAAACTGAGAA
GCTCATACTGCGGTGATATTACATTCTTTAATGAGGCTGAGGGGCAATGA
AGGCTAGGGTTGAATACATCAAATTACCTAGATGTTACACAAAAACTTAT
AGAAAAATCGAAGCGAAAAGAACAACGACGGTACAATAGAATTAACGTT
AGAGGAAACAATGCAAGTAATATCCTTTAAACTACCCCCGGCGTTAAATG
CAAAACTAGAACAAATTGCGATCAAAGAAAAGAAAAGCAAGAGTGAAATT
ATTCGAATAGCGTTAGCGAGGTATGTAGAAAATGTTTAGATGCCCCATCT
GCGGGTTCAAAACGCTGAGATTGTTCGCGCTTAAACAACATACTCGAAGG
GAGCATGTGTTGGTCAAATGTCCCATATGCGGGTTCACGGGGAAGCATTT
ATCTCAACATTTCTATAGTAGGTATGATATTGACCATCTCATATACTGCT
ACCTATTCTCTTCTTTCAGATTGCCTAAGAATGTTAGGTTAGCAATAAAG
AGAAAATTAGAGGTTGAGTGAATAATGTATCAATGTCTACGTTGTGGTGG
TATATTTAATAAAAGAAGAGAAGTGGTTGAGCATTTGCTTGTAGGGCATA
AGCACAAGGATAGACTAACACTGGACTTTTATTATATCTACTTCAGGGTG
AGAGGACAATGAACCTAATTGATATCATCTTATTTTACGGCTTTCAATTC
AACGATTATTGGACAACTGTCTTAGGGTTGAGAGTGGGTGCGGAAGAGAA
GAATCCCATAGCGGGTCTGTTCATTTCATCACCGTATCGTTTAGCGTTGT
TTAAGTTTGGCCTTATCACCATTGGTATGTTTATATTAATTTATGTTGTT
AGATTCAAGACATGGACAGAGATCGTATTGACTGTAACAGACGTTGTCGA
ATGCCTTGTCACGCTGAATAATACCCTTACGATTAGGAGGTACAAAAGGA
GGGGCGTTAGAGGATGACGGAGTCAGACGTTGACTCAGGTAGTAAAAAAT
ACCTGAGTAACCATAAGGGGATTTTTATTCATGTCACACTGGAAGAGTTA
AAGCGTTACCACCAACTTACGCCGGAACAGAAGAGGTTGATAAGGGCAAT
CGTCAAAACGCTTATTCATAACCCGCAACTGTTGGATGAAAGCAGTTATC
TTTACAGATTGCTCGCGAGTAAAGCGATTTCACAGTTTGTCTGCCCGCTT
TGTCTAATGCCCTTCAGCTCTTCCGTATCACTAAAGCAACACATCCGTTA
TACTGAACACACAAAGGTTTGCCCGGTGTGTAAAAAGGAGTTTACCTCAA
CCGATTCAGCCCTAGACCATGTTTGCAAAAAGCATAATATCTGCGTTAGT
TAGGCTCTTTTTAAAGTCTACCTTCTTTTTCGCTTACAATGAGGAAGTCC
CTTCTAGCCCTACTAACCCTATCCCTAGCGTTACTATCGTTTTTAATAAC
ACCATCGATGGCATTGAATTCTGGCGGTTCACCGATACCGATATATTATA
ACTATTATAACTACTATAGCCTTAACGCAGAAGGGTTTGGATTCAGTTTC
AATAATAGCAATAATTGGGTTGAAACGAACTTTATCTCAATAACCATAAA
CTTACCTAGTTCATTACCAAATAACTATCAAATCAATAATGCCTATTCTA
TCGTAGTAGGATTATCACCCATATCCGGTTAGCAATATAAACATTTTTAAT
AGCCCATTAGAAGCATATGTTGAACTATTCTCAAACCCACCGAATACATA
TCCAAATGAAATAGGATTTGTAGTTAGTTACGGCTCAACTGTATTTTATA
GTTATACCACACTGTATAGCAGTTTTGCGGGCACACAACTAACAATAACT
```

```
ATATCATATACCGGAAATGGGTTTGGTGTGCAATTCTCTGACAGTAACGG

GTTCTCTCACTCAGTTTCGGTAAGTTCGGTAAACTTTGTACCATATGGTG

CTCTAATACTCGGATCACTAATCCCGAACGGGAACTATTACTACTACCCA

GTAGGTAACATGTTACCGAATGCATCGGTGAACTTCTCATATACGATCTC

AAGTTTCACAATAGAAGGAAACCCGGCCACATCCGTCGATATTACCACAC

TTGGATTAGAAGGAAACACTGCAATATATACTTCAAGTAGCAATTGGTTC

AAATGGGTATCCGGTAGTGTGGTTATCACAAATGCCGTTGCCTATACCTA

TACCGATTTGGCTAGAATAGGAGGAAGTGCACAAATAAACTATACTGCAT

CGCAGCTATATTAAGCAAAATCTTTTTTTACCTCTTTTTAAATCTGTCTT

ATATGAAAAACTGTTTACAGTTGTAGGTTCTATTTTCTCTGGTTTGGGG

ATTTGGCTTAAGTCAATAGACCAGTCATTTTATTTAACGAAAGTATTGTA

TAACGGAAAAGTAATTGAAATAGTTCTAACGCCCGAGACAAATGAAGTCG

TGAAATCTTCCAACGGTGTTATGAACGCAAGTGTAACTTCTCTACCTTCC

ACAATTCTATACCAAGCACAATCCGTGCCTTCAATAAATGGAGGAACTCT

TAGTGTAATAAATACCACAGTTCAACCGCCATGGTATGCTAACTTATGGC

CTGAAGTCTTAACAATAGGTATAGTGATGTTGGGAATTGCAATATTCAGC

TGGATTAAACTTAAATTTAGAAGATAGCCCTTTTTAAAGCCATAAATTTT

TTATCGCTTAATGAAGTGGGGACTATTATTCTTAATAATGTTTATATCCA

TTTTTTCCCTCAACTCTTTAGCCCTATTAATCGGCGGAGGAGGGCCCAAC

AATAATGGTGCGGGAGTTTACACTCAGACTATAACAGTTAACGGAGGAAC

CGTACGAACTACTCTTAACGGTTCAACGCTTTCTACCGCACCATGGCTCA

ACCCCTCTTACGTAAGCGTCTACAACACATACTACCTTCAGGTTTTGCCG

AACCAAGAGTATATTGACAACAACGTTTCGTTATCCCTAAATACGGCTAA

CATTGCGTTAAACGTCACTTGGTTATTGGCGTCCTCAAGCAATACGGGAT

CCTACGGTGCAATCGCCATAGGCTACGGAGTGAACTTTCCCGCGGGGTTT

GTCAATAACTACGGTCCTTCCGCACCCTTACACGCCGGACGGAATCGTAAT

ATATCTCATGAAAGGAGGCATGCCGACCTATCGTTTATTCGTATACTTCA

ATGGAGTTGAGCAGTTAAACGTTTCAGTCGGGTCAATCAGTGTGGGACAA

AAAATAGGTTTAGGGTTCTTTTATCTACAGAACACACTTTACGTTTACTA

CTATAACGGTACTTTAAAGACTTGGTCATTAACGCCCGGTACGCTGATTA

CTATAAATAGTAATTACGTTATAGACGCACAGAATATAGGGCCGGGCTAC

GGCTACGGTCAATGGGTAATAGTTAATTATCAATATGCGATGCCGGTTAC

TGCACAACTGACGGTTAGTTATTTCGCATTAGGGTACAATGTATATCATT

TCTTAATGGCTTATGCGGGTGCTGGAAACCCGGTAAACATAACTGCGAAT

AACGGGCTTCTTACAGTATAACGGGTATAGTTGCAGAGAAGAACTTTAC

GATAACGGGAATTCAGCAAGGCCTAGCCTATGCTTTCAGCTTGTTAGGGA

AACCGAATGGCTTATACTTATTATATATGGGGCCAATTGAGGGCAGCCCA

CCAACGTGGTATGTAAACGTAACCGTAGGGCTTCAGATCGTTACACCCCA

GAAAACGATAAACTACAACTTAACAATACCAGTAATCGTTGAGGGCTATG

CGTTATACCCTTCTGTTAACGTACCTTCCGGAACTTACCTAAGCGGACAG

ACTATTAGCTTTACCCTCTCATCGTTCTTGGGATACCCTTCAGGCTTAGG

CTATTACACCGCAGTAAATCTAATCGCAAACGTAACAATAAACGGTGTGA

GTCATGCTATCCCCTATAGTTTCACCCCGATAGTGCAAACCCCGATAACT

TATTACTACACTGTTATAGTGGATGAAGGACAATTTGCATTAATAGATTA

TCAAGGGAGTTTCACAGTCCTACCCGCACAGAGTCAGCCCGTGATATTCA

TTACTTCTTATCCTAGAATTGGGCTATTAGGACAAACGATAACTGTGACT

TTCCAGTTCACTTATAATAGTCCCGTAGCGAATGTAACTCAATCAGCGTT

TACGCAATCATCTAATATTCTCGCTTTTGCCTATGCGAAAATGGTAACAA

CAAACGCTATAGTTCAGTTCAAGGCGTATTGGCTAAGTGCTAATGACGGG

TTGGTGATTATAACTCAAACGAATAACTATCTAATTCCGTTTAATAGCAG

TATAACGGGCTTAAACTTCGCAAACAATAGTGTTAATACGTTAACGTTTC

AGATTGTAACGGGTAACTATGTACAAATAACTAGCTCAGCGGGAGGCGTG

CTTACCCTAAGCAATACTAGTCCGATTATAGGAATAGGGTTCTATTACGG

TTCCGGTGTCCTACACCTGAACTGGTTCTTCGTTAGCGGTATCATTTTGC

AGTCTGCAACGGCAAATCAGGCTTACGTTATTTTGACGGGACTAACCCA

AATACGCTTTCACAGTATACGACGGGCTATACTAACGCTTCGGGGTTCGG

TACTGTAACGCTGAAGTTGAGTTACACTCCTTACGAACTTGTGGATGTAG

ACTGGTACGGCGTTACATACGCTTTGTTAAACATTAGCGTTTCAAACACT

ACTACAGTAAGCAGTACTACGACCGTGAACACAACAACGCTTAACTATAA

CTACACTAAGCCTTTCAGCAATAACATAGCACCTAACAGTCAGCTTTATG

ACTTCTCAGCGTATCAGCCGTGGGCGAAATTATCGGGATTGTGGTCGTG

GTCGTCATAGCTCTGCTGGGCTGGAAGTTCGGCGGGTCTGCGGGAGCTTC

GGGTGGTGCGGTTATGGGGTTAATCGCAGTCAGCTACTTAGGTTTACTGC

CTTGGTACCTATTCTACATCTTCGTATTCGGTATCGCTCTATTACTTGCT

AAAGTATTTGTAGACCGTTTCATGGGGAGGGAGGAATGACGGACGCAATC

AGTTTAGCCTTGCAAACGGGCTTAGGGCCGGTGGTAGGGGTAATTATCAT

ACTGGCAATGATGGGCTAACGTATAAGATAGCGGGAAAGATCCCGGCAA

TCATAACGGGAATAGCCTCGGCTTTCGTCCTAATGTTTATGGATTTTTTA

CCGTTATTTTGGGGTATCGCAATAATCTTCGGGTTAATCGCGGGTATGGT

GGTGACAAGGGATGGGGACTAAGTTAGTCGTTTACGTCTTATTGTTTGAC

GTCTTCCTATCGTTAGTGGTAGGTGCCTACTCGGGTATAGCACCGCCAAG

TATTCCACCGGTACCTACATATGCTTCAGCCCAACTCACGGCAAGTCTAA

TCACATGGACAGTGGGATGGCCTCCTATTACATTATGGCCTCAGATAACG

CTTATTCCGCCGTTTTCGATTTTGGGTGCAAACTTCCCCGGCTTAACCAT

TCCTAGCTTAACGATACCCGGTGTAACGCTCTTCTCAATAAGCTTCAGCT

GGTTAGCCCCAATTATTTATATTGCAAATTGGATCATTTGGGTCTTTCAG

ACTGTTGCTAGTGTGCTATCTTATTTACTTAATATCTTTACGGGTTCGGT

AGGTCTATTGAGTAGTGTACCCGTCTTAGGGCCATTTTTGACCGCCTTCG

TGTTGATAGTTAACTTCGTGTTAGTGTGGGAATTAATCAAGTTAATTAGG

GGGTCGGAATGACGGAGTATAACGCAAACAGTATAAGGGCTAAGATACTG

AGGCGTAAAATCCTTCAACTGATTGCGGAAAACTACGTTTTGTCAGCGTC
```

```
GTTAATCTCTCACACACTCTTACTCTCATACGCCACAGTGCTTAGGCACT
TGCGTATCCTTAACGATGAGGGCTATATCGAATTGTATAAGCAAGGTAGG
ACGCTATACGCAAAAATCCGCGATAATGCGAAACAAATTCAGATTCTGAA
TTCAGAACTGGAGGGGTTTAAAAACGTAAGCGGGAAGCCGATATTGACCA
AGGATGAGACTCCTAAGGAGTTTGGCAAGAAAGATAGCCTCACTCAAAGA
GGCTAAGGTTGCACTAAAAGTAGCAAGCGACCCCAGAAAGTACTTCAACG
AAGAACAGATGACTGAGGCTTACAGGATATTCTGGCAGACATGGGACGGG
GACATAATTAGAAGTGCTAGAAGGTTCGTGGAAGTAGCAAAGGCAAACCC
CAAGCTCACAAAAGGTGAAGCAACCAACATAGGCGTATTGTTGGGCTTAT
TCATCTTCATACTAATAGGTATAGTACTATTGCCCGTAATCGTTAGCCAA
GTCAACAACCTCACAAGCGGTACTTCACCCCAAGTAACCGGTACTAACGC
CACACTCCTGAACTTAGTGCCGTTATTCTATATCCTAGTCCTCATAATAG
TCCCCGCAGTCGTGGCGTATAAGATATACAAAGACTGAGGTGTGAGGGAT
GGAAATCAGTTTAAAGCCAATCATTTTTTTGGTCGTTTTTATCATCGTAG
GGATAGCACTATTCGGCCCTATAAACAGTGTTGTAAATAACGTTACCACA
TCGGGAACCTACACTACTATAGTTTCCGGTACTGTTACTACGTCTTCATT
TGTGTCAAATCCGCAATACGTAGGTAGCAATAACGCTACTATCGTAGCCT
TAGTGCCGTTATTCTATATCCTAGTCCTCATAATAGTCCCCGCAGTCGTG
GCGTATAAGTTGTATAAGGAGGAGTGATATGAAGTGGGTGCAAAAGGCGA
TAAAGAGACCCGGGAGGGTACATCGCTACCTTATGAGGCTCTACGGCAAA
CGGGCGTTTACAAAAGACGGTGACATAAAGGCAAGTTATCTCGATAAGGC
GATAAAGCACGTTAAAAAAGCTAAGATCCCGAAAGAGAAGAAACGTAGTT
TACTGTCAGCCCTACTGTTAGCGAAAAGGCTTAAGCGGATGCACCGCAAG
TAGGCCCTTTATAAAGTCATATTCTTTTTCTTTCCCTGATGAGTGCGTTA
GGGGATGTAATCTACATCTTGGGTTTTCTCTTTCCGGCTTTAGGGCTAAT
CAGCCGAAACTATCTTGTTAACTTAATGGCATTCATAATAGGAACAGTCG
CCTTTTTGGTCTTCGTCCAAGGCTATACCGATATAGCGTTCAGCAGTTCG
ACGTTTTACTTAGGAGTACTGCCTCTACTACTTGGTCTCGTCAACTTAGG
CTATTTCTTCAATTGGTTGAGGGAGGAAAGGATATGAGGTGGGGTAGAAG
AGATGATAGGGATACCGGCAAAATACTTCGAAATAGGAGTCGTAATAGAT
TCAACATTTATCATTATGTCTCTACTGTTAAGAAAGTCAAAGAGACAGAG
AGAGAACTCCTTCGACTTACGCAAACATGGAAGGCTATTAGGCTTATATC
TTATAATAGCGTCGGCATCAGCATTAATCGTCTCACATCTCGCCTTATAC
ACAAACTACATGAACTACTTAACGGGCTTATCTCTTAATGCGTTTCTGTT
TTATCTTGGGTTGAGGTGTTTGCATGTCTGATGGGAAACTCCTTTCTGCT
TTCGAGGAGGAATTAAGAAAAGCCCAAAGCCTAGAGGAATTAAAGCAAAA
GTATGAGGAAGCCCAAAAACAAATAGCTGACGGCAAAGTACTAAAGAGGC
TATACAAGGTTTATGAGAAAAGGCAAACAGAATTAATGCTTCAGCAATAT
AGGCAGATAAAGGCTGAACTGGAAAAGAGGAAAAAGGTAAAGAAAAAGGA
TAAAGCCGACATAAGGGTTAGAGTAGTAAAGAAGTGGATAAATTCACGCT
```
```
TATTCAGTGCTGAGCATTACGTCGCATTACTGCAAGAAAATCAAGACGGC
TTATCGATACTATTTCTAAGAAGAGCAAAACTTATAGAAAATCAAGGCTA
TCTAATGCTAGAAGTGAAGAAGTTAAGGAAGGCATGGGTTTTAACGGCTG
AACCTATACTCCTTGAAAGGTTAAAATTCCCATTCGGCAAAAAGTTTGTA
GCCGTGCATTTCGTTTTACCCAATTATCCTTACACACTTCAGCTTAAACC
GGATGAAAAACTGAAAGAGTTAGCAGTTAAGGCGATAAACGGGCCTCAAA
TAATGAGCGCAATGATACGTACAAAGTTCTTCGAAGCGTTAGCTAGGGTA
GGAAGCGGGCCTGATCTGATGATGCTCATAATCGGCGTTGTCATGGGGAT
TGGCATAGGCGTAGCGATAGGTTTCGGTATAGCTAACGCAAACTTAACGC
ATTTGCTATCTCAACACGTTACGAACACTACAGTGACACATACTACGACC
ACAACGACTTCACCCTCATTCACGATTCCCTCAAACTCCTCAAAAGGGGT
GAGCTAAAATGGTCTCAGTAACGAAATAATAACATATGGACGAGAAGCA
ATAGAAAGAATAATATGCAAATATTTTAAAGATTCGAAAATAGAAAAGAT
ATTATTCTTGCCGAGTGAGGAAGACGTAAAGGCAAAATATATCATTGGAC
GGGTAGGGTTTATAAGGATTAGTAATACGTGGTCTGGAATTGTCGTAGTT
GACGGGTACAAATACCTTTCGTTGCTGAAGTCCACCTTAATGGCAAGAT
TGATATTTACCTTTATCCTCAAAAGGACTTCTACTTAGCACATTTGGTGG
GTGAGCTGAATGGCTAAAAGAACGGCTTAACAGAACTAGAGCAATTAAA
GAAAGAGAACGAAGAGTTGAGAAAGAAGTTAGAAGAGTTAGAGGCGTTGA
TCAATAACGATAGCGATGACGACGAAGAGTTGCAGGAAATCGAAAACCCG
TACACCGTTACAAACCGTGCAATAGATGAATTAGTAAGCCCAAAGGACAC
AATGTTCTATTTGTCGGGAAACCAGATATCGTTAATCTTAAGTGCTTTTG
AATTCGCCCGCTTACCGACGTACTTCGGTGAGGAACCGGTAACGGAGTTA
GCGGAATACGCCCATAAGTTGAAACATTATCTCGTTTCGAAAGGAGGAAG
AGGAAGGAGGGATATACTGAGAGTCCTACGCGTTAGTTCAGGTCAGACAA
GAGAGAACGTAAACAAATCAATTCTGAAACAATTATTTGACCATGGTAAG
GAACATGAAGATGAAGAGTAATGAATGGTTATGGTTAGGGACTAAA
TTATAAACGCCCATAAGACTAACGGCTTTGAAAGTGCGATTATTTCGGG
AAACAAGGTACGGGAAAGACTACTTACGCCCTTAAGGTGGCAAAAGAAGT
TTACCAGAGATTAGGACATGAACCGGACAAGGCATGGGAACTGGCCCTTG
ACTCTTTATTCTTTGAGCTTAAAGATGCATTGAGGATAATGAAAATATTC
AGGCAAAATGATAGGACAATACCAATAATAATTTTCGACGATGCTGGGAT
ATGGCTTCAAAAATATTTATGGTATAAGGAAGAGATGATAAAGTTTTACC
GTATATATAACATTATTAGGAATATAGTAAGCGGGGTGATCTTCACTACC
CCTTCCCCTAACGATATAGCGTTTTATGTGAGGGAAAAGGGGTGGAAGCT
GATAATGATAACGAGAAACGGAAGACAACCTGACGGTACGCCAAAGGCAG
TAGCTAAAATAGCGGTGAATAAGATAACGATTATAAAAGGAAAAATAACA
AATAAGATGAAATGGAGGACAGTAGACGATTATACGGTCAAGCTTCCGGA
TTGGGTATATAAAGAATATGTGGAAAGAAGAAAGGTTTATGAGGAAAAT
TGTTGGAGGAGTTGGATGAGGTTTTAGATAGTGATAACAAAACGGAAAC
CCGTCAAACCCATCACTACTAACGAAAATTGACGACGTAACAAGATAGTG
```

ATACGGGTAATGTCAGACCCCTTTTAGCCATTCCGCATACTTTTTATATT
GCTCTTTCGCTATGCCGAAGAGCGATACGTAATGTTGCGTTAAAACGCGT
GTCGGTTTACGCCCTTGAATAAAATCGATAATATCTAACGGTACGCTTAG
CTCAGCCATCTTAGACGCTACGAATTTGCGGAAGTACTTTATCGCTATAG
CGTCCTTATGACGTCGTTCAAAGTCCGCTATTGCCCACTTCGTCACCTCT
ACTCTCTTCAGAGGCGTTATGTGGAATACATAGAAGACGCCCTTATATCC
CCTAGTCCAACTAAGCGGATAATAACAGACGTCGTTACCGCAAATGTCCC
TTTCGGGTTCCTTCAGCACTTTCAGTATTTCGCTCAGCCTAACGCCCGAC
TCGAGAGCGATACGGTAGATGAAGTAGACGTTTTCGCTATAGTCTTTTGC
TAATTGTAACGTCCTTTTTATCTCTTCCAACGTTGGAATGTAGATATCAG
CGTTCGCCTTCTTCACCTTTACCGCTTTCAATATTTTATCCGCAAATTCA
TCATGTATGATATTGCGTGACGCTAAGAAACGTGCAAAGAGTCGGTAAGC
CTTCTGTGCGTCTCTCGTCTCTTTATACGGCTTTGATATAGCATTGATGT
AGTCCTTTGCAGTTTTTTCGCTTATCCCCCTTTCGTTCATGAGATAGTCG
TAGAACGCCTTTATGTTGCCGTCCGTCGCGTATTGGCGCAAATTGGCAAC
CAACGCTATTTTACGTCGTTCAGTTCCCTCTTTTCCGCCTCCGGAGCCGG
AGGTCCCGGGTTCAAATCCCGGCGGGTCCGCTTGTAGGGGAGTATCCCCT
ACGACCCCTAATTTCATTTTTAGATATGATTCAACGACGTCAGCTAAAGG
ACCCACGTAACGCTCTTTTACCTCACCGTTTTCATACTCTAGCTTGTAAA
CATAATACCGCCCTTTCCTCTCGCGTAAAATATAATCCCCGTATTTATAA
CGCGTCTTATCTTTCGTCATTTCGCCTCACAGTATTATGGTTGCCAAAAC
GGGCTTATAAGCATTGGCAACCCGTTAATTTTTGCCGTTAAAACACGTTG
AATTGAAAGAAGACGGCAAAGAATCCACACAGGTAATACTAAAAAAGTAG
TATTACTTACATTAGAAGGACTCATTTGTCCACCTTGTATTCTAGCCATG
CTATCTCTGCCTTCAGCTCATCTAGCTTCCCCTTTATGTCTGTCAGGTCA
AGGGGAACTCCTCTCATTAACCTGAGTTCGTTTTCGATTTTTTCAAGCTC
CTTTTCCAACTCCTCTAGTTTCTCTAATTCCTTTAGTCGTTCTTCCAATT
TCTTTTTCCAATTTCCCCTTTGCGTCATTTATAATTATGCTTACTACCCAA
ACAATTCCTAAATCAGAAATAATTATTAACTCCTCTGAGTTGAATATCAT
TTTCCGCCCCTCGCTAAATACTCCTTAAAGCTCTGATAGAACCCCTTCAG
ACTAACCCGTAAGTCTGTTAGGTTCTTCCAGTATTGTAATGGGATTAAGT
AATAGTAGCTTACTGCATCTCTCTCAAATTTGTCCTTCTTAATCTTTCCT
TGCTTTTCTAAGTTGAGTATTTGCAGTGCTGAGATACATTTTAACTTGTC
CTCAGCATCTGAATAGTGTATAAACCAAACCCTCCCCATAACCTCATTCT
GCTTTGCAACTTCTACTTTAGTGCTTAATATTGCGTAAACGCTTTCGCCG
TATCTTTCTTTGCTCTGTTCTTCAGTCCATGAACTTCCCGTAATATCTAT
CCAAATTAAAGGATAATATTCTGTCTTAGCCTTAACGTATAAAGTCAAAT
CGTATTTATCTTGCAGACCGCTATAGTATTGCTCATTTATTACATTAGTT
AAAGTCCCCACGCCAGTTGGGCGGATATAAACATCAAAGTCTAACAAACC
CTTAGCCCGCCACTTTGATAAAGAGATTAAGAGCTTTCCAAAAACTAGGT
ATTCTCGCCCTAAATAAGTTGAAGGGAGGATATAATCCTCAGCTTGATTA
CCCCAATACTTTAGCTTAAAATTAGTTTCAGCCATCTCACTCACCATATT
GAAACGTGGGCTAGTATGTGAATCAGTACTGATGCTATTGCAAATAACAC
ACTTGCAGTAGCAATTCCTATTACAATCCATTTACCATAATCCACCTTAG
TTTGTTGGTCAATATACTCGTTGATGATCTTTAGTATTTCTGGCTTTAGT
TCTGATAATGAAAGGAAGACAGAGGCATAAAGTACTAAGGAGGATGTGAA
CAGATTATCCGCCTTTTCTGAAAGTTTATAAAGCTCATATCTTGCTCTCT
CATAATCTTCATAATTAATAATTTCATCAAACTTTTCTACTTGCTCTTCA
TATTCTTTCTTCAGAGAGTAAGGAGTTGTCTTTTCAATTACTCCTAATTT
TATTAACTTCTTAACAGCTTCCTTAAATCCTTGTTTATTGCTAGCATACG
CTAAAGGGTCTTTTCCTTCTTGAGAAGCTCTATAGATAACTATAGCACCA
TAAACAATATTTACAATATCGTATGGTAAGGAATACGCACCGATTTGGGC
AATATCTTCAACTCTTCTTTGATCCATCTAGTTCACCTCTTTTTGATTTG
TTTGTAGGTTTCTATCGCAGTTTTCAGCGATATCGCAAATAGCTTCCCCT
TTTCCGTTAGGTATAGCCTCTTTTCGCCTCTTTCTTGACGCTCTTTCACG
AAGCCCTCTTGTATTAGGAACTTTTTTGCATCATAAAAGGTGGCAGTGGA
CATGGGAAATTCTGCGTTTACTTTCTTGTATAGGTCATATGTTGCTATTC
CTTCATTATCATATAGATAAGCCAATACTATGGCTTCGGGGTAGAAGAAT
GGTGTACTTTTCATATCCTCCTCACTCCTCAGCCTCTAATAGCTTAACTG
CCTCCTCTATCAACTGTCCCATTGTCTTTCCAGTCTTTGCCTTAAGCCTC
TGCAGTAAATGGTAAAAGATTTTACTTATTCCGTTCTCTTCTGAGAACC
GCTTGCTTTTTACGATTAAATTCCACATATCATCTAAGATAGAGTGTTGT
GGTTCTAGCTTCCTCGTGTAGATTTTCCCCTATTAATGTTAGTTTATAAA
GACCGGCTATTTTTTCACTAATT

The nucleotide sequence of pSMY1 is:

(SEQ ID NO: 11)
TCATTTTTTCCTAAAAATTGCTCCTTTACATTTCATCACCTTATCCTCGATAATCTTATTTATAGTTCTTAATGC

TGTTAATGGATTCCCTGCATTATAAATACTTCTTCCAATGATTTCATAATCCGCTCCAGCACATACTGCATCGCC

ATAACTTCCACCTTGACTACCCATACCCGGAGAGACTATGGTCATTTTTTCGAAGTCTCTCCTATACTGCGTTAT

ATGATCTAATTTAGTCCCTCCAACTACTATTCCTTTTGGGCTTATCTCTCTTATAACGTTTTTAATATAGTCTGC

GAATAACGTACTCCATCCTTCATGTGACATTACGGCAACTAAGTATAAATTTTTAGAGTTTGCATCAAGATATCT

TTTTAATTCATCTAGAGATCCCTTAACGCCTATAAAGGAATGTGCTATGAACGAGTTGGCGAAAGATAATCTTTC

```
AACTATGCTTTTCATTATGTATCCGATATCTGCAAGCTTAAAATCAACAATAATTTCCTCCACGTCTAAACCAAT

TAAGAGCTCTCTAGTTTTATCCACTCCTAGATCTAAAACTAAAGGTAAACCAACTTTTATCCCATATAACTCATT

TTCCATCTCTTTAAGAACTTGATATGAGAGAGGTTTATCCATTGCTAATATTACTCTACTTTTCAACATTCTTCA

CCAAATAATCTAGAATTGACTTCTTTTCATTATCCTTAAGTTTATCACTCTTCAACAATTCATCTAGAATTTCTG

AAATTTTAAATAGAGAGTGTAATTTGACTCCTAGTTTTTCCAATCTTTGTGAAGCCCCTTCTTGTCTATCTATGA

TTACTAGTGCGTCTGAAACTTTACCTCCACCGTTAAGAATCTCCAATGTTGCTTTCTCTATGGATACTCCTGTAG

TTGCAACGTCATCTACTAACAATACTCTTTTTCCTTTTACATCGAGTTCTAATGTACGATTAGTTCCATGACCTT

TCTTTTCTATTCTAATATATCCCATAGGCTCTTTAAGGTTACAAGCTATGAATGCCGATAAGGGAACTCCTCCAG

TGGCTATTCCTACTATTATATCATGGGGTATATCTTTTGCTTTCTTTATAGCTTGATTAACTATATCGTAAAATT

CTGGATAATTTGGTAAAGGTCTTAAGTCTAAGTAATATGGACTAACCTTACCTGATGTTAAAACGAAACTTCCTA

TTAATAATAATTTCCTTTCGAGTAAGACTTCTGCGAAATTCATACGTAGAGACTCTGCGAAAAAGAATTTAAATA

TACTTCTATCATAACCAGTTATAAGGGCTTTGTGAGATTAAGACACGTAGTTTCGTCGCTTGACTTGACCAGAGA

TGACTACTTTAGAATATTCGAACTTGCAGACAAGTTCTATGATGTAAAAAAACTAAATTATCTATCAGGGAAAGT

AGTTTCATTAGCATTCTTTGAGCCAAGTACTAGAACTGCTCAAAGCTTTCATACTGCAGCAATAAAATTAGGTGC

TGATGTGATAGGATTTGCATCCGAGGAGTCTACTTCGATAGCAAAAGGTGAAAATTTGGCTGATACCATTAGGAT

GCTAAACAACTATTCAAACTGTATTGTAATGAGACATAAGTTTGATGGGGCAGCATTATTCCCTAGTCCAGTGTG

GTGGAATTCTGCAGATATCAACAAGTTTGTACAAAAAAGCTGAACGAGAAACGTAAAATGATATAAATATCAATA

TATTAAATTAGATTTTGCATAAAAAAACAGACTACATAATACTGTAAAACACAACATATCCAGTCACTATGGCGGC

CGCATTAGGCACCCCAGGCTTTACACTTTATGCTTCCGGCTCGTATAATGTGTGGATTTTGAGTTAGGATCCgGT

CGAGATTTTCAGGAGCTAAGGAAGCTAAAaTGGAGAAAAAAATCACTGGATATACCACCGTTGATATATCCCAAT

GGCATCGTAAAGAACATTTTGAGGCATTTCAGTCAGTTGCTCAATGTACCTATAACCAGACCGTTCAGCTGGATA

TTACGGCCTTTTTAAAGACCGTAAAGAAAATAAGCACAAGTTTTATCCGGCCTTTATTCACATTCTTGCCCGCC

TGATGAATGCTCATCCGGAATTCCGTATGGCAATGAAAGACGGTGAGCTGGTGATATGGGATAGTGTTCACCCTT

GTTACACCGTTTTCCATGAGCAAACTGAAACGTTTTCATCGCTCTGGAGTGAATACCACGACGATTTCCGGCAGT

TTCTACACATATATTCGCAAGATGTGGCGTGTTACGGTGAAAACCTGGCCTATTTCCCTAAAGGGTTTATTGAGA

ATATGTTTTTCGTCTCAGCCAATCCCTGGGTGAGTTTCACCAGTTTTGATTTAAACGTGGCCAATATGGACAACT

TCTTCGCCCCCGTTTTCACCATGGGCAAATATTATACGCAAGGCGACAAGGTGCTGATGCCGCTGGCGATTCAGG

TTCATCATGCCGTTTGTGATGGCTTTCCATGTCGGCAGAATGCTTAATGAATTACAACAGTACTGCGATGAGTGG

CAGGGCGGGGCGTAaAGATCTGGATCCGGCTTACTAAAAGCCAGATAACAGTATGCGTATTTGCGCGCTGATTTT

TGCGGTATAAGAATATATACTGATATGTATACCCGAAGTATGTCAAAAAGAGGTATGCTATGAAGCAGCGTATTA

CAGTGACAGTTGACAGCGACAGCTATCAGTTGCTCAAGGCATATATGATGTCAATATCTCCGGTCTGGTAAGCAC

AACCATGCAGAATGAAGCCCGTCGTCTGCGTGCCGAACGCTGGAAAGCGGAAAATCAGGAAGGGATGGCTGAGGT

CGCCCGGTTTATTGAAATGAACGGCTCTTTTGCTGACGAGAACAGGGGCTGGTGAAATGCAGTTTAAGGTTTACA

CCTATAAAGAGAGAGCCGTTATCGTCTGTTTGTGGATGTACAGAGTGATATTATTGACACGCCCGGGCGACGGA

TGGTGATCCCCCTGGCCAGTGCACGTCTGCTGTCAGATAAAGTCTCCCGTGAACTTTACCCGGTGGTGCATATCG

GGGATGAAAGCTGGCGCATGATGACCACCGATATGGCCAGTGTGCCGGTCTCCGTTATCGGGGAAGAAGTGGCTG

ATCTCAGCCACCGCGAAAATGACATCAAAAACGCCATTAACCTGATGTTCTGGGGAATATAAATGTCAGGCTCCC

TTATACACAGCCAGTCTGCAGGTCGACCATAGTGACTGGATATGTTGTGTTTTACAGTATTATGTAGTCTGTTTT

TTATGCAAAATCTAATTTAATATATTGATATTTATATCATTTTACGTTTCTCGTTCAGCTTTCTTGTACAAAGTG

GTTGATATCCAGCACAGTGGCgccggCCGCCACCGCGGTGGAGCTCGAATTCGTAATCATGTCATAGCTGTTTCC
```

-continued

```
TGTGTGAAATTGTTATCCGCTCACAATTCCACACAACATACGAGCCGGAAGCATAAAGTGTAAAGCCTGGGGTGC

CTAATGAGTGAGCTAACTCACATTAATTGCGTTGCGCTCACTGCCCGCTTTCCAGTCGGGAAACCTGTCGTGCCA

GCTGCATTAATGAATCGGCCAACGCGCGGGGAGAGGCGGTTTGCGTATTGGGCGCTCTTCCGCTTCCTCGCTCAC

TGACTCGCTGCGCTCGGTCGTTCGGCTGCGGCAGCGGTATCAGCTCACTCAAAGGCGGTAATACGGTTATCCAC

AGAATCAGGGGATAACGCAGGAAAGAACATGTGAGCAAAAGGCCAGCAAAAGGCCAGGAACCGTAAAAAGGCCGC

GTTGCTGGCGTTTTTCCATAGGCTCCGCCCCCTGACGAGCATCACAAAAATCGACGCTCAAGTCAGAGGTGGCG

AAACCCGACAGGACTATAAAGATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTCATAGCTCACGCTGTAGGTA

TCTCAGTTCGGTGTAGGTCGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACGCGCAGAAAAAAAGGATCTCA

AGAAGATCCTTTGATCTTTTCTACGGGGTCTGACGCTCAGTGGAACGAAAACTCACGTTAAGGGATTTTGGTCAT

GAGATTATCAAAAGGATCTTCACCTAGATCCTTTTAAATTAAAAATGAAGTTTTAAATCAATCTAAAGTATATA

TGAGTAAACTTGGTCTGACAGTTACCAATGCTTAATCAGTGAGGCACCTATCTCAGCGATCTGTCTATTTCGTTC

ATCCATAGTTGCCTGACTCCCCGTCGTGTAGATAACTACGATACGGGAGGGCTTACCATCTGGCCCCAGTGCTGC

AATGATACCGCGAGACCCACGCTCACCGGCTCCAGATTTATCAGCAATAAACCAGCCAGCCGGAAGGGCCGAGCG

CAGAAGTGGTCCTGCAACTTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACGCTCGTCGTTTGGTATGGC

TTCATTCAGCTCCGGTTCCCAACGATCAAGGCGAGTTACATGATCCCCCATGTTGTGCAAAAAAGCGGTTAGCTC

CTTCGGTCCTCCGATCGTTGTCAGAAGTAAGTTGGCCGCAGTGTTATCACTCATGGTTATGGCAGCACTGCATAA

TTCTCTTACTGTCATGCCATCCGTAAGATGCTTTTCTGTGACTGGTGAGTACTCAACCAAGTCATTCTGAGAATA

GTGTATGCGGCGACCGAGTTGCTCTTGCCCGGCGTCAATACGGGATAATACCGCGCCACATAGCAGAACTTTAAA

AGTGCTCATCATTGGAAAACGTTCTTCGGGGCGAAAACTCTCAAGGATCTTACCGCTGTTGAGATCCAGTTCGAT

GTAACCCACTCGTGCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCTTCCTTTTTCAATA

TTATTGAAGCATTTATCAGGGTTATTGTCTCATGAGCGGATACATATTTGAATGTATTTAGAAAAATAAACAAAT

AGGGGTTCCGCGCACATTTCCCCGAAAAGTGCCACCTGACGTCTAAGAAACCATTATTATCATGACATTAACCTA

TAAAAATAGGCGTATCACGAGGCCCTTTCGTCTCGCGCGTTTCGGTGATGACGGTGAAAACCTCTGACACATGCA

GCTCCCGGAGACGGTCACAGCTTGTCTGTAAGCGGATGCCGGGAGCAGACAAGCCCGTCAGGGCGCGTCAGCGGG

TGTTGGCGGGTGTCGGGGCTGGCTTAACTATGCGGCATCAGAGCAGATTGTACTGAGAGTGCACCATATGCGGTG

TGAAATACCGCACAGATGCGTAAGGAGAAAATACCGCATCAGGCGCCATTCGCCATTCAGGCTGCGCAACTGTTG

GGAAGGGCGATCGGTGCGGGCCTCTTCGCTATTACGCCAGCTGGCGAAAGGGGGATGTGCTGCAAGGCGATTAAG

TTGGGTAACGCCAGGGTTTTCCCAGTCACGACGTTGTAAAACGACGGCCAGTGCCAAGCTTGCATGCCTGCAGAG

TCTCATATGTTTCCTCACTTATTGAAATGTTAAGCCTTTTGACTATCCTATCTTTCCTCTTCTCTATCATTTAGG

TCACCTTGTTTATTGTTATTTGAAATACGTATCCGTCTTCGTCACATCGAAGTATAATTTTGTATCCATTATTAG

CATATTCTACGTCAAAGTTCCCACAACAATAATTCGGGTCTTCGGACTCGTTATAGACTTTGCTCCAACCATCTT

TTTGTAGTGCCTCTTCTAAGTAGTCTACTCTGATGAAGCCTTCATCATATTCGTTCAGTACCCTAAAGCTTATAC

TATCAATGCCTAATACGTCTAATAGCTTCAACAGATCGAATATAGGAACTTGACCATCATTTCAGCTCACCTTA

ATGAGCTGATATAATTCCGCTTCTATCTTTTGAACTTGGAAGTATGCCTTGCCTAGCTTTTGCTTATCCATATTG
```

```
CCCGTTATTCTATCAATCTTAATCTCGTGGATTAATGATAATAGCTCTCTGACATCCTCATCAAGCATTTCAAAT
AATTCTTTCTCTAAGACTTCTTTACTCATTGTTTTTCACCTTAGCAAACTCATCTAACGTTGTTTGTCTCAGTTC
TCTTTTCTTTATCAAATAAAATTCCGAATGTCCCTTCTTATTGTTATTACTGTACTTCATGTCAGTTCACTGCTT
TGCCTTTATAAATCCTTGATCCGTTTGCTCAAAATTTGCGGGCTGGGCATCAAATATCTTAGCTATATTGTCTTG
TGTTTGCTCTTGTTTTTGTTCTTCTTTCTGCTCTTGCTTAATCCATTTGAACGTTGTCTTTCTGTTTTTGTATTG
TACTTCACACTCGTCTGGATGTCTTTCGCAAATAGCTTTCAATGCTCTCTGTATGTTATACGCACTCGGGACTGA
AATCTCAAATTGAGCTAGTATATCCTCTAACGTTAATTCACCTTTCTTTTCAAGAATTTTATACATTATTTCCGC
CATCTTGTATGAATTTAGAGTTTGTGCCATATTCCCATCCCACTCTATCTATACTCTATGTATAAATTAGTATTT
AAGTCTTACTCTATCTATACTCTATCTATCTCTATATACACAGTGTTTGGGTAACTGGCAAAATTCTGTCTGA
CTGCTGTCTGACAAGAGTTTACTCTATCTCTCTATATCTATATACACAAACAGAGTTAGTCGACTCTGTGTATCT
TATGTATCTTATACAAAAAATATGGGATGTGCAAAATCTGAGCTACTAATACTGCTTGAATATATAGATAGAGAG
TGTAAGGACTACGAGAGTTGTAAAAGAATAATAGTAGAGCTAGAAGAGAGAGTGAAGAAAATAGCTTTCGTAGAA
GCAATAAATGATTTGTTCTAAACTACTTTTTTCTCTCTATCTCTATATCTATATATATACATAACTAAAACTAAA
AGAATAAACAAAAAACTAACAAAATCAACTCACCATTATACAAACTCAGAAAAACTATTTTTTTGTTATACTCTT
ACCCCATATATATATAGATATATAGATAGAGAGAGATAGAGTATAGTAGGGCATTTAAGATTTTAGAAGTTCTTC
AATGCGTCTTCTGATTGCATCTGCAACAAACTCTTGTCTGCTTATATATCCGCCCTTGCCTGACGCTATTAGTTC
ATCTATTTGTTTTGCTAATTCGATTGGAATCGAAACGGTCACATATTCTTTTTTGACTGATTTCCTCGGCATACG
CTATCTATACTATATTAATATGATAATATTAAATGATTCACGATATATAGATAGAGTATAGATAGAGTAAAGTTT
AAATACTTATATAGATAGAGTATAGATAGAGGGTTCAAAAAATGGTTTCACCCCAAACCCGAAAAGAAGAAGAGT
TATTAGAAAAACAAAATTCAGTTTTTTATTTGTTAACTTTAGGAAGGAAACCGTATGGTTCATATTTGCATATAA
AAATTGAACTAGACGAAGATGAAAAATTAGAGAAGGAAATCTATGCGGATAACATTAAGCTAGAGAATGAATTAA
GACAACTGAAGAGGTTGTATGAAGTATATCAGAGCGTAGAGATTGACGATGCTCAGAAAGCAATACAGAAGGAAG
CATTACTGACGATAGCGAAAATACTAAGTGTTTTTGACTTCTGAGGAGGCTGAGGGCAATGAAGGCTGAGGAAA
CAATCGTGGAACAGATTCAGGACATAATTCAAAAACTTCGCTATTATACAGGAAGATCAAATAGACATTTCAAGA
TGATTAGAAACTATTATGAGGAGTGTATAATAATAGTAGACGCTGAGGAGTTTATACAAGAAAATAACACTCTAA
GCATTACTGTATATTCTGAGGATCTTATATATTATACTGTTGATATCCCGCTGAATTTCATTAAACATGTATTCG
TATCCGCTTCGATTGATCAGCTCAATGATCAGCTTCAGCTAAAATATAATGAGGGTCTGATTAGAGTTTCTCTTA
CTTTGAACGATGACTTATGTGAGAAACTGAGAAGCTCATACTGCGGTGATATTACATTCTTTAATGAGGCTGAGG
GGCAATGAAGGCTAGGGTTGAATACATCAAATTACCTAGATGTTACACAAAAACTTATAGAAAAATCGAAGCGAA
AAAGAACAACGACGGTACAATAGAATTAACGTTAGAGGAAACAATGCAAGTAATATCCTTTAAACTACCCCCGGC
GTTAAATGCAAAACTAGAACAAATTGCGATCAAAGAAAAGAAAAGCAAGAGTGAAATTATTCGAATAGCGTTAGC
GAGGTATGTAGAAAATGTTTAGATGCCCCATCTGCGGGTTCAAAACGCTGAGATTGTTCGCGCTTAAACAACATA
CTCGAAGGGAGCATGTGTTGGTCAAATGTCCCATATGCGGGTTCACGGGAAGCATTTATCTCAACATTTCTATA
GTAGGTATGATATTGACCATCTCATATACTGCTACCTATTCTCTTCTTTCAGATTGCCTAAGAATGTTAGGTTAG
CAATAAAGAGAAAATTAGAGGTTGAGTGAATAATGTATCAATGTCTACGTTGTGGTGGTATATTTAATAAAAGAA
GAGAAGTGGTTGAGCATTTGCTTGTAGGGCATAAGCACAAGGATAGACTAACACTGGACTTTTATTATATCTACT
TCAGGGTGAGAGGACAATGAACCTAATTGATATCATCTTATTTTACGGCTTTCAATTCAACGATTATTGGACAAC
TGTCTTAGGGTTGAGAGTGGGTGCGGAAGAGAAGAATCCCATAGCGGGTCTGTTCATTTCATCACCGTATCGTTT
AGCGTTGTTTAAGTTTGGCCTTATCACCATTGGTATGTTTATATTAATTTATGTTGTTAGATTCAAGACATGGAC
AGAGATCGTATTGACTGTAACAGACGTTGTCGAATGCCTTGTCACGCTGAATAATACCCTTACGATTAGGAGGTA
```

-continued

```
CAAAAGGAGGGGCGTTAGAGGATGACGGAGTCAGACGTTGACTCAGGTAGTAAAAAATACCTGAGTAACCATAAG
GGGATTTTTATTCATGTCACACTGGAAGAGTTAAAGCGTTACCACCAACTTACGCCGGAACAGAAGAGGTTGATA
AGGGCAATCGTCAAAACGCTTATTCATAACCCGCAACTGTTGGATGAAAGCAGTTATCTTTACAGATTGCTCGCG
AGTAAAGCGATTTCACAGTTTGTCTGCCCGCTTTGTCTAATGCCCTTCAGCTCTTCCGTATCACTAAAGCAACAC
ATCCGTTATACTGAACACACAAAGGTTTGCCCGGTGTGTAAAAAGGAGTTTACCTCAACCGATTCAGCCCTAGAC
CATGTTTGCAAAAAGCATAATATCTGCGTTAGTTAGGCTCTTTTTAAAGTCTACCTTCTTTTTCGCTTACAATGA
GGAAGTCCCTTCTAGCCCTACTAACCCTATCCCTAGCGTTACTATCGTTTTTAATAACACCATCGATGGCATTGA
ATTCTGGCGGTTCACCGATACCGATATATTATAACTATTATAACTACTATAGCCTTAACGCAGAAGGGTTTGGAT
TCAGTTTCAATAATAGCAATAATTGGGTTGAAACGAACTTTATCTCAATAACCATAAACTTACCTAGTTCATTAC
CAAATAACTATCAAATCAATAATGCCTATTCTATCGTAGTAGGATTATCACCATATCCGGTTAGCAATATAAACA
TTTTTAATAGCCCATTAGAAGCATATGTTGAACTATTCTCAAACCCACCGAATACATATCCAAATGAAATAGGAT
TTGTAGTTAGTTACGGCTCAACTGTATTTTATAGTTATACCACACTGTATAGCAGTTTTGCGGGCACACAACTAA
CAATAACTATATCATATACCGGAAATGGGTTTGGTGTGCAATTCTCTGACAGTAACGGGTTCTCTCACTCAGTTT
CGGTAAGTTCGGTAAACTTTGTACCATATGGTGCTCTAATACTCGGATCACTAATCCCGAACGGGAACTATTACT
ACTACCCAGTAGGTAACATGTTACCGAATGCATCGGTGAACTTCTCATATACGATCTCAAGTTTCACAATAGAAG
GAAACCCGGCCACATCCGTCGATATTACCACACTTGGATTAGAAGGAAACACTGCAATATATACTTCAAGTAGCA
ATTGGTTCAAATGGGTATCCGGTAGTGTGGTTATCACAAATGCCGTTGCCTATACCTATACCGATTTGGCTAGAA
TAGGAGGAAGTGCACAAATAAACTATACTGCATCGCAGCTATATTAAGCAAAATCTTTTTTTACCTCTTTTTAAA
TCTGTCTTATATGAAAAAACTGTTTACAGTTGTAGGTTCTATTTTCTCTGGTTTGGGGATTTGGCTTAAGTCAAT
AGACCAGTCATTTTATTTAACGAAAGTATTGTATAACGGAAAAGTAATTGAAATAGTTCTAACGCCCGAGACAAA
TGAAGTCGTGAAATCTTCCAACGGTGTTATGAACGCAAGTGTAACTTCTCTACCTTCCACAATTCTATACCAAGC
ACAATCCGTGCCTTCAATAAATGGAGGAACTCTTAGTGTAATAAATACCACAGTTCAACCGCCATGGTATGCTAA
CTTATGGCCTGAAGTCTTAACAATAGGTATAGTGATGTTGGGAATTGCAATATTCAGCTGGATTAAACTTAAATT
TAGAAGATAGCCCTTTTTAAAGCCATAAATTTTTTATCGCTTAATGAAGTGGGGACTATTATTCTTAATAATGTT
TATATCCATTTTTTCCCTCAACTCTTTAGCCCTATTAATCGGCGGAGGAGGGCCCAACAATAATGGTGCGGGAGT
TTACACTCAGACTATAACAGTTAACGGAGGAACCGTACGAACTACTCTTAACGGTTCAACGCTTTCTACCGCACC
ATGGCTCAACCCCTCTTACGTAAGCGTCTACAACACATACTACCTTCAGGTTTTGCCGAACCAAGAGTATATTGA
CAACAACGTTTCGTTATCCCTAAATACGGCTAACATTGCGTTAAACGTCACTTGGTTATTGGCGTCCTCAAGCAA
TACGGGATCCTACGGTGCAATCGCCATAGGCTACGGAGTGAACTTTCCCGCGGGGTTTGTCAATAACTACGGTCC
TTCCGCACCTTACACGCCGGACGGAATCGTAATATATCTCATGAAAGGAGGCATGCCGACCTATCGTTTATTCGT
ATACTTCAATGGAGTTGAGCAGTTAAACGTTTCAGTCGGGTCAATCAGTGTGGGACAAAAAATAGGTTTAGGGTT
CTTTTATCTACAGAACACACTTTACGTTTACTACTATAACGGTACTTTAAAGACTTGGTCATTAACGCCCGGTAC
GCTGATTACTATAAATAGTAATTACGTTATAGACGCACAGAATATAGGGCCGGGCTACGGCTACGGTCAATGGGT
AATAGTTAATTATCAATATGCGATGCCGGTTACTGCACAACTGACGGTTAGTTATTTCGCATTAGGGTACAATGT
ATATCATTTCTTAATGGCTTATGCGGGTGCTGGAAACCCGGTAAACATAACTGCGAATAACGGGGCTTCTTACAG
TATAACGGGTATAGTTGCAGAGAAGAACTTTACGATAACGGGAATTCAGCAAGGCCTAGCCTATGCTTTCAGCTT
GTTAGGGAAACCGAATGGCTTATACTTATTATATATGGGGCAATTGAGGGCAGCCCACCAACGTGGTATGTAAA
CGTAACCGTAGGGCTTCAGATCGTTACACCCCAGAAAACGATAAACTACAACTTAACAATACCAGTAATCGTTGA
GGGCTATGCGTTATACCCTTCTGTTAACGTACCTTCCGGAACTTACCTAAGCGGACAGACTATTAGCTTTACCCT
CTCATCGTTCTTGGGATACCCTTCAGGCTTAGGCTATTACACCGCAGTAAATCTAATCGCAAACGTAACAATAAA
CGGTGTGAGTCATGCTATCCCCTATAGTTTCACCCCGATAGTGCAAACCCCGATAACTTATTACTACACTGTTAT
```

-continued

```
AGTGGATGAAGGACAATTTGCATTAATAGATTATCAAGGGAGTTTCACAGTCCTACCCGCACAGAGTCAGCCCGT
GATATTCATTACTTCTTATCCTAGAATTGGGCTATTAGGACAAACGATAACTGTGACTTTCCAGTTCACTTATAA
TAGTCCCGTAGCGAATGTAACTCAATCAGCGTTTACGCAATCATCTAATATTCTCGCTTTTGCCTATGCGAAAAT
GGTAACAACAAACGCTATAGTTCAGTTCAAGGCGTATTGGCTAAGTGCTAATGACGGGTTGGTGATTATAACTCA
AACGAATAACTATCTAATTCCGTTTAATAGCAGTATAACGGGCTTAAACTTCGCAAACAATAGTGTTAATACGTT
AACGTTTCAGATTGTAACGGGTAACTATGTACAAATAACTAGCTCAGCGGGAGGCGTGCTTACCCTAAGCAATAC
TAGTCCGATTATAGGAATAGGGTTCTATTACGGTTCCGGTGTCCTACACCTGAACTGGTTCTTCGTTAGCGGTAT
CATTTTGCAGTCTGCAACGGCAAATCAGGCTTACGTTATTTTGACGGGGACTAACCCAAATACGCTTTCACAGTA
TACGACGGGCTATACTAACGCTTCGGGGTTCGGTACTGTAACGCTGAAGTTGAGTTACACTCCTTACGAACTTGT
GGATGTAGACTGGTACGGCGTTACATACGCTTTGTTAAACATTAGCGTTTCAAACACTACTACAGTAAGCAGTAC
TACGACCGTGAACACAACAACGCTTAACTATAACTACACTAAGCCTTTCAGCAATAACATAGCACCTAACAGTCA
GCTTTATGACTTCTCAGCGTATCAGCCGTGGGCGGAAATTATCGGGATTGTGGTCGTGGTCGTCATAGCTCTGCT
GGGCTGGAAGTTCGGCGGGTCTGCGGGAGCTTCGGGTGGTGCGGTTATGGGGTTAATCGCAGTCAGCTACTTAGG
TTTACTGCCTTGGTACCTATTCTACATCTTCGTATTCGGTATCGCTCTATTACTTGCTAAAGTATTTGTAGACCG
TTTCATGGGGAGGGAGGAATGACGGACGCAATCAGTTTAGCCTTGCAAACGGGCTTAGGGCCGGTGGTAGGGGTA
ATTATCATACTGGCAATGATGGGGCTAACGTATAAGATAGCGGGAAAGATCCCGGCAATCATAACGGGAATAGCC
TCGGCTTTCGTCCTAATGTTTATGGATTTTTTACCGTTATTTTGGGGTATCGCAATAATCTTCGGGTTAATCGCG
GGTATGGTGGTGACAAGGGATGGGGACTAAGTTAGTCGTTTACGTCTTATTGTTTGACGTCTTCCTATCGTTAGT
GGTAGGTGCCTACTCGGGTATAGCACCGCCAAGTATTCCACCGGTACCTACATATGCTTCAGCCCAACTCACGGC
AAGTCTAATCACATGGACAGTGGGATGGCCTCCTATTACATTATGGCCTCAGATAACGCTTATTCCGCCGTTTTC
GATTTTGGGTGCAAACTTCCCCGGCTTAACCATTCCTAGCTTAACGATACCCGGTGTAACGCTCTTCTCAATAAG
CTTCAGCTGGTTAGCCCCAATTATTTATATTGCAAATTGGATCATTTGGGTCTTTCAGACTGTTGCTAGTGTGCT
ATCTTATTTACTTAATATCTTTACGGGTTCGGTAGGTCTATTGAGTAGTGTACCCGTCTTAGGGCCATTTTTGAC
CGCCTTCGTGTTGATAGTTAACTTCGTGTTAGTGTGGGAATTAATCAAGTTAATTAGGGGGTCGGAATGACGGAG
TATAACGCAAACAGTATAAGGGCTAAGATACTGAGGCGTAAAATCCTTCAACTGATTGCGGAAAACTACGTTTTG
TCAGCGTCGTTAATCTCTCACACACTCTTACTCTCATACGCCACAGTGCTTAGGCACTTGCGTATCCTTAACGAT
GAGGGCTATATCGAATTGTATAAGCAAGGTAGGACGCTATACGCAAAAATCCGCGATAATGCGAAACAAATTCAG
ATTCTGAATTCAGAACTGGAGGGGTTTAAAAACGTAAGCGGGAAGCCGATATTGACCAAGGATGAGACTCCTAAG
GAGTTTGGCAAGAAAGATAGCCTCACTCAAAGAGGCTAAGGTTGCACTAAAAGTAGCAAGCGACCCCAGAAAGTA
CTTCAACGAAGAACAGATGACTGAGGCTTACAGGATATTCTGGCAGACATGGGACGGGGACATAATTAGAAGTGC
TAGAAGGTTCGTGGAAGTAGCAAAGGCAAACCCCAAGCTCACAAAAGGTGAAGCAACCAACATAGGCGTATTGTT
GGGCTTATTCATCTTCATACTAATAGGTATAGTACTATTGCCCGTAATCGTTAGCCAAGTCAACAACCTCACAAG
CGGTACTTCACCCCAAGTAACCGGTACTAACGCCACACTCCTGAACTTAGTGCCGTTATTCTATATCCTAGTCCT
CATAATAGTCCCCGCAGTCGTGGCGTATAAGATATACAAAGACTGAGGTGTGAGGGATGGAAATCAGTTTAAAGC
CAATCATTTTTTGGTCGTTTTTATCATCGTAGGGATAGCACTATTCGGCCCTATAAACAGTGTTGTAAATAACG
TTACCACATCGGGAACCTACACTACTATAGTTTCCGGTACTGTTACTACGTCTTCATTTGTGTCAAATCCGCAAT
ACGTAGGTAGCAATAACGCTACTATCGTAGCCTTAGTGCCGTTATTCTATATCCTAGTCCTCATAATAGTCCCCG
CAGTCGTGGCGTATAAGTTGTATAAGGAGGAGTGATATGAAGTGGGTGCAAAAGGCGATAAAGAGACCCGGGAGG
GTACATCGCTACCTTATGAGGCTCTACGGCAAACGGGCGTTTACAAAAGACGGTGACATAAAGGCAAGTTATCTC
GATAAGGCGATAAAGCACGTTAAAAAAGCTAAGATCCCGAAAGAGAAGAAACGTAGTTTACTGTCAGCCCTACTG
```

-continued

```
TTAGCGAAAAGGCTTAAGCGGATGCACCGCAAGTAGGCCCTTTATAAAGTCATATTCTTTTTCTTTCCCTGATGA
GTGCGTTAGGGGATGTAATCTACATCTTGGGTTTTCTCTTTCCGGCTTTAGGGCTAATCAGCCGAAACTATCTTG
TTAACTTAATGGCATTCATAATAGGAACAGTCGCCTTTTTGGTCTTCGTCCAAGGCTATACCGATATAGCGTTCA
GCAGTTCGACGTTTTACTTAGGAGTACTGCCTCTACTACTTGGTCTCGTCAACTTAGGCTATTTCTTCAATTGGT
TGAGGGAGGAAAGGATATGAGGTGGGGTAGAAGAGATGATAGGGATACCGGCAAAATACTTCGAAATAGGAGTCG
TAATAGATTCAACATTTATCATTATGTCTCTACTGTTAAGAAAGTCAAAGAGACAGAGAGAGAACTCCTTCGACT
TACGCAAACATGGAAGGCTATTAGGCTTATATCTTATAATAGCGTCGGCATCAGCATTAATCGTCTCACATCTCG
CCTTATACACAAACTACATGAACTACTTAACGGGCTTATCTCTTAATGCGTTTCTGTTTTATCTTGGGTTGAGGT
GTTTGCATGTCTGATGGGAAACTCCTTTCTGCTTTCGAGGAGGAATTAAGAAAAGCCCAAAGCCTAGAGGAATTA
AAGCAAAAGTATGAGGAAGCCCAAAAACAAATAGCTGACGGCAAAGTACTAAAGAGGCTATACAAGGTTTATGAG
AAAAGGCAAACAGAATTAATGCTTCAGCAATATAGGCAGATAAAGGCTGAACTGGAAAAGAGGAAAAAGGTAAAG
AAAAAGGATAAAGCCGACATAAGGGTTAGAGTAGTAAAGAAGTGGATAAATTCACGCTTATTCAGTGCTGAGCAT
TACGTCGCATTACTGCAAGAAAATCAAGACGGCTTATCGATACTATTTCTAAGAAGAGCAAAACTTATAGAAAAT
CAAGGCTATCTAATGCTAGAAGTGAAGAAGTTAAGGAAGGCATGGGTTTTAACGGCTGAACCTATACTCCTTGAA
AGGTTAAAATTCCCATTCGGCAAAAAGTTTGTAGCCGTGCATTTCGTTTTACCCAATTATCCTTACACACTTCAG
CTTAAACCGGATGAAAAACTGAAAGAGTTAGCAGTTAAGGCGATAAACGGGCCTCAAATAATGAGCGCAATGATA
CGTACAAAGTTCTTCGAAGCGTTAGCTAGGGTAGGAAGCGGGCCTGATCTGATGATGCTCATAATCGGCGTTGTC
ATGGGGATTGGCATAGGCGTAGCGATAGGTTTCGGTATAGCTAACGCAAACTTAACGCATTTGCTATCTCAACAC
GTTACGAACACTACAGTGACACATACTACGACCACAACGACTTCACCCTCATTCACGATTCCCTCAAACTCCTCA
AAAGGGGTGAGCTAAAATGGTCTCAGTAACAGAAATAATAACATATGGACGAGAAGCAATAGAAAGAATAATATG
CAAATATTTTAAAGATTCGAAAATAGAAAAGATATTATTCTTGCCGAGTGAGGAAGACGTAAAGGCAAAATATAT
CATTGGACGGGTAGGGTTTATAAGGATTAGTAATACGTGGTCTGGAATTGTCGTAGTTGACGGGGTACAAATACC
TTTCGTTGCTGAAGTCCACCTTAATGGCAAGATTGATATTTACCTTTATCCTCAAAAGGACTTCTACTTAGCACA
TTTGGTGGGTGAGCTGAATGGCTAAAAAGAACGGCTTAACAGAACTAGAGCAATTAAAGAAAGAGAACGAAGAGT
TGAGAAAGAAGTTAGAAGAGTTAGAGGCGTTGATCAATAACGATAGCGATGACGACGAAGAGTTGCAGGAAATCG
AAAACCCGTACACCGTTACAAACCGTGCAATAGATGAATTAGTAAGCCCAAAGGACACAATGTTCTATTTGTCGG
GAAACCAGATATCGTTAATCTTAAGTGCTTTTGAATTCGCCCGCTTACCGACGTACTTCGGTGAGGAACCGGTAA
CGGAGTTAGCGGAATACGCCCATAAGTTGAAACATTATCTCGTTTCGAAAGGAGGAAGAGGAAGGAGGGATATAC
TGAGAGTCCTACGCGTTAGTTCAGGTCAGACAAGAGAGAACGTAAACAAATCAATTCTGAAACAATTATTTGACC
ATGGTAAGGAACATGAAGATGAAGAAGAGTAATGAATGGTTATGGTTAGGGACTAAAATTATAAACGCCCATAAG
ACTAACGGCTTTGAAAGTGCGATTATTTTCGGGAAACAAGGTACGGGAAAGACTACTTACGCCCTTAAGGTGGCA
AAAGAAGTTTACCAGAGATTAGGACATGAACCGGACAAGGCATGGGAACTGGCCCTTGACTCTTTATTCTTTGAG
CTTAAAGATGCATTGAGGATAATGAAAATATTCAGGCAAAATGATAGGACAATACCAATAATAATTTTCGACGAT
GCTGGGATATGGCTTCAAAAATATTTATGGTATAAGGAAGAGATGATAAAGTTTTACCGTATATATAACATTATT
AGGAATATAGTAAGCGGGGTGATCTTCACTACCCCTTCCCCTAACGATATAGCGTTTTATGTGAGGGAAAAGGGG
TGGAAGCTGATAATGATAACGAGAAACGGAAGACAACCTGACGGTACGCCAAAGGCAGTAGCTAAAATAGCGGTG
AATAAGATAACGATTATAAAAGGAAAAATAACAAATAAGATGAAATGGAGGACAGTAGACGATTATACGGTCAAG
CTTCCGGATTGGGTATATAAAGAATATGTGGAAAGAAGAAAGGTTTATGAGGAAAAATTGTTGGAGGAGTTGGAT
GAGGTTTTAGATAGTGATAACAAAACGGAAAACCCGTCAAACCCATCACTACTAACGAAAATTGACGACGTAACA
AGATAGTGATACGGGTAATGTCAGACCCCTTTTAGCCATTCCGCATACTTTTTATATTGCTCTTTCGCTATGCCG
AAGAGCGATACGTAATGTTGCGTTAAAACGCGTGTCGGTTTACGCCCTTGAATAAAATCGATAATATCTAACGGT
```

-continued

```
ACGCTTAGCTCAGCCATCTTAGACGCTACGAATTTGCGGAAGTACTTTATCGCTATAGCGTCCTTATGACGTCGT
TCAAAGTCCGCTATTGCCCACTTCGTCACCTCTACTCTCTTCAGAGGCGTTATGTGGAATACATAGAAGACGCCC
TTATATCCCCTAGTCCAACTAAGCGGATAATAACAGACGTCGTTACCGCAAATGTCCCTTTCGGGTTCCTTCAGC
ACTTTCAGTATTTCGCTCAGCCTAACGCCCGACTCGAGAGCGATACGGTAGATGAAGTAGACGTTTTCGCTATAG
TCTTTTGCTAATTGTAACGTCCTTTTTATCTCTTCCAACGTTGGAATGTAGATATCAGCGTTCGCCTTCTTCACC
TTTACCGCTTTCAATATTTTATCCGCAAATTCATCATGTATGATATTGCGTGACGCTAAGAAACGTGCAAAGAGT
CGGTAAGCCTTCTGTGCGTCTCTCGTCTCTTTATACGGCTTTGATATAGCATTGATGTAGTCCTTTGCAGTTTTT
TCGCTTATCCCCCTTTCGTTCATGAGATAGTCGTAGAACGCCTTTATGTTGCCGTCCGTCGCGTATTGGCGCAAA
TTGGCAACCAACGCTATTTTACGTCGTTCAGTTCCCTCTTTTCCGCCTCCGGAGCCGGAGGTCCCGGGTTCAAAT
CCCGGCGGGTCCGCTTGTAGGGGAGTATCCCCTACGACCCCTAATTTCATTTTTAGATATGATTCAACGACGTCA
GCTAAAGGACCCACGTAACGCTCTTTTACCTCACCGTTTTCATACTCTAGCTTGTAAACATAATACCGCCCTTTC
CTCTCGCGTAAAATATAATCCCCGTATTTATAACGCGTCTTATCTTTCGTCATTTCGCCTCACAGTATTATGGTT
GCCAAAACGGGCTTATAAGCATTGGCAACCCGTTAATTTTTGCCGTTAAAACACGTTGAATTGAAAGAAGACGGC
AAAGAATCCACACAGGTAATACTAAAAAAGTAGTATTACTTACATTAGAAGGACTCATTTGTCCACCTTGTATTC
TAGCCATGCTATCTCTGCCTTCAGCTCATCTAGCTTCCCCTTTATGTCTGTCAGGTCAAGGGGAACTCCTCTCAT
TAACCTGAGTTCGTTTTCGATTTTTTCAAGCTCCTTTTCCAACTCCTCTAGTTTCTCTAATTCCTTTAGTCGTTC
TTCCAATTTCTTTTCCAATTTCCCCTTTGCGTCATTTATAATTATGCTTACTACCCAAACAATTCCTAAATCAGA
AATAATTATTAACTCCTCTGAGTTGAATATCATTTTCCGCCCCTCGCTAAATACTCCTTAAAGCTCTGATAGAAC
CCCTTCAGACTAACCCGTAAGTCTGTTAGGTTCTTCCAGTATTGTAATGGGATTAAGTAATAGTAGCTTACTGCA
TCTCTCTCAAATTTGTCCTTCTTAATCTTTCCTTGCTTTTCTAAGTTGAGTATTTGCAGTGCTGAGATACATTTT
AACTTGTCCTCAGCATCTGAATAGTGTATAAACCAAACCCTCCCCATAACCTCATTCTGCTTTGCAACTTCTACT
TTAGTGCTTAATATTGCGTAAACGCTTTCGCCGTATCTTTCTTTGCTCTGTTCTTCAGTCCATGAACTTCCCGTA
ATATCTATCCAAATTAAAGGATAATATTCTGTCTTAGCCTTAACGTATAAAGTCAAATCGTATTTATCTTGCAGA
CCGCTATAGTATTGCTCATTTATTACATTAGTTAAAGTCCCCACGCCAGTTGGGCGGATATAAACATCAAAGTCT
AACAAACCCTTAGCCCGCCACTTTGATAAAGAGATTAAGAGCTTTCCAAAAACTAGGTATTCTCGCCCTAAATAA
GTTGAAGGGAGGATATAATCCTCAGCTTGATTACCCCAATACTTTAGCTTAAAATTAGTTTCAGCCATCTCACTC
ACCATATTGAAACGTGGGCTAGTATGTGAATCAGTACTGATGCTATTGCAAATAACACACTTGCAGTAGCAATTC
CTATTACAATCCATTTACCATAATCCACCTTAGTTTGTTGGTCAATATACTCGTTGATGATCTTTAGTATTTCTG
GCTTTAGTTCTGATAATGAAAGGAAGACAGAGGCATAAAGTACTAAGGAGGATGTGAACAGATTATCCGCCTTTT
CTGAAAGTTTATAAAGCTCATATCTTGCTCTCTCATAATCTTCATAATTAATAATTTCATCAAACTTTTCTACTT
GCTCTTCATATTCTTTCTTCAGAGAGTAAGGAGTTGTCTTTTCAATTACTCCTAATTTTATTAACTTCTTAACAG
CTTCCTTAAATCCTTGTTTATTGCTAGCATACGCTAAAGGGTCTTTTCCTTCTTGAGAAGCTCTATAGATAACTA
TAGCACCATAAACAATATTTACAATATCGTATGGTAAGGAATACGCACCGATTTGGGCAATATCTTCAACTCTTC
TTTGATCCATCTAGTTCACCTCTTTTTGATTTGTTTGTAGGTTTCTATCGCAGTTTTCAGCGATATCGCAAATAG
CTTCCCCTTTTCCGTTAGGTATAGCCTCTTTTCGCCTCTTTCTTGACGCTCTTTCACGAAGCCCTCTTGTATTAG
GAACTTTTTTGCATCATAAAAGGTGGCAGTGGACATGGGAAATTCTGCGTTTACTTTCTTGTATAGGTCATATGT
TGCTATTCCTTCATTATCATATAGATAAGCCAATACTATGGCTTCGGGGTAGAAGAATGGTGTACTTTTCATATC
CTCCTCACTCCTCAGCCTCTAATAGCTTAACTGCCTCCTCTATCAACTGTCCCATTGTCTTTCCAGTCTTTGCCT
TAAGCCTCTGCAGTAAATGGTAAAAAGATTTTACTTATTCCGTTCTCTTCTGAGAACCGCTTGCTTTTTACGATT
```

-continued

```
AAATTCCACATATCATCTAAGATAGAGTGTTGTGGTTCTAGCTTCCTCGTGTAGATTTTCCCCTATTAATGTTAG
TTTATAAAGACCGGCTATTTTTTCACTAATT
```

The nucleotide sequence of pSMY-A is:

(SEQ ID NO: 12)
```
TCATTTTTTCCTAAAAATTGCTCCTTTACATTTCATCACCTTATCCTCGATAATCTTATTTATAGTTCTTAATGC
TGTTAATGGATTCCCTGCATTATAAATACTTCTTCCAATGATTTCATAATCCGCTCCAGCACATACTGCATCGCC
ATAACTTCCACCTTGACTACCCATACCCGGAGAGACTATGGTCATTTTTTCGAAGTCTCTCCTATACTGCGTTAT
ATGATCTAATTTAGTCCCTCCAACTACTATTCCTTTTGGGCTTATCTCTCTTATAACGTTTTTAATATAGTCTGC
GAATAACGTACTCCATCCTTCATGTGACATTACGGCAACTAAGTATAAATTTTTAGAGTTTGCATCAAGATATCT
TTTTAATTCATCTAGAGATCCCTTAACGCCTATAAAGGAATGTGCTATGAACGAGTTGGCGAAAGATAATCTTTC
AACTATGCTTTTCATTATGTATCCGATATCTGCAAGCTTAAAATCAACAATAATTTCCTCCACGTCTAAACCAAT
TAAGAGCTCTCTAGTTTTATCCACTCCTAGATCTAAAACTAAAGGTAAACCAACTTTTATCCCATATAACTCATT
TTCCATCTCTTTAAGAACTTGATATGAGAGAGGTTTATCCATTGCTAATATTACTCTACTTTTCAACATTCTTCA
CCAAATAATCTAGAATTGACTTCTTTTCATTATCCTTAAGTTTATCACTCTTCAACAATTCATCTAGAATTTCTG
AAATTTTAAATAGAGAGTGTAATTTGACTCCTAGTTTTTCCAATCTTTGTGAAGCCCCTTCTTGTCTATCTATGA
TTACTAGTGCGTCTGAAACTTTACCTCCACCGTTAAGAATCTCCAATGTTGCTTTCTCTATGGATACTCCTGTAG
TTGCAACGTCATCTACTAACAATACTCTTTTTCCTTTTACATCGAGTTCTAATGTACGATTAGTTCCATGACCTT
TCTTTTCTATTCTAATATATCCCATAGGCTCTTTAAGGTTACAAGCTATGAATGCCGATAAGGGAACTCCTCCAG
TGGCTATTCCTACTATTATATCATGGGGTATATCTTTTGCTTTCTTTATAGCTTGATTAACTATATCGTAAAATT
CTGGATAATTTGGTAAAGGTCTTAAGTCTAAGTAATATGGACTAACCTTACCTGATGTTAAAACGAAACTTCCTA
TTAATAATAATTTCCTTTCGAGTAAGACTTCTGCGAAATTCATACGTAGAGACTCTGCGAAAAAGAATTTAAATA
TACTTCTATCATAACCAGTTATAAGGGCTTTGTGAGATTAAGACACGTAGTTTCGTCGCTTGACTTGACCAGAGA
TGACTACTTTAGAATATTCGAACTTGCAGACAAGTTCTATGATGTAAAAAAACTAAATTATCTATCAGGGAAAGT
AGTTTCATTAGCATTCTTTGAGCCAAGTACTAGAACTGCTCAAAGCTTTCATACTGCAGCAATAAAATTAGGTGC
TGATGTGATAGGATTTGCATCCGAGGAGTCTACTTCGATAGCAAAAGGTGAAAATTTGGCTGATACCATTAGGAT
GCTAAACAACTATTCAAACTGTATTGTAATGAGACATAAGTTTGATGGGGCAGCATTATTCCctaggggCCCCAT
CTGGAAAAATAATGAGGAGAGTATTTAGAGATGAAGCTTAGAAGATCTTAGATAATCTGAGTTTGATCTTTTATG
TGCATTGTGGTCATGTTGAATTTTCACGATCATTTAAGGACTCCCATAAACATAAATTATGTATCAAAACATTAA
TTGAAATATAGATAATAGTTATATTATAGTTATTTTTAGAAAAACATCCAATATGTTAACAAAACGTCTTTTACG
GAAATATATAAATGTTAAACAAGTTAGGTATACTATTTATAAAATAGTTAGGTCATAAAAGTACCCGAGAACTAG
TCCAGTGTGGTGGAATTCTGCAGATATCAACAAGTTTGTACAAAAAAGCTGAACGAGAAACGTAAAATGATATAA
ATATCAATATATTAAATTAGATTTTGCATAAAAAACAGACTACATAATACTGTAAAACACAACATATCCAGTCAC
TATGGCGGCCGCATTAGGCACCCCAGGCTTTACACTTTATGCTTCCGGCTCGTATAATGTGTGGATTTTGAGTTA
GGATCCgGTCGAGATTTTCAGGAGCTAAGGAAGCTAAAaTGGAGAAAAAAATCACTGGATATACCACCGTTGATA
TATCCCAATGGCATCGTAAAGAACATTTTGAGGCATTTCAGTCAGTTGCTCAATGTACCTATAACCAGACCGTTC
AGCTGGATATTACGGCCTTTTTAAAGACCGTAAAGAAAAATAAGCACAAGTTTTATCCGGCCTTTATTCACATTC
TTGCCCGCCTGATGAATGCTCATCCGGAATTCCGTATGGCAATGAAAGACGGTGAGCTGGTGATATGGGATAGTG
TTCACCCTTGTTACACCGTTTTCCATGAGCAAACTGAAACGTTTTCATCGCTCTGGAGTGAATACCACGACGATT
TCCGGCAGTTTCTACACATATATTCGCAAGATGTGGCGTGTTACGGTGAAAACCTGGCCTATTTCCCTAAAGGGT
TTATTGAGAATATGTTTTTCGTCTCAGCCAATCCCTGGGTGAGTTTCACCAGTTTTGATTTAAACGTGGCCAATA
```

-continued

```
TGGACAACTTCTTCGCCCCCGTTTTCACCATGGGCAAATATTATACGCAAGGCGACAAGGTGCTGATGCCGCTGG
CGATTCAGGTTCATCATGCCGTTTGTGATGGCTTTCCATGTCGGCAGAATGCTTAATGAATTACAACAGTACTGC
GATGAGTGGCAGGGCGGGGCGTAaAGATCTGGATCCGGCTTACTAAAAGCCAGATAACAGTATGCGTATTTGCGC
GCTGATTTTTGCGGTATAAGAATATATACTGATATGTATACCCGAAGTATGTCAAAAAGAGGTATGCTATGAAGC
AGCGTATTACAGTGACAGTTGACAGCGACAGCTATCAGTTGCTCAAGGCATATATGATGTCAATATCTCCGGTCT
GGTAAGCACAACCATGCAGAATGAAGCCCGTCGTCTGCGTGCCGAACGCTGGAAAGCGGAAAATCAGGAAGGGAT
GGCTGAGGTCGCCCGGTTTATTGAAATGAACGGCTCTTTTGCTGACGAGAACAGGGGCTGGTGAAATGCAGTTTA
AGGTTTACACCTATAAAAGAGAGAGCCGTTATCGTCTGTTTGTGGATGTACAGAGTGATATTATTGACACGCCCG
GGCGACGGATGGTGATCCCCCTGGCCAGTGCACGTCTGCTGTCAGATAAAGTCTCCCGTGAACTTTACCCGGTGG
TGCATATCGGGGATGAAAGCTGGCGCATGATGACCACCGATATGGCCAGTGTGCCGGTCTCCGTTATCGGGGAAG
AAGTGGCTGATCTCAGCCACCGCGAAAATGACATCAAAAACGCCATTAACCTGATGTTCTGGGGAATATAAATGT
CAGGCTCCCTTATACACAGCCAGTCTGCAGGTCGACCATAGTGACTGGATATGTTGTGTTTTACAGTATTATGTA
GTCTGTTTTTTATGCAAAATCTAATTTAATATATTGATATTTATATCATTTTACGTTTCTCGTTCAGCTTTCTTG
TACAAAGTGGTTGATATCCAGCACAGTGGCgCCGGCCGCCACCGCGGTGGAGCTCGAATTCGTAATCATGTCATA
GCTGTTTCCTGTGTGAAATTGTTATCCGCTCACAATTCCACACAACATACGAGCCGGAAGCATAAAGTGTAAAGC
CTGGGGTGCCTAATGAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACTACGG
CTACACTAGAAGGACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAGTGTTATCACTCATGGTTATGGCAGC
ACTGCATAATTCTCTTACTGTCATGCCATCCGTAAGATGCTTTTCTGTGACTGGTGAGTACTCAACCAAGTCATT
CTGAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGAGC
```

-continued

AAAAACAGGAAGGCAAAATGCCGCAAAAAAGGGAATAAGGGCGACACGGAAATGTTGAATACTCATACTCTTCCT

TTTTCAATATTATTGAAGCATTTATCAGGGTTATTGTCTCATGAGCGGATACATATTTGAATGTATTTAGAAAAA

TAAACAAATAGGGGTTCCGCGCACATTTCCCCGAAAAGTGCCACCTGACGTCTAAGAAACCATTATTATCATGAC

ATTAACCTATAAAAATAGGCGTATCACGAGGCCCTTTCGTCTCGCGCGTTTCGGTGATGACGGTGAAAACCTCTG

ACACATGCAGCTCCCGGAGACGGTCACAGCTTGTCTGTAAGCGGATGCCGGGAGCAGACAAGCCCGTCAGGGCGC

GTCAGCGGGTGTTGGCGGGTGTCGGGGCTGGCTTAACTATGCGGCATCAGAGCAGATTGTACTGAGAGTGCACCA

TATGCGGTGTGAAATACCGCACAGATGCGTAAGGAGAAAATACCGCATCAGGCGCCATTCGCCATTCAGGCTGCG

CAACTGTTGGGAAGGGCGATCGGTGCGGGCCTCTTCGCTATTACGCCAGCTGGCGAAAGGGGGATGTGCTGCAAG

GCGATTAAGTTGGGTAACGCCAGGGTTTTCCCAGTCACGACGTTGTAAAACGACGGCCAGTGCCAAGCTTGCATG

CCTGCAGAGTCTCATATGTTTCCTCACTTATTGAAATGTTAAGCCTTTTGACTATCCTATCTTTCCTCTTCTCTA

TCATTTAGGTCACCTTGTTTATTGTTATTTGAAATACGTATCCGTCTTCGTCACATCGAAGTATAATTTTGTATC

CATTATTAGCATATTCTACGTCAAAGTTCCCACAACAATAATTCGGGTCTTCGGACTCGTTATAGACTTTGCTCC

AACCATCTTTTTGTAGTGCCTCTTCTAAGTAGTCTACTCTGATGAAGCCTTCATCATATTCGTTCAGTACCCTAA

AGCTTATACTATCAATGCCTAATACGTCTAATAGCTTCAACAGATCGAATATAGGAACTTGCACCATCATTTCAG

CTCACCTTAATGAGCTGATATAATTCCGCTTCTATCTTTTGAACTTGGAAGTATGCCTTGCCTAGCTTTTGCTTA

TCCATATTGCCCGTTATTCTATCAATCTTAATCTCGTGGATTAATGATAATAGCTCTCTGACATCCTCATCAAGC

ATTTCAAATAATTCTTTCTCTAAGACTTCTTTTACTCATTGTTTTTCACCTTAGCAAACTCATCTAACGTTGTTTG

TCTCAGTTCTCTTTTCTTTATCAAATAAAATTCCGAATGTCCCTTCTTATTGTTATTACTGTACTTCATGTCAGT

TCACTGCTTTGCCTTTATAAATCCTTGATCCGTTTGCTCAAAATTTGCGGGCTGGGCATCAAATATCTTAGCTAT

ATTGTCTTGTGTTTGCTCTTGTTTTTGTTCTTCTTTCTGCTCTTGCTTAATCCATTTGAACGTTGTCTTTCTGTT

TTTGTATTGTACTTCACACTCGTCTGGATGTCTTTCGCAAATAGCTTTCAATGCTCTCTGTATGTTATACGCACT

CGGGACTGAAATCTCAAATTGAGCTAGTATATCCTCTAACGTTAATTCACCTTTCTTTTCAAGAATTTTATACAT

TATTTCCGCCATCTTGTATGAATTTAGAGTTTGTGCCATATTCCCATCCCACTCTATCTATACTCTATGTATAAA

TTAGTATTTAAGTCTTACTCTATCTATACTCTATCTATCTCTATATACACAGTGTTTGGGTAACTGGCAAAAT

TCTGTCTGACTGCTGTCTGACAAGAGTTTACTCTATCTCTCTATATCTATATACACAAACAGAGTTAGTCGACTC

TGTGTATCTTATGTATCTTATACAAAAAATATGGGATGTGCAAAATCTGAGCTACTAATACTGCTTGAATATATA

GATAGAGAGTGTAAGGACTACGAGAGTTGTAAAAGAATAATAGTAGAGCTAGAAGAGAGAGTGAAGAAAATAGCT

TTCGTAGAAGCAATAAATGATTTGTTCTAAACTACTTTTTTCTCTCTATCTCTATATCTATATATATACATAACT

AAAACTAAAAGAATAAACAAAAAACTAACAAAATCAACTCACCATTATACAAACTCAGAAAAACTATTTTTTTGT

TATACTCTTACCCCATATATATATAGATATATAGATAGAGAGAGATAGAGTATAGTAGGGCATTTAAGATTTTAG

AAGTTCTTCAATGCGTCTTCTGATTGCATCTGCAACAAACTCTTGTCTGCTTATATATCCGCCCTTGCCTGACGC

TATTAGTTCATCTATTTGTTTTGCTAATTCGATTGGAATCGAAACGGTCACATATTCTTTTTTGACTGATTTCCT

CGGCATACGCTATCTATACTATATTAATATGATAATATTAAATGATTCACGATATATAGATAGAGTATAGATAGA

GTAAAGTTTAAATACTTATATAGATAGAGTATAGATAGAGGGTTCAAAAAATGGTTTCACCCCAAACCCGAAAAG

AAGAAGAGTTATTAGAAAAACAAAATTCAGTTTTTTATTTGTTAACTTTAGGAAGGAAACCGTATGGTTCATATT

TGCATATAAAAATTGAACTAGACGAAGATGAAAAATTAGAGAAGGAAATCTATGCGGATAACATTAAGCTAGAGA

ATGAATTAAGACAACTGAAGAGGTTGTATGAAGTATATCAGAGCGTAGAGATTGACGATGCTCAGAAAGCAATAC

AGAAGGAAGCATTACTGACGATAGCGAAAATACTAAGTGTTTTTGACTTCTGAGGAGGCTGAGGGGCAATGAAGG

CTGAGGAAACAATCGTGGAACAGATTCAGGACATAATTCAAAAACTTCGCTATTATACAGGAAGATCAAATAGAC

ATTTCAAGATGATTAGAAACTATTATGAGGAGTGTATAATAATAGTAGACGCTGAGGAGTTTATACAAGAAATA

ACACTCTAAGCATTACTGTATATTCTGAGGATCTTATATATTATACTGTTGATATCCCGCTGAATTTCATTAAAC

-continued

ATGTATTCGTATCCGCTTCGATTGATCAGCTCAATGATCAGCTTCAGCTAAAATATAATGAGGGTCTGATTAGAG

TTTCTCTTACTTTGAACGATGACTTATGTGAGAAACTGAGAAGCTCATACTGCGGTGATATTACATTCTTTAATG

AGGCTGAGGGGCAATGAAGGCTAGGGTTGAATACATCAAATTACCTAGATGTTACACAAAAACTTATAGAAAAAT

CGAAGCGAAAAAGAACAACGACGGTACAATAGAATTAACGTTAGAGGAAACAATGCAAGTAATATCCTTTAAACT

ACCCCCGGCGTTAAATGCAAAACTAGAACAAATTGCGATCAAAGAAAAGAAAAGCAAGAGTGAAATTATTCGAAT

AGCGTTAGCGAGGTATGTAGAAAATGTTTAGATGCCCCATCTGCGGGTTCAAAACGCTGAGATTGTTCGCGCTTA

AACAACATACTCGAAGGGAGCATGTGTTGGTCAAATGTCCCATATGCGGGTTCACGGGAAGCATTTATCTCAAC

ATTTCTATAGTAGGTATGATATTGACCATCTCATATACTGCTACCTATTCTCTTCTTTCAGATTGCCTAAGAATG

TTAGGTTAGCAATAAAGAGAAAATTAGAGGTTGAGTGAATAATGTATCAATGTCTACGTTGTGGTGGTATATTTA

ATAAAAGAAGAGAAGTGGTTGAGCATTTGCTTGTAGGGCATAAGCACAAGGATAGACTAACACTGGACTTTTATT

ATATCTACTTCAGGGTGAGAGGACAATGAACCTAATTGATATCATCTTATTTTACGGCTTTCAATTCAACGATTA

TTGGACAACTGTCTTAGGGTTGAGAGTGGGTGCGGAAGAGAAGAATCCCATAGCGGGTCTGTTCATTTCATCACC

GTATCGTTTAGCGTTGTTTAAGTTTGGCCTTATCACCATTGGTATGTTTATATTAATTTATGTTGTTAGATTCAA

GACATGGACAGAGATCGTATTGACTGTAACAGACGTTGTCGAATGCCTTGTCACGCTGAATAATACCCTTACGAT

TAGGAGGTACAAAAGGAGGGGCGTTAGAGGATGACGGAGTCAGACGTTGACTCAGGTAGTAAAAAATACCTGAGT

AACCATAAGGGGATTTTTATTCATGTCACACTGGAAGAGTTAAAGCGTTACCACCAACTTACGCCGGAACAGAAG

AGGTTGATAAGGGCAATCGTCAAAACGCTTATTCATAACCCGCAACTGTTGGATGAAAGCAGTTATCTTTACAGA

TTGCTCGCGAGTAAAGCGATTTCACAGTTTGTCTGCCCGCTTTGTCTAATGCCCTTCAGCTCTTCCGTATCACTA

AAGCAACACATCCGTTATACTGAACACACAAAGGTTTGCCCGGTGTGTAAAAAGGAGTTTACCTCAACCGATTCA

GCCCTAGACCATGTTTGCAAAAAGCATAATATCTGCGTTAGTTAGGCTCTTTTTAAAGTCTACCTTCTTTTTCGC

TTACAATGAGGAAGTCCCTTCTAGCCCTACTAACCCTATCCCTAGCGTTACTATCGTTTTTAATAACACCATCGA

TGGCATTGAATTCTGGCGGTTCACCGATACCGATATATTATAACTATTATAACTACTATAGCCTTAACGCAGAAG

GGTTTGGATTCAGTTTCAATAATAGCAATAATTGGGTTGAAACGAACTTTATCTCAATAACCATAAACTTACCTA

GTTCATTACCAAATAACTATCAAATCAATAATGCCTATTCTATCGTAGTAGGATTATCACCATATCCGGTTAGCA

ATATAAACATTTTTAATAGCCCATTAGAAGCATATGTTGAACTATTCTCAAACCCACCGAATACATATCCAAATG

AAATAGGATTTGTAGTTAGTTACGGCTCAACTGTATTTTATAGTTATACCACACTGTATAGCAGTTTTGCGGGCA

CACAACTAACAATAACTATATCATATACCGGAAATGGGTTTGGTGTGCAATTCTCTGACAGTAACGGGTTCTCTC

ACTCAGTTTCGGTAAGTTCGGTAAACTTTGTACCATATGGTGCTCTAATACTCGGATCACTAATCCCGAACGGGA

ACTATTACTACTACCCAGTAGGTAACATGTTACCGAATGCATCGGTGAACTTCTCATATACGATCTCAAGTTTCA

CAATAGAAGGAAACCCGGCCACATCCGTCGATATTACCACACTTGGATTAGAAGGAAACACTGCAATATATACTT

CAAGTAGCAATTGGTTCAAATGGGTATCCGGTAGTGTGGTTATCACAAATGCCGTTGCCTATACCTATACCGATT

TGGCTAGAATAGGAGGAAGTGCACAAATAAACTATACTGCATCGCAGCTATATTAAGCAAAATCTTTTTTTACCT

CTTTTTAAATCTGTCTTATATGAAAAAACTGTTTACAGTTGTAGGTTCTATTTTCTCTGGTTTGGGGATTTGGCT

TAAGTCAATAGACCAGTCATTTTATTTAACGAAAGTATTGTATAACGGAAAAGTAATTGAAATAGTTCTAACGCC

CGAGACAAATGAAGTCGTGAAATCTTCCAACGGTGTTATGAACGCAAGTGTAACTTCTCTACCTTCCACAATTCT

ATACCAAGCACAATCCGTGCCTTCAATAAATGGAGGAACTCTTAGTGTAATAAATACCACAGTTCAACCGCCATG

GTATGCTAACTTATGGCCTGAAGTCTTAACAATAGGTATAGTGATGTGGGAATTGCAATATTCAGCTGGATTAA

ACTTAAATTTAGAAGATAGCCCTTTTTAAAGCCATAAATTTTTATCGCTTAATGAAGTGGGGACTATTATTCTT

AATAATGTTTATATCCATTTTTTCCCTCAACTCTTTAGCCCTATTAATCGGCGGAGGAGGGCCCAACAATAATGG

TGCGGGAGTTTACACTCAGACTATAACAGTTAACGGAGGAACCGTACGAACTACTCTTAACGGTTCAACGCTTTC

-continued

```
TACCGCACCATGGCTCAACCCCTCTTACGTAAGCGTCTACAACACATACTACCTTCAGGTTTTGCCGAACCAAGA

GTATATTGACAACAACGTTTCGTTATCCCTAAATACGGCTAACATTGCGTTAAACGTCACTTGGTTATTGGCGTC

CTCAAGCAATACGGGATCCTACGGTGCAATCGCCATAGGCTACGGAGTGAACTTTCCCGCGGGGTTTGTCAATAA

CTACGGTCCTTCCGCACCTTACACGCCGGACGGAATCGTAATATATCTCATGAAAGGAGGCATGCCGACCTATCG

TTTATTCGTATACTTCAATGGAGTTGAGCAGTTAAACGTTTCAGTCGGGTCAATCAGTGTGGGACAAAAAATAGG

TTTAGGGTTCTTTTATCTACAGAACACACTTTACGTTTACTACTATAACGGTACTTTAAAGACTTGGTCATTAAC

GCCCGGTACGCTGATTACTATAAATAGTAATTACGTTATAGACGCACAGAATATAGGGCCGGGCTACGGCTACGG

TCAATGGGTAATAGTTAATTATCAATATGCGATGCCGGTTACTGCACAACTGACGGTTAGTTATTTCGCATTAGG

GTACAATGTATATCATTTCTTAATGGCTTATGCGGGTGCTGGAAACCCGGTAAACATAACTGCGAATAACGGGGC

TTCTTACAGTATAACGGGTATAGTTGCAGAGAAGAACTTTACGATAACGGGAATTCAGCAAGGCCTAGCCTATGC

TTTCAGCTTGTTAGGGAAACCGAATGGCTTATACTTATTATATATGGGGCCAATTGAGGGCAGCCCACCAACGTG

GTATGTAAACGTAACCGTAGGGCTTCAGATCGTTACACCCCAGAAAACGATAAACTACAACTTAACAATACCAGT

AATCGTTGAGGGCTATGCGTTATACCCTTCTGTTAACGTACCTTCCGGAACTTACCTAAGCGGACAGACTATTAG

CTTTACCCTCTCATCGTTCTTGGGATACCCTTCAGGCTTAGGCTATTACACCGCAGTAAATCTAATCGCAAACGT

AACAATAAACGGTGTGAGTCATGCTATCCCCTATAGTTTCACCCCGATAGTGCAAACCCCGATAACTTATTACTA

CACTGTTATAGTGGATGAAGGACAATTTGCATTAATAGATTATCAAGGGAGTTTCACAGTCCTACCCGCACAGAG

TCAGCCCGTGATATTCATTACTTCTTATCCTAGAATTGGGCTATTAGGACAAACGATAACTGTGACTTTCCAGTT

CACTTATAATAGTCCCGTAGCGAATGTAACTCAATCAGCGTTTACGCAATCATCTAATATTCTCGCTTTTGCCTA

TGCGAAAATGGTAACAACAAACGCTATAGTTCAGTTCAAGGCGTATTGGCTAAGTGCTAATGACGGGTTGGTGAT

TATAACTCAAACGAATAACTATCTAATTCCGTTTAATAGCAGTATAACGGGCTTAAACTTCGCAAACAATAGTGT

TAATACGTTAACGTTTCAGATTGTAACGGGTAACTATGTACAAATAACTAGCTCAGCGGGAGGCGTGCTTACCCT

AAGCAATACTAGTCCGATTATAGGAATAGGGTTCTATTACGGTTCCGGTGTCCTACACCTGAACTGGTTCTTCGT

TAGCGGTATCATTTTGCAGTCTGCAACGGCAAATCAGGCTTACGTTATTTTGACGGGGACTAACCCAAATACGCT

TTCACAGTATACGACGGGCTATACTAACGCTTCGGGGTTCGGTACTGTAACGCTGAAGTTGAGTTACACTCCTTA

CGAACTTGTGGATGTAGACTGGTACGGCGTTACATACGCTTTGTTAAACATTAGCGTTTCAAACACTACTACAGT

AAGCAGTACTACGACCGTGAACACAACAACGCTTAACTATAACTACACTAAGCCTTTCAGCAATAACATAGCACC

TAACAGTCAGCTTTATGACTTCTCAGCGTATCAGCCGTGGGCGGAAATTATCGGGATTGTGGTCGTGGTCGTCAT

AGCTCTGCTGGGCTGGAAGTTCGGCGGGTCTGCGGGAGCTTCGGGTGGTGCGGTTATGGGGTTAATCGCAGTCAG

CTACTTAGGTTTACTGCCTTGGTACCTATTCTACATCTTCGTATTCGGTATCGCTCTATTACTTGCTAAAGTATT

TGTAGACCGTTTCATGGGAGGGAGGAATGACGGACGCAATCAGTTTAGCCTTGCAAACGGGCTTAGGGCCGGTG

GTAGGGGTAATTATCATACTGGCAATGATGGGCTAACGTATAAGATAGCGGGAAAGATCCCGGCAATCATAACG

GGAATAGCCTCGGCTTTCGTCCTAATGTTTATGGATTTTTTACCGTTATTTTGGGGTATCGCAATAATCTTCGGG

TTAATCGCGGGTATGGTGGTGACAAGGGATGGGGACTAAGTTAGTCGTTTACGTCTTATTGTTTGACGTCTTCCT

ATCGTTAGTGGTAGGTGCCTACTCGGGTATAGCACCGCCAAGTATTCCACCGGTACCTACATATGCTTCAGCCCA

ACTCACGGCAAGTCTAATCACATGGACAGTGGGATGGCCTCCTATTACATTATGGCCTCAGATAACGCTTATTCC

GCCGTTTTCGATTTTGGGTGCAAACTTCCCCGGCTTAACCATTCCTAGCTTAACGATACCCGGTGTAACGCTCTT

CTCAATAAGCTTCAGCTGGTTAGCCCCAATTATTTATATTGCAAATTGGATCATTTGGGTCTTTCAGACTGTTGC

TAGTGTGCTATCTTATTTACTTAATATCTTTACGGGTTCGGTAGGTCTATTGAGTAGTGTACCCGTCTTAGGGCC

ATTTTTGACCGCCTTCGTGTTGATAGTTAACTTCGTGTTAGTGTGGGAATTAATCAAGTTAATTAGGGGGTCGGA

ATGACGGAGTATAACGCAAACAGTATAAGGGCTAAGATACTGAGGCGTAAAATCCTTCAACTGATTGCGGAAAAC

TACGTTTTGTCAGCGTCGTTAATCTCTCACACACTCTTACTCTCATACGCCACAGTGCTTAGGCACTTGCGTATC
```

-continued

CTTAACGATGAGGGCTATATCGAATTGTATAAGCAAGGTAGGACGCTATACGCAAAAATCCGCGATAATGCGAAA

CAAATTCAGATTCTGAATTCAGAACTGGAGGGGTTTAAAAACGTAAGCGGGAAGCCGATATTGACCAAGGATGAG

ACTCCTAAGGAGTTTGGCAAGAAAGATAGCCTCACTCAAAGAGGCTAAGGTTGCACTAAAAGTAGCAAGCGACCC

CAGAAAGTACTTCAACGAAGAACAGATGACTGAGGCTTACAGGATATTCTGGCAGACATGGGACGGGACATAAT

TAGAAGTGCTAGAAGGTTCGTGGAAGTAGCAAAGGCAAACCCCAAGCTCACAAAAGGTGAAGCAACCAACATAGG

CGTATTGTTGGGCTTATTCATCTTCATACTAATAGGTATAGTACTATTGCCCGTAATCGTTAGCCAAGTCAACAA

CCTCACAAGCGGTACTTCACCCCAAGTAACCGGTACTAACGCCACACTCCTGAACTTAGTGCCGTTATTCTATAT

CCTAGTCCTCATAATAGTCCCCGCAGTCGTGGCGTATAAGATATACAAAGACTGAGGTGTGAGGGATGGAAATCA

GTTTAAAGCCAATCATTTTTTTGGTCGTTTTTATCATCGTAGGGATAGCACTATTCGGCCCTATAAACAGTGTTG

TAAATAACGTTACCACATCGGGAACCTACACTACTATAGTTTCCGGTACTGTTACTACGTCTTCATTTGTGTCAA

ATCCGCAATACGTAGGTAGCAATAACGCTACTATCGTAGCCTTAGTGCCGTTATTCTATATCCTAGTCCTCATAA

TAGTCCCCGCAGTCGTGGCGTATAAGTTGTATAAGGAGGAGTGATATGAAGTGGGTGCAAAAGGCGATAAAGAGA

CCCGGGAGGGTACATCGCTACCTTATGAGGCTCTACGGCAAACGGGCGTTTACAAAAGACGGTGACATAAAGGCA

AGTTATCTCGATAAGGCGATAAAGCACGTTAAAAAAGCTAAGATCCCGAAAGAGAAGAAACGTAGTTTACTGTCA

GCCCTACTGTTAGCGAAAAGGCTTAAGCGGATGCACCGCAAGTAGGCCCTTTATAAAGTCATATTCTTTTTCTTT

CCCTGATGAGTGCGTTAGGGGATGTAATCTACATCTTGGGTTTTCTCTTTCCGGCTTTAGGGCTAATCAGCCGAA

ACTATCTTGTTAACTTAATGGCATTCATAATAGGAACAGTCGCCTTTTTGGTCTTCGTCCAAGGCTATACCGATA

TAGCGTTCAGCAGTTCGACGTTTTACTTAGGAGTACTGCCTCTACTACTTGGTCTCGTCAACTTAGGCTATTTCT

TCAATTGGTTGAGGGAGGAAAGGATATGAGGTGGGGTAGAAGAGATGATAGGGATACCGGCAAAATACTTCGAAA

TAGGAGTCGTAATAGATTCAACATTTATCATTATGTCTCTACTGTTAAGAAAGTCAAAGAGACAGAGAGAGAACT

CCTTCGACTTACGCAAACATGGAAGGCTATTAGGCTTATATCTTATAATAGCGTCGGCATCAGCATTAATCGTCT

CACATCTCGCCTTATACACAAACTACATGAACTACTTAACGGGCTTATCTCTTAATGCGTTTCTGTTTTATCTTG

GGTTGAGGTGTTTGCATGTCTGATGGGAAACTCCTTTCTGCTTTCGAGGAGGAATTAAGAAAAGCCCAAAGCCTA

GAGGAATTAAAGCAAAAGTATGAGGAAGCCCAAAAACAAATAGCTGACGGCAAAGTACTAAAGAGGCTATACAAG

GTTTATGAGAAAAGGCAAACAGAATTAATGCTTCAGCAATATAGGCAGATAAAGGCTGAACTGGAAAAGAGGAAA

AAGGTAAAGAAAAGGATAAAGCCGACATAAGGGTTAGAGTAGTAAAGAAGTGGATAAATTCACGCTTATTCAGT

GCTGAGCATTACGTCGCATTACTGCAAGAAAATCAAGACGGCTTATCGATACTATTTCTAAGAAGAGCAAAACTT

ATAGAAAATCAAGGCTATCTAATGCTAGAAGTGAAGAAGTTAAGGAAGGCATGGGTTTTAACGGCTGAACCTATA

CTCCTTGAAAGGTTAAAATTCCCATTCGGCAAAAAGTTTGTAGCCGTGCATTTCGTTTTACCCAATTATCCTTAC

ACACTTCAGCTTAAACCGGATGAAAAACTGAAAGAGTTAGCAGTTAAGGCGATAAACGGGCCTCAAATAATGAGC

GCAATGATACGTACAAAGTTCTTCGAAGCGTTAGCTAGGGTAGGAAGCGGGCCTGATCTGATGATGCTCATAATC

GGCGTTGTCATGGGATTGGCATAGGCGTAGCGATAGGTTTCGGTATAGCTAACGCAAACTTAACGCATTTGCTA

TCTCAACACGTTACGAACACTACAGTGACACATACTACGACCACAACGACTTCACCCTCATTCACGATTCCCTCA

AACTCCTCAAAAGGGGTGAGCTAAATGGTCTCAGTAACAGAAATAATAACATATGGACGAGAAGCAATAGAAAG

AATAATATGCAAATATTTTAAAGATTCGAAAATAGAAAGATATTATTCTTGCCGAGTGAGGAAGACGTAAAGGC

AAAATATATCATTGGACGGGTAGGGTTTATAAGGATTAGTAATACGTGGTCTGGAATTGTCGTAGTTGACGGGGT

ACAAATACCTTTCGTTGCTGAAGTCCACCTTAATGGCAAGATTGATATTTACCTTTATCCTCAAAAGGACTTCTA

CTTAGCACATTTGGTGGGTGAGCTGAATGGCTAAAAAGAACGGCTTAACAGAACTAGAGCAATTAAAGAAAGAGA

ACGAAGAGTTGAGAAAGAAGTTAGAAGAGTTAGAGGCGTTGATCAATAACGATAGCGATGACGACGAAGAGTTGC

AGGAAATCGAAAACCCGTACACCGTTACAAACCGTGCAATAGATGAATTAGTAAGCCCAAAGGACACAATGTTCT

-continued

```
ATTTGTCGGGAAACCAGATATCGTTAATCTTAAGTGCTTTTGAATTCGCCCGCTTACCGACGTACTTCGGTGAGG
AACCGGTAACGGAGTTAGCGGAATACGCCCATAAGTTGAAACATTATCTCGTTTCGAAAGGAGGAAGAGGAAGGA
GGGATATACTGAGAGTCCTACGCGTTAGTTCAGGTCAGACAAGAGAGAACGTAAACAAATCAATTCTGAAACAAT
TATTTGACCATGGTAAGGAACATGAAGATGAAGAAGAGTAATGAATGGTTATGGTTAGGGACTAAAATTATAAAC
GCCCATAAGACTAACGGCTTTGAAAGTGCGATTATTTTCGGGAAACAAGGTACGGGAAAGACTACTTACGCCCTT
AAGGTGGCAAAAGAAGTTTACCAGAGATTAGGACATGAACCGGACAAGGCATGGGAACTGGCCCTTGACTCTTTA
TTCTTTGAGCTTAAAGATGCATTGAGGATAATGAAAATATTCAGGCAAAATGATAGGACAATACCAATAATAATT
TTCGACGATGCTGGGATATGGCTTCAAAAATATTTATGGTATAAGGAAGAGATGATAAAGTTTTACCGTATATAT
AACATTATTAGGAATATAGTAAGCGGGGTGATCTTCACTACCCCTTCCCCTAACGATATAGCGTTTTATGTGAGG
GAAAAGGGGTGGAAGCTGATAATGATAACGAGAAACGGAAGACAACCTGACGGTACGCCAAAGGCAGTAGCTAAA
ATAGCGGTGAATAAGATAACGATTATAAAAGGAAAAATAACAAATAAGATGAAATGGAGGACAGTAGACGATTAT
ACGGTCAAGCTTCCGGATTGGGTATATAAAGAATATGTGGAAAGAAGAAAGGTTTATGAGGAAAAATTGTTGGAG
GAGTTGGATGAGGTTTTAGATAGTGATAACAAAACGGAAAACCCGTCAAACCCATCACTACTAACGAAAATTGAC
GACGTAACAAGATAGTGATACGGGTAATGTCAGACCCCTTTTAGCCATTCCGCATACTTTTTATATTGCTCTTTC
GCTATGCCGAAGAGCGATACGTAATGTTGCGTTAAAACGCGTGTCGGTTTACGCCCTTGAATAAAATCGATAATA
TCTAACGGTACGCTTAGCTCAGCCATCTTAGACGCTACGAATTTGCGGAAGTACTTTATCGCTATAGCGTCCTTA
TGACGTCGTTCAAAGTCCGCTATTGCCCACTTCGTCACCTCTACTCTCTTCAGAGGCGTTATGTGGAATACATAG
AAGACGCCCTTATATCCCCTAGTCCAACTAAGCGGATAATAACAGACGTCGTTACCGCAAATGTCCCTTTCGGGT
TCCTTCAGCACTTTCAGTATTTCGCTCAGCCTAACGCCCGACTCGAGAGCGATACGGTAGATGAAGTAGACGTTT
TCGCTATAGTCTTTTGCTAATTGTAACGTCCTTTTTATCTCTTCCAACGTTGGAATGTAGATATCAGCGTTCGCC
TTCTTCACCTTTACCGCTTTCAATATTTTATCCGCAAATTCATCATGTATGATATTGCGTGACGCTAAGAAACGT
GCAAAGAGTCGGTAAGCCTTCTGTGCGTCTCTCGTCTCTTTATACGGCTTTGATATAGCATTGATGTAGTCCTTT
GCAGTTTTTTCGCTTATCCCCCTTTCGTTCATGAGATAGTCGTAGAACGCCTTTATGTTGCCGTCCGTCGCGTAT
TGGCGCAAATTGGCAACCAACGCTATTTTACGTCGTTCAGTTCCCTCTTTTCCGCCTCCGGAGCCGGAGGTCCCG
GGTTCAAATCCCGGCGGGTCCGCTTGTAGGGGAGTATCCCCTACGACCCCTAATTTCATTTTTAGATATGATTCA
ACGACGTCAGCTAAAGGACCCACGTAACGCTCTTTTACCTCACCGTTTTCATACTCTAGCTTGTAAACATAATAC
CGCCCTTTCCTCTCGCGTAAAATATAATCCCCGTATTTATAACGCGTCTTATCTTTCGTCATTTCGCCTCACAGT
ATTATGGTTGCCAAAACGGGCTTATAAGCATTGGCAACCCGTTAATTTTTGCCGTTAAAACACGTTGAATTGAAA
GAAGACGGCAAAGAATCCACACAGGTAATACTAAAAAAGTAGTATTACTTACATTAGAAGGACTCATTTGTCCAC
CTTGTATTCTAGCCATGCTATCTCTGCCTTCAGCTCATCTAGCTTCCCCTTTATGTCTGTCAGGTCAAGGGGAAC
TCCTCTCATTAACCTGAGTTCGTTTTCGATTTTTTCAAGCTCCTTTTCCAACTCCTCTAGTTTCTCTAATTCCTT
TAGTCGTTCTTCCAATTTCTTTTCCAATTTCCCCTTTGCGTCATTTATAATTATGCTTACTACCCAAACAATTCC
TAAATCAGAAATAATTATTAACTCCTCTGAGTTGAATATCATTTTCCGCCCCTCGCTAAATACTCCTTAAAGCTC
TGATAGAACCCCTTCAGACTAACCCGTAAGTCTGTTAGGTTCTTCCAGTATTGTAATGGGATTAAGTAATAGTAG
CTTACTGCATCTCTCTCAAATTTGTCCTTCTTAATCTTTCCTTGCTTTTCTAAGTTGAGTATTTGCAGTGCTGAG
ATACATTTTAACTTGTCCTCAGCATCTGAATAGTGTATAAACCAAACCCTCCCCATAACCTCATTCTGCTTTGCA
ACTTCTACTTTAGTGCTTAATATTGCGTAAACGCTTTCGCCGTATCTTTCTTTGCTCTGTTCTTCAGTCCATGAA
CTTCCCGTAATATCTATCCAAATTAAAGGATAATATTCTGTCTTAGCCTTAACGTATAAAGTCAAATCGTATTTA
TCTTGCAGACCGCTATAGTATTGCTCATTTATTACATTAGTTAAAGTCCCCACGCCAGTTGGGCGGATATAAACA
TCAAAGTCTAACAAACCCTTAGCCCGCCACTTTGATAAAGAGATTAAGAGCTTTCCAAAAACTAGGTATTCTCGC
CCTAAATAAGTTGAAGGGAGGATATAATCCTCAGCTTGATTACCCCAATACTTTAGCTTAAAATTAGTTTCAGCC
```

-continued

```
ATCTCACTCACCATATTGAAACGTGGGCTAGTATGTGAATCAGTACTGATGCTATTGCAAATAACACACTTGCAG

TAGCAATTCCTATTACAATCCATTTACCATAATCCACCTTAGTTTGTTGGTCAATATACTCGTTGATGATCTTTA

GTATTTCTGGCTTTAGTTCTGATAATGAAAGGAAGACAGAGGCATAAAGTACTAAGGAGGATGTGAACAGATTAT

CCGCCTTTTCTGAAAGTTTATAAAGCTCATATCTTGCTCTCTCATAATCTTCATAATTAATAATTTCATCAAACT

TTTCTACTTGCTCTTCATATTCTTTCTTCAGAGAGTAAGGAGTTGTCTTTTCAATTACTCCTAATTTTATTAACT

TCTTAACAGCTTCCTTAAATCCTTGTTTATTGCTAGCATACGCTAAAGGGTCTTTTCCTTCTTGAGAAGCTCTAT

AGATAACTATAGCACCATAAACAATATTTACAATATCGTATGGTAAGGAATACGCACCGATTTGGGCAATATCTT

CAACTCTTCTTTGATCCATCTAGTTCACCTCTTTTTGATTTGTTTGTAGGTTTCTATCGCAGTTTTCAGCGATAT

CGCAAATAGCTTCCCCTTTTCCGTTAGGTATAGCCTCTTTTCGCCTCTTTCTTGACGCTCTTTCACGAAGCCCTC

TTGTATTAGGAACTTTTTTGCATCATAAAAGGTGGCAGTGGACATGGGAAATTCTGCGTTTACTTTCTTGTATAG

GTCATATGTTGCTATTCCTTCATTATCATATAGATAAGCCAATACTATGGCTTCGGGGTAGAAGAATGGTGTACT

TTTCATATCCTCCTCACTCCTCAGCCTCTAATAGCTTAACTGCCTCCTCTATCAACTGTCCCATTGTCTTTCCAG

TCTTTGCCTTAAGCCTCTGCAGTAAATGGTAAAAAGATTTTACTTATTCCGTTCTCTTCTGAGAACCGCTTGCTT

TTTACGATTAAATTCCACATATCATCTAAGATAGAGTGTTGTGGTTCTAGCTTCCTCGTGTAGATTTTCCCCTAT

TAATGTTAGTTTATAAAGACCGGCTATTTTTTCACTAATT
```

In some embodiments, the suitable medium comprises plant cell wall, or one or more component thereof, as a carbon source. In some embodiments, the components are cellulose and/or hemicellulose. In some embodiments, the components are xylan, glucuronoxylan, arabinoxylan, and/or xyloglucan. In some embodiments, the components are glucose, xylose, mannose, galactose, rhamnose, and/or arabinose. In some embodiments, the suitable medium comprises plant cell wall, or one or more components thereof, as essentially the sole carbon source. In some embodiments, when the suitable medium comprises a plant cell wall, or one or more component thereof, as a carbon source, the peptide or protein of interest encoded in the nucleic acid stable integrated into the host cell chromosome is a cellulase, or an enzyme for digesting the plant cell wall, or one or more component thereof, or a functional variant thereof, or a enzymatically active fragment thereof. In some embodiments, the peptide or protein of interest encoded in the nucleic acid stable integrated into the host cell chromosome is a thermostable or thermophilic enzyme or protein. In some embodiments, the peptide or protein of interest is enzymatically active at a temperature of equal to or more than about 70° C., 75° C., 80° C., 85° C., or 90° C. In some embodiments, the peptide or protein of interest is enzymatically active at a pH of equal to or less than about 4.0, 3.5, 3.0, 2.5, or 2.0.

Such enzymes include, but are not limited to, enzymes with the following enzymatic activities: glycoside hydrolase, cellulase, xylanase, endoglucanase, cellobiohydrolase (CBH), and β-glucosidase (BG). Suitable examples of such enzymes include, but are not limited to, those described in "Thermophiles biology and technology at high temperatures," F. Robb, G. Antranikian, D. Grogan, and A. Driessen, CRC Press 2007, which is hereby incorporated by reference. Other suitable examples of such enzymes include, but are not limited to, those described in U.S. Patent Application Ser. Nos. 61/172,653 ; 61/172,668; 61/246,439; Ser. Nos. 12/892,724; and 13/265,786; PCT International Patent Application No. PCT/US2010/032320; and, Park J I, Steen E J, Burd H, Evans S S, Redding-Johnson A M, et al. (2012) A Thermophilic Ionic Liquid-Tolerant Cellulase Cocktail for the Production of Cellulosic Biofuels. PLoS ONE 7(5): e37010. doi:10.1371/journal.pone.0037010; which are hereby incorporated by reference.

Other suitable enzymes include enzymes having a protease activity, such as a protease. Exemplary proteases include, but are limited to, the following:

An exemplary protease is Sso2551 comprising the amino acid sequence as follows:

(SEQ ID NO: 25)
MESRIIQVVVISTFLVLSVLFPLLSLAYSTTSINPSYPQSNVISALPSNT

NIILYFFIPPKNLNELYLIAQEVANHQIKPLSNAQLVSMFSNQDKVNESI

KYLESKGFTIIYRSPFEIMAEAPVSLVSSVFETSFVLAKSTNGEIYYKPA

GNVKIPSTLNNLLIGGLTNFTNVSLPLIQLGKLENGNLIPNKQAYSSFVY

TFQFSATWYTPKVIEGAYNITPLLNSTADKKVTIAIIDAYGDPEIYQDVN

LFDARFGLPPINLTVLPVGPYHPENGLFTGWFEEVALDVEAAHAAAPYSN

ILLVVAPSATLEGLFSAIDVVVSEDLAQVVSMSWGLPGILFGASGFYAVF

NGIIFPNYPYYDYYFELGSAEGITFLASSGDLGAYNDLPTVYGSANYPAS

SPFVTAVGGTSLFANITSGYISTYNSTGNFGAEIAWSVNPLYFGVIQGGV

SSGGGYSQLFPAPWYQRYVTHSNYRAIPDVAADANPYTGFTIYALGQEVV

IGGTSLSAPLWAGIIADIDGIIGHPLGLVNPILYEIYQNTTLYHQAFHQI

SLGYNGYYYANSSYNLVTGLGSPNAGMLGVIIKHSLSKSLAISVSTFETG

VFQPWYFYGSTFTIAAYITYPNNTIVSQGSFNAYIYTSEGYLATVPLSFN

GSYWVGNYTITPNNPPNLWEIVVNGSSDQFTGVGTVEVDVGESINIVSPI

PYPYSFPIPYNSPFGIEAWIYYPNGTPVVNQSVTAYLVSNDGKLLASIPL

TMMAPGLYEGSYALLPPLPQGTYLLIVNDSYGSAFSYVYFGEYNFGAILT

PINDGFPAASPGQNITIIDEVLTPELTGLFTSNVTAYIYNQHGNLIDQVK

```
LTPAPDEIQFGVYLLFFLYYANFTIPFDASPGFYNVVIQSISNTSTGLVK

ADFITSFYVSPANLTLNVKVNNVVYEGELLKIFANITYPNGTPVKYGMFT

ATILPTSLNYEQLIIGFEAGIPLQYNSTLGEWVGIYSIPSIFYGSIFQGS

SVYSLAGPWNVIVSGVSWNGYNLYSTPSSFNFVNVMPYTFINNIVVSSKS

LDSPLLSKINSTTYMLSNVKSNNITINGMNVILSNVIANTVTVKNSNIMI

TSSTINQLVLDNSSVSIIGSKIGGDNIAVVANDSNVTIVSSVIQDSKYAF

LQPNSVISLSGVNMYNVTSLSSIPAPRITYLSTTNVTTSKESIIVNITGE

YLRLLGVSMNNKPVGYSVISSSPSSISLSIPFNASQLSDGQYIFTVSISD

GLPYNLTFNLLNNYHLIIVQDHLKALQGSVNLLTVIAIISLIIAIIAVAL

LFVFTRRR
```

An exemplary protease is Sso2045 (Cannio et al., *Protein Pept Lett.* 2010 Jan.; 17(1):78-85) comprising the amino acid sequence as follows:

```
                                     (SEQ ID NO: 26)
MRLLKILLLAMLILPLFSFFTLSISLYDQIQLPPHYLFYISENATQGSGI

DVIFYTSSPITFMIMTPSQFYQFNQTGSSQSIYSITTNSLSKFFPLSGQY

YIVFYNNISNNPVTLNYYILTRPLPTGIADYGLKINNGVISPYIEKIKSV

IGAVEINKLLAYNSTPPAGVSQYSASIQLNVVLQVNTIGGSQQLWLQNVI

QIYTNNDSYIFLDNIWNFTGKISILSNSTVKGNGIVYVTNNGNDYYAYGT

NFSTLLIPSLKYLLINTSYTSQGPMISFGYMNQSGSPIWYDNVTILIPNT

LSAYILVDGYNFTAGGLAYDAELILGGGGNGEFTFFNESNVELAMIYQYL

NGTLAPPKFLFPFGLDTEESADNLYSISYNGVYLVSSGYQVINNLNENVS

QLRFNVVNYTKATDQNFPYIFTINVSGGVLPYKLNVTISNSSGNELSGYT

YVLFPSVSTYYLFLSPLSPGNYTVKIKLTDFNGNSKSYEFSLTINPPLKV

QILNVTNYIDLALPYFNFTSIISGGTKPYNIIITISNDSGILSETYKIIN

YTSITYYAVNMKGYSIGKYTIQIEVEDYAGSINISKYNFTINPNPYISTL

SYTSETDKGLREVIKAIGKGGSGSLIYYWYVNNSLVSSGIGDELYNFTPS

NIGEYNITVMVKDVLGVSSAKSVIIKVNPDPVVELSVPKTTIDSGAEFPV

NATVSLGTPPYYISWYINGSYVGNESIKELNLSSIGVYIITVTVRDSAGY

IINMSKPVLIVPPPSLSVKEQTQGNFIQYNTSIALSASVNGGTDPYYLIF

LNGKLVGNYSSTTQLQFKLQNGENNITLIAKDLWGKTAVKTLIVNSGYNY

VGIGIIAGIILIIVIVVILVISKRK
```

An exemplary protease is Sso2088 comprising the amino acid sequence as follows:

```
                                     (SEQ ID NO: 27)
MESKNVILKRVMLLLVLILSTTTFLTIIAQSQAQYYYIQTSSPQYTIIPG

SVFVEPLNSSQTLYIAVLLNFTNLASLQSYLNEIYLSAPQFHHWLTPSQF

REYYYPSRSYVNSLIKYLESYNLQFLGNYGLILVFSGTVGNIEKAFNTYI

NVYYYPFKNLYWFGLLGIKNIGPFYYYSNNVTPSLPFNIGKYVLGVVGID

SLDPKVVNVVTQTWHLPMVKAQSGLVSKAIISPITIEQYFNFTLAYERGY

TGGGSNIAIEGVPESFVNVSDIYSFWQLYGIPRTGHLNVIYFGNVTTGGQ

SGENELDAEWSGAFAPAANVTIVFSNGYVGGPQLVGNLLNYYYEYYYMVN

YLNPNVISISVTVPESFLAAYYPAMLDMIHNIMLQAAAQGISVLAASGDW

GYESDHPPPNFHIGTYNTIWYPESDPYVTSVGGIFLNASSNGSIVEISGW

DYSTGGNSVVYPAQIYEITSLIPFTPVIVRTYPDIAFVSAGGYNIPEFGF

GLPLVFQGQLFVWYGTSGAAPMTAAMVALAGTRLGALNFALYHISYQGII

ESPLGNFVGKVAWIPITSGNNPLPAHYGWNYVTGPGTYNAYAMVYDLLLY

SGLIES
```

An exemplary protease is Sso2037 comprising the amino acid sequence as follows:

```
                                     (SEQ ID NO: 28)
MQFRKTFLFLNIHFPYVLRNTLLILLLLLPTPLLAISLPTGVVAYDGPIF

TNQVLGYVNITSLQAYNASGSKFGVPPYGASLQLNVMLQVNTSNEEYYFW

LQNVADFITNESKMFFSENIWNSTTPLAGINNVIGKGEIYSTSDLFSHSS

YYAYGTYYIKYDFPFSFYLIVNESHNNQGVYVSFGYVILQNGNITPPNPT

FYDTVFIPVNNLTSASIIIANQTTPNLNLGIITYLGSYLDAELVWGGFGN

GASTTFLNMSSYLALLYMKNGKWVPFSQVYNYGSDTAESTNNLRVTIAKN

GDAYVTIGKQNPGLLTTNFNPSIPGFLYLNISSKIPFLVNNIISRTFSGY

VSAPIKLGFFMNYSINSSSFAVLNGNYPSLIEPNVSWFKILNIIPNYTYY

YLVRVNSSIPVIGTINGKQITLNDTNWFAQGTQIKIVNYTYYNGSDERYV

ISSILPSLSFNISSPLNVTINTIKQYRVIINSDLPTYLNDKRVNGSIWIN

TGTIVKLSASIPFYEVGRFIGTYNLTLGGTIVVNKPIVEKLQLSINNLLL

EITAIIIVIVIIMLILRKRR
```

An exemplary protease is Sso1886 comprising the amino acid sequence as follows:

```
                                     (SEQ ID NO: 29)
MLKHIVLVLLLLLLTPLVAISFPTGVVAYNGPICTNEVLGYANISSLLAY

NTSASQLGVPPYGASLQLNVMLEVNTSGGEYYFWLQNVADFITNESKVFF

GDNIWNSTTPFAGINNIVGKGEIYSTSDFFSHSSYYAYGTYYIKYNFPFS

FYLIINESYDTQGVYVSFGYVILQNGNISPPNPIFYDTVFIPIQNLSFAS

IIIANQTTPSANFGIVTYLGNYLDAELVWGGFGNGESTTFLNMSSYLALL

YMKSGEWVPFSQVYNYGSDTAESTNNLQVLIGKNGDAYVTIGRQNPGLLT

TKFNPSYPSFLYLNISSKIPFLLNKSLSHAFSGYVTTQIKLGFFKNYSIN

SSSFAVLNGNYPSLIEPNVSWFKVLNIIPNYTYYYLVKVNSQIPVIANVN

GKQITLNSTDWFAQGTQISILNYTYYNGSNERYIISSILPSSSFNVSLPL

NITLSTIKQYRVLVDSNLPVYLNGERVNGSVWINAGSSIQLSANVPFYEK

GIFTGTYNVTPGSIITVNGPIVETLILSINTELMGIVAVIVIAVVAIAIL

VLRRRR
```

An exemplary protease is Sso2194 comprising the amino acid sequence as follows:

(SEQ ID NO: 30)
MMYKVLLIIILLLPLSMPLSIPTTSQPSALAFPSGVTSYPLNTIIYTDFV
MGRINISYLNIGSSYLPGGEYFTTGNASLQLNAMVLGEYWAQNVILFHQI
SNNTFYATLIVNLWNLSGPFSNTTSNSLVYQGLGVICYQGPTFKVTLPLS
ISLFMEIVNSTLNFGYNINGQKGIYFRYPIIGLFQLGGLSLLGLPNDLEL
VWGGPGGGSVVFMNVSSIANLYYFNGNTLTIVPNAYSIGFDTAESAYGVK
VYSTFPSVFSPIVIETSGVNVPSVLWPIPPHVLVNQTSNKITVKLSISNK
SLSGQAVYLETGFPPSVISSAVTNSSGIAVFPNNNYSFYVVYFPGNFTLS
STYYFSSPILNSLSSKFRSYYQDLLNFLNSAQNSFKKGIKSVLSKQETSI
TTTTLTSTTSSSSQFGVNLYIVLYILAFVIGMVISAILIRFKL

An exemplary protease is Sso2181 comprising the amino acid sequence as follows:

(SEQ ID NO: 31)
MTWSIFLLILALSDIVLPLTITNINNQSITTLSPNYYLTVAIVFPPSNLT
LLQQYVQEHVILNQTQVEKLFIPTEEISKTLSQLRQSNISATSYMNVILA
SGTVSQLEKALNGKFYVYELNGKRFFEFFGSPVIPNAIVIGTNITSLILN
KPTTLYNVTQAVAYNALKPSQLLYAYNISWLHAHNITGKGTAIGILDFYG
NPYIQQQLQEFDKQYNIPNPPFFKIVPIGAYNPNNGISTGWAMEISLDVE
YAHVIAPDAGIVLYVANPNIPLPAIIAYIVQQDEVNVVSQSFGIPELYVD
LGLIPLSYVNSLMYEYWLGEVEGISFAAASGDAGGNGYNYFLAPQGSVIF
PASIPYVLAVGGSSVYIGGNKTMETAWSGESVLGASTGGYSTLFPAPWYQ
DSNGFRVVPDVVADANPYTGAFILYYYNQTYLVGGTSLATPIVSGIIDLM
TQSYGKLGFVNPFLYELRNTSALSPIGFGYNTPYYVNSSELNPVTGLGSI
NAGYLYQLLPKVIHSSSISVGVNNITYLDGQVVKVVANITGIRPSSVIGI
VYNGSSVVQQFSLSFNGTYWVGEFVAEGSGIEEVIVKAGNLEGSTYVTIG
YQAQFIFPPIALFPEPEPVPIVVQLIYPNGSLVRNPSNLTALIYKYDQMN
NKMSIISSVQLQRTSLINLSILGIQIESSYLTGVYQLPSNIISGVYFIKI
PNVFGFDEFVSGIYILDAVYPPVFTNPVVLSPGQNVTILAEALAIGSPNV
TVTFYNISGNKVYSIPVNAITYQNTLLYITQITLPKLKPGYYYVVTKAIY
NASNFTAEGVGLTQIYVSPYSLNVKVRIIPNNSIVYQNQQIYVIANITYP
NGTEVKYGSFSAIIVPSYLSSQFDNLQLQYSVPLTYINGSWIGQLEIPSG
SSTNSLGYSTYGISGYWDVYVEGISADGIPTNFPATLDVNTLSINPISPS
SQFVVLPYVYVSVFNGTIAFNEFIDKAIVVGHNATFINSIIRNLIVENGT
VTLINSKVQNVSLVNSEIIKINSTVGNNVNYITTIGNNHAKSSYPSLDSG
SILTIGIVLDIITIIALILIKRRKKFI

An exemplary protease is Sso0916 comprising the amino acid sequence as follows:

(SEQ ID NO: 32)
MKMKKSDIIIILFIALIYILMFSNIVQSASVEGVSMYPIFQNGALTFYVK
PISINEGNVIIYKSPYFNNYVIHRVIATDNGYYITQGVDKITNPIPDNRI
GLEPASGIPKNLVVGKIVEFGNFTFSIPYLGYISILFSSII

An exemplary protease is Sso1141 comprising the amino acid sequence as follows:

(SEQ ID NO: 33)
MYRYIFLMSMLLISIIPLVFASNPNMYQNPITLKEFREIGTLNANEEVIV
TIFVPLKNLDLLYYYASGASNPASPLYHKFLSPHEVQQLFLPTEEYNQIL
NYVKSSGFQVIFTASNSVIVIKGTVGQVEKYLGTKYAVYSNGSVTYYTNY
GYPKINAYVYSSNISAIFFAHPSTLITESTIKSFQQEINQTFPLEGYWPT
VLQKVYNVTTEGENTTIGILDFYGDPYIVQQLAYFDKITGLPNPPNFSVV
PIGPYNPNLGIVTGWAGEISLDVEVAHAIAPKANITLYIANPNIPLPAII
AYITSQNKVDTLSQSFSIPESLFSSLFNGPLFYSCIILSDEYYALGSAEG
ITFLASSGDAGGSGYSNGPIGTVGYPSTSPFVTSVGGTTVYVQFPNGSYY
QTAWSNYGFVPNNVNYGGSTGGVSIIEPKPWYQWGLPTPSTYPNGKLIPE
ISANANVYPGIYIVLPSNTTGITGGTSEASPLTAGVLATIESYTHHRIGL
LNPILTYMAENYYGKVIEPITFGYNIPWVATYGYNLVTGYGTINAGYFEK
ILPTLNLSKELNVIVSVYNTSIPTVSPQQFYPGQRILVTANITYPNGSPV
QTGEFKALIENYLGNLTTFNLTYNSLTKLWTGSGVLSNKASGILFVYVYG
SSDGLRGIGYYETFSGYYITFNYTTTFTPVYVELGNAELGITLSNSYFQA
PIGVMNITLNIYSYNITTNAYTFVTTLSVPIKNGVGVIDLPPDLSIGDLL
IIAEGNAYGFDAFTNGVYMQTLFILPQVVVEPGSVSPGQHITIEGSIIPP
VNLPSTTFQDALQGTNITAKLVSSNGVVINEANIPLSPNGIYFGYLYIPK
NTPSGLYNVLLFATYYSYTLNTTIRGFYYGQIYVSNQATISVKSVNYAFE
GQTVFIYANITNGTNEIKFGMFSATVYPSSLSFNYTTISSIIEIPLWYNP
KIGEWEGNFTLPSAISAGNLTYLAGQGYFGVPFKVLITGISALGNPTTTN
SGNAYTINVLPYTLFTNQTLDKTLPSYASLVNVKILNVSGNLLNDFLTNV
IIVNSNVKILNGNISNIVIRNSTVLIMQSNANNITLYNSTLYAIGGSING
LNVVNSKVVPINIHIQGLYPELPSISINLPSKNVTGTVNVTVNVIGEDVS
RINVYLNGNLINSFTTNGTHIVTINTQNYPDGGYNLTVTAIQSDGLSSSN
SSYLYFENGLTNLNTKVNVISNQLTNVSNSLSSSISSLRTASLEYQSISL
AIGIIAIVLAILALVRRRR

An exemplary protease is Sso1175 comprising the amino acid sequence as follows:

(SEQ ID NO: 34)
MYMKAKHLISLIVILTPLVTLLTSAVYTSGGITFYSPAYNGESYYTGQSI
TIDALLPQQFATDAATINFFFPNSSLAVTIPVQINGSGGIYVPNAYAFPN
VPGTWQITIEVAGGVAVGTINVNVIQRTPLVTVHLGYGVVGQALPQTPTI
TLTFPNGTTITVPLQGTVNVPSGTSYQVEQAITENNIRWATNYTSGTITP
ATTSITPTYYQQYLVTFNYTVQGGTGYSPPTVYYRSLGMNETAKAPASVW
VDANSAYIYSPELQSNVQGERWIAVNFTGIIKAPGEINEYYINQYLVTVQ
SQIPVYAIVNGANETLNSTNWFTQGTTIKLENITKYVSSVERYVIANFSP

```
SEVITVNQPTTIKVNTVTQYFINVNSPVQLKALINGANESLTAGWYNQGT

SIKIENLTYYVGNGERLILGKVLPSLEIIVNGSYTISTTTITQYFVNVSS

PIPVQVLINGSKTILNSSWINAGTSILVLNYTYNISPQERVIIVGISPSQ

SFTVNSPETLKLLTVTQYLVTINGVSKFYNSGSKIVLNASVPFYETATFK

GTYNVSPGATITVNQPITETLVESPNYLILGAIAAVIIIVVAVVVIILLR

R
```

An exemplary protease is Saci_1714 (Lin et al., *J Biol Chem.* 1990 Jan. 25; 265(3):1490-5) comprising the amino acid sequence as follows:

```
                                              (SEQ ID NO: 35)
MNFKSICLIILLSALIIPYIPQNIYFFPHRNTTGATISSGLYVNPYLYYT

SPPAPAGIASFGLYNYSGNVTPYVITTNEMLGYVNITSLLAYNREALRYG

VDPYSATLQFNIVLSVNTSNGVYAYWLQDVGQFQTNKNSLTFIDNVWNLT

GSLSTLSSSAITGNGQVASAGGGQTFYYDVGPSYTYSFPLSYIYIINMSY

TSNAVYVWIGYEIIQIGQTEYGTVNYYDKITIYQPNIISASLMINGNNYT

PNGLYYDAELVWGGGGNGAPTSFNSLNCTLGLYYISNGSITPVPSLYTFG

ADTAEAAYNVYTTMNNGVPIAYNGIENLTILTNNFSVILI
```

In some embodiments, the method comprises: (a) culturing the host cell in a suitable medium comprising a hemicellulose, or component thereof, as essentially the sole carbon source, and the peptide or protein of interest encoded in the nucleic acid is an enzyme described in one of the references cited earlier, such that the enzyme is expressed. In some embodiments, the nucleic acid encodes two, three, or more than three such enzymes and these enzymes are expressed.

In some embodiments, the culturing step comprises culturing the host cell in a medium having a temperature of equal to or more than about 70° C., 75° C., 80° C., 85° C., or 90° C. In some embodiments, the culturing step comprises culturing the host cell in a medium having a pH of equal to or less than about 4.0, 3.5, 3.0, 2.5, or 2.0. In some embodiments, the culturing step comprises culturing the host cell in a medium having a temperature of equal to or more than about 70° C., and a pH of equal to or less than about 4.0. In some embodiments, the culturing step comprises culturing the host cell in a medium comprising lignocellulosic or cellulosic biomass, such as switchgrass, bagasse, corn-stover, or forestry waste material. In some embodiments, the culturing step comprises culturing the host cell in a medium comprising lignocellulosic or cellulosic biomass, such as switchgrass, bagasse, corn-stover, or forestry waste material, at a temperature of equal to or more than about 70° C., and a pH of equal to or less than about 4.0. In some embodiments, the lignocellulosic or cellulosic biomass is essentially the sole carbon source in the medium.

In some embodiments, the novel vector is constructed using a Gateway® (Invitrogen) destination cassette inserted into the cloning vector for *Sulfolobus solfataricus*. Our cloning strategies employ PCR targeting and amplification of genes of interest using primers containing small inducible promoters to rapidly and efficiently clone and express recombinant genes. Recombinant proteins show native localization and modification and can be genetically targeted for secretion, membrane association or integration, and extracellular accumulation. These tools can be applied to generate cellulase enzymes that are active on cellulosic plant material in dilute sulfuric acid at elevated temperatures and acidic pH. The vectors of the present invention are useful in exploring extremophilic genomes and exploiting their useful gene products and their acid, heat, and detergent stability characteristics for industrial and energy applications.

*Sulfolobus* is used as a model system for genetics and microbiology of archaeal hyperthermophiles and acidophiles. Currently the economical degradation of cellulosic materials to liberate sugars for fermentation into ethanol is a major barrier to producing practical biofuels. Proteins from archaea and extremophilic bacteria have many practical applications as their enzymes are hyper-stable and can tolerate extreme conditions like those used in industrial processes. The present invention enables practical and efficient molecular genetics for this organism to generate acid and/or heat and detergent stable enzymes from archaea and bacteria.

Lignocellulosic Pretreatment Conditions Compatible with *Sulfolobus* Growth

Currently, one of the most efficient means to degrade cellulose into component sugars is the use of sulfuric acid and high (about 250° C.) temperatures, using chemical hydrolysis to liberate fermentable sugars. Alternatively, enzymatic hydrolysis produces fewer detrimental side-products but requires a feedstock pretreatment. Pretreatment typically involve exposure to dilute sulfuric acid at elevated temperatures (about 120° C.). *Sulfolobus* thrives in dilute sulfuric acid at relatively high temperatures (80° C.). *Sulfolobus* Growth media is a media sufficient for lignocellulosic feedstock pre-treatment to facilitate enzymatic saccharification (see FIGS. 6-9 and Tables 1 and 2). The present invention enables an integrated pretreatment/enzyme production/saccharification process, where lignocellulosic pretreatment, enzyme production, and enzymatic degradation under hot acidic conditions occur concurrently.

TABLE 1

List of recombinant heat and acid stable cellulase enzymes produced in *Sulfolobus* and their activities on relevant cellulosic substrates.

| Protein | Cellulolytic Activity | | | Hemicellulolytic Activity | | | | Optima | | | E. coli |
| | Azo-CMC | PNP-B-D-Cellobioside | PNP-B-D-Glucopyranoside | RBB-Xylan | PNP-B-D-Xylopyranoside | PNP-B-D-Glucuronide | PNP-A-L-Arabinofuranoside | | | | Expression |
| Gene # | Endo- | Biosidase | Biosidase | Endo- | Biosidase | Biosidase | Biosidase | pH | T | ½ Life | |
| Sso1353 | – | + | ++ | – | ++ | + | ++ | 6.0 | 90° C. | 2.2 h | Active |
| Sso1354 | +++ | – | – | +++ | – | – | – | 3.6 | 90° C. | 5.5 h | NOT active |
| Sso3007 | – | – | ++ | – | – | – | + | 6.5 | 80° C. | 2.5 h | NOT active |

TABLE 1-continued

List of recombinant heat and acid stable cellulase enzymes produced in Sulfolobus and their activities on relevant cellulosic substrates.

| | Cellulolytic Activity | | | Hemicellulolytic Activity | | | | Optima | | | E. coli Expression |
|---|---|---|---|---|---|---|---|---|---|---|---|
| Protein | Azo-CMC | PNP-B-D-Cellobioside | PNP-B-D-Glucopyranoside | RBB-Xylan | PNP-B-D-Xylopyranoside | PNP-B-D-Glucuronide | PNP-A-L-Arabinofuranoside | pH | T | ½ Life | |
| Gene # | Endo- | Biosidase | Biosidase | Endo- | Biosidase | Biosidase | Biosidase | | | | |
| Sso3019 | − | + | +++ | − | + | + | − | 6.8 | 80° C. | 0.85 h | ND |
| Sso3032 | − | − | ++ | − | +++ | − | ++++ | 6.8 | 70° C. | 10.5 h | Active |
| Sso3036 | − | − | − | − | − | ++++ | − | 6.8 | 90° C. | 7 h | ND |

Notably two of these six enzymes are inactive when produced in eubacterial strains.

*Sulfolobus* Growth media and lignocellulosic pretreatment solution comprise the following ingredients listed in Table 3.

TABLE 2

Ingredients of Sulfolobus Growth media and lignocellulosic pretreatment solution.

| Ingredient | Final concentration |
|---|---|
| Ammonium sulfate | 0.30% |
| Glycine | 0.07% |
| Potassium hydrogen phosphate | 0.05% |
| Potassium chloride | 0.01% |
| Sodium borate | 0.000002440% |
| Manganese chloride | 0.000000900% |
| Zinc sulfate | 0.000000110% |
| Cupric sulfate | 0.000000025% |
| Sodium molybdate | 0.000000015% |
| Vandyl sulfate | 0.000000015% |
| Cobalt chloride | 0.000000005% |
| Nickel sulfate | 0.000000005% |
| Magnesium chloride | 1 mM |
| Calcium nitrate | 0.3 mM |

The nucleic acid can further comprise a ribosomal binding site. The inclusion of a ribosomal binding site between multiple independently transcribed genes has been used to cause high-level expression of two genes simultaneously. Two or more genes assembled into an artificial polycistronic message can be expressed as proteins by inclusion of a ribosomal binding site between the two genes. The sequence of such a ribosomal binding site is: gaggtgagtcgga (SEQ ID NO:24).

Particular embodiments of the invention include, but are not limited to, the following:

A recombinant or isolated nucleic acid comprising: (a) a nucleotide sequence that is capable of stably integrating into the chromosome of an Archea or acidophilic hyperthermophilic eubacteria, and (b) a nucleotide sequence of interest. In some embodiments, the nucleic acids described above wherein the nucleotide sequence of interest comprises a single or multiple cloning site or a sequence to direct targeted integration via enzymatic processes. In some embodiments, the nucleic acids described above wherein the Archaea or eubacteria is hyperthermophilic. In some embodiments, the nucleic acids described above wherein the Archaea or eubacteria is capable of growth or is viable at a temperature equal to or more than about 70° C., 75° C., 80° C., 85° C., or 90° C. In some embodiments, the nucleic acids described above wherein the Archaea is capable of growth or is viable at a temperature equal to 80° C. In some embodiments, the nucleic acids described above wherein the Archaea or eubacteria is an acidophilic Archaea. In some embodiments, the nucleic acids described above wherein the Archaea or eubacteria is capable of growth or is viable at a pH equal to or less than about 4.0, 3.5, 3.0, 2.5, or 2.0. In some embodiments, the nucleic acids described above wherein the Archaea is capable of growth or is viable at a pH within the range of from about 2.0 to about 3.0. In some embodiments, the nucleic acids described above wherein the Archaea is of the kingdom Crenarchaeota. In some embodiments, the nucleic acids described above wherein the Archaea of the phylum Crenarchaeota. In some embodiments, the nucleic acids described above wherein the Archaea is of the class Thermoprotei. In some embodiments, the nucleic acids described above wherein the Archaea is of the order Sulfolobales. In some embodiments, the nucleic acids described above wherein the Archaea is of the family Sulfolobaceae. In some embodiments, the nucleic acids described above wherein the Archaea is of the genus *Sulfolobus*. In some embodiments, the nucleic acids described above wherein the Archaea is *Sulfolobus solfataricus, Sulfolobus islandicus, Sulfolobus acidocaldarius, Sulfolobus tokodaii, Metallosphaera yellowstonensis, Metallosphaera sedula,* or *Acidianus brierleyi.* In some embodiments, the nucleic acids described above wherein the nucleotide sequence that is capable of stably integrating into a chromosome of a *Sulfolobus* species. In some embodiments, the nucleic acids described above wherein the nucleotide sequence that is capable of stably integrating into the chromosome is the integration sequence of a Fusellovirus capable of infecting a *Sulfolobus* species. In some embodiments, the nucleic acids described above wherein the Fusellovirus is a *Sulfolobus* spindle-shaped virus. In some embodiments, the nucleic acids described above wherein the *Sulfolobus* spindle-shaped virus is SSV1, SSV2, SSV3, SSVL1, SSVK1, or SSVRH. In some embodiments, the nucleic acids described above wherein the nucleotide sequence that is capable of stably integration into the chromosome comprises the nucleotide sequence of SEQ ID NO:1-9. In some embodiments, the nucleic acids described above wherein the nucleotide sequence of interest encodes a peptide, protein or RNA, or a DNA sequence that binds a protein. In some embodiments, the nucleic acids described above wherein the nucleic acid further comprising a promoter operably linked to the nucleotide sequence encoding the peptide, protein or RNA. In some embodiments, the nucleic acids described above wherein the peptide or peptide comprises an export peptide signal at the 5' end of the peptide or protein. In some embodiments, the nucleic acids described above wherein the export peptide signal comprises an amino acid sequence encoded by a XPO, SP, Seq1, Seq2, Seq3, Seq4, or Seq5 nucleotide sequence. In some embodiments, the nucleic acids described above wherein the protein or peptide needs to be expressed, synthesized and/or folded at a temperature equal to or more than about 70° C., 75° C., 80° C., 85° C., or 90° C. in order to be correctly folded in order to be biological active. In some embodiments, the nucleic acids described above wherein the protein or peptide needs to be glycosylated or otherwise modified after translation by the host organism during or after expression, synthesis and/or folding in order to be biologically or biochemically active. In some embodiments, the nucleic acids described above wherein the resulting protein or peptide is stable in a detergent, or mixture thereof, such as Triton X-100, sodium dodecyl sulfate, or the like. In some embodiments, the nucleic acids described above wherein the protein or peptide is a cellulase or protease. In some embodiments, the nucleic acids described above wherein the nucleic acid further comprises one or more control sequences which permit stable maintenance of the nucleic acid as a vector in a non-*Sulfolobus* host cell. In some embodiments, the nucleic acids described above wherein the control sequence is a sequence comprising an origin of replication (ori) functional in *Escherichia coli* cells.

An Archaea host cell comprising the nucleic acid of the present invention stably integrated into the chromosome of the host cell. In some embodiments, the host cell described above wherein the nucleic acid of present invention as an extrachromosomal element in the host cell. In some embodiments, the host cell described above wherein the host cell is hyperthermophilic. In some embodiments, the host cell described above wherein the host cell is capable of growth or is viable at a temperature equal to or more than about 70° C., 75° C., 80° C., 85° C., or 90° C. In some embodiments, the host cell described above wherein the host cell is capable of growth or is viable at a temperature equal to 80° C. In some embodiments, the host cell described above wherein the host cell is acidophilic. In some embodiments, the host cell is capable of growth or is viable at a pH equal to or less than about 4.0, 3.5, 3.0, 2.5, or 2.0. In some embodiments, the host cell described above wherein the host cell is capable of growth or is viable at a pH within the range of from about 2.0 to about 6.0. In some embodiments, the host cell described above wherein the Archaea is of the kingdom Crenarchaeota. In some embodiments, the host cell described above wherein the Archaea is of the phylum Crenarchaeota. In some embodiments, the host cell described above wherein the Archaea is of the class Thermoprotei. In some embodiments, the host cell described above wherein the Archaea is of the order Sulfolobales. In some embodiments, the host cell described above wherein the Archaea is of the family Sulfolobaceae. In some embodiments, the host cell described above wherein the Archaea is of the genus *Sulfolobus*. In some embodiments, the host cell described above wherein the Archaea is *Sulfolobus solfataricus, Sulfolobus islandicus, Sulfolobus acidocaldarius, Sulfolobus tokodaii, Metallosphaera yellowstonensis, Metallosphaera sedula*, or *Acidianus brierleyi*. In some embodiments, the host cell described above wherein the nucleotide sequence of interest encodes a peptide, protein or RNA, and the peptide, protein or RNA is heterologous to the host cell.

A method of constructing the host cell of the present invention, comprising: (a) introducing a nucleic acid comprising: (i) a nucleotide sequence that is capable of stably integrating into the chromosome of a host cell that is an Archea or acidophilic hyperthermophilic eubacteria, and (ii) a nucleotide sequence of interest into an Archaea host cell, and (b) integrating the nucleic acid into a chromosome of the host cell or (c) maintaining the nucleic acid as an extrachromosomal element. In some embodiments, the method described above wherein the nucleic acid is a nucleic acid described above. In some embodiments, the method described above wherein the host cell is a host cell described above.

A method of expressing a peptide or protein or RNA of interest in an Archaea, comprising: (a) optionally constructing the nucleic acid of one of the present invention, (b) optionally introducing the nucleic acid into an Archaea host cell, (c) optionally integrating the nucleic acid into a chromosome of the host cell, (d) culturing the host cell in a suitable medium such that a peptide or protein or RNA of interest encoded in the nucleic acid is expressed, and (e) optionally isolating the peptide or protein or RNA from the host cell, (f) designing the nucleic acid such that a peptide or protein or RNA of interest encoded in the nucleic acid is targeted to the membrane, intrcellular or extracellular compartment and modified by glycosylation of other post-translational process as part of this cellular targeting. In some embodiments, the method described above wherein the peptide or protein of interest is a thermophilic enzyme, or enzymatically active fragment thereof, capable of catalyzing an enzymatic reaction. In some embodiments, the method described above wherein the peptide or protein of interest is a cellulase. In some embodiments, the method described above wherein the enzymatic reaction is an enzymatic degradation or catabolic reaction. In some embodiments, the method described above wherein the medium comprises a pretreated biomass. In some embodiments, the method described above wherein the nucleic acid is a nucleic acid described above. In some embodiments, the method described above wherein the host cell is a host cell described above.

REFERENCES CITED

1. Jenney F E, Jr., Adams M W. The impact of extremophiles on structural genomics (and vice versa). Extremophiles : life under extreme conditions. 2008;12(1):39-50.
2. Noll K M, Vargas M. Recent advances in genetic analyses of hyperthermophilic archaea and bacteria. Archives of microbiology. 1997;168(2):73-80.
3. Allers T, Mevarech M. Archaeal genetics—the third way. Nature reviews Genetics. 2005;6(1):58-73.
4. Lipscomb G L, Stirrett K, Schut G J, Yang F, Jenney F E, Jr., Scott R A, Adams M W, Westpheling J. Natural competence in the hyperthermophilic archaeon Pyrococcus furiosus facilitates genetic manipulation: construction of markerless deletions of genes encoding the two cytoplasmic hydrogenases. Applied and environmental microbiology. 2011;77(7):2232-8. PMCID: 3067412.
5. Hopkins R C, Sun J, Jenney F E, Jr., Chandrayan S K, McTernan P M, Adams M W. Homologous expression of a subcomplex of Pyrococcus furiosus hydrogenase that interacts with pyruvate ferredoxin oxidoreductase. PloS one. 2011;6(10):e26569. PMCID: 3200332.
6. Chandrayan S K, McTernan P M, Hopkins R C, Sun J, Jenney F E, Jr., Adams M W. Engineering Hyperthermophilic Archaeon Pyrococcus furiosus to Overproduce Its Cytoplasmic [NiFe]-Hydrogenase. The Journal of biological chemistry. 2012;287(5):3257-64. PMCID: 3270980.
7. Bridger S L, Clarkson S M, Stirrett K, DeBarry M B, Lipscomb G L, Schut G J, Westpheling J, Scott R A, Adams M W. Deletion strains reveal metabolic roles for key elemental sulfur-responsive proteins in Pyrococcus furiosus. Journal of bacteriology. 2011;193(23):6498-504. PMCID: 3232869.

8. Kurosawa N, Grogan D W. Homologous recombination of exogenous DNA with the *Sulfolobus* acidocaldarius genome: properties and uses. FEMS microbiology letters. 2005;253(1):141-9.
9. Albers S V, Driessen A J. Conditions for gene disruption by homologous recombination of exogenous DNA into the *Sulfolobus* solfataricus genome. Archaea. 2008;2(3): 145-9. PMCID: 2685593.
10. Berkner S, Lipps G. Genetic tools for *Sulfolobus* spp.: vectors and first applications. Archives of microbiology. 2008;190(3):217-30.
11. Albers S V, Jonuscheit M, Dinkelaker S, Urich T, Kletzin A, Tampe R, Driessen A J, Schleper C. Production of recombinant and tagged proteins in the hyperthermophilic archaeon *Sulfolobus* solfataricus. Applied and environmental microbiology. 2006;72(1):102-11. PMCID: 1352248.
12. Dworkin M, Falkow S. The prokaryotes : a handbook on the biology of bacteria. 3rd ed. New York ; London: Springer; 2006.
13. Jonuscheit M, Martusewitsch E, Stedman K M, Schleper C. A reporter gene system for the hyperthermophilic archaeon *Sulfolobus* solfataricus based on a selectable and integrative shuttle vector. Molecular microbiology. 2003; 48(5):1241-52.
14. Elferink M G, Schleper C, Zillig W. Transformation of the extremely thermoacidophilic archaeon *Sulfolobus* solfataricus via a self-spreading vector. FEMS microbiology letters. 1996;137(1):31-5.
15. Cannio R, Contursi P, Rossi M, Bartolucci S. An autonomously replicating transforming vector for *Sulfolobus* solfataricus. Journal of bacteriology. 1998;180(12): 3237-40. PMCID: 107829.
16. Aucelli T, Contursi P, Girfoglio M, Rossi M, Cannio R. A spreadable, non-integrative and high copy number shuttle vector for *Sulfolobus* solfataricus based on the genetic element pSSVx from *Sulfolobus* islandicus. Nucleic acids research. 2006;34(17):e114. PMCID: 1635272.
17. Leigh J A, Albers S V, Atomi H, Allers T. Model organisms for genetics in the domain Archaea: methanogens, halophiles, Thermococcales and Sulfolobales. FEMS microbiology reviews. 2011;35(4):577-608.
18. Martin A, Yeats S, Janekovic D, Reiter W D, Aicher W, Zillig W. SAV 1, a temperate u.v.-inducible DNA virus-like particle from the archaebacterium *Sulfolobus* acidocaldarius isolate B12. The EMBO journal. 1984;3(9): 2165-8. PMCID: 557659.
19. Schleper C, Kubo K, Zillig W. The particle SSV1 from the extremely thermophilic archaeon *Sulfolobus* is a virus: demonstration of infectivity and of transfection with viral DNA. Proceedings of the National Academy of Sciences of the United States of America. 1992;89(16):7645-9. PMCID: 49767.
20. Martusewitsch E, Sensen C W, Schleper C. High spontaneous mutation rate in the hyperthermophilic archaeon *Sulfolobus* solfataricus is mediated by transposable elements. Journal of bacteriology. 2000;182(9):2574-81. PMCID: 111323.
21. Lubelska J M, Jonuscheit M, Schleper C, Albers S V, Driessen A J. Regulation of expression of the arabinose and glucose transporter genes in the thermophilic archaeon *Sulfolobus* solfataricus. Extremophiles : life under extreme conditions. 2006;10(5):383-91.
22. Hopp T P, Prickett K S, Price V L, Libby R T, March C J, Cerretti D P, Urdal D L, Conlon P J. A Short Polypeptide Marker Sequence Useful for Recombinant Protein Identification and Purification. Bio-Technol. 1988;6(10): 1204-10.
23. Bradford M M. A rapid and sensitive method for the quantitation of microgram quantities of protein utilizing the principle of protein-dye binding. Analytical biochemistry. 1976;72:248-54.
24. Brizzard B. Epitope tagging. BioTechniques. 2008;44 (5):693-5.
25. Yoon S H, Reiss D J, Bare J C, Tenenbaum D, Pan M, Slagel J, Moritz R L, Lim S, Hackett M, Menon A L, Adams M W, Barnebey A, Yannone S M, Leigh J A, Baliga N S. Parallel evolution of transcriptome architecture during genome reorganization. Genome research. 2011;21(11):1892-904. PMCID: 3205574.
26. Lund P. Insights into chaperonin function from studies on archaeal thermosomes. Biochemical Society transactions. 2011;39(1):94-8.
27. Zhang Y, Buchholz F, Muyrers J P, Stewart A F. A new logic for DNA engineering using recombination in *Escherichia coli*. Nature genetics. 1998;20(2):123-8.
28. Degryse E. Evaluation of *Escherichia coli* recBC sbcBC mutants for cloning by recombination in vivo. Journal of biotechnology. 1995;39(2):181-7.
29. Trent J D, Kagawa H K, Yaoi T, Olle E, Zaluzec N J. Chaperonin filaments: the archaeal cytoskeleton? Proceedings of the National Academy of Sciences of the United States of America. 1997;94(10):5383-8. PMCID: 24687.
30. Cannio R, D'Angelo A, Rossi M, Bartolucci S. A superoxide dismutase from the archaeon *Sulfolobus* solfataricus is an extracellular enzyme and prevents the deactivation by superoxide of cell-bound proteins. European journal of biochemistry/FEBS. 2000;267(1):235-43.
31. Ursby T, Adinolfi B S, Al-Karadaghi S, De Vendittis E, Bocchini V. Iron superoxide dismutase from the archaeon *Sulfolobus* solfataricus: analysis of structure and thermostability. Journal of molecular biology. 1999;286(1):189-205.
32. Szabo Z, Sani M, Groeneveld M, Zolghadr B, Schelert J, Albers S V, Blum P, Boekema E J, Driessen A J. Flagellar motility and structure in the hyperthermoacidophilic archaeon *Sulfolobus* solfataricus. Journal of bacteriology. 2007;189(11):4305-9.

The above references are hereby incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Recombinant Acid/Heat Stable Cellulases in *Sulfolobus solfataricus*

Potential applications for acid/thermal-stable enzymes in industrial processes have long been recognized and initiated much interest in acidophilic and hyperthermophilic microbes such as the archaeal *Sulfolobales*. Here we report the development of an efficient and rapid means to produce recombinant acid/thermal-stable proteins that are highly resistant to detergent denaturation at high levels with *Sulfolobus solfataricus*. Building on previous works with *Sulfolobus* vectors, we have developed a PCR-based cloning approach to modify, express, target localization, and purify recombinant proteins from *Sulfolobus solfataricus*. Novel vectors are used here to generate over 80 *Sulfolobus* expression constructs with various affinity tags for detection, quantification, and purification. We define minimal promoters that can be incorporated into PCR primers to facilitate inducible protein expression over a >1500 fold range and yielding over 2.5 mg per liter of cell culture. Polycistronic co-expression of the alpha and gamma subunits of the thermosome yields protein levels approaching 5% of the total cell protein. We show recombinant protein localization to the intracellular, membrane, or extracellular compartments. An intracellular ATPase is efficiently targeted for secretion by inclusion of a small leader peptide. Finally, we use our vectors to generate active acid/heat stable cellulases that are highly glycosylated and secreted from *Sulfolobus* cells. We show the production of cellulolytic enzymes in *Sulfolobus* and degradation of lignocellulosic feedstocks with these enzymes. We also show production of xylose from plant xylan and glucose and xylan from raw switchgrass biomass in a single-step pretreatment-saccharification process. In addition we show the ability to mix multiple enzymes to alter the sugar products form plant lignocellulose in dilute sulfuric acid at high temperatures in these single-step pretreatment-saccharification reactions. These compsitions and methods have uses in industrial and bioenergy applications.

Construction of high-throughput expression vectors for *Sulfolobus solfataricus*. Vectors were built from established shuttle vectors and based on the *Sulfolobus* viral pathogen SSV1 (Martin, A., et al. SAV 1, a temperate u.v.-inducible DNA virus-like particle from the archaebacterium *Sulfolobus* acidocaldarius isolate B12. The *EMBO journal* 3, 2165-2168 (1984); Schleper, C., Kubo, K. & Zillig, W. The particle SSV1 from the extremely thermophilic archaeon *Sulfolobus* is a virus: demonstration of infectivity and of transfection with viral DNA. *Proceedings of the National Academy of Sciences of the United States of America* 89, 7645-7649 (1992)). The starting plasmid for this work was plasmid PMJ05, a derivative of the PMJ03 shuttle vector, which is effectively a pUC18 *E. coli* vector integrated into a SSV1 viral genome (Jonuscheit, M., Martusewitsch, E., Stedman, K. M. & Schleper, C. A reporter gene system for the hyperthermophilic archaeon *Sulfolobus* solfataricus based on a selectable and integrative shuttle vector. *Molecular microbiology* 48, 1241-1252 (2003); Martusewitsch, E., Sensen, C. W. & Schleper, C. High spontaneous mutation rate in the hyperthermophilic archaeon *Sulfolobus solfataricus* is mediated by transposable elements. *Journal of bacteriology* 182, 2574-2581 (2000)). The PMJ-vectors were designed with the PyrEF genes as selectable markers that complement uracil auxotrophy in the *Sulfolobus* PH1-16 strain (Albers, S. V., et al. Production of recombinant and tagged proteins in the hyperthermophilic archaeon *Sulfolobus solfataricus*. *Applied and environmental microbiology* 72, 102-111 (2006)). Limited use of the PMJ05 and related plasmids for recombinant protein expression and tagging of proteins in *Sulfolobus* has been demonstrated (Albers, S. V., et al. (2006)). To expand recombinant capabilities in *Sulfolobus*, we first replaced the tf55 promoter and LacS genes with either the AraS or tf55 promoter from *Sulfolobus* and the Gateway® destination-cassette (Invitrogen) to generate the pSMY-A and pSMY-T vectors respectively (FIG. 1 Panel a). An additional vector was constructed by cloning the destination cassette into the same sites producing the promoter-less pSMY1 vector. All three vectors were propagated in *E. coli*, purified, and sequenced prior to further experimentation in *Sulfolobus*. For all experiments the pSMY vectors were electroporated into the PH1-16 strain of *Sulfolobus* and selected in liquid and on plates to validate vector stability and selectable marker function in *Sulfolobus* as previously described (Schleper, C., et al. (1992); Albers, S. V., et al. (2006)).

The strategy for cloning and tagging genes of interest into the pSMY *Sulfolobus* expression vectors involves; 1) PCR amplification and modification of target genes using primers encoding promoters and/or epitope fusion tags, 2) direct cloning of the PCR products using TOPO° vectors (Invitrogen), and 3) in vitro recombination of the genes of interest into the *Sulfolobus* expression vectors (FIG. 1 Panel b). Validated reaction products are then transferred into the uracil auxotrophic strain of *Sulfolobus* (PH1-16) by electroporation and selected in media lacking uracil. The entire cloning process nominally requires ten days from PCR reactions to detectable protein expression in *Sulfolobus*.

Construction of high-throughput expression vectors for *Sulfolobus solfataricus*. Vectors were built from established shuttle vectors and based on the *Sulfolobus* viral pathogen SSV1 (18, 19). The starting plasmid for this work was plasmid PMJ05, a derivative of the PMJ03 shuttle vector, which is effectively a pUC18 *E. coli* vector integrated into a SSV1 viral genome (13, 20). The PMJ-vectors were designed with the PyrEF genes as selectable markers that complement uracil auxotrophy in the *Sulfolobus* PH1-16 strain (11). Limited use of the PMJ05 and related plasmids for recombinant protein expression and tagging of proteins in *Sulfolobus* has been demonstrated (11). To expand recombinant capabilities in *Sulfolobus*, we first replaced the tf55 promoter and LacS genes with either the AraS or tf55 promoter from *Sulfolobus* and the Gateway® destination-cassette (Invitrogen) to generate the pSMY-A and pSMY-T vectors respectively (FIG. 1 Panel a). An additional vector was constructed by cloning the destination cassette into the same sites producing the promoter-less pSMY1 vector. All three vectors were propagated in *E. coli*, purified, and sequenced prior to further experimentation in *Sulfolobus*. For all experiments the pSMY vectors were electroporated into the PH1-16 strain of *Sulfolobus* and selected in liquid and on plates to validate vector stability and selectable marker function in *Sulfolobus* as previously described (11, 19).

The strategy for cloning and tagging genes of interest into the pSMY *Sulfolobus* expression vectors involves; 1) PCR amplification and modification of target genes using primers encoding promoters and/or epitope fusion tags, 2) direct cloning of the PCR products using TOPO® vectors (Invitrogen), and 3) in vitro recombination of the genes of interest into the *Sulfolobus* expression vectors (FIG. 1 Panel b). Validated reaction products are then transferred into the uracil auxotrophic strain of *Sulfolobus* (PH1-16) by electroporation and selected in media lacking uracil. The entire cloning process nominally requires ten days from PCR reactions to detectable protein expression in *Sulfolobus*.

Figure 2:
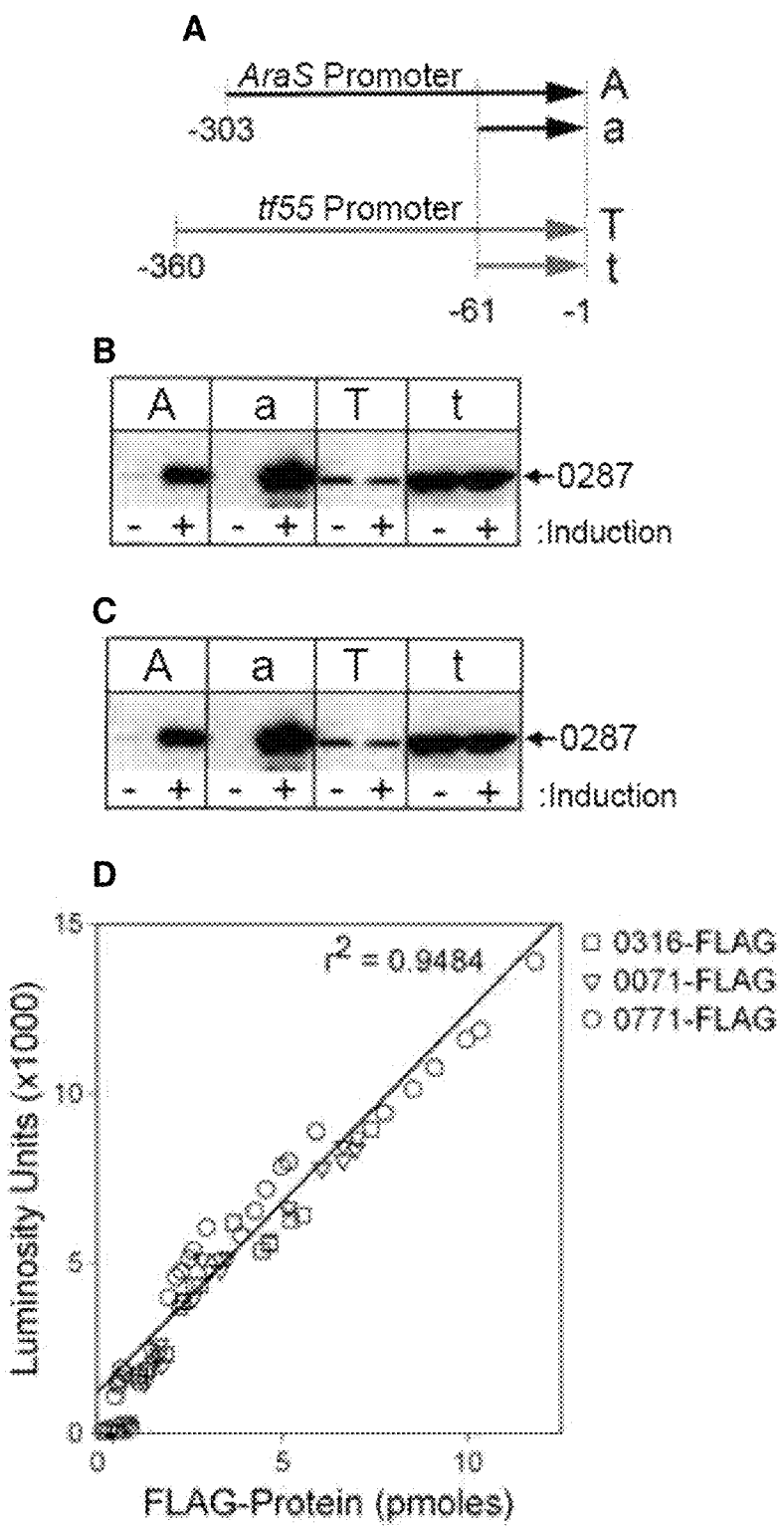
FIG. 2 shows shows examples of minimal inducible promoters and inducible expression from these promoters in *Sulfolobus* : (Panel A) A schematic map of inducible promoters and the minimal promoter sequences (61 nucleotides) as defined by work in this invention retaining inducible characteristics and having increased expression levels. Immunoblots of equivalent amounts of protein extracts from *Sulfolobus* cells with integrated expression vectors carrying genetically modified: (Panel B) Sso0287 gene fused to sequence encoding an epitope tag (FLAG), and (Panel C) three recombinant proteins expressed from integrated *Sulfolobus* vectors likewise epitope-fused and driven by four different promoters then proteins visualized by immunoblot. This figure represents 12 separate constructs; Sso1440, Sso 0771, and Sso0071 genes driven by the indicated promoters. Note the elevated protein levels in strains with the 61-nucleotide promoters ('a' and 't') which are first described here. (Panel B) Quantitation of protein expression levels by using purified recombinant proteins and chemiluminiscent immunoblots shows a linear relationship between luminosity and protein quantity. This relationship is used to quantify protein expression levels in *Sulfolobus*.

Quantitative analysis of expression from inducible *Sulfolobus* promoters. Four different *Sulfolobus* promoter sequences were designed and evaluated to establish optimal promoters to regulate protein expression levels. The thermosome α subunit promoter (tf55) and the arabinose sugar transporter operon promoters (AraS) have been used previously for recombinant protein expression in *Sulfolobus* (11, 21). To simplify the addition of inducible promoters to genes of interest using PCR, we designed 'minimal' 61 nucleotide versions of the tf55 and AraS promoters (FIG. 2 Panel A). Expression vectors driven by the four varied promoters were constructed with identical FLAG-Sso0287 coding sequences to test promoter functions in *Sulfolobus*. The Sso0287 gene encodes a 68 kDa cytoplasmic protein with unknown cellular functions and has previously been expressed in *Sulfolobus* using a related viral vector (11). Immunoblotting was used to evaluate the relative expression and induction levels among these four constructs (Fig.2 Panel B). The basal expression and inducibility of the various promoters was evaluated after 72 hours of growth under standard and inducing conditions (80 or 85° C. for tf55 constructs and +/−10 uM D-arabinose for AraS constructs). Both the full length and the 'minimal' AraS promoters were tightly controlled by D-arabinose under our experimental conditions (FIG. 2 Panel B). Notably, the minimal AraS promoter (61 base) appeared to have lower levels of baseline expression and higher expression after induction relative to the longer (303 base) AraS promoter. Likewise, the minimal tf55 promoter constructs appeared to have markedly higher expression levels than the larger promoter. In contrast to the AraS promoters, neither tf55 promoter showed inducible expression under our experimental conditions (FIG. 2 Panel B).

To further validate these results and establish whether promoters were the primary factor determining recombinant protein levels, we generated twelve additional expression constructs with four promoters driving three different genes. Constructs were generated for each of the four promoters described above, driving expression of; 1) RNA helicase (Sso1440), 2) cell division control protein 6 (cdc6) (Sso 0771), and 3) DNA polymerase subunit D (Sso0071). Sequence-validated constructs were electroporated into the *Sulfolobus* PH1-16 strain and protein levels evaluated by FLAG-immunoblots under inducing conditions (FIG. 2 Panel C). Protein levels for these 12 constructs were largely in concurrence with the FLAG-Sso0287 expression levels with the four promoters (FIG. 2 Panel B). More specifically, the relative expression levels under inducing conditions was; a>t>T≈A with relatively small variations between proteins (FIG. 2 Panel C). In nearly all cases Sso0771 protein had accumulated to greater levels than the other proteins, but the promoter appeared to be the principal determinant for protein levels in *Sulfolobus*. Notably, the 61-nucleotide AraS promoter retains inducibility and the smaller versions of both promoters show significantly higher expression than their larger counterparts. Such minimal promoters can likewise be derived from other genes and species for application to the production of hyper-stable proteins, RNAs and enzymes.

Recombinant protein yields greater than one milligram per liter in *Sulfolobus*. To quantify recombinant protein expression levels in *Sulfolobus*, three recombinant proteins (Sso0316, Sso0071, and Sso07710) were purified to near homogeneity using immunoaffinity chromatography and protein concentrations determined by Bradford assays (22, 23). Serial dilutions of pure proteins were used to establish the linear range of FLAG-immunoblot luminosity and molar protein amounts (FIG. 2 Panel D). Notably, all three FLAG-fusion proteins showed a consistent relationship between luminosity and molar protein amounts. Aliquots of purified FLAG-fusion protein standards were included on all subsequent immunoblots to calibrate luminosity to molar protein amounts. This approach was used to quantify protein expression levels of the Sso0287 protein driven by the promoters shown in FIG. 2 Panel B. The induction of Sso0287 protein was maximal under the control of the 61-nucleotide AraS promoter and was over 1500-fold relative to the control. Protein yields over 1.5 milligrams of protein per liter of *Sulfolobus* culture were observed (Table 3). Surprisingly, the control of protein expression was markedly greater for the minimal AraS promoter than the longer DNA sequences used previously (11).

TABLE 3

| Promoter | Induction | Expression (ug/L) | Fold Induction |
|---|---|---|---|
| A | − | 4.2 | 297.4 |
|  | + | 1243.9 |  |
| a | − | 1.0 | 1535.9 |
|  | + | 1576.5 |  |
| T | − | 33.6 | 1.7 |
|  | + | 57.6 |  |
| t | − | 635.1 | 1.0 |
|  | + | 632.8 |  |

Figure 3:
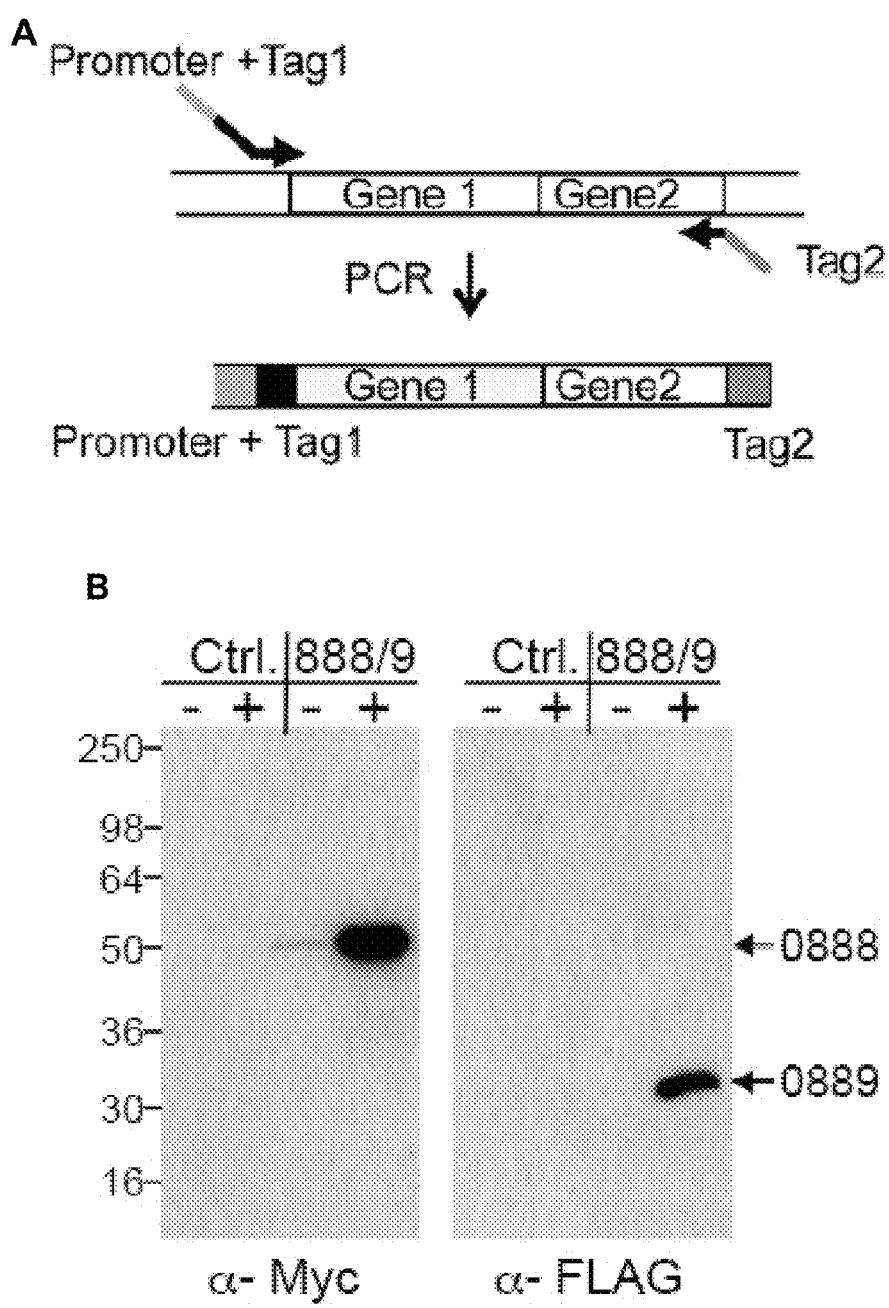
FIG. 3 shows construction and expression of multiple genes/proteins from a single *Sulfolobus* shuttle vector construct: (Panel A) A schematic diagram of a PCR-based strategy to clone and modify multiple genes into a polycistronic construct for simultaneous expression in *Sulfolobus*. (Panel B) Immunoblots of protein extracts from *Sulfolobus* cells carrying a vector with two genes (Sso0888 and Sso0889) arranged on a polycistronic construct for co-expression showing both genes produce protein. (Panel C) Immunoblots of protein extracts from *Sulfolobus* cells carrying four different polycistronic constructs (Sso0197-98, Sso2250-51, Sso2815-16, and Sso0888-89) showing reproducible polycistronic expression in *Sulfolobus*. (Panel D) Coomassie-stained SDS-PAGE gels (left) and immunoblots (right) of protein extracts from *Sulfolobus* cells carrying a vector with the genes encoding the thermosome β and γ proteins fused to epitope tags. This construct co-expresses genes that are not tandem but distil in the genome and have been built into a synthetic polycistronic construct for co-expression.
Figure 3:
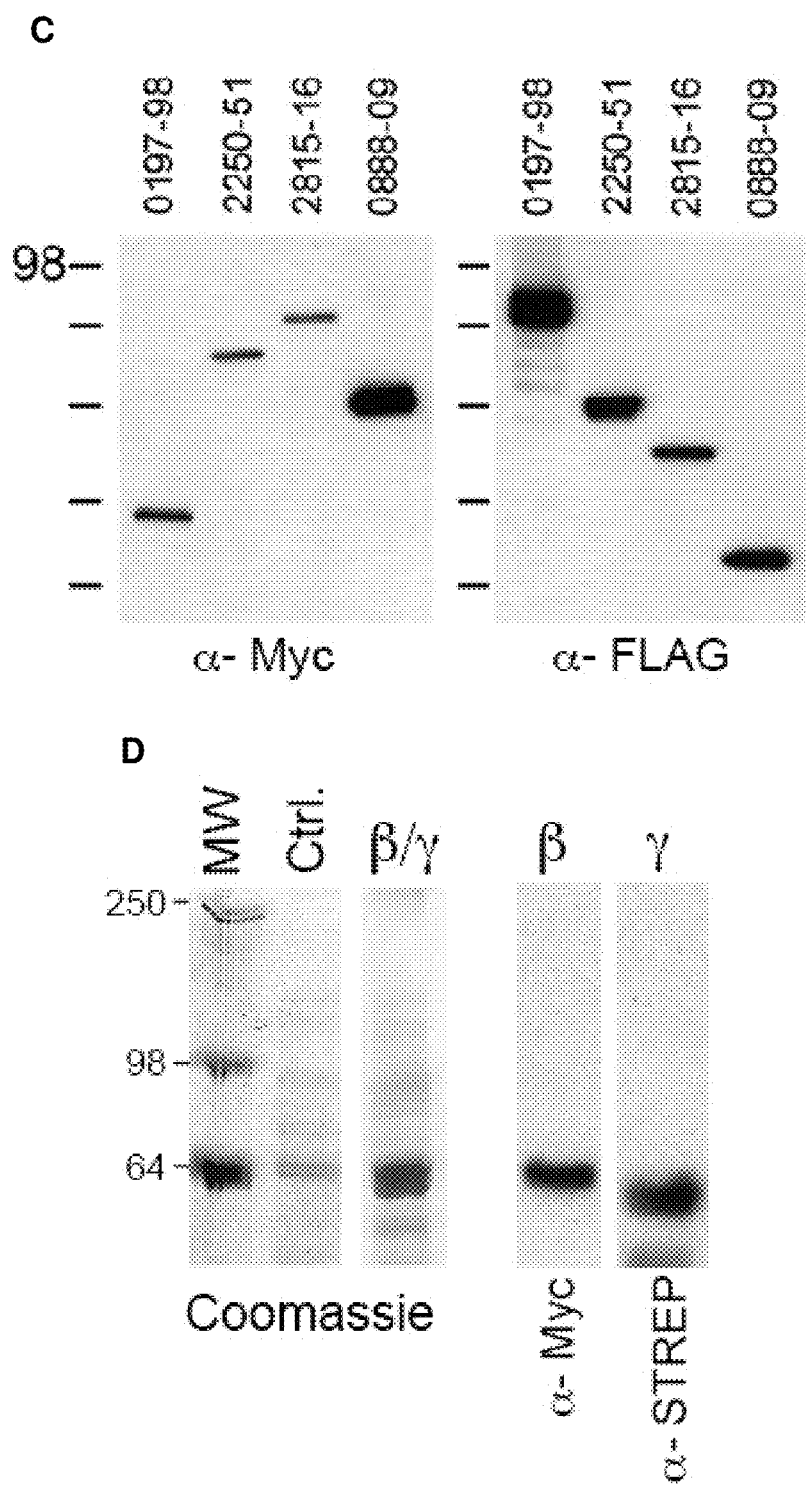

Co-expression of multiple genes from polycistronic constructs. Many proteins function as members of assemblies and are transcribed and translated from single polycistronic mRNAs. Such proteins often show reduced stability and function when overexpressed as individual polypeptides and can be particularly difficult to produce in heterologous hosts such as *E. coli*. We therefore generated a polycistronic expression construct to evaluate protein co-expression with our vectors. The polycistronic Sso0888-0889 genes encode tryptophan synthase subunits beta and alpha respectively and were amplified from genomic DNA using PCR designed to add an inducible promoter and a Myc or FLAG epitope tag (24) to Sso0888 and Sso0889 respectively (FIG. 3 Panel A). The cloning and tagging strategy was identical that described above but in this case PCR primers encoded amino-terminal fused Myc tag on the first gene (Sso0888) and a carboxyl-terminal fused FLAG epitope on the downstream gene (Sso0889). This strategy permits simultaneous and exclusive detection of each gene product by immunoblotting. Like the individually expressed genes, the polycistronic genes 0888-0889 showed tightly controlled and inducible expression behind the minimal AraS minimal promoter with no evidence of *Sulfolobus* proteins being reactive with these antibodies (FIG. 3 Panel B).

To establish the general utility of this approach, three additional polycistronic operons were constructed; 1) the operon encoding the hypothetical proteins Sso0197 which has conserved kinase domains and Sso0198, 2) the operon encoding the DNA repair protein Sso2250 and the co-transcribed hypothetical gene Sso2251, and 3) the ferredoxin oxidoreductase subunits alpha and beta encoded by Sso2815 and Sso2816 respectively. These constructs all expressed recombinant tagged proteins from both members of the polycistronic messages at approximately equal levels (FIG. 3 Panel C). Together, these data show the feasibility of protein co-expression in *Sulfolobus* using these vectors.

Operons often rearrange but maintain co-regulation of functionally and physically associated proteins (25). Such cases result in subunits of assemblies located at distil locations in the genome. The *Sulfolobus* thermosome subunits are an example of noncontiguous genes encoding proteins that assemble into a functional molecule (26). To evaluate our ability to co-express non-contiguous genes from a synthetic polycistronic mRNA, an artificial polycistronic construct containing thermosome subunits alpha (Sso0282) and gamma (Sso3000) was constructed. PCR products from individually amplified/tagged genes were assembled into a single polycistronic expression construct using seamless cloning (Invitrogen) (27, 28). To ensure high-level expression of both subunits, a ribosomal binding site was inserted between the two open reading frames on the polycistronic construct. Thermosomes are among the most abundant constitutively expressed proteins in *Sulfolobus* and can account for nearly 5% of the total cellular protein (29). The abundant thermosome polypeptides migrate at similar rates and appear as a prominent doublet of protein bands in *Sulfolobus* crude extracts. Recombinant thermosome subunits alpha and gamma expressed from the synthetic polycistronic vector resulted in dramatically increased thermosome levels visualized by coomassie blue-stained SDS-PAGE (FIG. 3 Panel D, left). Immunoblots confirmed recombinant thermosome expression of both the alpha and gamma subunits (FIG. 3 Panel E, right). Both subunits were expressed at approximately equal levels that were much higher than the endogenous thermosome and therefore markedly greater than 5% of the total cell protein (29).

Figure 4:
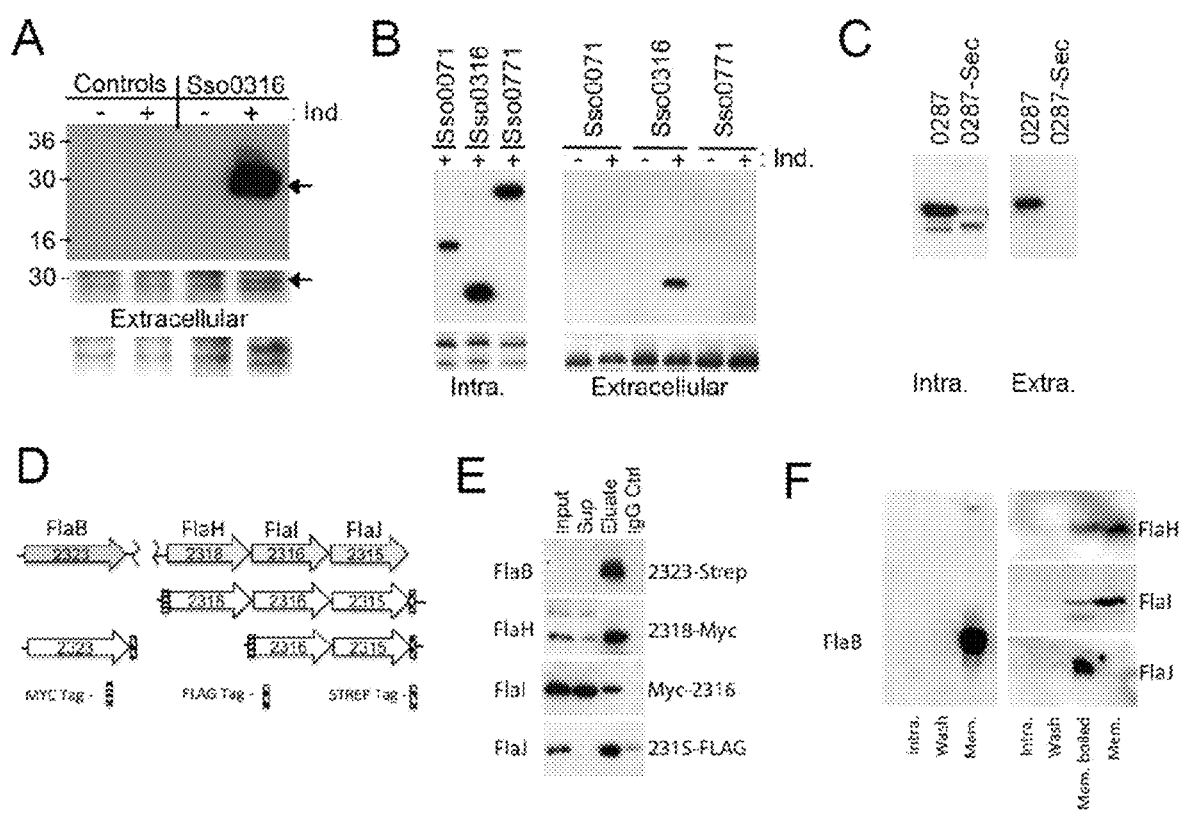
FIG. 4 shows recombinant protein secretion to the extracellular compartment and targeted localization to the membrane in *Sulfolobus*. (Panel A) Immunoblots and coomassie-blue stained SDS-PAGE gels of extracellular proteins from cultures of *Sulfolobus* with (+) or without (−) induction either carrying an empty vector (controls) or carrying a vector with Sso0316, a superoxide dismutase fused to an epitope tag. (Panel B) Intracellular and extracellular proteins from *Sulfolobus* with vectors carrying the noted genes, showing that only Sso0316 accumulates outside the cells. (Panel C) shows targeting of the intracellular protein Sso0287 to the extracellular space by inclusion of a secretion tag on the DNA construct. (Panel D) A schematic map of the epitope tagged pilin and flagellin genes from *Sulfolobus* constructed into vectors. (Panel E) Affinity purification of epitope tagged genes from *Sulfolobus* extracts showing expression. (Panel F) Localization of the recombinant genes to the cellular membranes.

Native localization of overexpressed recombinant proteins in *Sulfolobus*. The *Sulfolobus* gene Sso0316 encodes and extracellular tetrameric iron superoxide dismutase (30, 31). An overexpression construct of Sso0316 was generated to investigate whether overexpressed recombinant proteins properly localized within cell or in this case, into the surrounding medium. As described above, superoxide dismutase was placed under the control of the 61-nucleotide minimal AraS promoter and fused to a carboxy-terminal FLAG epitope tag and transferred into the pSMY1 vector. Two intracellular genes encoding a DNA replication protein (Sso0771) and an RNA polymerase subunit (Sso0071) were likewise cloned and tagged as control proteins. Extracellular partitions of *Sulfolobus* cultures for these three constructs was evaluated after 72 hours of growth under inducing conditions. Cell-free media was collected from cultures and 90% saturating ammonium sulfate used to precipitate extracellular proteins. Extracellular precipitates of controls showed nearly equal amounts of precipitating protein but none recognized by the FLAG antibody (FIG. 4 Panel A). In sharp contrast, the media from cells carrying the Sso0316 expression constructs revealed a tightly controlled expression and extracellular accumulation of the recombinant superoxide dismutase (FIG. 4 Panel A). Notably, the SOD-FLAG protein was visible on the coomassie stained gel.

To ensure that protein overexpression in *Sulfolobus* did not cause protein accumulation in the media due to leakage or cell lysis, extracellular fractions from three cultures overexpressing different proteins were compared. Protein localization was compared between the extracellular superoxide dismutase (SOD, Sso0316) and the intracellular DNA polymerase subunit D (PolD, Sso0071) and cell division control protein 6 (cdc6, Sso0771) (FIG. 4B). Induced cultures were portioned into cellular and extracellular fractions and immunoblots used to visualize recombinant proteins in crude culture fractions. Cdc6, PolD, and SOD were clearly evident in the intracellular partitions (FIG. 4B, left panel). In marked contrast, the extracellular partitions from the same cultures show only detectable levels of SOD under inducing conditions (FIG. 4B, right panel).

Membrane Localization of overexpressed genes in *Sulfolobus*. Subcellular localization of proteins is often intimately linked to proper function. To further assess the localization of recombinant proteins within *Sulfolobus* we constructed a series of constructs expressing the subunits of the flagellin and pilin membrane assembly genes (FIG. 5 Panel A). *Sulfolobus* flagellin proteins are known and contain integral membrane protein Fla? (Sso2315), an integral and extracellular protein FlaB (Sso2323), and the membrane-associated intracellular ATPase components FlaH and FlaI (Sso2318 and Sso2316) (32).

Figure 5:
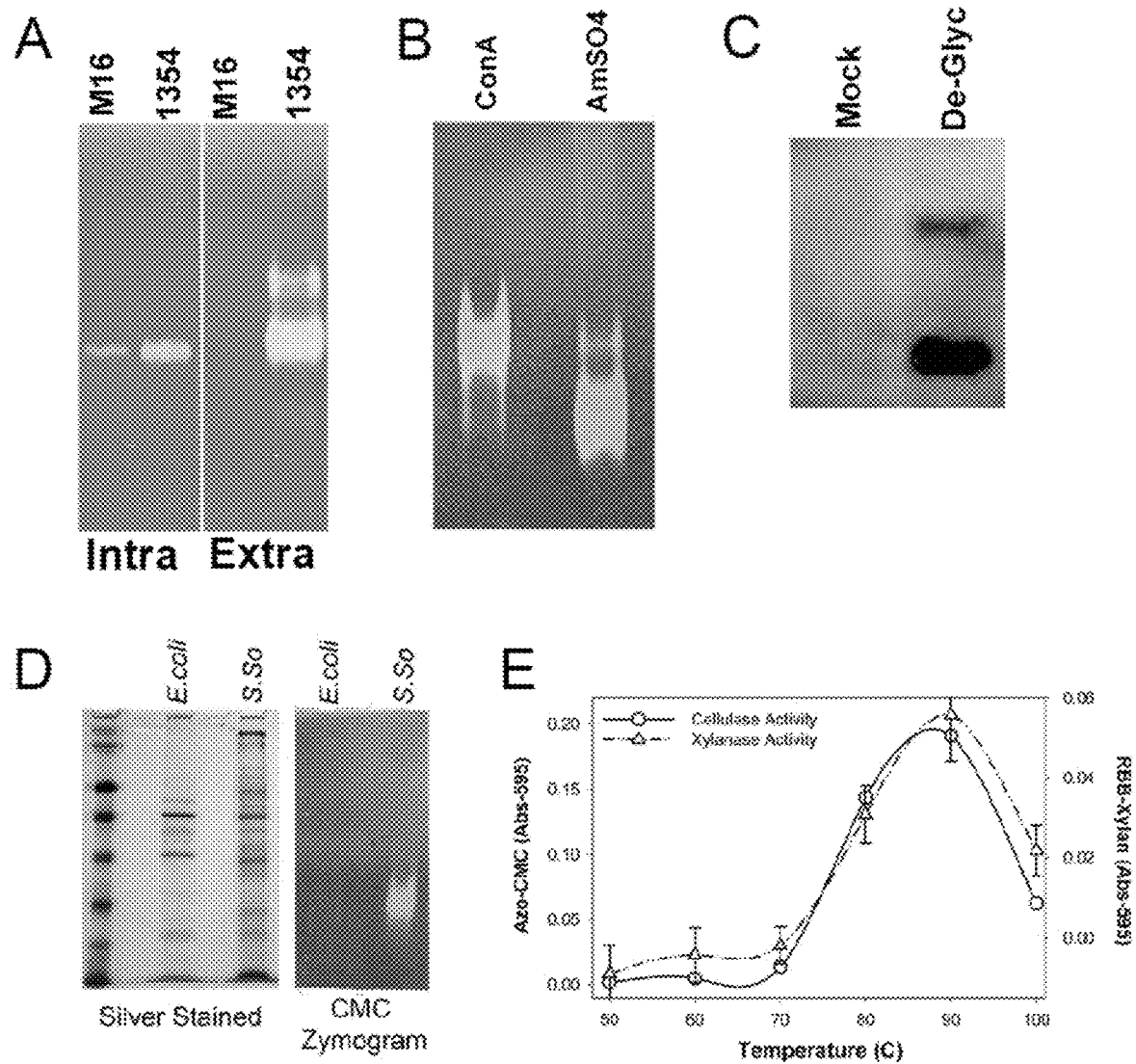
FIG. 5 shows the recombinant production, secretion and glycosylation of heat and acid stable cellulase in *Sulfolobus*. (Panel A) Zymograms of intracellular and extracellular proteins from cells alone (M16) and M16-cells carrying the subjects vector expressing cellulase-1354. Yellow areas are due to cellulase activity in the gel. (Panel B) Zymogram of extracellular protein from 1354 culture either bound to glycosylation-specific resin (Concanavalin A) of precipitated with ammonium sulfate (AmSO4). (Panel C) Immunoblot of equal amounts of 1354 protein either with mock-reacted (Mock) or treated with deglycosylation enzymes (De-Glyc). (Panel D) Comparison of activity from the same cellulase gene expressed in *E. coli* or *Sulfolobus* showing the recombinant protein is not active when produced with *E. coli* but active when produced in *Sulfolobus*. (Panel E) Activity assays of *Sulfolobus*-derived enzyme on xylan and cellulose substrates showing temperature optima of approximately 90° C. for both xylan degradation and cellulose degradation.
Figure 6:
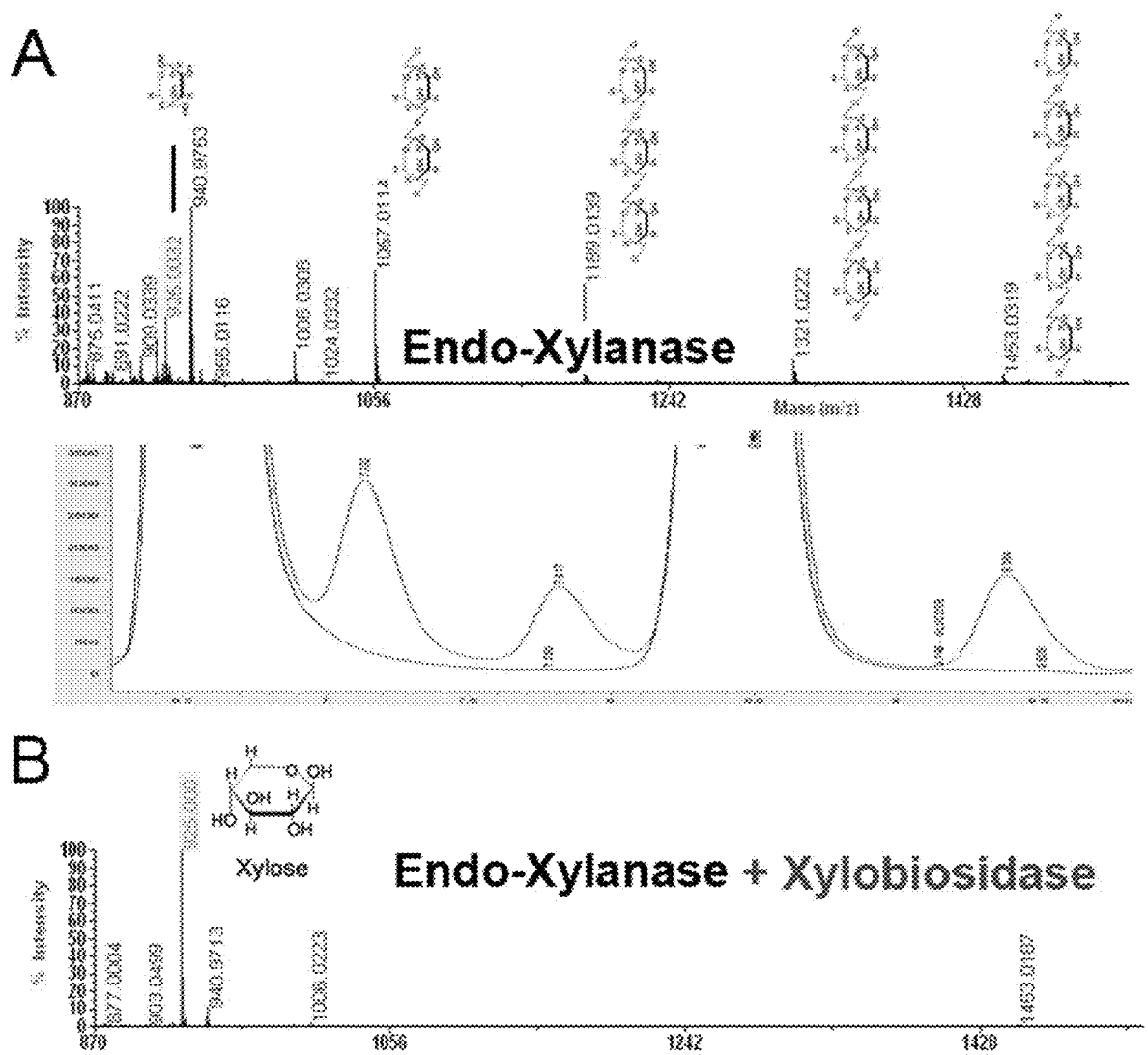
FIG. 6 shows the results of the use of *Sulfolobus* enzyme mixtures and reaction conditions to simultaneously pre-treat and degrade hemicellulose to monomeric sugar products. Identification of specific xylan degradation products using enzymes produced in *Sulfolobus* with HPLC chromatography and mass spectrometry. (Panel A) Active degradation of raw oat-spelt xylan with *Sulfolobus* enzyme Sso1354 at 80° C. and pH 3.5. Reactions were run on HPLC Aminex-H column (lower chromatogram) to identify breakdown products after incubation for over 12 hours with Sso1354 at 80° C. and pH 3.5 (red trace) as compared to a parallel mock reaction lacking enzyme (blue trace). Reactions were also subjected to chemical modification with mass-tags to facilitate ionization of sugar products in mass spectrometer and analyzed (top mass chromatogram). Multiple xylan degradation products were identified by accurate mass measurements and are illustrated above the corresponding signals showing 'endo-xylanase activity of Sso1354 at 80° C. and pH 3.5 on raw xylan. (Panel B) Mass spectrometry was carried out on reactions containing enzyme mixes with Sso1354 and Sso3032. The addition of Sso3032 produced a single sugar product, namely xylan from the mixture of xylose polymers produced from Sso1354 alone starting from raw xylan. These data show the ability to degrade raw hemicellulose in a single-step pretreatment and saccharification process using recombinant enzymes from *Sulfolobus*.
Figure 7:
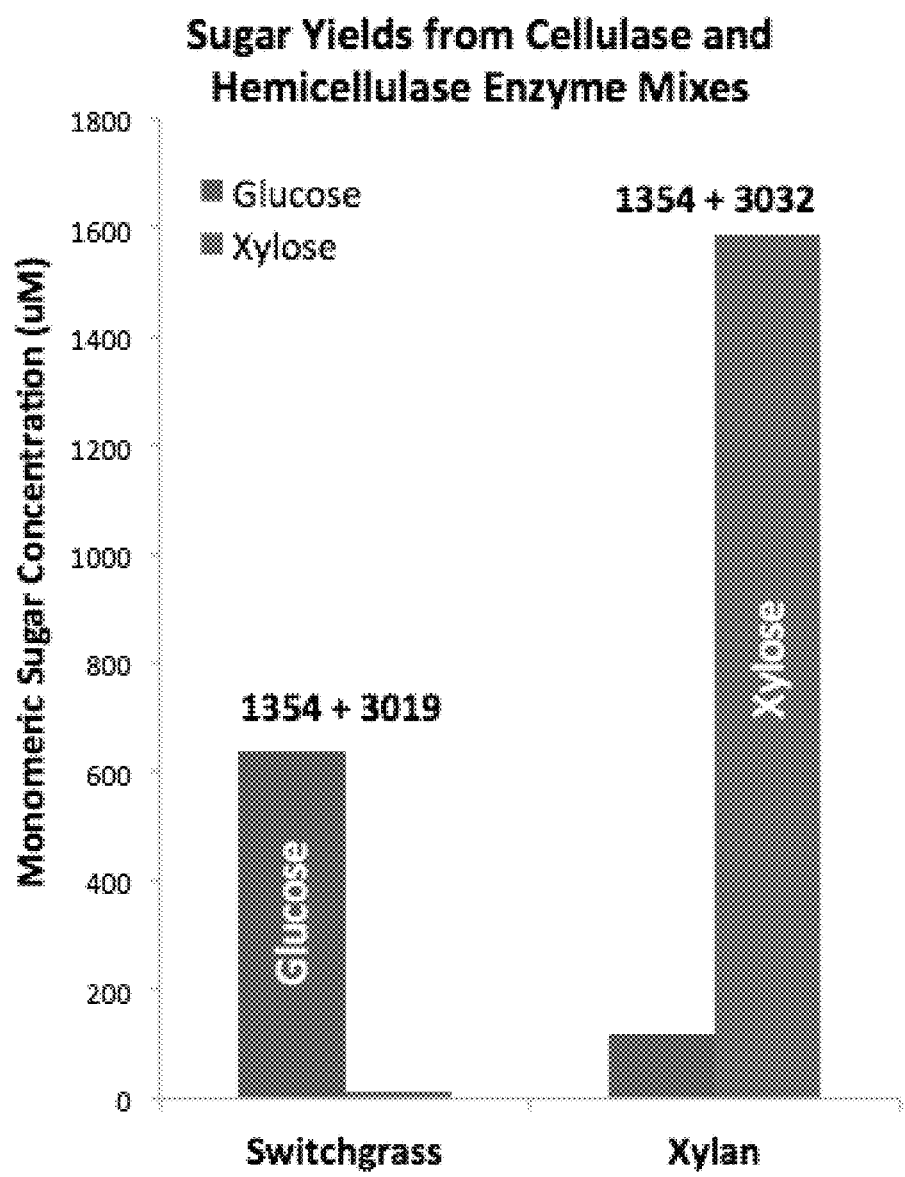
FIG. 7 shows results of the use of rationally designed *Sulfolobus* enzyme mixes for specific saccharification processes of raw plant materials. Here we show monomeric sugar yields from digestion of switchgrass and oat spelt xylan with rationally selected enzyme combinations to yield desired monomeric sugars, glucose and xylose, respectively.
Figure 8:
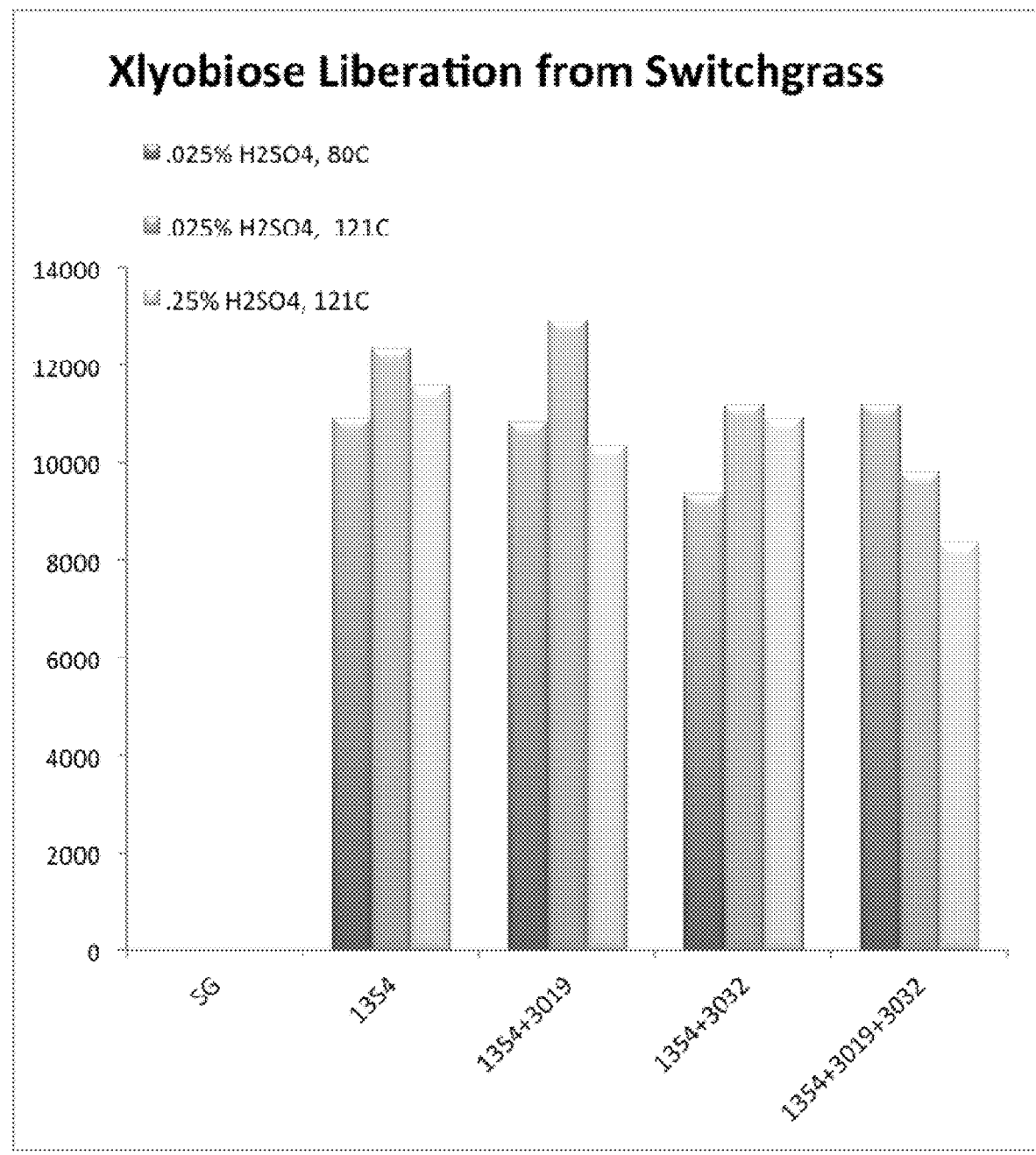
FIG. 8 shows xylobiose liberation from switchgrass.

Production of Purification-Free and immobilized Enzyme products. The combination of polycictronic constructs and targeted localization can be combined to produce extracellular solutions with high-levels of desired enzymatic activities with minimal purification or without purification. The application of single and/or multiple simultaneous gene expression can produce post-translationally modified enzyme mixes accumulating in the media and that do not require purification. Either filtration or centrifugation of cells from these cultures yields active enzyme mixes. We have reduced this to practice with single enzyme production where only concentration of the extracellular media is sufficient to produce active enzyme preparations (FIGS. 4-6). In addition, we have demonstrated the capability to target assembly of immobilized enzymes both integral and associated with host membranes for future applications. Such membrane targeting and assembly could be used for industrial applications to immobilize active heat/acid/detergent stable enzymes onto engineered organic and inorganic surfaces and/or immobilized membrane rafts to be applied to industrial processes.

Figure 9:
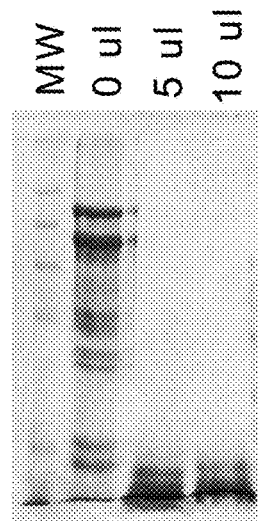
FIG. 9 shows the results of 1 ug of bovine serum albumen (BSA) is incubated for 30 min at 80° C. at pH=3.0 either alone (0 ul), with 5 ul or 10 ul of extracellular protease preparation. The reactions are quenched by boiling in 2% SDS and run on SDS-PAGE and stained with coomassie brilliant blue. BSA degradation by protease activity is evident in both cases for reactions in dilute sulfuric acid at 80° C.

Enzymatic saccharification and pre-treatment in the same dilute sulfuric acid and temperature conditions. Standard pretreatment conditions for lignocellulosic biomass use sulfuric acid concentrations of 0.275-0.8% (v/v) acid and a temperature of 121° C. or greater. Here we establish a pretreatment regimen compatible with *Sulfolobus* growth conditions with 0.025% (v/v) sulfuric acid and 80° C. and demonstrate that enzymatic saccharification of raw plant biomass is comparable to yields with the harsher treatments (FIG. 9). Solutions of 10% (m/v) pulverized switchgrass were made up in *Sulfolobus* growth media with either 0.025% or 0.025% sulfuric acid. The pretreatments were either 121° C. for 60 minutes or 80° C. for 10 hours. Saccharification to xylobiose was quantified after a 15-hour reaction with the noted *Sulfolobus* enzymes at 80° C. Sugar yields are from standard (0.25%, 121° C.) and the low-temp/low-acid pretreatments conditions (0.025%, 80° C.) are comparable with *Sulfolobus* enzymes (FIG. 9). These data reveal that pretreatment of lignocellulosic feedstocks in *Sulfolobus* growth conditions (80° C., and 0.025% sulfuric acid) is compatible with; 1) pretreatment, 2) enzymatic saccharification using heat/acid stable enzymes expressed in *Sulfolobus*, and 3) *Sulfolobus* cell growth.

Figure 10:
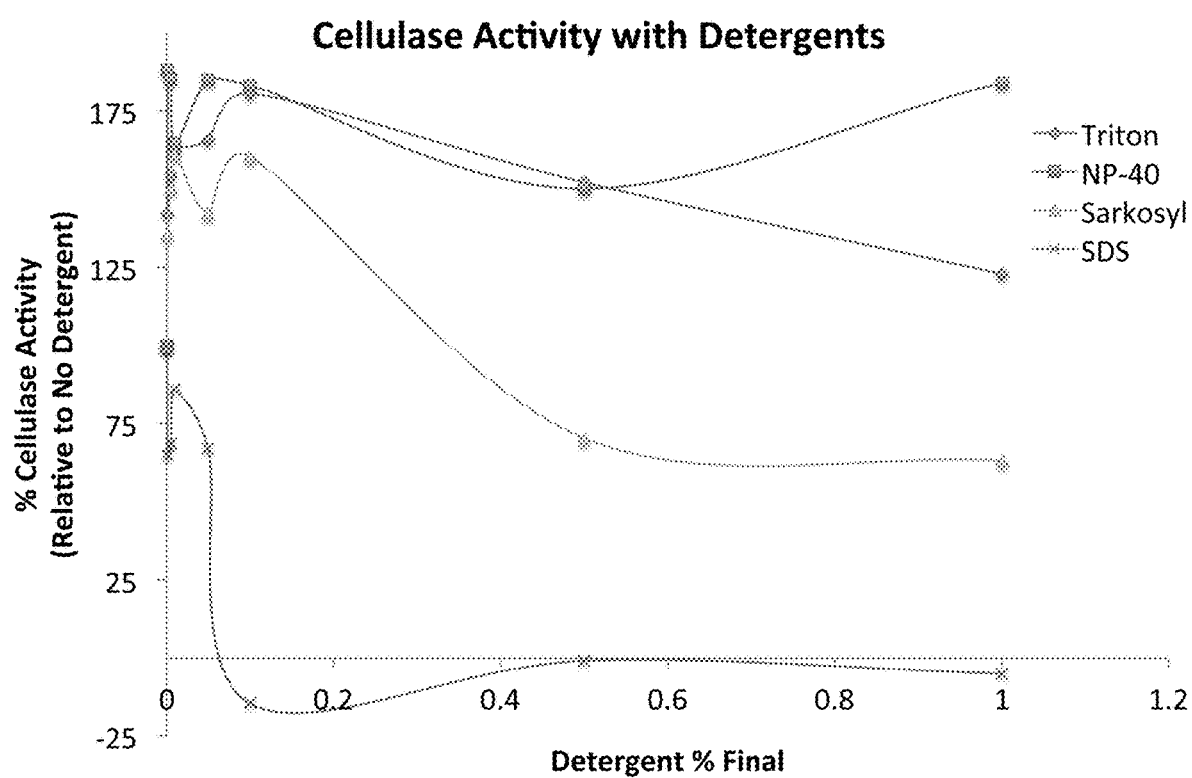
FIG. 10 shows that thermal and acid stable cellulase shows high degree of stability in various detergents under hot acidic conditions. Reactions are carried out at 80° C. and pH=3.0 with increasing amounts of detergents as indicated. Low detergent concentrations increased cellulase activity and activity is retained for most detergents up to and potentially beyond 1% v/v.

Cellulase stability in detergents. Thermal and acid stable cellulase also have a high degree of stability in various detergents (FIG. 10).

The biodiversity available for exploitation has been partly limited by the availability of genetically tractable model organisms to express and purify proteins. The development of genetic tools to complement well-established model organisms like *E. coli* and yeast systems holds promise to expand our understanding and application of extremophiles and extremophilic proteins for industrial, ecological, and energy applications.

EXAMPLE 2

Recombinant Acid/Heat Stable Proteases in *Sulfolobus solfataricus*

We have isolated active acid and heat stable extracellular protease from *Sulfolobus solfataricus*. The enzyme is an active protease in the 0.025-0.25% v/v $H_2SO_4$ at 80° C. isolated from the extracellular fraction of active cell cultures (FIG. 9). In some embodiments, the protease is fused to an epitope or other purification tags such as polyhistidine or FLAG among others targeted to the extracellular compartment as described herein. These enzymes can be produced recombinantly in Archaea as described herein.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A recombinant or isolated nucleic acid comprising: (a) a nucleotide sequence comprising a Fusellovirus integration sequence that integrates into a *Sulfolobus* species chromosome; and (b) a nucleotide sequence of interest, wherein the nucleotide sequence of interest is operably linked to a minimal promoter and encodes a protein that is biologically activate at a temperature equal to or more than about 70° C. and/or a pH equal to or less than about 4.0, wherein the minimal promoter is an AraS to tf55 promoter.

2. The nucleic acid of claim 1, wherein the Fusellovirus is a *Sulfolobus* spindle-shaped virus.

3. The nucleic acid of claim 2, wherein the *Sulfolobus* spindle-shaped virus is SSV1, SSV2, SSV3, SSVL1, SSVK1, or SSVRH.

4. The nucleic acid of claim 1, wherein the protein comprises an export peptide signal at the 5' end.

5. The nucleic acid of claim 1, wherein the protein needs to be expressed, synthesized and/or folded at a temperature equal to or more than about 70° C., 75° C., 80° C., 85° C., or 90° C. in order to be correctly folded and to be biologically active; and/or needs to be glycosylated during or after expression, synthesis and/or folding in order to be biologically active.

6. The nucleic acid of claim 1, further comprising one or more control sequences which permit stable maintenance of the nucleic acid as a vector in a non-*Sulfolobus* host cell.

7. An Archaea host cell comprising the nucleic acid of claim 1 stably integrated into the chromosome of the host cell.

8. The host cell of claim 7, wherein the host cell is hyperthermophilic or acidophilic.

9. The host cell of claim 7, wherein the host cell is capable of growth or is viable at a temperature equal to or more than about 70° C., 75° C., 80° C., 85° C., or 90° C.

10. The host cell of claim 7, wherein the host cell is capable of growth or is viable at a pH equal to or less than about 4.0, 3.5, 3.0, 2.5, or 2.0.

11. The host cell of claim 7, wherein the Archaea is of the genus *Sulfolobus*.

12. A method of genetically modifying a host cell comprising: (a) introducing a nucleic acid of claim 1 into a host cell that is an Archea or acidophilic hyperthermophilic eubacteria, and (b) integrating the nucleic acid into the chromosome of the host cell.

13. A method of expressing a protein of interest in an Archaea, comprising: culturing the host cell of claim 7 in a suitable medium such that the protein is expressed, and optionally isolating the protein from the host cell.

14. The method of claim 13, wherein the protein is a thermophilic enzyme, or enzymatically active fragment thereof, that catalyzes an enzymatic reaction.

15. The method of claim 14, wherein the protein is a cellulase.

* * * * *

```
                        SEQUENCE LISTING

<160> NUMBER OF SEQ ID NOS: 35

<210> SEQ ID NO 1
<211> LENGTH: 49
<212> TYPE: DNA
<213> ORGANISM: Artificial Sequence
<220> FEATURE:
<223> OTHER INFORMATION: synthetic nucleotide sequence

<400> SEQUENCE: 1
cgccgcggcc gggatttgaa cccgggtcac gggctcgaga ggcccgcat               49

<210> SEQ ID NO 2
<211> LENGTH: 49
<212> TYPE: DNA
<213> ORGANISM: Artificial Sequence
<220> FEATURE:
<223> OTHER INFORMATION: synthetic nucleotide sequence

<400> SEQUENCE: 2
tgccgcggcc gggatttgaa cccgggtcag gggctcgaga ggcccgcat               49

<210> SEQ ID NO 3
<211> LENGTH: 45
<212> TYPE: DNA
<213> ORGANISM: Artificial Sequence
<220> FEATURE:
<223> OTHER INFORMATION: synthetic nucleotide sequence

<400> SEQUENCE: 3
ggggcgcgga ctgaggctcc gctggcgaag gcctgcacgg gttca                   45

<210> SEQ ID NO 4
<211> LENGTH: 44
<212> TYPE: DNA
<213> ORGANISM: Artificial Sequence
<220> FEATURE:
<223> OTHER INFORMATION: synthetic nucleotide sequence

<400> SEQUENCE: 4
gggggcggac tgaggctccg ctggcgaagg cctgcacggg ttca                    44

<210> SEQ ID NO 5
<211> LENGTH: 28
<212> TYPE: DNA
<213> ORGANISM: Artificial Sequence
<220> FEATURE:
<223> OTHER INFORMATION: synthetic nucleotide sequence

<400> SEQUENCE: 5
tccgctggcg aaggcctgca cgggttca                                      28

<210> SEQ ID NO 6
<211> LENGTH: 48
<212> TYPE: DNA
<213> ORGANISM: Artificial Sequence
```

```
<220> FEATURE:
<223> OTHER INFORMATION: synthetic nucleotide sequence
<220> FEATURE:
<221> NAME/KEY: misc_feature
<222> LOCATION: (29)..(29)
<223> OTHER INFORMATION: S = C or G

<400> SEQUENCE: 6
gccgcggccg ggatttgaac ccgggtcasg ggctcgagag gcccgcat                 48

<210> SEQ ID NO 7
<211> LENGTH: 49
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (1)..(1)
<223> OTHER INFORMATION: Y = C or T
<220> FEATURE:
<221> NAME/KEY: misc_feature
<222> LOCATION: (30)..(30)
<223> OTHER INFORMATION: S = C or G

<400> SEQUENCE: 7
ygccgcggcc gggatttgaa cccgggtcas gggctcgaga ggcccgcat                49

<210> SEQ ID NO 8
<211> LENGTH: 28
<212> TYPE: DNA
<213> ORGANISM: Artificial Sequence
<220> FEATURE:
<223> OTHER INFORMATION: synthetic nucleotide sequence

<400> SEQUENCE: 8
tccgctggcg aaggcctgca cgggttca                                        28

<210> SEQ ID NO 9
<211> LENGTH: 44
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (4)..(4)
<223> OTHER INFORMATION: S = C or G

<400> SEQUENCE: 9
gggsgcggac tgaggctccg ctggcgaagg cctgcacggg ttca                      44

<210> SEQ ID NO 10
<211> LENGTH: 22073
<212> TYPE: DNA
<213> ORGANISM: Artificial Sequence
<220> FEATURE:
<223> OTHER INFORMATION: synthetic nucleotide vector sequence

<400> SEQUENCE: 10
tcattttttc ctaaaaattg ctcctttaca tttcatcacc ttatcctcga taatcttatt     60
tatagttctt aatgctgtta atggattccc tgcattataa atacttcttc caatgatttc    120
ataatccgct ccagcacata ctgcatcgcc ataacttcca ccttgactac ccatacccgg    180
agagactatg gtcatttttt cgaagtctct cctatactgc gttatatgat ctaatttagt    240
ccctccaact actattcctt tgggcttat ctctcttata acgttttaa tatagtctgc     300
```

```
gaataacgta ctccatcctt catgtgacat tacggcaact aagtataaat tttagagtt    360 tgcatcaaga tatcttttta attcatctag agatcccta acgcctataa aggaatgtgc    420
tatgaacgag ttggcgaaag ataatctttc aactatgctt ttcattatgt atccgatatc   480
tgcaagctta aaatcaacaa taatttcctc cacgtctaaa ccaattaaga gctctctagt   540
tttatccact cctagatcta aaactaaagg taaaccaact tttatcccat ataactcatt   600
ttccatctct ttaagaactt gatatgagag aggtttatcc attgctaata ttactctact   660
tttcaacatt cttcaccaaa taatctagaa ttgacttctt ttcattatcc ttaagtttat   720
cactcttcaa caattcatct agaatttctg aaattttaaa tagagagtgt aatttgactc   780
ctagtttttc caatctttgt gaagccccctt cttgtctatc tatgattact agtgcgtctg   840
aaactttacc tccaccgtta agaatctcca atgttgcttt ctctatggat actcctgtag   900
ttgcaacgtc atctactaac aatactcttt ttccttttac atcgagttct aatgtacgat    960
tagttccatg acctttcttt tctattctaa tatatcccat aggctcttta aggttacaag   1020
ctatgaatgc cgataaggga actcctccag tggctattcc tactattata tcatgggta   1080 tatcttttgc tttctttata gcttgattaa ctatatcgta aaattctgga taatttggta   1140
aaggtcttaa gtctaagtaa tatggactaa ccttacctga tgttaaaacg aaacttccta   1200
ttaataataa tttcctttcg agtaagactt ctgcgaaatt catacgtaga gactctgcga   1260
aaaagaattt aaatatactt ctatcataac cagttataag ggctttgtga gattaagaca   1320
cgtagtttcg tcgcttgact tgaccagaga tgactacttt agaatattcg aacttgcaga   1380
caagttctat gatgtaaaaa aactaaatta tctatcaggg aaagtagttt cattagcatt   1440
ctttgagcca agtactagaa ctgctcaaag cttttcatact gcagcaataa aattaggtgc   1500
tgatgtgata ggatttgcat ccgaggagtc tacttcgata gcaaaaggtg aaaatttggc   1560
tgataccatt aggatgctaa acaactattc aaactgtatt gtaatgagac ataagtttga   1620
tggggcagca ttattcccta ggccgtgatt tcgtaatatt gtaagttaaa tttagcgtag   1680
attttgttta ttatattttt tagaatttca cgaataaagc ttaagtaaga gggataagcg   1740
aataagatct tgtctttata tactattatc ttttctcggat aaagctctct tttaattctc   1800
ttggttatct catctttact gcatatttca cataatcttc ttcctcctac tacgtttatg   1860
gcatttcttt tgttacatct ttcgcacatc atattagagg agaatggatt tcctatttat   1920
ttaaaaaatt acttctcggt ttagctgaga gaaaaatttt tatataagcg atactaatgt   1980
tctcacggaa cggtgttgtg aggtactagt ccagtgtggt ggaattctgc agatatcaac   2040
aagtttgtac aaaaaagctg aacgagaaac gtaaaatgat ataaatatca atatattaaa   2100
ttagattttg cataaaaaac agactacata atactgtaaa acacaacata tccagtcact   2160
atggcggccg cattaggcac cccaggcttt acactttatg cttccggctc gtataatgtg   2220
tggattttga gttaggatcc gtcgagattt tcaggagcta aggaagctaa aatgagaaa    2280 aaaatcactg gatataccac cgttgatata tcccaatggc atcgtaaaga acattttgag   2340
gcatttcagt cagttgctca atgtacctat aaccagaccg ttcagctgga tattacggcc   2400
tttttaaaga ccgtaaagaa aaataagcac aagttttatc cggcctttat tcacattctt   2460
gcccgcctga tgaatgctca tccggaattc cgtatggcaa tgaaagacgg tgagctggtg   2520
atatgggata tgtgttcaccc ttgttacacc gttttccatg agcaaactga acgttttca    2580 tcgctctgga gtgaatacca cgacgatttc cggcagtttc tacacatata ttcgcaagat   2640
gtggcgtgtt acggtgaaaa cctggcctat ttccctaaag ggtttattga gaatatgttt   2700
```

```
ttcgtctcag ccaatccctg ggtgagtttc accagttttg atttaaacgt ggccaatatg    2760
gacaacttct tcgcccccgt tttcaccatg ggcaaatatt atacgcaagg cgacaaggtg    2820
ctgatgccgc tggcgattca ggttcatcat gccgtttgtg atggctttcc atgtcggcag    2880
aatgcttaat gaattacaac agtactgcga tgagtggcag ggcggggcgt aaagatctgg    2940
atccggctta ctaaaagcca gataacagta tgcgtatttg cgcgctgatt tttgcggtat    3000
aagaatatat actgatatgt atacccgaag tatgtcaaaa agaggtatgc tatgaagcag    3060
cgtattacag tgacagttga cagcgacagc tatcagttgc tcaaggcata tatgatgtca    3120
atatctccgt tctggtaagc acaaccatgc agaatgaagc ccgtcgtctg cgtgccgaac    3180
gctggaaagc ggaaaatcag gaagggatgg ctgaggtcgc ccggtttatt gaaatgaacg    3240
gctcttttgc tgacgagaac aggggctggt gaaatgcagt ttaaggttta cacctataaa    3300
agagagagcc gttatcgtct gtttgtggat gtacagagtg atattattga cacgcccggg    3360
cgacggatgt gatccccct ggccagtgca cgtctgctgt cagataaagt ctcccgtgaa    3420
ctttacccgg tggtgcatat cggggatgaa agctggcgca tgatgaccac cgatatggcc    3480
agtgtgccgc tctccgttat cggggaagaa gtggctgatc tcagccaccg cgaaaatgac    3540
atcaaaaacg ccattaacct gatgttctgg ggaatataaa tgtcaggctc ccttatacac    3600
agccagtctg caggtcgacc atagtgactg gatatgttgt gttttacagt attatgtagt    3660 ctgttttta tgcaaaatct aatttaatat attgatattt atatcatttt acgtttctcg    3720
ttcagctttc ttgtacaaag tggttgatat ccagcacagt ggcgccggcc gccaccgcgg    3780
tggagctcga attcgtaatc atgtcatagc tgtttcctgt gtgaaattgt tatccgctca    3840
caattccaca acatacga gccggaagca taaagtgtaa agcctggggt gcctaatgag    3900
tgagctaact cacattaatt gcgttgcgct cactgcccgc tttccagtcg ggaaacctgt    3960
cgtgccagct gcattaatga atcggccaac gcgcggggag aggcggtttg cgtattgggc    4020
gctcttccgc ttcctcgctc actgactcgc tgcgctcggt cgttcggctg cggcgagcgg    4080
tatcagctca ctcaaaggcg gtaatacggt tatccacaga atcaggggat aacgcaggaa    4140
agaacatgtg agcaaaaggc cagcaaaagg ccaggaaccg taaaaaggcc gcgttgctgg    4200
cgtttttcca taggctccgc cccctgacg agcatcacaa aaatcgacgc tcaagtcaga    4260
ggtggcgaaa cccgacagga ctataaagat accaggcgtt tccccctgga agctccctcg    4320
tgcgctctcc tgttccgacc ctgccgctta ccggatacct gtccgccttt ctcccttcgg    4380
gaagcgtggc gctttctcat agctcacgct gtaggtatct cagttcggtg taggtcgttc    4440
gctccaagct gggctgtgtg cacgaacccc ccgttcagcc cgaccgctgc gccttatccg    4500
gtaactatcg tcttgagtcc aacccggtaa gacacgactt atcgccactg gcagcagcca    4560
ctggtaacag gattagcaga gcgaggtatg taggcggtgc tacagagttc ttgaagtggt    4620
ggcctaacta cggctacact agaaggacag tatttggtat ctgcgctctg ctgaagccag    4680
ttaccttcgg aaaaagagtt ggtagctctt gatccggcaa acaaaccacc gctggtagcg    4740
gtggtttttt tgtttgcaag cagcagatta cgcgcagaaa aaaaggatct caagaagatc    4800
ctttgatctt ttctacgggg tctgacgctc agtggaacga aaactcacgt taagggattt    4860
tggtcatgag attatcaaaa aggatcttca cctagatcct tttaaattaa aaatgaagtt    4920
ttaaatcaat ctaaagtata tatgagtaaa cttggtctga cagttaccaa tgcttaatca    4980
gtgaggcacc tatctcagcg atctgtctat ttcgttcatc catagttgcc tgactccccg    5040
```

```
tcgtgtagat aactacgata cgggagggct taccatctgg ccccagtgct gcaatgatac    5100
cgcgagaccc acgctcaccg gctccagatt tatcagcaat aaaccagcca gccggaaggg    5160
ccgagcgcag aagtggtcct gcaactttat ccgcctccat ccagtctatt aattgttgcc    5220
gggaagctag agtaagtagt tcgccagtta atagtttgcg caacgttgtt gccattgcta    5280
caggcatcgt ggtgtcacgc tcgtcgtttg gtatggcttc attcagctcc ggttcccaac    5340
gatcaaggcg agttacatga tcccccatgt tgtgcaaaaa agcggttagc tccttcggtc    5400
ctccgatcgt tgtcagaagt aagttggccg cagtgttatc actcatggtt atggcagcac    5460
tgcataattc tcttactgtc atgccatccg taagatgctt ttctgtgact ggtgagtact    5520
caaccaagtc attctgagaa tagtgtatgc ggcgaccgag ttgctcttgc ccggcgtcaa    5580
tacgggataa taccgcgcca catagcagaa ctttaaaagt gctcatcatt ggaaaacgtt    5640
cttcggggcg aaaactctca aggatcttac cgctgttgag atccagttcg atgtaaccca    5700
ctcgtgcacc caactgatct tcagcatctt ttactttcac cagcgtttct gggtgagcaa    5760
aaacaggaag gcaaaatgcc gcaaaaaagg gaataagggc gacacggaaa tgttgaatac    5820
tcatactctt cctttttcaa tattattgaa gcatttatca gggttattgt ctcatgagcg    5880
gatacatatt tgaatgtatt tagaaaaata aacaaatagg ggttccgcgc acatttcccc    5940
gaaaagtgcc acctgacgtc taagaaacca ttattatcat gacattaacc tataaaaata    6000
ggcgtatcac gaggcccttt cgtctcgcgc gtttcggtga tgacggtgaa aacctctgac    6060
acatgcagct cccggagacg gtcacagctt gtctgtaagc ggatgccggg agcagacaag    6120
cccgtcaggg cgcgtcagcg ggtgttggcg ggtgtcgggg ctggcttaac tatgcggcat    6180
cagagcagat tgtactgaga gtgcaccata tgcggtgtga ataccgcac agatgcgtaa    6240 ggagaaaata ccgcatcagg cgccattcgc cattcaggct gcgcaactgt tgggaagggc    6300
gatcggtgcg ggcctcttcg ctattacgcc agctggcgaa aggggggatgt gctgcaaggc    6360 gattaagttg ggtaacgcca gggttttccc agtcacgacg ttgtaaaacg acggccagtg    6420
ccaagcttgc atgcctgcag agtctcatat gtttcctcac ttattgaaat gttaagcctt    6480
ttgactatcc tatctttcct cttctctatc atttaggtca ccttgtttat tgttatttga    6540
aatacgtatc cgtcttcgtc acatcgaagt ataattttgt atccattatt agcatattct    6600
acgtcaaagt tccacacaaca ataattcggg tcttcggact cgttatagac tttgctccaa    6660
ccatcttttt gtagtgcctc ttctaagtag tctactctga tgaagccttc atcatattcg    6720
ttcagtaccc taaagcttat actatcaatg cctaatacgt ctaatagctt caacagatcg    6780
aatataggaa cttgcaccat catttcagct caccttaatg agctgatata attccgcttc    6840
tatcttttga acttggaagt atgccttgcc tagcttttgc ttatccatat tgcccgttat    6900
tctatcaatc ttaatctcgt ggattaatga taatagctct ctgacatcct catcaagcat    6960
ttcaaataat tctttctcta agacttcttt actcattgtt tttcacctta gcaaactcat    7020
ctaacgttgt ttgtctcagt tctcttttct ttatcaaata aaattccgaa tgtcccttct    7080
tattgttatt actgtacttc atgtcagttc actgctttgc ctttataaat ccttgatccg    7140
tttgctcaaa atttgcgggc tgggcatcaa atatcttagc tatattgtct tgtgtttgct    7200
cttgtttttg ttcttctttc tgctcttgct taatccattt gaacgttgtc tttctgtttt    7260
tgtattgtac ttcacactcg tctggatgtc tttcgcaaat agcttcaat gctctctgta    7320 tgttatacgc actcgggact gaaatctcaa attgagctag tatatcctct aacgttaatt    7380
cacctttctt ttcaagaatt ttatacatta tttccgccat cttgtatgaa tttagagttt    7440
```

```
gtgccatatt cccatcccac tctatctata ctctatgtat aaattagtat ttaagtctta   7500
ctctatctat actctatcta tctctctata tacacagtgt ttgggtaact ggcaaaattc   7560
tgtctgactg ctgtctgaca agagtttact ctatctctct atatctatat acacaaacag   7620
agttagtcga ctctgtgtat cttatgtatc ttatacaaaa aatatgggat gtgcaaaatc   7680
tgagctacta atactgcttg aatatataga tagagagtgt aaggactacg agagttgtaa   7740
aagaataata gtagagctag aagagagagt gaagaaaata gctttcgtag aagcaataaa   7800
tgatttgttc taaactactt ttttctctct atctctatat ctatatatat acataactaa   7860
aactaaaaga ataaacaaaa aactaacaaa atcaactcac cattatacaa actcagaaaa   7920
actatttttt tgttatactc ttaccccata tatatataga tatatagata gagagagata   7980
gagtatagta gggcatttaa gatttttagaa gttcttcaat gcgtcttctg attgcatctg   8040
caacaaactc ttgtctgctt atatatccgc ccttgcctga cgctattagt tcatctatttt   8100 gttttgctaa ttcgattgga atcgaaacgg tcacatattc tttttttgact gatttcctcg   8160 gcatacgcta tctatactat attaatatga taatattaaa tgattcacga tatatagata   8220
gagtatagat agagtaaagt ttaaatactt atatagatag agtatagata gagggttcaa   8280
aaaatggttt caccccaaac ccgaaaagaa gaagagttat tagaaaaaca aaattcagtt   8340 tttttatttgt taactttagg aaggaaaccg tatggttcat atttgcatat aaaaattgaa   8400
ctagacgaag atgaaaaatt agagaaggaa atctatgcgg ataacattaa gctagagaat   8460
gaattaagac aactgaagag gttgtatgaa gtatatcaga gcgtagagat tgacgatgct   8520
cagaaagcaa tacagaagga agcattactg acgatagcga aaatactaag tgttttttgac   8580 ttctgaggag gctgaggggc aatgaaggct gaggaaacaa tcgtggaaca gattcaggac   8640
ataattcaaa aacttcgcta ttatacagga agatcaaata gacatttcaa gatgattaga   8700
aactattatg aggagtgtat aataatagta gacgctgagg agtttataca agaaaataac   8760
actctaagca ttactgtata ttctgaggat cttatatatt atactgttga tatcccgctg   8820
aatttcatta aacatgtatt cgtatccgct tcgattgatc agctcaatga tcagcttcag   8880
ctaaaatata atgagggtct gattagagtt tctcttactt tgaacgatga cttatgtgag   8940
aaactgagaa gctcatactg cggtgatatt acattctttta atgaggctga ggggcaatga   9000
aggctagggt tgaatacatc aaattaccta gatgttacac aaaaacttat agaaaatcg   9060 aagcgaaaaa gaacaacgac ggtacaatag aattaacgtt agaggaaaca atgcaagtaa   9120 tatccttttaa actaccccccg gcgttaaatg caaaactaga acaaattgcg atcaaagaaa   9180
agaaaagcaa gagtgaaatt attcgaatag cgttagcgag gtatgtagaa atgtttttaga   9240 tgccccatct gcgggttcaa aacgctgaga ttgttcgcgc ttaaacaaca tactcgaagg   9300
gagcatgtgt tggtcaaatg tcccatatgc gggttcacgg ggaagcattt atctcaacat   9360
ttctatagta ggtatgatat tgaccatctc atatactgct acctattctc ttcttttcaga   9420 ttgcctaaga atgttaggtt agcaataaag agaaaattag aggttgagtg aataatgtat   9480
caatgtctac gttgtggtgg tatatttaat aaaagaagag aagtggttga gcatttgctt   9540
gtagggcata agcacaagga tagactaaca ctggactttt attatatcta cttcagggtg   9600
agaggacaat gaacctaatt gatatcatct tattttacgg ctttcaattc aacgattatt   9660
ggacaactgt cttagggttg agagtggggtg cggaagagaa gaatcccata gcgggtctgt   9720
tcatttcatc accgtatcgt ttagcgttgt ttaagtttgg ccttatcacc attggtatgt   9780
```

-continued

```
ttatattaat ttatgttgtt agattcaaga catggacaga gatcgtattg actgtaacag    9840
acgttgtcga atgccttgtc acgctgaata atacccttac gattaggagg tacaaaagga    9900
ggggcgttag aggatgacgg agtcagacgt tgactcaggt agtaaaaaat acctgagtaa    9960
ccataagggg atttttattc atgtcacact ggaagagtta aagcgttacc accaacttac   10020
gccggaacag aagaggttga taagggcaat cgtcaaaacg cttattcata acccgcaact   10080
gttggatgaa agcagttatc tttacagatt gctcgcgagt aaagcgattt cacagtttgt   10140
ctgcccgctt tgtctaatgc ccttcagctc ttccgtatca ctaaagcaac acatccgtta   10200
tactgaacac acaaaggttt gcccggtgtg taaaaaggag tttacctcaa ccgattcagc   10260
cctagaccat gtttgcaaaa agcataatat ctgcgttagt taggctcttt ttaaagtcta   10320
ccttcttttt cgcttacaat gaggaagtcc cttctagccc tactaaccct atccctagcg   10380
ttactatcgt ttttaataac accatcgatg gcattgaatt ctggcggttc accgataccg   10440
atatattata actattataa ctactatagc cttaacgcag aagggtttgg attcagtttc   10500
aataatagca ataattgggt tgaaacgaac tttatctcaa taaccataaa cttacctagt   10560
tcattaccaa ataactatca aatcaataat gcctattcta tcgtagtagg attatcacca   10620
tatccggtta gcaatataaa cattttaat agcccattag aagcatatgt tgaactattc   10680
tcaaacccac cgaatacata tccaaatgaa ataggatttg tagttagtta cggctcaact   10740
gtatttata gttataccac actgtatagc agttttgcgg gcacacaact aacaataact   10800
atatcatata ccggaaatgg gtttggtgtg caattctctg acagtaacgg gttctctcac   10860
tcagtttcgg taagttcggt aaactttgta ccatatggtg ctctaatact cggatcacta   10920
atcccgaacg ggaactatta ctactaccca gtaggtaaca tgttaccgaa tgcatcggtg   10980
aacttctcat atacgatctc aagtttcaca atagaaggaa acccggccac atccgtcgat   11040
attaccacac ttggattaga aggaaacact gcaatatata cttcaagtag caattggttc   11100
aaatgggtat ccggtagtgt ggttatcaca atgccgttg cctataccta taccgatttg   11160
gctagaatag gaggaagtgc acaaataaac tatactgcat cgcagctata ttaagcaaaa   11220
tctttttta cctcttttta aatctgtctt atatgaaaaa actgtttaca gttgtaggtt   11280
ctattttctc tggtttgggg atttggctta agtcaataga ccagtcattt tatttaacga   11340
aagtattgta taacggaaaa gtaattgaaa tagttctaac gcccgagaca aatgaagtcg   11400
tgaaatcttc caacggtgtt atgaacgcaa gtgtaacttc tctaccttcc acaattctat   11460
accaagcaca atccgtgcct tcaataaatg gaggaactct tagtgtaata aataccacag   11520
ttcaaccgcc atggtatgct aacttatggc ctgaagtctt aacaataggt atagtgatgt   11580
tgggaattgc aatattcagc tggattaaac ttaaatttag aagatagccc ttttaaagc   11640
cataaatttt ttatcgctta atgaagtggg gactattatt cttaataatg tttatatcca   11700
ttttttccct caactcttta gccctattaa tcggcggagg agggcccaac aataatggtg   11760
cgggagttta cactcagact ataacagtta acggaggaac cgtacgaact actcttaacg   11820
gttcaacgct ttctaccgca ccatggctca accctctta cgtaagcgtc tacaacacat   11880
actaccttca ggttttgccg aaccaagagt atattgacaa caacgtttcg ttatccctaa   11940
atacggctaa cattgcgtta aacgtcactt ggttattggc gtcctcaagc aatacgggat   12000
cctacggtgc aatcgccata ggctacggag tgaactttcc cgcggggttt gtcaataact   12060
acggtccttc cgcaccttac acgccggacg gaatcgtaat atatctcatg aaaggaggca   12120
tgccgaccta tcgtttattc gtatacttca atggagttga gcagttaaac gtttcagtcg   12180
```

```
ggtcaatcag tgtgggacaa aaaataggtt tagggttctt ttatctacag aacacacttt   12240
acgtttacta ctataacggt acttttaaaga cttggtcatt aacgcccggt acgctgatta   12300
ctataaatag taattacgtt atagacgcac agaatatagg gccgggctac ggctacggtc   12360
aatgggtaat agttaattat caatatgcga tgccggttac tgcacaactg acggttagtt   12420
atttcgcatt agggtacaat gtatatcatt tcttaatggc ttatgcgggt gctggaaacc   12480
cggtaaacat aactgcgaat aacgggggctt cttacagtat aacgggtata gttgcagaga   12540
agaactttac gataacggga attcagcaag gcctagccta tgctttcagc ttgttaggga   12600
aaccgaatgg cttatactta ttatatatgg ggccaattga gggcagccca ccaacgtggt   12660
atgtaaacgt aaccgtaggg cttcagatcg ttacacccca gaaaacgata aactacaact   12720
taacaatacc agtaatcgtt gagggctatg cgttataccc ttctgttaac gtaccttccg   12780
gaacttacct aagcggacag actattagct ttaccctctc atcgttcttg ggatacccttt   12840 caggcttagg ctattacacc gcagtaaatc taatcgcaaa cgtaacaata aacggtgtga   12900
gtcatgctat cccctatagt ttcaccccga tagtgcaaac cccgataact tattactaca   12960
ctgttatagt ggatgaagga caatttgcat taatagatta tcaagggagt ttcacagtcc   13020
tacccgcaca gagtcagccc gtgatattca ttacttctta tcctagaatt gggctattag   13080
gacaaacgat aactgtgact ttccagttca cttataatag tcccgtagcg aatgtaactc   13140
aatcagcgtt tacgcaatca tctaatattc tcgcttttgc ctatgcgaaa atggtaacaa   13200
caaacgctat agttcagttc aaggcgtatt ggctaagtgc taatgacggg ttggtgatta   13260
taactcaaac gaataactat ctaattccgt ttaatagcag tataacgggc ttaaacttcg   13320
caaacaatag tgttaatacg ttaacgtttc agattgtaac gggtaactat gtacaaataa   13380
ctagctcagc gggaggcgtg cttaccctaa gcaatactag tccgattata ggaatagggt   13440
tctattacgg ttccggtgtc ctacacctga actggttctt cgttagcggt atcattttgc   13500
agtctgcaac ggcaaatcag gcttacgtta ttttgacggg gactaaccca aatacgcttt   13560
cacagtatac gacgggctat actaacgctt cggggttcgg tactgtaacg ctgaagttga   13620
gttacactcc ttacgaactt gtggatgtag actggtacgg cgttacatac gctttgttaa   13680
acattagcgt ttcaaaacact actacagtaa gcagtactac gaccgtgaac acaacaacgc   13740
ttaactataa ctacactaag cctttcagca ataacatagc acctaacagt cagctttatg   13800
acttctcagc gtatcagccg tgggcggaaa ttatcgggat tgtggtcgtg gtcgtcatag   13860
ctctgctggg ctgaaagttc ggcgggtctg cgggagcttc gggtggtgcg gttatggggt   13920
taatcgcagt cagctactta ggtttactgc cttggtacct attctacatc ttcgtattcg   13980
gtatcgctct attacttgct aaagtatttg tagaccgttt catggggagg gaggaatgac   14040
ggacgcaatc agtttagcct tgcaaacggg cttagggccg gtggtagggg taattatcat   14100
actggcaatg atgggggctaa cgtataagat agcgggaaag atcccggcaa tcataacggg   14160
aatagcctcg gctttcgtcc taatgtttat ggattttta ccgttatttt ggggtatcgc   14220
aataatcttc gggttaatcg cgggtatggt ggtgacaagg gatggggact aagttagtcg   14280
tttacgtctt attgtttgac gtcttcctat cgttagtggt aggtgcctac tcgggtatag   14340
caccgccaag tattccaccg gtacctacat atgcttcagc ccaactcacg gcaagtctaa   14400
tcacatggac agtgggatgg cctcctatta cattatggcc tcagataacg cttattccgc   14460
cgttttcgat tttgggtgca aacttccccg gcttaaccat tcctagctta acgataccg   14520
```

```
gtgtaacgct cttctcaata agcttcagct ggttagcccc aattatttat attgcaaatt   14580
ggatcatttg ggtctttcag actgttgcta gtgtgctatc ttatttactt aatatcttta   14640
cgggttcggt aggtctattg agtagtgtac ccgtcttagg gccattttg accgccttcg    14700 tgttgatagt taacttcgtg ttagtgtggg aattaatcaa gttaattagg gggtcggaat   14760
gacggagtat aacgcaaaca gtataagggc taagatactg aggcgtaaaa tccttcaact   14820
gattgcggaa aactacgttt tgtcagcgtc gttaatctct cacacactct tactctcata   14880
cgccacagtg cttaggcact tgcgtatcct taacgatgag ggctatatcg aattgtataa   14940
gcaaggtagg acgctatacg caaaaatccg cgataatgcg aaacaaattc agattctgaa   15000
ttcagaactg gaggggttta aaaacgtaag cgggaagccg atattgacca aggatgagac   15060
tcctaaggag tttggcaaga agatagcct cactcaaaga ggctaaggtt gcactaaaag    15120
tagcaagcga ccccagaaag tacttcaacg aagaacagat gactgaggct tacaggatat   15180
tctggcagac atgggacggg gacataatta gaagtgctag aaggttcgtg gaagtagcaa   15240
aggcaaaccc caagctcaca aaaggtgaag caaccaacat aggcgtattg ttgggcttat   15300
tcatcttcat actaataggt atagtactat tgcccgtaat cgttagccaa gtcaacaacc   15360
tcacaagcgg tacttcaccc caagtaaccg gtactaacgc cacactcctg aacttagtgc   15420
cgttattcta tatcctagtc ctcataatag tccccgcagt cgtggcgtat aagatataca   15480
aagactgagg tgtgagggat ggaaatcagt ttaaagccaa tcatttttt ggtcgttttt    15540 atcatcgtag ggatagcact attcggccct ataaacagtg ttgtaaataa cgttaccaca   15600
tcgggaacct acactactat agtttccggt actgttacta cgtcttcatt tgtgtcaaat   15660
ccgcaatacg taggtagcaa taacgctact atcgtagcct tagtgccgtt attctatatc   15720
ctagtcctca taatagtccc cgcagtcgtg gcgtataagt tgtataagga ggagtgtatat  15780 gaagtgggtg caaaaggcga taaagagacc cgggagggta catcgctacc ttatgaggct   15840
ctacggcaaa cgggcgttta caaaagacgg tgacataaag gcaagttatc tcgataaggc   15900
gataaagcac gttaaaaaag ctaagatccc gaaagagaag aaacgtagtt tactgtcagc   15960
cctactgtta gcgaaaaggc ttaagcggat gcaccgcaag taggccctt ataaagtcat    16020 attcttttc tttccctgat gagtgcgtta ggggatgtaa tctacatctt gggttttctc    16080
tttccggctt tagggctaat cagccgaaac tatcttgtta acttaatggc attcataata   16140
ggaacagtcg ccttttggt cttcgtccaa ggctataccg atatagcgtt cagcagttcg    16200
acgttttact taggagtact gcctctacta cttggtctcg tcaacttagg ctatttcttc   16260
aattggttga gggaggaaag gatatgaggt ggggtagaag agatgatagg gataccggca   16320
aaatacttcg aaataggagt cgtaatagat tcaacattta tcattatgtc tctactgtta   16380
agaaagtcaa agagacagag agagaactcc ttcgacttac gcaaacatgg aaggctatta   16440
ggcttatatc ttataatagc gtcggcatca gcattaatcg tctcacatct cgccttatac   16500
acaaactaca tgaactactt aacgggctta tctcttaatg cgtttctgtt ttatcttggg   16560
ttgaggtgtt tgcatgtctg atgggaaact cctttctgct ttcgaggagg aattaagaaa   16620
agcccaaagc ctagaggaat taaagcaaaa gtatgaggaa gcccaaaaac aaatagctga   16680
cggcaaagta ctaaagaggc tatacaaggt ttatgagaaa aggcaaacag aattaatgct   16740
tcagcaatat aggcagataa aggctgaact ggaaaagagg aaaaaggtaa agaaaaagga   16800
taaagccgac ataagggtta gagtagtaaa gaagtggata aattcacgct tattcagtgc   16860
tgagcattac gtcgcattac tgcaagaaaa tcaagacggc ttatcgatac tatttctaag   16920
```

```
aagagcaaaa cttatagaaa atcaaggcta tctaatgcta gaagtgaaga agttaaggaa    16980
ggcatgggtt ttaacggctg aacctatact ccttgaaagg ttaaaattcc cattcggcaa    17040
aaagtttgta gccgtgcatt tcgttttacc caattatcct tacacacttc agcttaaacc    17100
ggatgaaaaa ctgaaagagt tagcagttaa ggcgataaac gggcctcaaa taatgagcgc    17160
aatgatacgt acaaagttct tcgaagcgtt agctagggta ggaagcgggc ctgatctgat    17220
gatgctcata atcggcgttg tcatggggat tggcataggc gtagcgatag gtttcggtat    17280
agctaacgca aacttaacgc atttgctatc tcaacacgtt acgaacacta cagtgacaca    17340
tactacgacc acaacgactt caccctcatt cacgattccc tcaaactcct caaaaggggt    17400
gagctaaaat ggtctcagta acagaaataa taacatatgg acgagaagca atagaaagaa    17460
taatatgcaa atattttaaa gattcgaaaa tagaaaagat attattcttg ccgagtgagg    17520
aagacgtaaa ggcaaaatat atcattggac gggtaggggtt tataaggatt agtaatacgt    17580
ggtctggaat tgtcgtagtt gacggggtac aaataccttt cgttgctgaa gtccacctta    17640
atggcaagat tgatatttac cttta tcctc aaaaggactt ctacttagca catttggtgg    17700
gtgagctgaa tggctaaaaa gaacggctta acagaactag agcaattaaa gaaagagaac    17760
gaagagttga gaaagaagtt agaagagtta gaggcgttga tcaataacga tagcgatgac    17820
gacgaagagt tgcaggaaat cgaaaacccg tacaccgtta caaaccgtgc aatagatgaa    17880
ttagtaagcc caaaggacac aatgttctat ttgtcgggaa accagatatc gttaatctta    17940
agtgcttttg aattcgcccg cttaccgacg tacttcggtg aggaaccggt aacggagtta    18000
gcggaatacg cccataagtt gaaacattat ctcgtttcga aaggaggaag aggaaggagg    18060
gatatactga gagtcctacg cgttagttca ggtcagacaa gagagaacgt aaacaaatca    18120
attctgaaac aattatttga ccatggtaag gaacatgaag atgaagaaga gtaatgaatg    18180
gttatggtta gggactaaaa ttataaacgc ccataagact aacggctttg aaagtgcgat    18240 tatttt cggg aaacaaggta cgggaaagac tacttacgcc cttaaggtgg caaaagaagt    18300
ttaccagaga ttaggacatg aaccggacaa ggcatgggaa ctggcccttg actctttatt    18360 cttt gagctt aaagatgcat tgaggataat gaaaatattc aggcaaaatg ataggacaat    18420
accaataata attttcgacg atgctgggat atggcttcaa aaatatttat ggtataagga    18480
agagatgata aagttttacc gtatatataa cattattagg aatatagtaa gcggggtgat    18540
cttcactacc ccttccccta acgatatagc gttttatgtg agggaaaagg ggtggaagct    18600
gataatgata acgagaaacg gaagacaacc tgacggtacg ccaaaggcag tagctaaaat    18660
agcggtgaat aagataacga ttataaaagg aaaaataaca aataagatga aatggaggac    18720
agtagacgat tatacggtca agcttccgga ttgggtatat aaagaatatg tggaaagaag    18780
aaaggtttat gaggaaaaat tgttggagga gttggatgag gttttagata gtgataacaa    18840
aacgaaaaac ccgtcaaacc catcactact aacgaaaatt gacgacgtaa caagatagtg    18900
atacgggtaa tgtcagaccc cttttagcca ttccgcatac ttttt atatt gctctttcgc    18960 tatgccgaag agcgatacgt aatgttgcgt taaaacgcgt gtcggtttac gcccttgaat    19020
aaaatcgata atatctaacg gtacgcttag ctcagccatc ttagacgcta cgaatttgcg    19080
gaagtacttt atcgctatag cgtccttatg acgtcgttca aagtccgcta ttgcccactt    19140
cgtcacctct actctcttca gaggcgttat gtggaataca tagaagacgc ccttatatcc    19200
cctagtccaa ctaagcggat aataacagac gtcgttaccg caaatgtccc tttcgggttc    19260
```

```
cttcagcact ttcagtattt cgctcagcct aacgcccgac tcgagagcga tacggtagat    19320
gaagtagacg ttttcgctat agtcttttgc taattgtaac gtccttttta tctcttccaa    19380
cgttggaatg tagatatcag cgttcgcctt cttcaccttt accgctttca atattttatc    19440
cgcaaattca tcatgtatga tattgcgtga cgctaagaaa cgtgcaaaga gtcggtaagc    19500
cttctgtgcg tctctcgtct ctttatacgg ctttgatata gcattgatgt agtcctttgc    19560
agttttttcg cttatccccc tttcgttcat gagatagtcg tagaacgcct ttatgttgcc    19620
gtccgtcgcg tattggcgca aattggcaac caacgctatt ttacgtcgtt cagttccctc    19680
ttttccgcct ccggagccgg aggtcccggg ttcaaatccc ggcgggtccg cttgtagggg    19740
agtatcccct acgaccccta atttcatttt tagatatgat tcaacgacgt cagctaaagg    19800
acccacgtaa cgctctttta cctcaccgtt ttcatactct agcttgtaaa cataataccg    19860 cccttttcctc tcgcgtaaaa tataatcccc gtatttataa cgcgtcttat ctttcgtcat    19920
ttcgcctcac agtattatgg ttgccaaaac gggcttataa gcattggcaa cccgttaatt    19980
tttgccgtta aaacacgttg aattgaaaga agacggcaaa gaatccacac aggtaatact    20040
aaaaaagtag tattacttac attagaagga ctcatttgtc caccttgtat tctagccatg    20100
ctatctctgc cttcagctca tctagcttcc cctttatgtc tgtcaggtca aggggaactc    20160
ctctcattaa cctgagttcg ttttcgattt tttcaagctc cttttccaac tcctctagtt    20220
tctctaattc ctttagtcgt tcttccaatt tcttttccaa tttccccttt gcgtcattta    20280
taattatgct tactacccaa acaattccta aatcagaaat aattattaac tcctctgagt    20340
tgaatatcat tttccgcccc tcgctaaata ctccttaaag ctctgataga accccttcag    20400
actaacccgt aagtctgtta ggttcttcca gtattgtaat gggattaagt aatagtagct    20460
tactgcatct ctctcaaatt tgtccttctt aatctttcct tgcttttcta agttgagtat    20520
ttgcagtgct gagatacatt ttaacttgtc ctcagcatct gaatagtgta taaaccaaac    20580 cctcccata acctcattct gctttgcaac ttctacttta gtgcttaata ttgcgtaaac    20640
gctttcgccg tatctttctt tgctctgttc ttcagtccat gaacttcccg taatatctat    20700
ccaaattaaa ggataatatt ctgtcttagc cttaacgtat aaagtcaaat cgtatttatc    20760
ttgcagaccg ctatagtatt gctcatttat tacattagtt aaagtcccca cgccagttgg    20820
gcggatataa acatcaaagt ctaacaaacc cttagcccgc cactttgata aagagattaa    20880 gagcttttcca aaaactaggt attctcgccc taaataagtt gaagggagga tataatcctc    20940
agcttgatta ccccaatact ttagcttaaa attagtttca gccatctcac tcaccatatt    21000
gaaacgtggg ctagtatgtg aatcagtact gatgctattg caaataacac acttgcagta    21060
gcaattccta ttacaatcca tttaccataa tccaccttag tttgttggtc aatatactcg    21120
ttgatgatct ttagtatttc tggctttagt tctgataatg aaaggaagac agaggcataa    21180
agtactaagg aggatgtgaa cagattatcc gccttttctg aaagtttata aagctcatat    21240
cttgctctct cataatcttc ataattaata atttcatcaa acttttctac ttgctcttca    21300
tattctttct tcagagagta aggagttgtc ttttcaatta ctcctaattt tattaacttc    21360
ttaacagctt cctaaatcc ttgtttattg ctagcatacg ctaaagggtc ttttccttct    21420
tgagaagctc tatagataac tatagcacca taaacaatat ttacaatatc gtatggtaag    21480
gaatacgcac cgatttgggc aatatcttca actcttcttt gatccatcta gttcacctct    21540
ttttgatttg tttgtaggtt tctatcgcag ttttcagcga tatcgcaaat agcttcccct    21600
tttccgttag gtatagcctc ttttcgcctc tttcttgacg ctctttcacg aagccctctt    21660
```

```
gtattaggaa cttttttgca tcataaaagg tggcagtgga catgggaaat tctgcgttta    21720 cttcttgta taggtcatat gttgctattc cttcattatc atatagataa gccaatacta    21780
tggcttcggg gtagaagaat ggtgtacttt tcatatcctc ctcactcctc agcctctaat    21840
agcttaactg cctcctctat caactgtccc attgtctttc cagtctttgc cttaagcctc    21900
tgcagtaaat ggtaaaaaga ttttacttat tccgttctct tctgagaacc gcttgctttt    21960
tacgattaaa ttccacatat catctaagat agagtgttgt ggttctagct tcctcgtgta    22020
gattttcccc tattaatgtt agtttataaa gaccggctat ttttcacta att            22073

<210> SEQ ID NO 11
<211> LENGTH: 21706
<212> TYPE: DNA
<213> ORGANISM: Artificial Sequence
<220> FEATURE:
<223> OTHER INFORMATION: synthetic vector nucleotide sequence

<400> SEQUENCE: 11 tcatttttc ctaaaaattg ctcctttaca tttcatcacc ttatcctcga taatcttatt      60
tatagttctt aatgctgtta atggattccc tgcattataa atacttcttc caatgatttc    120
ataatccgct ccagcacata ctgcatcgcc ataacttcca ccttgactac ccatacccgg    180
agagactatg gtcatttttt cgaagtctct cctatactgc gttatatgat ctaatttagt    240
ccctccaact actattcctt tgggcttat ctctcttata acgttttaa tatagtctgc      300 gaataacgta ctccatcctt catgtgacat tacggcaact aagtataaat ttttagagtt    360
tgcatcaaga tatcttttta attcatctag agatccctta acgcctataa aggaatgtgc    420
tatgaacgag ttggcgaaag ataatctttc aactatgctt tcattatgt atccgatatc      480 tgcaagctta aaatcaacaa taatttcctc cacgtctaaa ccaattaaga gctctctagt    540
tttatccact cctagatcta aaactaaagg taaaccaact tttatcccat ataactcatt    600
ttccatctct ttaagaactt gatatgagag aggtttatcc attgctaata ttactctact    660
tttcaacatt cttcaccaaa taatctagaa ttgacttctt ttcattatcc ttaagtttat    720
cactcttcaa caattcatct agaattcctg aaattttaaa tagagagtgt aatttgactc    780 ctagttttc caatctttgt gaagcccctt cttgtctatc tatgattact agtgcgtctg      840
aaactttacc tccaccgtta agaatctcca atgttgcttt ctctatggat actcctgtag    900
ttgcaacgtc atctactaac aatactcttt ttccttttac atcgagttct aatgtacgat    960
tagttccatg acctttcttt tctattctaa tatatcccat aggctctta aggttacaag     1020 ctatgaatgc cgataaggga actcctccag tggctattcc tactattata tcatggggta    1080
tatcttttgc tttctttata gcttgattaa ctatatcgta aaattctgga taatttgta     1140 aaggtcttaa gtctaagtaa tatggactaa ccttacctga tgttaaaacg aaacttccta    1200
ttaataataa tttcctttcg agtaagactt ctgcgaaatt catacgtaga gactctgcga    1260
aaaagaattt aaatatactt ctatcataac cagttataag ggctttgtga gattaagaca    1320
cgtagtttcg tcgcttgact tgaccagaga tgactacttt agaatattcg aacttgcaga    1380
caagttctat gatgtaaaaa aactaaatta tctatcaggg aaagtagttt cattagcatt    1440
ctttgagcca agtactagaa ctgctcaaag ctttcatact gcagcaataa aattaggtgc    1500
tgatgtgata ggatttgcat ccgaggagtc tacttcgata gcaaaggtg aaaatttggc     1560 tgataccatt aggatgctaa acaactattc aaactgtatt gtaatgagac ataagtttga    1620
```

```
tggggcagca ttattcccta gtccagtgtg gtggaattct gcagatatca acaagtttgt    1680
acaaaaaagc tgaacgagaa acgtaaaatg atataaatat caatatatta aattagattt    1740
tgcataaaaa acagactaca taatactgta aaacacaaca tatccagtca ctatggcggc    1800
cgcattaggc accccaggct ttacacttta tgcttccggc tcgtataatg tgtggatttt    1860
gagttaggat ccggtcgaga ttttcaggag ctaaggaagc taaaatggag aaaaaaatca    1920
ctggatatac caccgttgat atatcccaat ggcatcgtaa agaacatttt gaggcatttc    1980
agtcagttgc tcaatgtacc tataaccaga ccgttcagct ggatattacg gcctttttaa    2040
agaccgtaaa gaaaaataag cacaagtttt atccggcctt tattcacatt cttgcccgcc    2100
tgatgaatgc tcatccggaa ttccgtatgg caatgaaaga cggtgagctg gtgatatggg    2160
atagtgttca cccttgttac accgttttcc atgagcaaac tgaaacgttt tcatcgctct    2220
ggagtgaata ccacgacgat ttccggcagt ttctacacat atattcgcaa gatgtggcgt    2280
gttacggtga aaacctggcc tatttcccta aagggtttat tgagaatatg ttttcgtct    2340 cagccaatcc ctgggtgagt ttcaccagtt ttgatttaaa cgtggccaat atggacaact    2400
tcttcgcccc cgttttcacc atgggcaaat attatacgca aggcgacaag gtgctgatgc    2460
cgctggcgat tcaggttcat catgccgttt gtgatggctt ccatgtcgg cagaatgctt    2520 aatgaattac aacagtactg cgatgagtgg cagggcgggg cgtaaagatc tggatccggc    2580
ttactaaaag ccagataaca gtatgcgtat ttgcgcgctg attttgtcgg tataagaata    2640
tatactgata tgtataccccg aagtatgtca aaaagaggta tgctatgaag cagcgtatta    2700
cagtgacagt tgacagcgac agctatcagt tgctcaaggc atatatgatg tcaatatctc    2760
cggtctggta agcacaacca tgcagaatga agcccgtcgt ctgcgtgccg aacgctggaa    2820
agcggaaaat caggaaggga tggctgaggt cgcccggttt attgaaatga acggctcttt    2880
tgctgacgag aacaggggct ggtgaaatgc agtttaaggt ttacacctat aaaagagaga    2940
gccgttatcg tctgtttgtg gatgtacaga gtgatattat tgacacgccc gggcgacgga    3000
tggtgatccc cctggccagt gcacgtctgc tgtcagataa agtctcccgt gaactttacc    3060
cggtggtgca tatcggggat gaaagctggc gcatgatgac caccgatatg gccagtgtgc    3120
cggtctccgt tatcggggaa gaagtggctg atctcagcca ccgcgaaaat gacatcaaaa    3180
acgccattaa cctgatgttc tggggaatat aaatgtcagg ctcccttata cacagccagt    3240
ctgcaggtcg accatagtga ctggatatgt tgtgttttac agtattatgt agtctgtttt    3300
ttatgcaaaa tctaatttaa tatattgata tttatatcat tttacgtttc tcgttcagct    3360
ttcttgtaca aagtggttga tatccagcac agtggcgccg gcgccaccg cggtggagct    3420 cgaattcgta atcatgtcat agctgtttcc tgtgtgaaat tgttatccgc tcacaattcc    3480
acacaacata cgagccggaa gcataaagtg taaagcctgg ggtgcctaat gagtgagcta    3540
actcacatta attgcgttgc gctcactgcc cgctttccag tcgggaaacc tgtcgtgcca    3600
gctgcattaa tgaatcggcc aacgcgcggg gagaggcggt ttgcgtattg ggcgctcttc    3660
cgcttcctcg ctcactgact cgctgcgctc ggtcgttcgg ctgcggcgag cggtatcagc    3720
tcactcaaag gcggtaatac ggttatccac agaatcaggg gataacgcag gaaagaacat    3780
gtgagcaaaa ggccagcaaa aggccaggaa ccgtaaaaag gccgcgttgc tggcgttttt    3840
ccataggctc cgcccccctg acgagcatca caaaaatcga cgctcaagtc agaggtggcg    3900
aaacccgaca ggactataaa gataccaggc gtttccccct ggaagctccc tcgtgcgctc    3960
tcctgttccg accctgccgc ttaccggata cctgtccgcc tttctccctt cgggaagcgt    4020
```

```
ggcgctttct catagctcac gctgtaggta tctcagttcg gtgtaggtcg ttcgctccaa    4080
gctgggctgt gtgcacgaac cccccgttca gcccgaccgc tgcgccttat ccggtaacta    4140
tcgtcttgag tccaacccgg taagacacga cttatcgcca ctggcagcag ccactggtaa    4200
caggattagc agagcgaggt atgtaggcgg tgctacagag ttcttgaagt ggtggcctaa    4260
ctacggctac actagaagga cagtatttgg tatctgcgct ctgctgaagc cagttacctt    4320
cggaaaaaga gttggtagct cttgatccgg caaacaaacc accgctggta gcggtggttt    4380
ttttgtttgc aagcagcaga ttacgcgcag aaaaaaagga tctcaagaag atcctttgat    4440
cttttctacg gggtctgacg ctcagtgaac gaaaactca cgttaaggga ttttggtcat    4500
gagattatca aaaaggatct tcacctagat ccttttaaat taaaaatgaa gttttaaatc    4560
aatctaaagt atatatgagt aaacttggtc tgacagttac caatgcttaa tcagtgaggc    4620
acctatctca gcgatctgtc tatttcgttc atccatagtt gcctgactcc ccgtcgtgta    4680
gataactacg atacgggagg gcttaccatc tggccccagt gctgcaatga taccgcgaga    4740
cccacgctca ccggctccag atttatcagc aataaaccag ccagccggaa gggccgagcg    4800
cagaagtggt cctgcaactt tatccgcctc catccagtct attaattgtt gccgggaagc    4860
tagagtaagt agttcgccag ttaatagttt gcgcaacgtt gttgccattg ctacaggcat    4920
cgtggtgtca cgctcgtcgt ttggtatggc ttcattcagc tccggttccc aacgatcaag    4980
gcgagttaca tgatccccca tgttgtgcaa aaaagcggtt agctccttcg gtcctccgat    5040
cgttgtcaga agtaagttgg ccgcagtgtt atcactcatg gttatggcag cactgcataa    5100
ttctcttact gtcatgccat ccgtaagatg cttttctgtg actggtgagt actcaaccaa    5160
gtcattctga gaatagtgta tgcggcgacc gagttgctct tgcccggcgt caatacggga    5220
taataccgcg ccacatagca gaactttaaa agtgctcatc attggaaaac gttcttcggg    5280
gcgaaaactc tcaaggatct taccgctgtt gagatccagt tcgatgtaac ccactcgtgc    5340
acccaactga tcttcagcat cttttacttt caccagcgtt tctgggtgag caaaaacagg    5400
aaggcaaaat gccgcaaaaa agggaataag ggcgacacgg aaatgttgaa tactcatact    5460 cttcctttt caatattatt gaagcattta tcagggttat tgtctcatga gcggatacat    5520
atttgaatgt atttagaaaa ataaacaaat aggggttccg cgcacatttc cccgaaaagt    5580
gccacctgac gtctaagaaa ccattattat catgacatta acctataaaa ataggcgtat    5640
cacgaggccc tttcgtctcg cgcgtttcgg tgatgacggt gaaaacctct gacacatgca    5700
gctcccggag acggtcacag cttgtctgta agcggatgcc gggagcagac aagcccgtca    5760
gggcgcgtca gcgggtgttg gcgggtgtcg ggctggctt aactatgcgg catcagagca    5820
gattgtactg agagtgcacc atatgcggtg tgaaataccg cacagatgcg taaggagaaa    5880
ataccgcatc aggcgccatt cgccattcag gctgcgcaac tgttgggaag ggcgatcggt    5940
gcgggcctct tcgctattac gccagctggc gaaaggggga tgtgctgcaa ggcgattaag    6000
ttgggtaacg ccagggtttt cccagtcacg acgttgtaaa acgacggcca gtgccaagct    6060
tgcatgcctg cagagtctca tatgtttcct cacttattga aatgttaagc cttttgacta    6120
tcctatcttt cctcttctct atcatttagg tcaccttgtt tattgttatt tgaaatacgt    6180
atccgtcttc gtcacatcga agtataattt tgtatccatt attagcatat tctacgtcaa    6240
agttcccaca acaataattc gggtcttcgg actcgttata gactttgctc caaccatctt    6300
tttgtagtgc ctcttctaag tagtctactc tgatgaagcc ttcatcatat tcgttcagta    6360
```

```
ccctaaagct tatactatca atgcctaata cgtctaatag cttcaacaga tcgaatatag    6420
gaacttgcac catcatttca gctcaccttc atgagctgat ataattccgc ttctatcttt    6480
tgaacttgga agtatgcctt gcctagcttt tgcttatcca tattgcccgt tattctatca    6540
atcttaatct cgtggattaa tgataatagc tctctgacat cctcatcaag catttcaaat    6600
aattctttct ctaagacttc tttactcatt gttttcacc ttagcaaact catctaacgt    6660
tgtttgtctc agttctcttt tctttatcaa ataaaattcc gaatgtccct tcttattgtt    6720
attactgtac ttcatgtcag ttcactgctt tgcctttata atccttgat ccgtttgctc    6780
aaaatttgcg ggctgggcat caaatatctt agctatattg tcttgtgttt gctcttgttt    6840
ttgttcttct ttctgctctt gcttaatcca tttgaacgtt gtctttctgt ttttgtattg    6900
tacttcacac tcgtctggat gtctttcgca aatagctttc aatgctctct gtatgttata    6960
cgcactcggg actgaaatct caaattgagc tagtatatcc tctaacgtta attcacctt    7020
cttttcaaga attttataca ttatttccgc catcttgtat gaatttagag tttgtgccat    7080
attcccatcc cactctatct atactctatg tataaattag tatttaagtc ttactctatc    7140
tatactctat ctatctctct atatacacag tgtttgggta actggcaaaa ttctgtctga    7200
ctgctgtctg acaagagttt actctatctc tctatatcta tatacacaaa cagagttagt    7260
cgactctgtg tatcttatgt atcttataca aaaaatatgg gatgtgcaaa atctgagcta    7320
ctaatactgc ttgaatatat agatagagag tgtaaggact acgagagttg taaaagaata    7380
atagtagagc tagaagagag agtgaagaaa atagctttcg tagaagcaat aaatgatttg    7440
ttctaaacta ctttttttctc tctatctcta tatctatata tatacataac taaaactaaa    7500
agaataaaca aaaactaac aaaatcaact caccattata caaactcaga aaaactattt    7560
ttttgttata ctcttacccc atatatat agatatatag atagagagag atagagtata    7620
gtagggcatt taagatttta gaagttcttc aatgcgtctt ctgattgcat ctgcaacaaa    7680
ctcttgtctg cttatatatc cgcccttgcc tgacgctatt agttcatcta tttgttttgc    7740
taattcgatt ggaatcgaaa cggtcacata ttctttttg actgatttcc tcggcatacg    7800
ctatctatac tatattaata tgataatatt aaatgattca cgatatatag atagagtata    7860
gatagagtaa agtttaaata cttatataga tagagtatag atagagggtt caaaaaatgg    7920
tttcaccccca aacccgaaaaa gaagaagagt tattagaaaa acaaaattca gttttttatt    7980
tgttaacttt aggaaggaaa ccgtatggtt catatttgca tataaaaatt gaactagacg    8040
aagatgaaaa attagagaag gaaatctatg cggataacat taagctagag aatgaattaa    8100
gacaactgaa gaggttgtat gaagtatatc agagcgtaga gattgacgat gctcagaaag    8160
caatacagaa ggaagcatta ctgacgatag cgaaaatact aagtgttttt gacttctgag    8220
gaggctgagg ggcaatgaag gctgaggaaa caatcgtgga acagattcag gacataattc    8280
aaaaacttcg ctattataca ggaagatcaa atagacattt caagatgatt agaaactatt    8340
atgaggagtg tataataata gtagacgctg aggagtttat acaagaaaat aacactctaa    8400
gcattactgt atattctgag gatcttatat attatactgt tgatatcccg ctgaatttca    8460
ttaaacatgt attccgtatcc gcttcgattg atcagctcaa tgatcagctt cagctaaaat    8520
ataatgaggg tctgattaga gtttctctta ctttgaacga tgacttatgt gagaaactga    8580
gaagctcata ctgcggtgat attacattct ttaatgaggc tgaggggcaa tgaaggctag    8640
ggttgaatac atcaaattac ctagatgtta cacaaaaact tatagaaaaa tcgaagcgaa    8700
aaagaacaac gacggtacaa tagaattaac gttagaggaa acaatgcaag taatatcctt    8760
```

```
taaactaccc ccggcgttaa atgcaaaact agaacaaatt gcgatcaaag aaaagaaaag    8820
caagagtgaa attattcgaa tagcgttagc gaggtatgta gaaatgtttt agatgcccca    8880
tctgcgggtt caaaacgctg agattgttcg cgcttaaaca acatactcga agggagcatg    8940
tgttggtcaa atgtcccata tgcgggttca cggggaagca tttatctcaa catttctata    9000
gtaggtatga tattgaccat ctcatatact gctacctatt ctcttctttc agattgccta    9060
agaatgttag gttagcaata aagagaaaat tagaggttga gtgaataatg tatcaatgtc    9120
tacgttgtgg tggtatattt aataaaagaa gagaagtggt tgagcatttg cttgtagggc    9180
ataagcacaa ggatagacta acactggact tttattatat ctacttcagg gtgagaggac    9240
aatgaaccta attgatatca tcttatttta cggctttcaa ttcaacgatt attggacaac    9300
tgtcttaggg ttgagagtgg gtgcggaaga gaagaatccc atagcgggtc tgttcatttc    9360
atcaccgtat cgtttagcgt tgtttaagtt tggccttatc accattggta tgtttatatt    9420
aatttatgtt gttagattca agacatggac agagatcgta ttgactgtaa cagacgttgt    9480
cgaatgcctt gtcacgctga ataatacccct tacgattagg aggtacaaaa ggaggggcgt    9540
tagaggatga cggagtcaga cgttgactca ggtagtaaaa aatacctgag taaccataag    9600
gggattttta ttcatgtcac actggaagag ttaaagcgtt accaccaact tacgccggaa    9660
cagaagaggt tgataagggc aatcgtcaaa acgcttattc ataacccgca actgttggat    9720
gaaagcagtt atctttacag attgctcgcg agtaaagcga tttcacagtt tgtctgcccg    9780
ctttgtctaa tgcccttcag ctcttccgta tcactaaagc aacacatccg ttatactgaa    9840
cacacaaagg tttgcccggt gtgtaaaaag gagtttacct caaccgattc agccctagac    9900
catgttgca aaaagcataa tatctgcgtt agttaggctc tttttaaagt ctaccttctt    9960
tttcgcttac aatgaggaag tcccttctag ccctactaac cctatcccta gcgttactat   10020
cgttttaat aacaccatcg atggcattga attctggcgg ttcaccgata ccgatatatt   10080
ataactatta taactactat agccttaacg cagaagggtt tggattcagt ttcaataata   10140
gcaataattg ggttgaaacg aactttatct caataaccat aaacttacct agttcattac   10200
caaataacta tcaaatcaat aatgcctatt ctatcgtagt aggattatca ccatatccgg   10260
ttagcaatat aaacatttttt aatagcccat tagaagcata tgttgaacta ttctcaaacc   10320
caccgaatac atatccaaat gaaataggat ttgtagttag ttacggctca actgtatttt   10380
atagttatac cacactgtat agcagttttg cgggcacaca actaacaata actatatcat   10440
ataccggaaa tgggtttggt gtgcaattct ctgacagtaa cgggttctct cactcagttt   10500
cggtaagttc ggtaaacttt gtaccatatg gtgctctaat actcggatca ctaatcccga   10560
acgggaacta ttactactac ccagtaggta acatgttacc gaatgcatcg gtgaacttct   10620
catatacgat ctcaagtttc acaatagaag gaaacccggc cacatccgtc gatattacca   10680
cacttggatt agaaggaaac actgcaatat atacttcaag tagcaattgg ttcaaatggg   10740
tatccggtag tgtggttatc acaaatgccg ttgcctatac ctataccgat ttggctagaa   10800
taggaggaag tgcacaaata aactatactg catcgcagct atattaagca aaatctttttt   10860
ttacctcttt ttaaatctgt cttatatgaa aaaactgttt acagttgtag gttctatttt   10920
ctctggtttg gggatttggc ttaagtcaat agaccagtca ttttatttaa cgaaagtatt   10980
gtataacgga aaagtaattg aaatagttct aacgcccgag acaaatgaag tcgtgaaatc   11040
ttccaacggt gttatgaacg caagtgtaac ttctctacct tccacaattc tataccaagc   11100
```

```
acaatccgtg ccttcaataa atggaggaac tcttagtgta ataaatacca cagttcaacc    11160
gccatggtat gctaacttat ggcctgaagt cttaacaata ggtatagtga tgttgggaat    11220
tgcaatattc agctggatta aacttaaatt tagaagatag ccctttttaa agccataaat    11280
tttttatcgc ttaatgaagt ggggactatt attcttaata atgtttatat ccattttttc    11340
cctcaactct ttagccctat taatcggcgg aggagggccc aacaataatg gtgcgggagt    11400
ttacactcag actataacag ttaacggagg aaccgtacga actactctta acggttcaac    11460
gctttctacc gcaccatggc tcaacccctc ttacgtaagc gtctacaaca catactacct    11520
tcaggttttg ccgaaccaag agtatattga caacaacgtt tcgttatccc taaatacggc    11580
taacattgcg ttaaacgtca cttggttatt ggcgtcctca agcaatacgg atcctacgg    11640 tgcaatcgcc ataggctacg gagtgaactt cccgcgggg tttgtcaata actacggtcc    11700
ttccgcacct tacacgccgg acggaatcgt aatatatctc atgaaggag gcatgccgac    11760 ctatcgttta ttcgtatact tcaatggagt tgagcagtta aacgtttcag tcgggtcaat    11820
cagtgtggga caaaaaatag gtttaggggtt cttttatcta cagaacacac tttacgttta    11880
ctactataac ggtactttaa agacttggtc attaacgccc ggtacgctga ttactataaa    11940
tagtaattac gttatagacg cacagaatat agggccgggc tacggctacg gtcaatgggt    12000
aatagttaat tatcaatatg cgatgccggt tactgcacaa ctgacggtta gttatttcgc    12060
attagggtac aatgtatatc atttcttaat ggcttatgcg ggtgctggaa acccggtaaa    12120
cataactgcg aataacgggg cttcttacag tataacgggt atagttgcag agaagaactt    12180
tacgataacg ggaattcagc aaggcctagc ctatgctttc agcttgttag ggaaaccgaa    12240
tggcttatac ttattatata tggggccaat tgagggcagc ccaccaacgt ggtatgtaaa    12300
cgtaaccgta gggcttcaga tcgttacacc ccagaaaacg ataaactaca acttaacaat    12360
accagtaatc gttgagggct atgcgttata cccttctgtt aacgtaccett ccggaactta    12420 cctaagcgga cagactatta gctttaccct ctcatcgttc ttgggatacc cttcaggctt    12480
aggctattac accgcagtaa atctaatcgc aaacgtaaca ataaacggtg tgagtcatgc    12540
tatcccctat agtttcaccc cgatagtgca aaccccgata acttattact acactgttat    12600
agtggatgaa ggacaatttg cattaataga ttatcaaggg agtttcacag tcctacccgc    12660
acagagtcag cccgtgatat tcattacttc ttatcctaga attgggctat taggacaaac    12720
gataactgtg actttccagt tcacttataa tagtcccgta gcgaatgtaa ctcaatcagc    12780
gtttacgcaa tcatctaata ttctcgcttt tgcctatgcg aaaatggtaa caacaaacgc    12840
tatagttcag ttcaaggcgt attggctaag tgctaatgac gggttggtga ttataactca    12900
aacgaataac tatctaattc cgtttaatag cagtataacg ggcttaaact tcgcaaacaa    12960
tagtgttaat acgttaacgt ttcagattgt aacgggtaac tatgtacaaa taactagctc    13020
agcgggaggc gtgcttaccc taagcaatac tagtccgatt ataggaatag ggttctatta    13080
cggttccggt gtcctacacc tgaactggtt cttcgttagc ggtatcattt tgcagtctgc    13140
aacggcaaat caggcttacg ttattttgac ggggactaac ccaaatacgc tttcacagta    13200
tacgacgggc tatactaacg cttcgggggtt cggtactgta acgctgaagt tgagttacac    13260
tccttacgaa cttgtggatg tagactggta cggcgttaca tacgctttgt taaacattag    13320
cgtttcaaac actactacag taagcagtac tacgaccgtg aacacaacaa cgcttaacta    13380
taactacact aagcctttca gcaataacat agcacctaac agtcagcttt atgacttctc    13440
agcgtatcag ccgtgggcgg aaattatcgg gattgtggtc gtggtcgtca tagctctgct    13500
```

```
gggctggaag ttcggcgggt ctgcgggagc ttcgggtggt gcggttatgg ggttaatcgc    13560
agtcagctac ttaggtttac tgccttggta cctattctac atcttcgtat tcggtatcgc    13620
tctattactt gctaaagtat ttgtagaccg tttcatgggg agggaggaat gacggacgca    13680
atcagtttag ccttgcaaac gggcttaggg ccggtggtag gggtaattat catactggca    13740
atgatggggc taacgtataa gatagcggga aagatcccgg caatcataac gggaatagcc    13800
tcggctttcg tcctaatgtt tatgattttt ttaccgttat tttggggtat cgcaataatc    13860
ttcgggttaa tcgcgggtat ggtggtgaca agggatgggg actaagttag tcgtttacgt    13920
cttattgttt gacgtcttcc tatcgttagt ggtaggtgcc tactcgggta tagcaccgcc    13980
aagtattcca ccggtaccta catatgcttc agcccaactc acggcaagtc taatcacatg    14040
gacagtggga tggcctccta ttacattatg gcctcagata acgcttattc cgccgttttc    14100
gattttgggt gcaaacttcc ccggcttaac cattcctagc ttaacgatac ccggtgtaac    14160
gctcttctca ataagcttca gctggttagc cccaattatt tatattgcaa attggatcat    14220
ttgggtcttt cagactgttg ctagtgtgct atcttattta cttaatatct ttacggggttc   14280 ggtaggtcta ttgagtagtg tacccgtctt agggccattt ttgaccgcct tcgtgttgat    14340
agttaacttc gtgttagtgt gggaattaat caagttaatt aggggtcgg aatgacggag     14400 tataacgcaa acagtataag ggctaagata ctgaggcgta aaatccttca actgattgcg    14460
gaaaactacg ttttgtcagc gtcgttaatc tctcacacac tcttactctc atacgccaca    14520
gtgcttaggc acttgcgtat ccttaacgat gagggctata tcgaattgta taagcaaggt    14580
aggacgctat acgcaaaaat ccgcgataat gcgaaacaaa ttcagattct gaattcagaa    14640
ctggaggggt ttaaaaacgt aagcgggaag ccgatattga ccaaggatga gactcctaag    14700
gagtttggca agaaagatag cctcactcaa agaggctaag gttgcactaa aagtagcaag    14760
cgacccagca aagtacttca acgaagaaca gatgactgag gcttacagga tattctggca    14820
gacatgggac ggggacataa ttagaagtgc tagaaggttc gtggaagtag caaaggcaaa    14880
ccccaagctc acaaaaggtg aagcaaccaa cataggcgta ttgttgggct tattcatctt    14940
catactaata ggtatagtac tattgcccgt aatcgttagc caagtcaaca acctcacaag    15000
cggtacttca ccccaagtaa ccggtactaa cgccacactc ctgaacttag tgccgttatt    15060
ctatatccta gtcctcataa tagtccccgc agtcgtggcg tataagatat acaaagactg    15120
aggtgtgagg gatggaaatc agtttaaagc caatcatttt tttggtcgtt tttatcatcg    15180
tagggatagc actattcggc cctataaaca gtgttgtaaa taacgttacc acatcggaa     15240 cctacactac tatagtttcc ggtactgtta ctacgtcttc atttgtgtca aatccgcaat    15300
acgtaggtag caataacgct actatcgtag ccttagtgcc gttattctat atccagtcc     15360 tcataatagt ccccgcagtc gtggcgtata agttgtataa ggaggagtga tatgaagtgg    15420
gtgcaaaagg cgataaagag acccggggagg gtacatcgct accttatgag gctctacggc    15480
aaacgggcgt ttacaaaaga cggtgacata aaggcaagtt atctcgataa ggcgataaag    15540
cacgttaaaa aagctaagat cccgaaagag aagaaacgta gtttactgtc agccctactg    15600
ttagcgaaaa ggcttaagcg gatgcaccgc aagtaggccc tttataaagt catattcttt    15660
ttctttccct gatgagtgcg ttaggggatg taatctacat cttgggtttt ctctttccgg    15720
ctttagggct aatcagccga aactatcttg ttaacttaat ggcattcata ataggaacag    15780 tcgcctttt ggtcttcgtc caaggctata ccgatatagc gttcagcagt tcgacgtttt     15840
```

```
acttaggagt actgcctcta ctacttggtc tcgtcaactt aggctatttc ttcaattggt    15900
tgagggagga aaggatatga ggtggggtag aagagatgat agggataccg gcaaaatact    15960
tcgaaatagg agtcgtaata gattcaacat ttatcattat gtctctactg ttaagaaagt    16020
caaagagaca gagagagaac tccttcgact tacgcaaaca tggaaggcta ttaggcttat    16080
atcttataat agcgtcggca tcagcattaa tcgtctcaca tctcgcctta tacacaaact    16140
acatgaacta cttaacgggc ttatctctta atgcgtttct gttttatctt gggttgaggt    16200
gtttgcatgt ctgatgggaa actcctttct gctttcgagg aggaattaag aaaagcccaa    16260
agcctagagg aattaaagca aaagtatgag gaagcccaaa aacaaatagc tgacggcaaa    16320
gtactaaaga ggctatacaa ggtttatgag aaaaggcaaa cagaattaat gcttcagcaa    16380
tataggcaga taaaggctga actgaaaaag aggaaaaagg taagaaaaaa ggataaagcc    16440
gacataaggg ttagagtagt aaagaagtgg ataaattcac gcttattcag tgctgagcat    16500
tacgtcgcat tactgcaaga aaatcaagac ggcttatcga tactatttct aagaagagca    16560
aaacttatag aaaatcaagg ctatctaatg ctagaagtga agaagttaag gaaggcatgg    16620
gttttaacgg ctgaacctat actccttgaa aggttaaaat tcccattcgg caaaaagttt    16680
gtagccgtgc atttcgtttt acccaattat ccttacacac ttcagcttaa accggatgaa    16740
aaactgaaag agttagcagt taaggcgata aacgggcctc aaataatgag cgcaatgata    16800
cgtacaaagt tcttcgaagc gttagctagg gtaggaagcg ggcctgatct gatgatgctc    16860
ataatcggcg ttgtcatggg gattggcata ggcgtagcga taggtttcgg tatagctaac    16920
gcaaacttaa cgcatttgct atctcaacac gttacgaaca ctacagtgac acatactacg    16980
accacaacga cttcacccct attcacgatt ccctcaaact cctcaaaagg ggtgagctaa    17040
aatggtctca gtaacagaaa taataacata tggacgagaa gcaatagaaa gaataatatg    17100
caaatatttt aaagattcga aaatagaaaa gatattattc ttgccgagtg aggaagacgt    17160
aaaggcaaaa tatatcattg gacgggtagg gtttataagg attagtaata cgtggtctgg    17220
aattgtcgta gttgacgggg tacaaatacc tttcgttgct gaagtccacc ttaatggcaa    17280
gattgatatt tacctttatc ctcaaaagga cttctactta gcacatttgg tgggtgagct    17340
gaatggctaa aaagaacggc ttaacagaac tagagcaatt aaagaaagag aacgaagagt    17400
tgagaaagaa gttagaagag ttagaggcgt tgatcaataa cgatagcgat gacgacgaag    17460
agttgcagga aatcgaaaac ccgtacaccg ttacaaaccg tgcaatagat gaattagtaa    17520
gcccaaagga cacaatgttc tatttgtcgg gaaaccagat atcgttaatc ttaagtgctt    17580
ttgaattcgc ccgcttaccg acgtacttcg gtgaggaacc ggtaacggag ttagcggaat    17640
acgcccataa gttgaaacat tatctcgttt cgaaaggagg aagaggaagg agggatatac    17700
tgagagtcct acgcgttagt tcaggtcaga caagagagaa cgtaaacaaa tcaattctga    17760
aacaattatt tgaccatggt aaggaacatg aagatgaaga agagtaatga atggttatgg    17820
ttagggacta aaattataaa cgcccataag actaacggct ttgaaagtgc gattattttc    17880
gggaaacaag gtacgggaaa gactacttac gcccttaagg tggcaaaaga agtttaccag    17940
agattaggac atgaaccgga caaggcatgg gaactggccc ttgactcttt attctttgag    18000
cttaaagatg cattgaggat aatgaaaata ttcaggcaaa atgataggac aataccaata    18060
ataattttcg acgatgctgg gatatggctt caaaaatatt tatggtataa ggaagagatg    18120
ataaagtttt accgtatata taacattatt aggaatatag taagcggggt gatcttcact    18180
accccttccc ctaacgatat agcgttttat gtgagggaaa agggtggaa gctgataatg    18240
```

```
ataacgagaa acggaagaca acctgacggt acgccaaagg cagtagctaa aatagcggtg   18300
aataagataa cgattataaa aggaaaaata acaaataaga tgaaatggag dacagtagac   18360
gattatacgg tcaagcttcc ggattgggta tataaagaat atgtggaaag aagaaaggtt   18420
tatgaggaaa aattgttgga ggagttggat gaggttttag atagtgataa caaaacggaa   18480
aacccgtcaa acccatcact actaacgaaa attgacgacg taacaagata gtgatacggg   18540
taatgtcaga cccctttag ccattccgca tactttttat attgctcttt cgctatgccg   18600
aagagcgata cgtaatgttg cgttaaaacg cgtgtcggtt tacgcccttg aataaaatcg   18660
ataatatcta acggtacgct tagctcagcc atcttagacg ctacgaattt gcggaagtac   18720
tttatcgcta tagcgtcctt atgacgtcgt tcaaagtccg ctattgccca cttcgtcacc   18780
tctactctct tcagaggcgt tatgtggaat acatagaaga cgcccttata tccctagtc    18840 caactaagcg gataataaca gacgtcgtta ccgcaaatgt ccctttcggg ttccttcagc   18900
actttcagta tttcgctcag cctaacgccc gactcgagag cgatacggta gatgaagtag   18960
acgttttcgc tatagtcttt tgctaattgt aacgtccttt ttatctcttc caacgttgga   19020
atgtagatat cagcgttcgc cttcttcacc tttaccgctt tcaatatttt atccgcaaat   19080
tcatcatgta tgatattgcg tgacgctaag aaacgtgcaa agagtcggta agccttctgt   19140
gcgtctctcg tctctttata cggctttgat atagcattga tgtagtcctt tgcagttttt   19200
tcgcttatcc cccttcgtt catgagatag tcgtagaacg cctttatgtt gccgtccgtc    19260
gcgtattggc gcaaattggc aaccaacgct attttacgtc gttcagttcc ctctttccg    19320 cctccggagc cggaggtccc gggttcaaat cccggcgggt ccgcttgtag gggagtatcc   19380
cctacgaccc ctaatttcat ttttagatat gattcaacga cgtcagctaa aggacccacg   19440
taacgctctt ttacctcacc gttttcatac tctagcttgt aaacataata ccgccctttc   19500
ctctcgcgta aaatataatc cccgtattta taacgcgtct tatctttcgt catttcgcct   19560
cacagtatta tggttgccaa acgggctta taagcattgg caacccgtta attttgccg    19620 ttaaaacacg ttgaattgaa agaagacggc aaagaatcca cacaggtaat actaaaaaag   19680
tagtattact tacattagaa ggactcattt gtccaccttg tattctagcc atgctatctc   19740
tgccttcagc tcatctagct tccccttat gtctgtcagg tcaagggaa ctcctctcat    19800 taacctgagt tcgttttcga tttttttcaag ctccttttcc aactcctcta gtttctctaa   19860
ttcctttagt cgttcttcca atttctttc caatttcccc tttgcgtcat ttataattat    19920
gcttactacc caaacaattc ctaaatcaga aataattatt aactcctctg agttgaatat   19980
cattttccgc ccctcgctaa atactcctta aagctctgat agaacccctt cagactaacc   20040
cgtaagtctg ttaggttctt ccagtattgt aatgggatta agtaatagta gcttactgca   20100
tctctctcaa atttgtcctt cttaatcttt ccttgctttt ctaagttgag tatttgcagt   20160
gctgagatac attttaactt gtcctcagca tctgaatagt gtataaacca aaccctcccc   20220
ataacctcat tctgctttgc aacttctact ttagtgctta atattgcgta aacgctttcg   20280
ccgtatcttt ctttgctctg ttcttcagtc catgaacttc ccgtaatatc tatccaaatt   20340
aaaggataat attctgtctt agccttaacg tataaagtca aatcgtattt atcttgcaga   20400
ccgctatagt attgctcatt tattacatta gttaaagtcc ccacgccagt tgggcggata   20460
taaacatcaa agtctaacaa acccttagcc cgccactttg ataaagagat taagagcttt   20520
ccaaaaacta ggtattctcg ccctaaataa gttgaaggga ggatataatc ctcagcttga   20580
```

```
ttaccccaat actttagctt aaaattagtt tcagccatct cactcaccat attgaaacgt    20640
gggctagtat gtgaatcagt actgatgcta ttgcaaataa cacacttgca gtagcaattc    20700
ctattacaat ccatttacca taatccacct tagtttgttg gtcaatatac tcgttgatga    20760
tctttagtat ttctggcttt agttctgata atgaaaggaa gacagaggca taaagtacta    20820
aggaggatgt gaacagatta tccgcctttt ctgaaagttt ataaagctca tatcttgctc    20880
tctcataatc ttcataatta ataatttcat caaacttttc tacttgctct tcatattctt    20940
tcttcagaga gtaaggagtt gtcttttcaa ttactcctaa ttttattaac ttcttaacag    21000
cttccttaaa tccttgttta ttgctagcat acgctaaagg gtcttttcct tcttgagaag    21060
ctctatagat aactatagca ccataaacaa tatttacaat atcgtatggt aaggaatacg    21120
caccgatttg ggcaatatct tcaactcttc tttgatccat ctagttcacc tcttttgat    21180 ttgtttgtag gtttctatcg cagttttcag cgatatcgca aatagcttcc ccttttccgt    21240
taggtatagc ctcttttcgc ctctttcttg acgctctttc acgaagccct cttgtattag    21300
gaactttttt gcatcataaa aggtggcagt ggacatggga aattctgcgt ttactttctt    21360
gtataggtca tatgttgcta ttccttcatt atcatataga taagccaata ctatggcttc    21420
ggggtagaag aatggtgtac ttttcatatc ctcctcactc ctcagcctct aatagcttaa    21480
ctgcctcctc tatcaactgt cccattgtct ttccagtctt tgccttaagc ctctgcagta    21540
aatggtaaaa agatttact tattccgttc tcttctgaga accgcttgct ttttacgatt      21600
aaattccaca tatcatctaa gatagagtgt tgtggttcta gcttcctcgt gtagattttc    21660
ccctattaat gttagtttat aaagaccggc tattttttca ctaatt                   21706

<210> SEQ ID NO 12
<211> LENGTH: 22015
<212> TYPE: DNA
<213> ORGANISM: Artificial Sequence
<220> FEATURE:
<223> OTHER INFORMATION: synthetic vector nucleotide sequence

<400> SEQUENCE: 12
tcattttttc ctaaaaattg ctcctttaca tttcatcacc ttatcctcga taatcttatt       60
tatagttctt aatgctgtta atggattccc tgcattataa atacttcttc caatgatttc      120
ataatccgct ccagcacata ctgcatcgcc ataacttcca ccttgactac ccatacccgg      180
agagactatg gtcattttt cgaagtctct cctatactgc gttatatgat ctaatttagt       240
ccctccaact actattcctt tgggcttat ctctcttata acgtttttaa tatagtctgc       300
gaataacgta ctccatcctt catgtgacat tacggcaact aagtataaat ttttagagtt      360
tgcatcaaga tatctttta attcatctag agatccctta acgcctataa aggaatgtgc       420
tatgaacgag ttggcgaaag ataatctttc aactatgctt ttcattatgt atccgatatc      480
tgcaagctta aaatcaacaa taatttcctc cacgtctaaa ccaattaaga gctctctagt      540
tttatccact cctagatcta aaactaaagg taaaccaact tttatcccat ataactcatt      600
ttccatctct ttaagaactt gatatgagag aggtttatcc attgctaata ttactctact      660
tttcaacatt cttcaccaaa taatctagaa ttgacttctt ttcattatcc ttaagtttat      720
cactcttcaa caattcatct agaatttctg aaattttaaa tagagagtgt aatttgactc      780
ctagtttttc caatctttgt gaagcccctt cttgtctatc tatgattact agtgcgtctg      840
aaactttacc tccaccgtta agaatctcca atgttgcttt ctctatggat actcctgtag      900
ttgcaacgtc atctactaac aatactcttt ttcctttac atcgagttct aatgtacgat      960
```

```
tagttccatg accttctttt tctattctaa tatatcccat aggctcttta aggttacaag    1020
ctatgaatgc cgataaggga actcctccag tggctattcc tactattata tcatggggta    1080
tatcttttgc tttctttata gcttgattaa ctatatcgta aaattctgga taatttggta    1140
aaggtcttaa gtctaagtaa tatggactaa ccttacctga tgttaaaacg aaacttccta    1200
ttaataataa tttcctttcg agtaagactt ctgcgaaatt catacgtaga gactctgcga    1260
aaaagaattt aaatatactt ctatcataac cagttataag ggctttgtga gattaagaca    1320
cgtagtttcg tcgcttgact tgaccagaga tgactacttt agaatattcg aacttgcaga    1380
caagttctat gatgtaaaaa aactaaatta tctatcaggg aaagtagttt cattagcatt    1440
ctttgagcca agtactagaa ctgctcaaag ctttcatact gcagcaataa aattaggtgc    1500
tgatgtgata ggatttgcat ccgaggagtc tacttcgata gcaaaaggtg aaaatttggc    1560
tgataccatt aggatgctaa acaactattc aaactgtatt gtaatgagac ataagtttga    1620
tggggcagca ttattcccta ggggccccat ctggaaaaat aatgaggaga gtatttagag    1680
atgaagctta aagatctta gataatctga gtttgatctt ttatgtgcat tgtggtcatg    1740
ttgaattttc acgatcattt aaggactccc ataaacataa attatgtatc aaaacattaa    1800
ttgaaatata gataatagtt atattatagt tatttttaga aaaacatcca atatgttaac    1860
aaaacgtctt ttacggaaat atataaatgt taaacaagtt aggtatacta tttataaaat    1920
agttaggtca taaaagtacc cgagaactag tccagtgtgg tggaattctg cagatatcaa    1980
caagtttgta caaaaaagct gaacgagaaa cgtaaaatga tataaatatc aatatattaa    2040
attagatttt gcataaaaaa cagactacat aatactgtaa aacacaacat atccagtcac    2100
tatggcggcc gcattaggca ccccaggctt tacactttat gcttccggct cgtataatgt    2160
gtggattttg agttaggatc cggtcgagat tttcaggagc taaggaagct aaaatggaga    2220
aaaaaatcac tggatatacc accgttgata tatcccaatg gcatcgtaaa gaacattttg    2280
aggcatttca gtcagttgct caatgtacct ataaccagac cgttcagctg gatattacgg    2340 ccttttttaaa gaccgtaaag aaaaataagc acaagtttta tccggccttt attcacattc    2400
ttgcccgcct gatgaatgct catccggaat tccgtatggc aatgaaagac ggtgagctgg    2460
tgatatggga tagtgttcac ccttgttaca ccgttttcca tgagcaaact gaaacgtttt    2520
catcgctctg gagtgaatac cacgacgatt ccggcagtt tctacacata tattcgcaag    2580
atgtggcgtg ttacggtgaa aacctggcct atttccctaa agggtttatt gagaatatgt    2640
ttttcgtctc agccaatccc tgggtgagtt tcaccagttt tgatttaaac gtggccaata    2700
tggacaactt cttcgccccc gttttcacca tgggcaaata ttatacgcaa ggcgacaagg    2760
tgctgatgcc gctggcgatt caggttcatc atgccgtttg tgatggcttt ccatgtcggc    2820
agaatgctta atgaattaca acagtactgc gatgagtggc agggcggggc gtaagatct    2880 ggatccggct tactaaaagc cagataacag tatgcgtatt tgcgcgctga ttttgcggt    2940 ataagaatat atactgatat gtatacccga agtatgtcaa aaagaggtat gctatgaagc    3000
agcgtattac agtgacagtt gacagcgaca gctatcagtt gctcaaggca tatatgatgt    3060
caatatctcc ggtctggtaa gcacaaccat gcagaatgaa gcccgtcgtc tgcgtgccga    3120
acgctggaaa gcggaaaatc aggaagggat ggctgaggtc gcccggttta ttgaaatgaa    3180
cggctctttt gctgacgaga acaggggctg gtgaaatgca gtttaaggtt tacacctata    3240
aaagagagag ccgttatcgt ctgtttgtgg atgtacagag tgatattatt gacacgcccg    3300
```

-continued

```
ggcgacggat ggtgatcccc ctggccagtg cacgtctgct gtcagataaa gtctcccgtg    3360
aactttaccc ggtggtgcat atcggggatg aaagctggcg catgatgacc accgatatgg    3420
ccagtgtgcc ggtctccgtt atcggggaag aagtggctga tctcagccac cgcgaaaatg    3480
acatcaaaaa cgccattaac ctgatgttct ggggaatata atgtcaggc tcccttatac     3540 acagccagtc tgcaggtcga ccatagtgac tggatatgtt gtgttttaca gtattatgta    3600
gtctgttttt tatgcaaaat ctaatttaat atattgatat ttatatcatt ttacgtttct    3660
cgttcagctt tcttgtacaa agtggttgat atccagcaca gtggcgccgg ccgccaccgc    3720
ggtggagctc gaattcgtaa tcatgtcata gctgtttcct gtgtgaaatt gttatccgct    3780
cacaattcca cacaacatac gagccggaag cataaagtgt aaagcctggg gtgcctaatg    3840
agtgagctaa ctcacattaa ttgcgttgcg ctcactgccc gctttccagt cgggaaacct    3900
gtcgtgccag ctgcattaat gaatcggcca acgcgcgggg agaggcggtt tgcgtattgg    3960
gcgctcttcc gcttcctcgc tcactgactc gctgcgctcg tcgttcggc tgcggcgagc     4020 ggtatcagct cactcaaagg cggtaatacg gttatccaca gaatcagggg ataacgcagg    4080
aaagaacatg tgagcaaaag gccagcaaaa ggccaggaac cgtaaaaagg ccgcgttgct    4140
ggcgtttttc cataggctcc gcccccctga cgagcatcac aaaaatcgac gctcaagtca    4200
gaggtggcga aacccgacag gactataaag ataccaggcg tttccccctg gaagctccct    4260
cgtgcgctct cctgttccga ccctgccgct taccggatac ctgtccgcct ttctcccttc    4320
gggaagcgtg gcgctttctc atagctcacg ctgtaggtat ctcagttcgg tgtaggtcgt    4380
tcgctccaag ctgggctgtg tgcacgaacc ccccgttcag cccgaccgct gcgccttatc    4440
cggtaactat cgtcttgagt ccaacccggt aagacacgac ttatcgccac tggcagcagc    4500
cactggtaac aggattagca gagcgaggta tgtaggcggt gctacagagt tcttgaagtg    4560
gtggcctaac tacggctaca ctagaaggac agtatttggt atctgcgctc tgctgaagcc    4620
agttaccttc ggaaaaagag ttggtagctc ttgatccggc aaacaaacca ccgctggtag    4680
cggtggtttt tttgtttgca agcagcagat tacgcgcaga aaaaaaggat ctcaagaaga    4740
tcctttgatc ttttctacgg ggtctgacgc tcagtggaac gaaaactcac gttaagggat    4800
tttggtcatg agattatcaa aaaggatctt cacctagatc cttttaaatt aaaaatgaag    4860
ttttaaatca atctaaagta tatatgagta aacttggtct gacagttacc aatgcttaat    4920
cagtgaggca cctatctcag cgatctgtct atttcgttca tccatagttg cctgactccc    4980
cgtcgtgtag ataactacga tacgggaggg cttaccatct ggccccagtg ctgcaatgat    5040
accgcgagac ccacgctcac cggctccaga tttatcagca ataaaccagc cagccggaag    5100
ggccgagcgc agaagtggtc ctgcaacttt atccgcctcc atccagtcta ttaattgttg    5160
ccgggaagct agagtaagta gttcgccagt taatagtttg cgcaacgttg ttgccattgc    5220
tacaggcatc gtggtgtcac gctcgtcgtt tggtatggct tcattcagct ccggttccca    5280
acgatcaagg cgagttacat gatccccat gttgtgcaaa aaagcggtta gctccttcgg    5340
tcctccgatc gttgtcagaa gtaagttggc cgcagtgtta tcactcatgg ttatggcagc    5400
actgcataat tctcttactg tcatgccatc cgtaagatgc ttttctgtga ctggtgagta    5460
ctcaaccaag tcattctgag aatagtgtat gcggcgaccg agttgctctt gcccggcgtc    5520
aatacgggat aataccgcgc cacatagcag aactttaaaa gtgctcatca ttggaaaacg    5580
ttcttcgggg cgaaaactct caaggatctt accgctgttg agatccagtt cgatgtaacc    5640
cactcgtgca cccaactgat cttcagcatc ttttactttc accagcgttt ctgggtgagc    5700
```

```
aaaaacagga aggcaaaatg ccgcaaaaaa gggaataagg gcgacacgga aatgttgaat    5760
actcatactc ttccttttc aatattattg aagcatttat cagggttatt gtctcatgag    5820
cggatacata tttgaatgta tttagaaaaa taaacaaata ggggttccgc gcacatttcc    5880
ccgaaaagtg ccacctgacg tctaagaaac cattattatc atgacattaa cctataaaaa    5940
taggcgtatc acgaggccct ttcgtctcgc gcgtttcggt gatgacggtg aaaacctctg    6000
acacatgcag ctcccggaga cggtcacagc ttgtctgtaa gcggatgccg ggagcagaca    6060
agcccgtcag ggcgcgtcag cgggtgttgg cgggtgtcgg ggctggctta actatgcggc    6120
atcagagcag attgtactga gagtgcacca tatgcggtgt gaaataccgc acagatgcgt    6180
aaggagaaaa taccgcatca ggcgccattc gccattcagg ctgcgcaact gttgggaagg    6240
gcgatcggtg cgggcctctt cgctattacg ccagctggcg aaagggggat gtgctgcaag    6300
gcgattaagt tgggtaacgc cagggttttc ccagtcacga cgttgtaaaa cgacggccag    6360
tgccaagctt gcatgcctgc agagtctcat atgtttcctc acttattgaa atgttaagcc    6420
ttttgactat cctatctttc ctcttctcta tcatttaggt caccttgttt attgttattt    6480
gaaatacgta tccgtcttcg tcacatcgaa gtataatttt gtatccatta ttagcatatt    6540
ctacgtcaaa gttcccacaa caataattcg ggtcttcgga ctcgttatag actttgctcc    6600
aaccatcttt ttgtagtgcc tcttctaagt agtctactct gatgaagcct tcatcatatt    6660
cgttcagtac cctaaagctt atactatcaa tgcctaatac gtctaatagc ttcaacagat    6720
cgaatatagg aacttgcacc atcatttcag ctcaccttaa tgagctgata taattccgct    6780
tctatctttt gaacttggaa gtatgccttg cctagctttt gcttatccat attgcccgtt    6840
attctatcaa tcttaatctc gtggattaat gataatagct ctctgacatc ctcatcaagc    6900
atttcaaata attctttctc taagacttct ttactcattg ttttttcacct tagcaaactc    6960 atctaacgtt gtttgtctca gttctctttt ctttatcaaa taaaattccg aatgtcccttt    7020 cttattgtta ttactgtact tcatgtcagt tcactgcttt gcctttataa atccttgatc    7080
cgtttgctca aaatttgcgg gctgggcatc aaatatctta gctatattgt cttgtgtttg    7140
ctcttgtttt tgttcttctt tctgctcttg cttaatccat ttgaacgttg tctttctgtt    7200
tttgtattgt acttcacact cgtctggatg tctttcgcaa atagctttca atgctctctg    7260
tatgttatac gcactcggga ctgaaatctc aaattgagct agtatatcct ctaacgttaa    7320
ttcacctttc ttttcaagaa ttttatacat tatttccgcc atcttgtatg aatttagagt    7380
ttgtgccata ttcccatccc actctatcta tactctatgt ataaattagt atttaagtct    7440
tactctatct atactctatc tatctctcta tatacacagt gtttgggtaa ctggcaaaat    7500
tctgtctgac tgctgtctga caagagttta ctctatctct ctatatctat atacacaaac    7560
agagttagtc gactctgtgt atcttatgta tcttatacaa aaaatatggg atgtgcaaaa    7620
tctgagctac taatactgct tgaatatata gatagagagt gtaaggacta cgagagttgt    7680
aaaagaataa tagtagagct agaagagaga gtgaagaaaa tagctttcgt agaagcaata    7740
aatgatttgt tctaaactac tttttttctct ctatctctat atctatatat atacataact    7800
aaaactaaaa gaataaacaa aaaactaaca aaatcaactc accattatac aaactcagaa    7860
aaactatttt tttgttatac tcttaccccca tatatatata gatatataga tagagagaga    7920
tagagtatag tagggcattt aagatttttag aagttcttca atgcgtcttc tgattgcatc    7980
tgcaacaaac tcttgtctgc ttatatatcc gcccttgcct gacgctatta gttcatctat    8040
```

```
ttgttttgct aattcgattg gaatcgaaac ggtcacatat tcttttttga ctgatttcct    8100
cggcatacgc tatctatact atattaatat gataatatta aatgattcac gatatataga    8160
tagagtatag atagagtaaa gtttaaatac ttatatagat agagtataga tagagggttc    8220
aaaaaatggt ttcaccccaa acccgaaaag aagaagagtt attagaaaaa caaaattcag    8280
ttttttattt gttaacttta ggaaggaaac cgtatggttc atatttgcat ataaaaattg    8340
aactagacga agatgaaaaa ttagagaagg aaatctatgc ggataacatt aagctagaga    8400
atgaattaag acaactgaag aggttgtatg aagtatatca gagcgtagag attgacgatg    8460
ctcagaaagc aatacagaag gaagcattac tgacgatagc gaaaatacta agtgtttttg    8520
acttctgagg aggctgaggg gcaatgaagg ctgaggaaac aatcgtggaa cagattcagg    8580
acataattca aaaacttcgc tattatacag gaagatcaaa tagacatttc aagatgatta    8640
gaaactatta tgaggagtgt ataataatag tagacgctga ggagtttata caagaaaata    8700
acactctaag cattactgta tattctgagg atcttatata ttatactgtt gatatcccgc    8760
tgaatttcat taaacatgta ttcgtatccg cttcgattga tcagctcaat gatcagcttc    8820
agctaaaata taatgagggt ctgattagag tttctcttac tttgaacgat gacttatgtg    8880
agaaactgag aagctcatac tgcggtgata ttacattctt taatgaggct gaggggcaat    8940
gaaggctagg gttgaataca tcaaattacc tagatgttac acaaaaactt atagaaaaat    9000
cgaagcgaaa agaacaacg acggtacaat agaattaacg ttagaggaaa caatgcaagt    9060
aatatccttt aaactacccc cggcgttaaa tgcaaaacta gaacaaattg cgatcaaaga    9120
aaagaaaagc aagagtgaaa ttattcgaat agcgttagcg aggtatgtag aaaatgttta    9180
gatgccccat ctgcgggttc aaaacgctga gattgttcgc gcttaaacaa catactcgaa    9240
gggagcatgt gttggtcaaa tgtcccatat gcgggttcac ggggaagcat ttatctcaac    9300
atttctatag taggtatgat attgaccatc tcatatactg ctacctattc tcttctttca    9360
gattgcctaa gaatgttagg ttagcaataa agagaaaatt agaggttgag tgaataatgt    9420
atcaatgtct acgttgtggt ggtatattta ataaagaag agaagtggtt gagcatttgc    9480
ttgtagggca taagcacaag gatagactaa cactggactt ttattatatc tacttcaggg    9540
tgagaggaca atgaacctaa ttgatatcat cttatttac ggctttcaat tcaacgatta    9600
ttggacaact gtcttagggt tgagagtggg tgcggaagag aagaatccca tagcgggtct    9660
gttcatttca tcaccgtatc gtttagcgtt gtttaagttt ggccttatca ccattggtat    9720
gtttatatta atttatgttg ttagattcaa gacatggaca gagatcgtat tgactgtaac    9780
agacgttgtc gaatgccttg tcacgctgaa taatacccct acgattagga ggtacaaaag    9840
gaggggcgtt agaggatgac ggagtcgacg gttgactcag gtagtaaaaa ataccctgagt    9900 aaccataagg ggatttttat tcatgtcaca ctggaagagt taaagcgtta ccaccaactt    9960
acgccggaac agaagaggtt gataagggca atcgtcaaaa cgcttattca taacccgcaa   10020
ctgttggatg aaagcagtta tctttacaga ttgctcgcga gtaaagcgat ttcacagttt   10080
gtctgcccgc tttgtctaat gcccttcagc tcttccgtat cactaaagca acacatccgt   10140
tatactgaac acacaaaggt ttgcccggtg tgtaaaaagg agtttacctc aaccgattca   10200
gccctagacc atgtttgcaa aaagcataat atctgcgtta gttaggctct ttttaaagtc   10260
taccttcttt ttcgcttaca atgaggaagt cccttctagc cctactaacc ctatccctag   10320
cgttactatc gtttttaata acaccatcga tggcattgaa ttctggcggt tcaccgatac   10380
cgatatatta taactattat aactactata gccttaacgc agaagggttt ggattcagtt   10440
```

```
tcaataatag caataattgg gttgaaacga actttatctc aataaccata aacttaccta   10500
gttcattacc aaataactat caaatcaata atgcctattc tatcgtagta ggattatcac   10560
catatccggt tagcaatata aacatttta atagcccatt agaagcatat gttgaactat    10620
tctcaaaccc accgaataca tatccaaatg aaataggatt tgtagttagt tacggctcaa   10680
ctgtatttta tagttatacc acactgtata gcagttttgc gggcacacaa ctaacaataa   10740
ctatatcata taccggaaat gggtttggtg tgcaattctc tgacagtaac gggttctctc   10800
actcagtttc ggtaagttcg gtaaactttg taccatatgg tgctctaata ctcggatcac   10860
taatcccgaa cgggaactat tactactacc cagtaggtaa catgttaccg aatgcatcgg   10920
tgaacttctc atatacgatc tcaagtttca caatagaagg aaacccggcc acatccgtcg   10980
atattaccac acttggatta gaaggaaaca ctgcaatata tacttcaagt agcaattggt   11040
tcaaatgggt atccggtagt gtggttatca caaatgccgt tgcctatacc tataccgatt   11100
tggctagaat aggaggaagt gcacaaataa actatactgc atcgcagcta tattaagcaa   11160 aatcttttt tacctctttt taaatctgtc ttatatgaaa aaactgttta cagttgtagg    11220 ttctatttc tctggtttgg ggatttggct taagtcaata gaccagtcat tttatttaac    11280
gaaagtattg tataacggaa aagtaattga aatagttcta acgcccgaga caaatgaagt   11340
cgtgaaatct tccaacggtg ttatgaacgc aagtgtaact tctctacctt ccacaattct   11400
ataccaagca caatccgtgc cttcaataaa tggaggaact cttagtgtaa taaataccac   11460
agttcaaccg ccatggtatg ctaacttatg gcctgaagtc ttaacaatag gtatagtgat   11520
gttgggaatt gcaatattca gctggattaa acttaaattt agaagatagc cctttttaaa   11580
gccataaatt ttttatcgct taatgaagtg gggactatta ttcttaataa tgtttatatc   11640 catttttcc ctcaactctt tagccctatt aatcggcgga ggagggccca acaataatgg    11700
tgcgggagtt tacactcaga ctataacagt taacggagga accgtacgaa ctactcttaa   11760
cggttcaacg cttctaccg caccatggct caacccctct tacgtaagcg tctacaacac    11820
atactacctt caggttttgc cgaaccaaga gtatattgac aacaacgttt cgttatccct   11880
aaatacggct aacattgcgt taaacgtcac ttggttattg gcgtcctcaa gcaatacggg   11940
atcctacggt gcaatcgcca taggctacgg agtgaacttt cccgcgggg ttgtcaataa    12000 ctacggtcct tccgcacctt acacgccgga cggaatcgta atatatctca tgaaaggagg   12060
catgccgacc tatcgtttat tcgtatactt caatggagtt gagcagttaa acgtttcagt   12120
cgggtcaatc agtgtgggac aaaaaatagg tttagggttc ttttatctac agaacacact   12180
ttacgtttac tactataacg gtactttaaa gacttggtca ttaacgcccg gtacgctgat   12240
tactataaat agtaattacg ttatagacgc acagaatata gggccgggct acggctacgg   12300
tcaatgggta atagttaatt atcaatatgc gatgccggtt actgcacaac tgacggttag   12360
ttatttcgca ttagggtaca atgtatatca tttcttaatg gcttatgcgg gtgctggaaa   12420
cccggtaaac ataactgcga ataacggggc ttcttacagt ataacgggta tagttgcaga   12480
gaagaacttt acgataacgg gaattcagca aggcctagcc tatgctttca gcttgttagg   12540
gaaaccgaat ggcttatact tattatatat ggggccaatt gagggcagcc caccaacgtg   12600
gtatgtaaac gtaaccgtag ggcttcagat cgttacaccc cagaaaacga taaactacaa   12660
cttaacaata ccagtaatcg ttgagggcta tgcgttatac ccttctgtta acgtaccttc   12720
cggaacttac ctaagcggac agactattag ctttacccctc tcatcgttct tgggatacc   12780
```

```
ttcaggctta ggctattaca ccgcagtaaa tctaatcgca aacgtaacaa taaacggtgt   12840
gagtcatgct atcccctata gtttcacccc gatagtgcaa accccgataa cttattacta   12900
cactgttata gtggatgaag gacaatttgc attaatagat tatcaaggga gtttcacagt   12960
cctacccgca cagagtcagc ccgtgatatt cattacttct tatcctagaa ttgggctatt   13020
aggacaaacg ataactgtga cttccagtt cacttataat agtcccgtag cgaatgtaac   13080
tcaatcagcg tttacgcaat catctaatat tctcgctttt gcctatgcga aaatggtaac   13140
aacaaacgct atagttcagt tcaaggcgta ttggctaagt gctaatgacg ggttggtgat   13200
tataactcaa acgaataact atctaattcc gtttaatagc agtataacgg cttaaaactt   13260
cgcaaacaat agtgttaata cgttaacgtt tcagattgta acgggtaact atgtacaaat   13320
aactagctca gcgggaggcg tgcttaccct aagcaatact agtccgatta taggaatagg   13380
gttctattac ggttccggtg tcctacacct gaactggttc ttcgttagcg gtatcatttt   13440
gcagtctgca acgcaaatc aggcttacgt tattttgacg gggactaacc caaatacgct   13500
ttcacagtat acgacgggct atactaacgc ttcggggttc ggtactgtaa cgctgaagtt   13560
gagttacact ccttacgaac ttgtggatgt agactggtac ggcgttacat acgctttgtt   13620
aaacattagc gtttcaaaca ctactacagt aagcagtact acgaccgtga acacaacaac   13680
gcttaactat aactcacta agcctttcag caataacata gcacctaaca gtcagcttta   13740
tgacttctca gcgtatcagc cgtgggcgga aattatcggg attgtggtcg tggtcgtcat   13800
agctctgctg ggctggaagt tcggcgggtc tgcgggagct tcgggtggtg cggttatggg   13860
gttaatcgca gtcagctact taggtttact gccttggtac ctattctaca tcttcgtatt   13920
cggtatcgct ctattacttg ctaaagtatt tgtagaccgt ttcatgggga gggaggaatg   13980
acggacgcaa tcagtttagc cttgcaaacg ggcttagggc cggtggtagg ggtaattatc   14040
atactggcaa tgatggggct aacgtataag atagcgggaa agatcccggc aatcataacg   14100
ggaatagcct cggctttcgt cctaatgttt atggattttt taccgttatt ttggggtatc   14160
gcaataatct tcgggttaat cgcgggtatg gtggtgacaa gggatgggga ctaagttagt   14220
cgtttacgtc ttattgtttg acgtcttcct atcgttagtg gtaggtgcct actcgggtat   14280
agcaccgcca agtattccac cggtacctac atatgcttca gcccaactca cggcaagtct   14340
aatcacatgg acagtgggat ggcctcctat tacattatgg cctcagataa cgcttattcc   14400
gccgttttcg attttgggtg caaacttccc cggcttaacc attcctagct taacgatacc   14460
cggtgtaacg ctcttctcaa taagcttcag ctggttagcc ccaattattt atattgcaaa   14520
ttggatcatt tgggtctttc agactgttgc tagtgtgcta tcttatttac ttaatatctt   14580
tacgggttcg gtaggtctat tgagtagtgt acccgtctta gggccatttt tgaccgcctt   14640
cgtgttgata gttaacttcg tgttagtgtg ggaattaatc aagttaatta ggggtcgga   14700 atgacggagt ataacgcaaa cagtataagg gctaagatac tgaggcgtaa aatccttcaa   14760
ctgattgcgg aaaactacgt tttgtcagcg tcgttaatct ctcacacact cttactctca   14820
tacgccacag tgcttaggca cttgcgtatc cttaacgatg agggctatat cgaattgtat   14880
aagcaaggta ggacgctata cgcaaaaatc cgcgataatg cgaaacaaat tcagattctg   14940
aattcagaac tggaggggtt taaaaacgta agcgggaagc cgatattgac caaggatgag   15000
actcctaagg agtttggcaa gaaagatagc ctcactcaaa gaggctaagg ttgcactaaa   15060
agtagcaagc gaccccagaa agtacttcaa cgaagaacag atgactgagg cttacaggat   15120
attctggcag acatgggacg gggacataat tagaagtgct agaaggttcg tggaagtagc   15180
```

```
aaaggcaaac cccaagctca caaaaggtga agcaaccaac ataggcgtat tgttgggctt   15240
attcatcttc atactaatag gtatagtact attgcccgta atcgttagcc aagtcaacaa   15300
cctcacaagc ggtacttcac cccaagtaac cggtactaac gccacactcc tgaacttagt   15360
gccgttattc tatatcctag tcctcataat agtccccgca gtcgtggcgt ataagatata   15420
caaagactga ggtgtgaggg atggaaatca gtttaaagcc aatcattttt ttggtcgttt   15480
ttatcatcgt agggatagca ctattcggcc ctataaacag tgttgtaaat aacgttacca   15540
catcgggaac ctacactact atagtttccg gtactgttac tacgtcttca tttgtgtcaa   15600
atccgcaata cgtaggtagc aataacgcta ctatcgtagc cttagtgccg ttattctata   15660
tcctagtcct cataatagtc cccgcagtcg tggcgtataa gttgtataag gaggagtgat   15720
atgaagtggg tgcaaaaggc gataaagaga cccgggaggg tacatcgcta ccttatgagg   15780
ctctacggca aacgggcgtt tacaaaagac ggtgacataa aggcaagtta tctcgataag   15840
gcgataaagc acgttaaaaa agctaagatc ccgaaagaga agaaacgtag tttactgtca   15900
gccctactgt tagcgaaaag gcttaagcgg atgcaccgca agtaggccct ttataaagtc   15960
atattctttt tctttccctg atgagtgcgt taggggatgt aatctacatc ttgggttttc   16020
tctttccggc tttagggcta atcagccgaa actatcttgt taacttaatg gcattcataa   16080
taggaacagt cgccttttttg gtcttcgtcc aaggctatac cgatatagcg ttcagcagtt   16140
cgacgtttta cttaggagta ctgcctctac tacttggtct cgtcaactta ggctatttct   16200
tcaattggtt gagggaggaa aggatatgag gtggggtaga agagatgata gggataccgg   16260
caaaatactt cgaaatagga gtcgtaatag attcaacatt tatcattatg tctctactgt   16320
taagaaagtc aaagagacag agagagaact ccttcgactt acgcaaacat ggaaggctat   16380
taggcttata tcttataata gcgtcggcat cagcattaat cgtctcacat ctcgcccttat  16440 acacaaacta catgaactac ttaacgggct tatctcttaa tgcgtttctg ttttatcttg   16500
ggttgaggtg tttgcatgtc tgatgggaaa ctcctttctg ctttcgagga ggaattaaga   16560
aaagcccaaa gcctagagga attaaagcaa aagtatgagg aagcccaaaa acaaatagct   16620
gacggcaaag tactaaagag gctatacaag gtttatgaga aaaggcaaac agaattaatg   16680
cttcagcaat ataggcagat aaaggctgaa ctggaaaaga ggaaaaaggt aaagaaaaag   16740
gataaagccg acataagggt tagagtagta aagaagtgga taaattcacg cttattcagt   16800
gctgagcatt acgtcgcatt actgcaagaa aatcaagacg gcttatcgat actatttcta   16860
agaagagcaa aacttataga aaatcaaggc tatctaatgc tagaagtgaa gaagttaagg   16920
aaggcatggg ttttaacggc tgaacctata ctccttgaaa ggttaaaatt cccattcggc   16980
aaaaagtttg tagccgtgca tttcgtttta cccaattatc cttacacact tcagcttaaa   17040
ccggatgaaa aactgaaaga gttagcagtt aaggcgataa acgggcctca aataatgagc   17100
gcaatgatac gtacaaagtt cttcgaagcg ttagctaggg taggaagcgg gcctgatctg   17160
atgatgctca taatcggcgt tgtcatgggg attggcatag gcgtagcgat aggtttcggt   17220
atagctaacg caaacttaac gcatttgcta tctcaacacg ttacgaacac tacagtgaca   17280
catactacga ccacaacgac ttcaccctca ttcacgattc cctcaaactc ctcaaaaggg   17340
gtgagctaaa atggtctcag taacagaaat aataacatat ggacgagaag caatagaaag   17400
aataatatgc aaatatttta aagattcgaa aatagaaaag atattattct tgccgagtga   17460
ggaagacgta aaggcaaaat atatcattgg acgggtaggg tttataagga ttagtaatac   17520
```

```
gtggtctgga attgtcgtag ttgacggggt acaaatacct ttcgttgctg aagtccacct    17580
taatggcaag attgatattt acctttatcc tcaaaaggac ttctacttag cacatttggt    17640
gggtgagctg aatggctaaa agaacggct taacagaact agagcaatta aagaaagaga    17700
acgaagagtt gagaaagaag ttagaagagt tagaggcgtt gatcaataac gatagcgatg    17760
acgacgaaga gttgcaggaa atcgaaaacc cgtacaccgt tacaaaccgt gcaatagatg    17820
aattagtaag cccaaaggac acaatgttct atttgtcggg aaaccagata tcgttaatct    17880
taagtgcttt tgaattcgcc cgcttaccga cgtacttcgg tgaggaaccg gtaacggagt    17940
tagcggaata cgcccataag ttgaaacatt atctcgtttc gaaggagga agaggaagga    18000 gggatatact gagagtccta cgcgttagtt caggtcagac aagagagaac gtaaacaaat    18060
caattctgaa acaattattt gaccatggta aggaacatga agatgaagaa gagtaatgaa    18120
tggttatggt tagggactaa aattataaac gcccataaga ctaacggctt tgaaagtgcg    18180
attattttcg ggaaacaagg tacgggaaag actacttacg cccttaaggt ggcaaaagaa    18240
gtttaccaga gattaggaca tgaaccggac aaggcatggg aactggccct tgactcttta    18300
ttctttgagc ttaaagatgc attgaggata atgaaaatat tcaggcaaaa tgataggaca    18360
ataccaataa taattttcga cgatgctggg atatggcttc aaaaatattt atggtataag    18420
gaagagatga taaagtttta ccgtatatat aacattatta ggaatatagt aagcggggtg    18480
atcttcacta cccctttcccc taacgatata gcgttttatg tgagggaaaa ggggtggaag    18540
ctgataatga taacgagaaa cggaagacaa cctgacggta cgccaaaggc agtagctaaa    18600
atagcggtga ataagataac gattataaaa ggaaaaataa caaataagat gaaatggagg    18660
acagtagacg attatacggt caagcttccg gattgggtat ataaagaata tgtggaaaga    18720
agaaaggttt atgaggaaaa attgttggag gagttggatg aggttttaga tagtgataac    18780
aaaacggaaa acccgtcaaa cccatcacta ctaacgaaaa ttgacgacgt aacaagatag    18840
tgatacgggt aatgtcagac cccttttagc cattccgcat acttttttata ttgctctttc    18900 gctatgccga agagcgatac gtaatgttgc gttaaaacgc gtgtcggttt acgcccttga    18960
ataaaatcga taatatctaa cggtacgctt agctcagcca tcttagacgc tacgaatttg    19020
cggaagtact ttatcgctat agcgtcctta tgacgtcgtt caaagtccgc tattgcccac    19080
ttcgtcacct ctactctctt cagaggcgtt atgtggaata catagaagac gcccttatat    19140
cccctagtcc aactaagcgg ataataacag acgtcgttac cgcaaatgtc cctttcgggt    19200
tccttcagca ctttcagtat ttcgctcagc ctaacgcccg actcgagagc gatacggtag    19260
atgaagtaga cgttttcgct atagtctttt gctaattgta acgtcctttt tatctcttcc    19320
aacgttggaa tgtagatatc agcgttcgcc ttcttcacct ttaccgcttt caatatttta    19380
tccgcaaatt catcatgtat gatattgcgt gacgctaaga aacgtgcaaa gagtcggtaa    19440
gccttctgtg cgtctctcgt ctctttatac ggctttgata tagcattgat gtagtccttt    19500 gcagttttt cgcttatccc cctttcgttc atgagatagt cgtagaacgc ctttatgttg    19560
ccgtccgtcg cgtattggcg caaattggca accaacgcta ttttacgtcg ttcagttccc    19620 tctttttccgc ctccggagcc ggaggtcccg ggttcaaatc ccggcgggtc cgcttgtagg    19680
ggagtatccc ctacgacccc taatttcatt tttagatatg attcaacgac gtcagctaaa    19740
ggacccacgt aacgctcttt tacctcaccg ttttcatact ctagcttgta aacataatac    19800
cgccctttcc tctcgcgtaa aatataatcc ccgtatttat aacgcgtctt atctttcgtc    19860
atttcgcctc acagtattat ggttgccaaa acgggcttat aagcattggc aacccgttaa    19920
```

```
ttttttgccgt taaaacacgt tgaattgaaa gaagacggca aagaatccac acaggtaata    19980
ctaaaaaagt agtattactt acattagaag gactcatttg tccaccttgt attctagcca    20040
tgctatctct gccttcagct catctagctt cccctttatg tctgtcaggt caagggggaac   20100 tcctctcatt aacctgagtt cgttttcgat tttttcaagc tccttttcca actcctctag    20160
tttctctaat tcctttagtc gttcttccaa tttcttttcc aatttcccct ttgcgtcatt    20220
tataattatg cttactaccc aaacaattcc taaatcagaa ataattatta actcctctga    20280
gttgaatatc attttccgcc cctcgctaaa tactccttaa agctctgata gaacccttc     20340 agactaaccc gtaagtctgt taggttcttc cagtattgta atgggattaa gtaatagtag    20400
cttactgcat ctctctcaaa tttgtccttc ttaatctttc cttgcttttc taagttgagt    20460
atttgcagtg ctgagataca ttttaacttg tcctcagcat ctgaatagtg tataaaccaa    20520
accctcccca taacctcatt ctgctttgca acttctactt tagtgcttaa tattgcgtaa    20580
acgctttcgc cgtatctttc tttgctctgt cttcagtcc atgaacttcc cgtaatatct     20640
atccaaatta aaggataata ttctgtctta gcctaacgt ataaagtcaa atcgtattta     20700
tcttgcagac cgctatagta ttgctcattt attacattag ttaaagtccc cacgccagtt    20760
gggcggatat aaacatcaaa gtctaacaaa cccttagccc gccactttga taaagagatt    20820
aagagctttc caaaaactag gtattctcgc cctaaataag ttgaagggag gatataatcc    20880
tcagcttgat taccccaata ctttagctta aaattagttt cagccatctc actcaccata    20940
ttgaaacgtg ggctagtatg tgaatcagta ctgatgctat tgcaaataac acacttgcag   21000
tagcaattcc tattacaatc catttaccat aatccaccttt agtttgttgg tcaatatact   21060
cgttgatgat ctttagtatt tctggcttta gttctgataa tgaaaggaag acagaggcat   21120
aaagtactaa ggaggatgtg aacagattat ccgccttttc tgaaagttta taaagctcat    21180
atcttgctct ctcataatct tcataattaa taatttcatc aaactttttct acttgctctt   21240 catattcttt cttcagagag taaggagttg tcttttcaat tactcctaat tttattaact   21300
tcttaacagc ttccttaaat ccttgtttat tgctagcata cgctaaaggg tcttttcctt    21360
cttgagaagc tctatagata actatagcac cataaacaat atttacaata tcgtatggta    21420
aggaatacgc accgatttgg gcaatatctt caactcttct ttgatccatc tagttcacct    21480 cttttttgatt tgtttgtagg tttctatcgc agttttcagc gatatcgcaa atagcttccc   21540
cttttccgtt aggtatagcc tcttttcgcc tctttcttga cgctctttca cgaagccctc    21600
ttgtattagg aacttttttg catcataaaa ggtggcagtg gacatgggaa attctgcgtt    21660
tactttcttg tataggtcat atgttgctat tccttcatta tcatatagat aagccaatac    21720
tatggcttcg gggtagaaga atggtgtact tttcatatcc tcctcactcc tcagcctcta    21780
atagcttaac tgcctcctct atcaactgtc ccattgtctt tccagtctttt gccttaagcc    21840 tctgcagtaa atggtaaaaa gattttactt attccgttct cttctgagaa ccgcttgctt    21900
tttacgatta aattccacat atcatctaag atagagtgtt gtggttctag cttcctcgtg    21960 tagatttttcc cctattaatg ttagtttata aagaccggct attttttcac taatt         22015
```

<210> SEQ ID NO 13
<211> LENGTH: 61
<212> TYPE: DNA
<213> ORGANISM: Artificial Sequence
<220> FEATURE:
<223> OTHER INFORMATION: synthetic Mini Promoter nucleotide sequence

```
<400> SEQUENCE: 13
atgttaaaca agttaggtat actatttata aaatagttag gtcataaaag tacccgagaa      60
t                                                                     61

<210> SEQ ID NO 14
<211> LENGTH: 61
<212> TYPE: DNA
<213> ORGANISM: Artificial Sequence
<220> FEATURE:
<223> OTHER INFORMATION: synthetic Mini Promoter nucleotide sequence

<400> SEQUENCE: 14
gctgagagaa aaattttttat ataagcgata ctaatgttct cacggaacgg tgttgtgagg     60
t                                                                     61

<210> SEQ ID NO 15
<211> LENGTH: 119
<212> TYPE: DNA
<213> ORGANISM: Artificial Sequence
<220> FEATURE:
<223> OTHER INFORMATION: synthetic nucleotide sequence

<400> SEQUENCE: 15
atgactctcc aaattcagtt taaaaagtac gagctacctc cattacccta caagatagat      60
gcattagaac cgtatataag taaagatata attgatgtac attataacgg acatcataa      119

<210> SEQ ID NO 16
<211> LENGTH: 75
<212> TYPE: DNA
<213> ORGANISM: Artificial Sequence
<220> FEATURE:
<223> OTHER INFORMATION: synthetic nucleotide sequence

<400> SEQUENCE: 16
atgaataagc tgattcctat atttgtcgtg gtaataattg tactaggcat aattgtgtct      60
atagaatttg gaaag                                                      75

<210> SEQ ID NO 17
<211> LENGTH: 93
<212> TYPE: DNA
<213> ORGANISM: Artificial Sequence
<220> FEATURE:
<223> OTHER INFORMATION: synthetic nucleotide sequence

<400> SEQUENCE: 17
atgaataaat tatatattgt gcttccggta attgtgataa tagccattgg cgttatgggg      60
ggaatcattt acttgcatca acagtctctc agc                                  93

<210> SEQ ID NO 18
<211> LENGTH: 90
<212> TYPE: DNA
<213> ORGANISM: Artificial Sequence
<220> FEATURE:
<223> OTHER INFORMATION: synthetic nucleotide sequence

<400> SEQUENCE: 18
atgaataaaa ccctcggtct aatcctaacc tctgtattcc tactatccac tttaggcata     60
ataactggat ttgtaatacc aacacaagct                                      90

<210> SEQ ID NO 19
<211> LENGTH: 87
```

```
<212> TYPE: DNA
<213> ORGANISM: Artificial Sequence
<220> FEATURE:
<223> OTHER INFORMATION: synthetic nucleotide sequence

<400> SEQUENCE: 19
ttggttgtga aaaaacatt  cgttttatct accttgatat taatttcagt tgtagcgtta    60
gtgagtacag cagtttatac atctggt                                         87

<210> SEQ ID NO 20
<211> LENGTH: 90
<212> TYPE: DNA
<213> ORGANISM: Artificial Sequence
<220> FEATURE:
<223> OTHER INFORMATION: synthetic nucleotide sequence

<400> SEQUENCE: 20
atgaagctaa ttgaaatgct aaaggagata acccaagtcc cagggatttc agggtatgag    60
gaaagagtta gagagaaaat tattgaatgg                                      90

<210> SEQ ID NO 21
<211> LENGTH: 90
<212> TYPE: DNA
<213> ORGANISM: Artificial Sequence
<220> FEATURE:
<223> OTHER INFORMATION: synthetic nucleotide sequence

<400> SEQUENCE: 21
atggtagatt gggaactaat gaaaaaaata atagaatctc caggagtttc tgggtatgaa    60
cacctgggaa ttagagacct tgtggtagat                                      90

<210> SEQ ID NO 22
<211> LENGTH: 30
<212> TYPE: PRT
<213> ORGANISM: Artificial Sequence
<220> FEATURE:
<223> OTHER INFORMATION: synthetic amino acid sequence

<400> SEQUENCE: 22

Met Lys Leu Ile Glu Met Leu Lys Glu Ile Thr Gln Val Pro Gly Ile
1               5                   10                  15

Ser Gly Tyr Glu Glu Arg Val Arg Glu Lys Ile Ile Glu Trp
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: synthetic amino acid sequence

<400> SEQUENCE: 23

Met Val Asp Trp Glu Leu Met Lys Lys Ile Ile Glu Ser Pro Gly Val
1               5                   10                  15

Ser Gly Tyr Glu His Leu Gly Ile Arg Asp Leu Val Val Asp
            20                  25                  30

<210> SEQ ID NO 24
<211> LENGTH: 13
<212> TYPE: DNA
<213> ORGANISM: Artificial Sequence
<220> FEATURE:
<223> OTHER INFORMATION: synthetic nucleotide sequence for ribosomal
      binding site
```

<400> SEQUENCE: 24
gaggtgagtc gga                                                                              13

<210> SEQ ID NO 25
<211> LENGTH: 1308
<212> TYPE: PRT
<213> ORGANISM: Sulfolobus solfataricus

<400> SEQUENCE: 25

Met Glu Ser Arg Ile Ile Gln Val Val Ile Ser Thr Phe Leu Val
1               5                   10                  15

Leu Ser Val Leu Phe Pro Leu Leu Ser Leu Ala Tyr Ser Thr Thr Ser
            20                  25                  30

Ile Asn Pro Ser Tyr Pro Gln Ser Asn Val Ile Ser Ala Leu Pro Ser
        35                  40                  45

Asn Thr Asn Ile Ile Leu Tyr Phe Phe Ile Pro Pro Lys Asn Leu Asn
    50                  55                  60

Glu Leu Tyr Leu Ile Ala Gln Glu Val Ala Asn His Gln Ile Lys Pro
65                  70                  75                  80

Leu Ser Asn Ala Gln Leu Val Ser Met Phe Ser Asn Gln Asp Lys Val
                85                  90                  95

Asn Glu Ser Ile Lys Tyr Leu Glu Ser Lys Gly Phe Thr Ile Ile Tyr
            100                 105                 110

Arg Ser Pro Phe Glu Ile Met Ala Glu Ala Pro Val Ser Leu Val Ser
        115                 120                 125

Ser Val Phe Glu Thr Ser Phe Val Leu Ala Lys Ser Thr Asn Gly Glu
    130                 135                 140

Ile Tyr Tyr Lys Pro Ala Gly Asn Val Lys Ile Pro Ser Thr Leu Asn
145                 150                 155                 160

Asn Leu Leu Ile Gly Gly Leu Thr Asn Phe Thr Asn Val Ser Leu Pro
                165                 170                 175

Leu Ile Gln Leu Gly Lys Leu Glu Asn Gly Asn Leu Ile Pro Asn Lys
            180                 185                 190

Gln Ala Tyr Ser Ser Phe Val Tyr Thr Phe Gln Phe Ser Ala Thr Trp
        195                 200                 205

Tyr Thr Pro Lys Val Ile Glu Gly Ala Tyr Asn Ile Thr Pro Leu Leu
    210                 215                 220

Asn Ser Thr Ala Asp Lys Lys Val Thr Ile Ala Ile Asp Ala Tyr
225                 230                 235                 240

Gly Asp Pro Glu Ile Tyr Gln Asp Val Asn Leu Phe Asp Ala Arg Phe
                245                 250                 255

Gly Leu Pro Pro Ile Asn Leu Thr Val Leu Pro Val Gly Pro Tyr His
            260                 265                 270

Pro Glu Asn Gly Leu Phe Thr Gly Trp Phe Glu Glu Val Ala Leu Asp
        275                 280                 285

Val Glu Ala Ala His Ala Ala Ala Pro Tyr Ser Asn Ile Leu Leu Val
    290                 295                 300

Val Ala Pro Ser Ala Thr Leu Glu Gly Leu Phe Ser Ala Ile Asp Val
305                 310                 315                 320

Val Val Ser Glu Asp Leu Ala Gln Val Val Ser Met Ser Trp Gly Leu
                325                 330                 335

Pro Gly Ile Leu Phe Gly Ala Ser Gly Phe Tyr Ala Val Phe Asn Gly
            340                 345                 350

-continued

```
Ile Ile Phe Pro Asn Tyr Pro Tyr Asp Tyr Tyr Phe Glu Leu Gly
            355                 360                 365

Ser Ala Glu Gly Ile Thr Phe Leu Ala Ser Ser Gly Asp Leu Gly Ala
370                 375                 380

Tyr Asn Asp Leu Pro Thr Val Tyr Gly Ser Ala Asn Tyr Pro Ala Ser
385                 390                 395                 400

Ser Pro Phe Val Thr Ala Val Gly Gly Thr Ser Leu Phe Ala Asn Ile
                405                 410                 415

Thr Ser Gly Tyr Ile Ser Thr Tyr Asn Ser Thr Gly Asn Phe Gly Ala
                420                 425                 430

Glu Ile Ala Trp Ser Val Asn Pro Leu Tyr Phe Gly Val Ile Gln Gly
                435                 440                 445

Gly Val Ser Ser Gly Gly Tyr Ser Gln Leu Phe Pro Ala Pro Trp
            450                 455                 460

Tyr Gln Arg Tyr Val Thr His Ser Asn Tyr Arg Ala Ile Pro Asp Val
465                 470                 475                 480

Ala Ala Asp Ala Asn Pro Tyr Thr Gly Phe Thr Ile Tyr Ala Leu Gly
                485                 490                 495

Gln Glu Val Val Ile Gly Gly Thr Ser Leu Ser Ala Pro Leu Trp Ala
                500                 505                 510

Gly Ile Ile Ala Asp Ile Asp Gly Ile Ile Gly His Pro Leu Gly Leu
            515                 520                 525

Val Asn Pro Ile Leu Tyr Glu Ile Tyr Gln Asn Thr Thr Leu Tyr His
            530                 535                 540

Gln Ala Phe His Gln Ile Ser Leu Gly Tyr Asn Gly Tyr Tyr Tyr Ala
545                 550                 555                 560

Asn Ser Ser Tyr Asn Leu Val Thr Gly Leu Gly Ser Pro Asn Ala Gly
                565                 570                 575

Met Leu Gly Val Ile Ile Lys His Ser Leu Ser Lys Ser Leu Ala Ile
                580                 585                 590

Ser Val Ser Thr Phe Glu Thr Gly Val Phe Gln Pro Trp Tyr Phe Tyr
            595                 600                 605

Gly Ser Thr Phe Thr Ile Ala Ala Tyr Ile Thr Tyr Pro Asn Asn Thr
610                 615                 620

Ile Val Ser Gln Gly Ser Phe Asn Ala Tyr Ile Tyr Thr Ser Glu Gly
625                 630                 635                 640

Tyr Leu Ala Thr Val Pro Leu Ser Phe Asn Gly Ser Tyr Trp Val Gly
                645                 650                 655

Asn Tyr Thr Ile Thr Pro Asn Asn Pro Pro Asn Leu Trp Glu Ile Val
                660                 665                 670

Val Asn Gly Ser Ser Asp Gln Phe Thr Gly Val Gly Thr Val Glu Val
            675                 680                 685

Asp Val Gly Glu Ser Ile Asn Ile Val Ser Pro Ile Pro Tyr Pro Tyr
            690                 695                 700

Ser Phe Pro Ile Pro Tyr Asn Ser Pro Phe Gly Ile Glu Ala Trp Ile
705                 710                 715                 720

Tyr Tyr Pro Asn Gly Thr Pro Val Val Asn Gln Ser Val Thr Ala Tyr
                725                 730                 735

Leu Val Ser Asn Asp Gly Lys Leu Leu Ala Ser Ile Pro Leu Thr Met
                740                 745                 750

Met Ala Pro Gly Leu Tyr Glu Gly Ser Tyr Ala Leu Leu Pro Pro Leu
            755                 760                 765

Pro Gln Gly Thr Tyr Leu Leu Ile Val Asn Asp Ser Tyr Gly Ser Ala
```

-continued

```
            770                 775                 780
Phe Ser Tyr Val Tyr Phe Gly Glu Tyr Asn Phe Gly Ala Ile Leu Thr
785                 790                 795                 800

Pro Ile Asn Asp Gly Phe Pro Ala Ala Ser Pro Gly Gln Asn Ile Thr
                805                 810                 815

Ile Ile Asp Glu Val Leu Thr Pro Glu Leu Thr Gly Leu Phe Thr Ser
                820                 825                 830

Asn Val Thr Ala Tyr Ile Tyr Asn Gln His Gly Asn Leu Ile Asp Gln
                835                 840                 845

Val Lys Leu Thr Pro Ala Pro Asp Glu Ile Gln Phe Gly Val Tyr Leu
850                 855                 860

Leu Phe Phe Leu Tyr Tyr Ala Asn Phe Thr Ile Pro Phe Asp Ala Ser
865                 870                 875                 880

Pro Gly Phe Tyr Asn Val Val Ile Gln Ser Ile Ser Asn Thr Ser Thr
                885                 890                 895

Gly Leu Val Lys Ala Asp Phe Ile Thr Ser Phe Tyr Val Ser Pro Ala
                900                 905                 910

Asn Leu Thr Leu Asn Val Lys Val Asn Asn Val Val Tyr Glu Gly Glu
                915                 920                 925

Leu Leu Lys Ile Phe Ala Asn Ile Thr Tyr Pro Asn Gly Thr Pro Val
930                 935                 940

Lys Tyr Gly Met Phe Thr Ala Thr Ile Leu Pro Thr Ser Leu Asn Tyr
945                 950                 955                 960

Glu Gln Leu Ile Ile Gly Phe Glu Ala Gly Ile Pro Leu Gln Tyr Asn
                965                 970                 975

Ser Thr Leu Gly Glu Trp Val Gly Ile Tyr Ser Ile Pro Ser Ile Phe
                980                 985                 990

Tyr Gly Ser Ile Phe Gln Gly Ser  Ser Val Tyr Ser Leu  Ala Gly Pro
                995                 1000                1005

Trp Asn  Val Ile Val Ser Gly  Val Ser Trp Asn Gly  Tyr Asn Leu
    1010                1015                1020

Tyr Ser  Thr Pro Ser Ser Phe  Asn Phe Val Asn Val  Met Pro Tyr
    1025                1030                1035

Thr Phe  Ile Asn Asn Ile Val  Val Ser Ser Lys Ser  Leu Asp Ser
    1040                1045                1050

Pro Leu  Leu Ser Lys Ile Asn  Ser Thr Thr Tyr Met  Leu Ser Asn
    1055                1060                1065

Val Lys  Ser Asn Asn Ile Thr  Ile Asn Gly Met Asn  Val Ile Leu
    1070                1075                1080

Ser Asn  Val Ile Ala Asn Thr  Val Thr Val Lys Asn  Ser Asn Ile
    1085                1090                1095

Met Ile  Thr Ser Ser Thr Ile  Asn Gln Leu Val Leu  Asp Asn Ser
    1100                1105                1110

Ser Val  Ser Ile Ile Gly Ser  Lys Ile Gly Gly Asp  Asn Ile Ala
    1115                1120                1125

Val Val  Ala Asn Asp Ser Asn  Val Thr Ile Val Ser  Ser Val Ile
    1130                1135                1140

Gln Asp  Ser Lys Tyr Ala Phe  Leu Gln Pro Asn Ser  Val Ile Ser
    1145                1150                1155

Leu Ser  Gly Val Asn Met Tyr  Asn Val Thr Ser Leu  Ser Ser Ile
    1160                1165                1170

Pro Ala  Pro Arg Ile Thr Tyr  Leu Ser Thr Thr Asn  Val Thr Thr
    1175                1180                1185
```

```
Ser Lys Glu Ser Ile Ile Val Asn Ile Thr Gly Glu Tyr Leu Arg
    1190                1195                1200

Leu Leu Gly Val Ser Met Asn Asn Lys Pro Val Gly Tyr Ser Val
    1205                1210                1215

Ile Ser Ser Ser Pro Ser Ser Ile Ser Leu Ser Ile Pro Phe Asn
    1220                1225                1230

Ala Ser Gln Leu Ser Asp Gly Gln Tyr Ile Phe Thr Val Ser Ile
    1235                1240                1245

Ser Asp Gly Leu Pro Tyr Asn Leu Thr Phe Asn Leu Leu Asn Asn
    1250                1255                1260

Tyr His Leu Ile Ile Val Gln Asp His Leu Lys Ala Leu Gln Gly
    1265                1270                1275

Ser Val Asn Leu Leu Thr Val Ile Ala Ile Ile Ser Leu Ile Ile
    1280                1285                1290

Ala Ile Ile Ala Val Ala Leu Leu Phe Val Phe Thr Arg Arg Arg
    1295                1300                1305

<210> SEQ ID NO 26
<211> LENGTH: 875
<212> TYPE: PRT
<213> ORGANISM: Sulfolobus solfataricus

<400> SEQUENCE: 26

Met Arg Leu Leu Lys Ile Leu Leu Leu Ala Met Leu Ile Leu Pro Leu
1               5                   10                  15

Phe Ser Phe Phe Thr Leu Ser Ile Ser Leu Tyr Asp Gln Ile Gln Leu
                20                  25                  30

Pro Pro His Tyr Leu Phe Tyr Ile Ser Glu Asn Ala Thr Gln Gly Ser
            35                  40                  45

Gly Ile Asp Val Ile Phe Tyr Thr Ser Ser Pro Ile Thr Phe Met Ile
        50                  55                  60

Met Thr Pro Ser Gln Phe Tyr Gln Phe Asn Gln Thr Gly Ser Ser Gln
65                  70                  75                  80

Ser Ile Tyr Ser Ile Thr Thr Asn Ser Leu Ser Lys Phe Phe Pro Leu
                85                  90                  95

Ser Gly Gln Tyr Tyr Ile Val Phe Tyr Asn Asn Ile Ser Asn Asn Pro
            100                 105                 110

Val Thr Leu Asn Tyr Tyr Ile Leu Thr Arg Pro Leu Pro Thr Gly Ile
        115                 120                 125

Ala Asp Tyr Gly Leu Lys Ile Asn Asn Gly Val Ile Ser Pro Tyr Ile
    130                 135                 140

Glu Lys Ile Lys Ser Val Ile Gly Ala Val Glu Ile Asn Lys Leu Leu
145                 150                 155                 160

Ala Tyr Asn Ser Thr Pro Pro Ala Gly Val Ser Gln Tyr Ser Ala Ser
                165                 170                 175

Ile Gln Leu Asn Val Val Leu Gln Val Asn Thr Ile Gly Gly Ser Gln
            180                 185                 190

Gln Leu Trp Leu Gln Asn Val Ile Gln Ile Tyr Thr Asn Asn Asp Ser
        195                 200                 205

Tyr Ile Phe Leu Asp Asn Ile Trp Asn Phe Thr Gly Lys Ile Ser Ile
    210                 215                 220

Leu Ser Asn Ser Thr Val Lys Gly Asn Gly Ile Val Tyr Val Thr Asn
225                 230                 235                 240

Asn Gly Asn Asp Tyr Tyr Ala Tyr Gly Thr Asn Phe Ser Thr Leu Leu
```

-continued

```
                245                 250                 255
Ile Pro Ser Leu Lys Tyr Leu Leu Ile Asn Thr Ser Tyr Thr Ser Gln
            260                 265                 270
Gly Pro Met Ile Ser Phe Gly Tyr Met Asn Gln Ser Gly Ser Pro Ile
        275                 280                 285
Trp Tyr Asp Asn Val Thr Ile Leu Ile Pro Asn Thr Leu Ser Ala Tyr
    290                 295                 300
Ile Leu Val Asp Gly Tyr Asn Phe Thr Ala Gly Leu Ala Tyr Asp
305                 310                 315                 320
Ala Glu Leu Ile Leu Gly Gly Gly Asn Gly Glu Phe Thr Phe Phe
            325                 330                 335
Asn Glu Ser Asn Val Glu Leu Ala Met Ile Tyr Gln Tyr Leu Asn Gly
            340                 345                 350
Thr Leu Ala Pro Pro Lys Phe Leu Phe Pro Phe Gly Leu Asp Thr Glu
        355                 360                 365
Glu Ser Ala Asp Asn Leu Tyr Ser Ile Ser Tyr Asn Gly Val Tyr Leu
    370                 375                 380
Val Ser Ser Gly Tyr Gln Val Ile Asn Asn Leu Asn Glu Asn Val Ser
385                 390                 395                 400
Gln Leu Arg Phe Asn Val Val Asn Tyr Thr Lys Ala Thr Asp Gln Asn
            405                 410                 415
Phe Pro Tyr Ile Phe Thr Ile Asn Val Ser Gly Gly Val Leu Pro Tyr
            420                 425                 430
Lys Leu Asn Val Thr Ile Ser Asn Ser Gly Asn Glu Leu Ser Gly
        435                 440                 445
Tyr Thr Tyr Val Leu Phe Pro Ser Val Ser Thr Tyr Tyr Leu Phe Leu
    450                 455                 460
Ser Pro Leu Ser Pro Gly Asn Tyr Thr Val Lys Ile Lys Leu Thr Asp
465                 470                 475                 480
Phe Asn Gly Asn Ser Lys Ser Tyr Glu Phe Ser Leu Thr Ile Asn Pro
            485                 490                 495
Pro Leu Lys Val Gln Ile Leu Asn Val Thr Asn Tyr Ile Asp Leu Ala
        500                 505                 510
Leu Pro Tyr Phe Asn Phe Thr Ser Ile Ile Ser Gly Gly Thr Lys Pro
    515                 520                 525
Tyr Asn Ile Ile Ile Thr Ile Ser Asn Asp Ser Gly Ile Leu Ser Glu
    530                 535                 540
Thr Tyr Lys Ile Ile Asn Tyr Thr Ser Ile Thr Tyr Tyr Ala Val Asn
545                 550                 555                 560
Met Lys Gly Tyr Ser Ile Gly Lys Tyr Thr Ile Gln Ile Glu Val Glu
            565                 570                 575
Asp Tyr Ala Gly Ser Ile Asn Ile Ser Lys Tyr Asn Phe Thr Ile Asn
        580                 585                 590
Pro Asn Pro Tyr Ile Ser Thr Leu Ser Tyr Thr Ser Glu Thr Asp Lys
    595                 600                 605
Gly Leu Arg Glu Val Ile Lys Ala Ile Gly Lys Gly Ser Gly Ser
        610                 615                 620
Leu Ile Tyr Tyr Trp Tyr Val Asn Asn Ser Leu Val Ser Ser Gly Ile
625                 630                 635                 640
Gly Asp Glu Leu Tyr Asn Phe Thr Pro Ser Asn Ile Gly Glu Tyr Asn
            645                 650                 655
Ile Thr Val Met Val Lys Asp Val Leu Gly Val Ser Ser Ala Lys Ser
            660                 665                 670
```

```
Val Ile Ile Lys Val Asn Pro Asp Pro Val Val Glu Leu Ser Val Pro
            675                 680                 685

Lys Thr Thr Ile Asp Ser Gly Ala Glu Phe Pro Val Asn Ala Thr Val
    690                 695                 700

Ser Leu Gly Thr Pro Pro Tyr Tyr Ile Ser Trp Tyr Ile Asn Gly Ser
705                 710                 715                 720

Tyr Val Gly Asn Glu Ser Ile Lys Glu Leu Asn Leu Ser Ser Ile Gly
                725                 730                 735

Val Tyr Ile Ile Thr Val Thr Val Arg Asp Ser Ala Gly Tyr Ile Ile
            740                 745                 750

Asn Met Ser Lys Pro Val Leu Ile Val Pro Pro Ser Leu Ser Val
            755                 760                 765

Lys Glu Gln Thr Gln Gly Asn Phe Ile Gln Tyr Asn Thr Ser Ile Ala
    770                 775                 780

Leu Ser Ala Ser Val Asn Gly Gly Thr Asp Pro Tyr Tyr Leu Ile Phe
785                 790                 795                 800

Leu Asn Gly Lys Leu Val Gly Asn Tyr Ser Ser Thr Gln Leu Gln
                805                 810                 815

Phe Lys Leu Gln Asn Gly Glu Asn Asn Ile Thr Leu Ile Ala Lys Asp
            820                 825                 830

Leu Trp Gly Lys Thr Ala Val Lys Thr Leu Ile Val Asn Ser Gly Tyr
            835                 840                 845

Asn Tyr Val Gly Ile Gly Ile Ala Gly Ile Ile Leu Ile Ile Val
    850                 855                 860

Ile Val Val Ile Leu Val Ile Ser Lys Arg Lys
865                 870                 875

<210> SEQ ID NO 27
<211> LENGTH: 606
<212> TYPE: PRT
<213> ORGANISM: Sulfolobus solfataricus

<400> SEQUENCE: 27

Met Glu Ser Lys Asn Val Ile Leu Lys Arg Val Met Leu Leu Leu Val
1               5                   10                  15

Leu Ile Leu Ser Thr Thr Thr Phe Leu Thr Ile Ile Ala Gln Ser Gln
            20                  25                  30

Ala Gln Tyr Tyr Tyr Ile Gln Thr Ser Ser Pro Gln Tyr Thr Ile Ile
        35                  40                  45

Pro Gly Ser Val Phe Val Glu Pro Leu Asn Ser Ser Gln Thr Leu Tyr
    50                  55                  60

Ile Ala Val Leu Leu Asn Phe Thr Asn Leu Ala Ser Leu Gln Ser Tyr
65                  70                  75                  80

Leu Asn Glu Ile Tyr Leu Ser Ala Pro Gln Phe His His Trp Leu Thr
                85                  90                  95

Pro Ser Gln Phe Arg Glu Tyr Tyr Pro Ser Arg Ser Tyr Val Asn
            100                 105                 110

Ser Leu Ile Lys Tyr Leu Glu Ser Tyr Asn Leu Gln Phe Leu Gly Asn
        115                 120                 125

Tyr Gly Leu Ile Leu Val Phe Ser Gly Thr Val Gly Asn Ile Glu Lys
    130                 135                 140

Ala Phe Asn Thr Tyr Ile Asn Val Tyr Tyr Pro Phe Lys Asn Leu
145                 150                 155                 160

Tyr Trp Phe Gly Leu Leu Gly Ile Lys Asn Ile Gly Pro Phe Tyr Tyr
```

```
                165                 170                 175
Tyr Ser Asn Asn Val Thr Pro Ser Leu Pro Phe Asn Ile Gly Lys Tyr
            180                 185                 190
Val Leu Gly Val Val Gly Ile Asp Ser Leu Asp Pro Lys Val Val Asn
            195                 200                 205
Val Val Thr Gln Thr Trp His Leu Pro Met Val Lys Ala Gln Ser Gly
            210                 215                 220
Leu Val Ser Lys Ala Ile Ile Ser Pro Ile Thr Ile Glu Gln Tyr Phe
225                 230                 235                 240
Asn Phe Thr Leu Ala Tyr Glu Arg Gly Tyr Thr Gly Gly Gly Ser Asn
                245                 250                 255
Ile Ala Ile Glu Gly Val Pro Glu Ser Phe Val Asn Val Ser Asp Ile
                260                 265                 270
Tyr Ser Phe Trp Gln Leu Tyr Gly Ile Pro Arg Thr Gly His Leu Asn
                275                 280                 285
Val Ile Tyr Phe Gly Asn Val Thr Thr Gly Gly Gln Ser Gly Glu Asn
            290                 295                 300
Glu Leu Asp Ala Glu Trp Ser Gly Ala Phe Ala Pro Ala Ala Asn Val
305                 310                 315                 320
Thr Ile Val Phe Ser Asn Gly Tyr Val Gly Gly Pro Gln Leu Val Gly
                325                 330                 335
Asn Leu Leu Asn Tyr Tyr Glu Tyr Tyr Tyr Met Val Asn Tyr Leu
            340                 345                 350
Asn Pro Asn Val Ile Ser Ile Ser Val Thr Val Pro Glu Ser Phe Leu
            355                 360                 365
Ala Ala Tyr Tyr Pro Ala Met Leu Asp Met Ile His Asn Ile Met Leu
            370                 375                 380
Gln Ala Ala Ala Gln Gly Ile Ser Val Leu Ala Ala Ser Gly Asp Trp
385                 390                 395                 400
Gly Tyr Glu Ser Asp His Pro Pro Asn Phe His Ile Gly Thr Tyr
                405                 410                 415
Asn Thr Ile Trp Tyr Pro Glu Ser Asp Pro Tyr Val Thr Ser Val Gly
            420                 425                 430
Gly Ile Phe Leu Asn Ala Ser Ser Asn Gly Ser Ile Val Glu Ile Ser
            435                 440                 445
Gly Trp Asp Tyr Ser Thr Gly Gly Asn Ser Val Val Tyr Pro Ala Gln
            450                 455                 460
Ile Tyr Glu Ile Thr Ser Leu Ile Pro Phe Thr Pro Val Ile Val Arg
465                 470                 475                 480
Thr Tyr Pro Asp Ile Ala Phe Val Ser Ala Gly Gly Tyr Asn Ile Pro
                485                 490                 495
Glu Phe Gly Phe Gly Leu Pro Leu Val Phe Gln Gly Gln Leu Phe Val
            500                 505                 510
Trp Tyr Gly Thr Ser Gly Ala Ala Pro Met Thr Ala Ala Met Val Ala
            515                 520                 525
Leu Ala Gly Thr Arg Leu Gly Ala Leu Asn Phe Ala Leu Tyr His Ile
            530                 535                 540
Ser Tyr Gln Gly Ile Ile Glu Ser Pro Leu Gly Asn Phe Val Gly Lys
545                 550                 555                 560
Val Ala Trp Ile Pro Ile Thr Ser Gly Asn Asn Pro Leu Pro Ala His
                565                 570                 575
Tyr Gly Trp Asn Tyr Val Thr Gly Pro Gly Thr Tyr Asn Ala Tyr Ala
                580                 585                 590
```

```
Met Val Tyr Asp Leu Leu Tyr Ser Gly Leu Ile Glu Ser
    595                 600                 605

<210> SEQ ID NO 28
<211> LENGTH: 570
<212> TYPE: PRT
<213> ORGANISM: Sulfolobus solfataricus

<400> SEQUENCE: 28

Met Gln Phe Arg Lys Thr Phe Leu Phe Leu Asn Ile His Phe Pro Tyr
1               5                   10                  15

Val Leu Arg Asn Thr Leu Leu Ile Leu Leu Leu Leu Pro Thr Pro
            20                  25                  30

Leu Leu Ala Ile Ser Leu Pro Thr Gly Val Val Ala Tyr Asp Gly Pro
            35                  40                  45

Ile Phe Thr Asn Gln Val Leu Gly Tyr Val Asn Ile Thr Ser Leu Gln
    50                  55                  60

Ala Tyr Asn Ala Ser Gly Ser Lys Phe Gly Val Pro Pro Tyr Gly Ala
65                  70                  75                  80

Ser Leu Gln Leu Asn Val Met Leu Gln Val Asn Thr Ser Asn Glu Glu
                85                  90                  95

Tyr Tyr Phe Trp Leu Gln Asn Val Ala Asp Phe Ile Thr Asn Glu Ser
            100                 105                 110

Lys Met Phe Phe Ser Glu Asn Ile Trp Asn Ser Thr Thr Pro Leu Ala
        115                 120                 125

Gly Ile Asn Asn Val Ile Gly Lys Gly Glu Ile Tyr Ser Thr Ser Asp
    130                 135                 140

Leu Phe Ser His Ser Ser Tyr Tyr Ala Tyr Gly Thr Tyr Tyr Ile Lys
145                 150                 155                 160

Tyr Asp Phe Pro Phe Ser Phe Tyr Leu Ile Val Asn Glu Ser His Asn
                165                 170                 175

Asn Gln Gly Val Tyr Val Ser Phe Gly Tyr Val Ile Leu Gln Asn Gly
            180                 185                 190

Asn Ile Thr Pro Pro Asn Pro Thr Phe Tyr Asp Thr Val Phe Ile Pro
        195                 200                 205

Val Asn Asn Leu Thr Ser Ala Ser Ile Ile Ala Asn Gln Thr Thr
    210                 215                 220

Pro Asn Leu Asn Leu Gly Ile Ile Thr Tyr Leu Gly Ser Tyr Leu Asp
225                 230                 235                 240

Ala Glu Leu Val Trp Gly Gly Phe Gly Asn Gly Ala Ser Thr Thr Phe
                245                 250                 255

Leu Asn Met Ser Ser Tyr Leu Ala Leu Leu Tyr Met Lys Asn Gly Lys
            260                 265                 270

Trp Val Pro Phe Ser Gln Val Tyr Asn Tyr Gly Ser Asp Thr Ala Glu
        275                 280                 285

Ser Thr Asn Asn Leu Arg Val Thr Ile Ala Lys Asn Gly Asp Ala Tyr
    290                 295                 300

Val Thr Ile Gly Lys Gln Asn Pro Gly Leu Leu Thr Thr Asn Phe Asn
305                 310                 315                 320

Pro Ser Ile Pro Gly Phe Leu Tyr Leu Asn Ile Ser Lys Ile Pro
                325                 330                 335

Phe Leu Val Asn Asn Ile Ile Ser Arg Thr Phe Ser Gly Tyr Val Ser
            340                 345                 350

Ala Pro Ile Lys Leu Gly Phe Phe Met Asn Tyr Ser Ile Asn Ser Ser
```

```
                355                 360                 365
Ser Phe Ala Val Leu Asn Gly Asn Tyr Pro Ser Leu Ile Glu Pro Asn
370                 375                 380

Val Ser Trp Phe Lys Ile Leu Asn Ile Ile Pro Asn Tyr Thr Tyr Tyr
385                 390                 395                 400

Tyr Leu Val Arg Val Asn Ser Ser Ile Pro Val Ile Gly Thr Ile Asn
                405                 410                 415

Gly Lys Gln Ile Thr Leu Asn Asp Thr Asn Trp Phe Ala Gln Gly Thr
            420                 425                 430

Gln Ile Lys Ile Val Asn Tyr Thr Tyr Asn Gly Ser Asp Glu Arg
        435                 440                 445

Tyr Val Ile Ser Ser Ile Leu Pro Ser Leu Ser Phe Asn Ile Ser Ser
450                 455                 460

Pro Leu Asn Val Thr Ile Asn Thr Ile Lys Gln Tyr Arg Val Ile Ile
465                 470                 475                 480

Asn Ser Asp Leu Pro Thr Tyr Leu Asn Asp Lys Arg Val Asn Gly Ser
                485                 490                 495

Ile Trp Ile Asn Thr Gly Thr Ile Val Lys Leu Ser Ala Ser Ile Pro
            500                 505                 510

Phe Tyr Glu Val Gly Arg Phe Ile Gly Thr Tyr Asn Leu Thr Leu Gly
        515                 520                 525

Gly Thr Ile Val Val Asn Lys Pro Ile Val Glu Lys Leu Gln Leu Ser
530                 535                 540

Ile Asn Asn Leu Leu Leu Glu Ile Thr Ala Ile Ile Val Ile Val
545                 550                 555                 560

Ile Ile Met Leu Ile Leu Arg Lys Arg Arg
                565                 570

<210> SEQ ID NO 29
<211> LENGTH: 556
<212> TYPE: PRT
<213> ORGANISM: Sulfolobus solfataricus

<400> SEQUENCE: 29

Met Leu Lys His Ile Val Leu Val Leu Leu Leu Leu Leu Thr Pro
1               5                   10                  15

Leu Val Ala Ile Ser Phe Pro Thr Gly Val Ala Tyr Asn Gly Pro
            20                  25                  30

Ile Cys Thr Asn Glu Val Leu Gly Tyr Ala Asn Ile Ser Ser Leu Leu
            35                  40                  45

Ala Tyr Asn Thr Ser Ala Ser Gln Leu Gly Val Pro Pro Tyr Gly Ala
50                  55                  60

Ser Leu Gln Leu Asn Val Met Leu Glu Val Asn Thr Ser Gly Gly Glu
65                  70                  75                  80

Tyr Tyr Phe Trp Leu Gln Asn Val Ala Asp Phe Ile Thr Asn Glu Ser
                85                  90                  95

Lys Val Phe Phe Gly Asp Asn Ile Trp Asn Ser Thr Pro Phe Ala
            100                 105                 110

Gly Ile Asn Asn Ile Val Gly Lys Gly Glu Ile Tyr Ser Thr Ser Asp
            115                 120                 125

Phe Phe Ser His Ser Ser Tyr Tyr Ala Tyr Gly Thr Tyr Tyr Ile Lys
        130                 135                 140

Tyr Asn Phe Pro Phe Ser Phe Tyr Leu Ile Ile Asn Glu Ser Tyr Asp
145                 150                 155                 160
```

Thr Gln Gly Val Tyr Val Ser Phe Gly Tyr Val Ile Leu Gln Asn Gly
                165                 170                 175

Asn Ile Ser Pro Pro Asn Pro Ile Phe Tyr Asp Thr Val Phe Ile Pro
            180                 185                 190

Ile Gln Asn Leu Ser Phe Ala Ser Ile Ile Ala Asn Gln Thr Thr
        195                 200                 205

Pro Ser Ala Asn Phe Gly Ile Val Thr Tyr Leu Gly Asn Tyr Leu Asp
    210                 215                 220

Ala Glu Leu Val Trp Gly Gly Phe Gly Asn Gly Glu Ser Thr Thr Phe
225                 230                 235                 240

Leu Asn Met Ser Ser Tyr Leu Ala Leu Leu Tyr Met Lys Ser Gly Glu
                245                 250                 255

Trp Val Pro Phe Ser Gln Val Tyr Asn Tyr Gly Ser Asp Thr Ala Glu
            260                 265                 270

Ser Thr Asn Asn Leu Gln Val Leu Ile Gly Lys Asn Gly Asp Ala Tyr
        275                 280                 285

Val Thr Ile Gly Arg Gln Asn Pro Gly Leu Leu Thr Thr Lys Phe Asn
    290                 295                 300

Pro Ser Tyr Pro Ser Phe Leu Tyr Leu Asn Ile Ser Ser Lys Ile Pro
305                 310                 315                 320

Phe Leu Leu Asn Lys Ser Leu Ser His Ala Phe Ser Gly Tyr Val Thr
                325                 330                 335

Thr Gln Ile Lys Leu Gly Phe Phe Lys Asn Tyr Ser Ile Asn Ser Ser
            340                 345                 350

Ser Phe Ala Val Leu Asn Gly Asn Tyr Pro Ser Leu Ile Glu Pro Asn
        355                 360                 365

Val Ser Trp Phe Lys Val Leu Asn Ile Ile Pro Asn Tyr Thr Tyr Tyr
    370                 375                 380

Tyr Leu Val Lys Val Asn Ser Gln Ile Pro Val Ile Ala Asn Val Asn
385                 390                 395                 400

Gly Lys Gln Ile Thr Leu Asn Ser Thr Asp Trp Phe Ala Gln Gly Thr
                405                 410                 415

Gln Ile Ser Ile Leu Asn Tyr Thr Tyr Tyr Asn Gly Ser Asn Glu Arg
            420                 425                 430

Tyr Ile Ile Ser Ser Ile Leu Pro Ser Ser Phe Asn Val Ser Leu
        435                 440                 445

Pro Leu Asn Ile Thr Leu Ser Thr Ile Lys Gln Tyr Arg Val Leu Val
    450                 455                 460

Asp Ser Asn Leu Pro Val Tyr Leu Asn Gly Glu Arg Val Asn Gly Ser
465                 470                 475                 480

Val Trp Ile Asn Ala Gly Ser Ser Ile Gln Leu Ser Ala Asn Val Pro
                485                 490                 495

Phe Tyr Glu Lys Gly Ile Phe Thr Gly Thr Tyr Asn Val Thr Pro Gly
            500                 505                 510

Ser Ile Ile Thr Val Asn Gly Pro Ile Val Glu Thr Leu Ile Leu Ser
        515                 520                 525

Ile Asn Thr Glu Leu Met Gly Ile Val Ala Val Ile Val Ile Ala Val
    530                 535                 540

Val Ala Ile Ala Ile Leu Val Leu Arg Arg Arg Arg
545                 550                 555

<210> SEQ ID NO 30
<211> LENGTH: 443
<212> TYPE: PRT

-continued

<213> ORGANISM: Sulfolobus solfataricus

<400> SEQUENCE: 30

```
Met Met Tyr Lys Val Leu Leu Ile Ile Leu Leu Leu Pro Leu Ser
1               5                   10                  15

Met Pro Leu Ser Ile Pro Thr Thr Ser Gln Pro Ser Ala Leu Ala Phe
            20                  25                  30

Pro Ser Gly Val Thr Ser Tyr Pro Leu Asn Thr Ile Ile Tyr Thr Asp
            35                  40                  45

Phe Val Met Gly Arg Ile Asn Ile Ser Tyr Leu Asn Ile Gly Ser Ser
    50                  55                  60

Tyr Leu Pro Gly Gly Glu Tyr Phe Thr Thr Gly Asn Ala Ser Leu Gln
65                  70                  75                  80

Leu Asn Ala Met Val Leu Gly Glu Tyr Trp Ala Gln Asn Val Ile Leu
                85                  90                  95

Phe His Gln Ile Ser Asn Asn Thr Phe Tyr Ala Thr Leu Ile Val Asn
            100                 105                 110

Leu Trp Asn Leu Ser Gly Pro Phe Ser Asn Thr Thr Ser Asn Ser Leu
        115                 120                 125

Val Tyr Gln Gly Leu Gly Val Ile Cys Tyr Gln Gly Pro Thr Phe Lys
    130                 135                 140

Val Thr Leu Pro Leu Ser Ile Ser Leu Phe Met Glu Ile Val Asn Ser
145                 150                 155                 160

Thr Leu Asn Phe Gly Tyr Asn Ile Asn Gly Gln Lys Gly Ile Tyr Phe
                165                 170                 175

Arg Tyr Pro Ile Ile Gly Leu Phe Gln Leu Gly Gly Leu Ser Leu Leu
            180                 185                 190

Gly Leu Pro Asn Asp Leu Glu Leu Val Trp Gly Gly Pro Gly Gly Gly
        195                 200                 205

Ser Val Val Phe Met Asn Val Ser Ser Ile Ala Asn Leu Tyr Tyr Phe
    210                 215                 220

Asn Gly Asn Thr Leu Thr Ile Val Pro Asn Ala Tyr Ser Ile Gly Phe
225                 230                 235                 240

Asp Thr Ala Glu Ser Ala Tyr Gly Val Lys Val Tyr Ser Thr Phe Pro
                245                 250                 255

Ser Val Phe Ser Pro Ile Val Ile Glu Thr Ser Gly Val Asn Val Pro
            260                 265                 270

Ser Val Leu Trp Pro Ile Pro Pro His Val Leu Val Asn Gln Thr Ser
        275                 280                 285

Asn Lys Ile Thr Val Lys Leu Ser Ile Ser Asn Lys Ser Leu Ser Gly
    290                 295                 300

Gln Ala Val Tyr Leu Glu Thr Gly Phe Pro Pro Ser Val Ile Ser Ser
305                 310                 315                 320

Ala Val Thr Asn Ser Ser Gly Ile Ala Val Phe Pro Asn Asn Asn Tyr
                325                 330                 335

Ser Phe Tyr Val Val Tyr Phe Pro Gly Asn Phe Thr Leu Ser Ser Thr
            340                 345                 350

Tyr Tyr Phe Ser Ser Pro Ile Leu Asn Ser Leu Ser Ser Lys Phe Arg
        355                 360                 365

Ser Tyr Tyr Gln Asp Leu Leu Asn Phe Leu Asn Ser Ala Gln Asn Ser
    370                 375                 380

Phe Lys Lys Gly Ile Lys Ser Val Leu Ser Lys Gln Glu Thr Ser Ile
385                 390                 395                 400
```

```
Thr Thr Thr Thr Leu Thr Ser Thr Ser Ser Ser Gln Phe Gly
            405             410             415

Val Asn Leu Tyr Ile Val Leu Tyr Ile Leu Ala Phe Val Ile Gly Met
        420             425             430

Val Ile Ser Ala Ile Leu Ile Arg Phe Lys Leu
        435             440

<210> SEQ ID NO 31
<211> LENGTH: 1077
<212> TYPE: PRT
<213> ORGANISM: Sulfolobus solfataricus

<400> SEQUENCE: 31

Met Thr Trp Ser Ile Phe Leu Ile Leu Ala Leu Ser Asp Ile Val
1               5                   10                  15

Leu Pro Leu Thr Ile Thr Asn Ile Asn Asn Gln Ser Ile Thr Thr Leu
            20                  25                  30

Ser Pro Asn Tyr Tyr Leu Thr Val Ala Ile Val Phe Pro Pro Ser Asn
        35                  40                  45

Leu Thr Leu Leu Gln Gln Tyr Val Gln Glu His Val Ile Leu Asn Gln
 50                  55                  60

Thr Gln Val Glu Lys Leu Phe Ile Pro Thr Glu Gly Ile Ser Lys Thr
65                  70                  75                  80

Leu Ser Gln Leu Arg Gln Ser Asn Ile Ser Ala Thr Ser Tyr Met Asn
                85                  90                  95

Val Ile Leu Ala Ser Gly Thr Val Ser Gln Leu Glu Lys Ala Leu Asn
            100                 105                 110

Gly Lys Phe Tyr Val Tyr Glu Leu Asn Gly Lys Arg Phe Phe Glu Phe
        115                 120                 125

Phe Gly Ser Pro Val Ile Pro Asn Ala Ile Val Ile Gly Thr Asn Ile
    130                 135                 140

Thr Ser Leu Ile Leu Asn Lys Pro Thr Thr Leu Tyr Asn Val Thr Gln
145                 150                 155                 160

Ala Val Ala Tyr Asn Ala Leu Lys Pro Ser Gln Leu Leu Tyr Ala Tyr
                165                 170                 175

Asn Ile Ser Trp Leu His Ala His Asn Ile Thr Gly Lys Gly Thr Ala
            180                 185                 190

Ile Gly Ile Leu Asp Phe Tyr Gly Asn Pro Tyr Ile Gln Gln Gln Leu
        195                 200                 205

Gln Glu Phe Asp Lys Gln Tyr Asn Ile Pro Asn Pro Phe Phe Lys
    210                 215                 220

Ile Val Pro Ile Gly Ala Tyr Asn Pro Asn Asn Gly Ile Ser Thr Gly
225                 230                 235                 240

Trp Ala Met Glu Ile Ser Leu Asp Val Glu Tyr Ala His Val Ile Ala
                245                 250                 255

Pro Asp Ala Gly Ile Val Leu Tyr Val Ala Asn Pro Asn Ile Pro Leu
            260                 265                 270

Pro Ala Ile Ile Ala Tyr Ile Val Gln Gln Asp Glu Val Asn Val Val
        275                 280                 285

Ser Gln Ser Phe Gly Ile Pro Glu Leu Tyr Val Asp Leu Gly Leu Ile
    290                 295                 300

Pro Leu Ser Tyr Val Asn Ser Leu Met Tyr Glu Tyr Trp Leu Gly Glu
305                 310                 315                 320

Val Glu Gly Ile Ser Phe Ala Ala Ala Ser Gly Asp Ala Gly Gly Asn
                325                 330                 335
```

```
Gly Tyr Asn Tyr Phe Leu Ala Pro Gln Gly Ser Val Ile Phe Pro Ala
            340                 345                 350

Ser Ile Pro Tyr Val Leu Ala Val Gly Gly Ser Ser Val Tyr Ile Gly
            355                 360                 365

Gly Asn Lys Thr Met Glu Thr Ala Trp Ser Gly Glu Ser Val Leu Gly
370                 375                 380

Ala Ser Thr Gly Gly Tyr Ser Thr Leu Phe Pro Ala Pro Trp Tyr Gln
385                 390                 395                 400

Asp Ser Asn Gly Phe Arg Val Val Pro Asp Val Val Ala Asp Ala Asn
            405                 410                 415

Pro Tyr Thr Gly Ala Phe Ile Leu Tyr Tyr Asn Gln Thr Tyr Leu
            420                 425                 430

Val Gly Gly Thr Ser Leu Ala Thr Pro Ile Val Ser Gly Ile Ile Asp
            435                 440                 445

Leu Met Thr Gln Ser Tyr Gly Lys Leu Gly Phe Val Asn Pro Phe Leu
            450                 455                 460

Tyr Glu Leu Arg Asn Thr Ser Ala Leu Ser Pro Ile Gly Phe Gly Tyr
465                 470                 475                 480

Asn Thr Pro Tyr Tyr Val Asn Ser Ser Glu Leu Asn Pro Val Thr Gly
            485                 490                 495

Leu Gly Ser Ile Asn Ala Gly Tyr Leu Tyr Gln Leu Leu Pro Lys Val
            500                 505                 510

Ile His Ser Ser Ser Ile Ser Val Gly Val Asn Asn Ile Thr Tyr Leu
            515                 520                 525

Asp Gly Gln Val Val Lys Val Ala Asn Ile Thr Gly Ile Arg Pro
530                 535                 540

Ser Ser Val Ile Gly Ile Val Tyr Asn Gly Ser Ser Val Val Gln Gln
545                 550                 555                 560

Phe Ser Leu Ser Phe Asn Gly Thr Tyr Trp Val Gly Glu Phe Val Ala
            565                 570                 575

Glu Gly Ser Gly Ile Glu Glu Val Ile Val Lys Ala Gly Asn Leu Glu
            580                 585                 590

Gly Ser Thr Tyr Val Thr Ile Gly Tyr Gln Ala Gln Phe Ile Phe Pro
            595                 600                 605

Pro Ile Ala Leu Phe Pro Glu Pro Glu Pro Val Pro Ile Val Val Gln
610                 615                 620

Leu Ile Tyr Pro Asn Gly Ser Leu Val Arg Asn Pro Ser Asn Leu Thr
625                 630                 635                 640

Ala Leu Ile Tyr Lys Tyr Asp Gln Met Asn Asn Lys Met Ser Ile Ile
            645                 650                 655

Ser Ser Val Gln Leu Gln Arg Thr Ser Leu Ile Asn Leu Ser Ile Leu
            660                 665                 670

Gly Ile Gln Ile Glu Ser Ser Tyr Leu Thr Gly Val Tyr Gln Leu Pro
            675                 680                 685

Ser Asn Ile Ile Ser Gly Val Tyr Phe Ile Lys Ile Pro Asn Val Phe
            690                 695                 700

Gly Phe Asp Glu Phe Val Ser Gly Ile Tyr Ile Leu Asp Ala Val Tyr
705                 710                 715                 720

Pro Pro Val Phe Thr Asn Pro Val Val Leu Ser Pro Gly Gln Asn Val
            725                 730                 735

Thr Ile Leu Ala Glu Ala Leu Ala Ile Gly Ser Pro Asn Val Thr Val
            740                 745                 750
```

```
Thr Phe Tyr Asn Ile Ser Gly Asn Lys Val Tyr Ser Ile Pro Val Asn
            755                 760                 765

Ala Ile Thr Tyr Gln Asn Thr Leu Leu Tyr Ile Thr Gln Ile Thr Leu
    770                 775                 780

Pro Lys Leu Lys Pro Gly Tyr Tyr Val Val Thr Lys Ala Ile Tyr
785                 790                 795                 800

Asn Ala Ser Asn Phe Thr Ala Glu Gly Val Gly Leu Thr Gln Ile Tyr
                805                 810                 815

Val Ser Pro Tyr Ser Leu Asn Val Lys Val Arg Ile Ile Pro Asn Asn
            820                 825                 830

Ser Ile Val Tyr Gln Asn Gln Gln Ile Tyr Val Ile Ala Asn Ile Thr
        835                 840                 845

Tyr Pro Asn Gly Thr Glu Val Lys Tyr Gly Ser Phe Ser Ala Ile Ile
850                 855                 860

Val Pro Ser Tyr Leu Ser Ser Gln Phe Asp Asn Leu Gln Leu Gln Tyr
865                 870                 875                 880

Ser Val Pro Leu Thr Tyr Ile Asn Gly Ser Trp Ile Gly Gln Leu Glu
                885                 890                 895

Ile Pro Ser Gly Ser Ser Thr Asn Ser Leu Gly Tyr Ser Thr Tyr Gly
            900                 905                 910

Ile Ser Gly Tyr Trp Asp Val Tyr Val Glu Gly Ile Ser Ala Asp Gly
        915                 920                 925

Ile Pro Thr Asn Phe Pro Ala Thr Leu Asp Val Asn Thr Leu Ser Ile
    930                 935                 940

Asn Pro Ile Ser Pro Ser Ser Gln Phe Val Val Leu Pro Tyr Val Tyr
945                 950                 955                 960

Val Ser Val Phe Asn Gly Thr Ile Ala Phe Asn Glu Phe Ile Asp Lys
                965                 970                 975

Ala Ile Val Val Gly His Asn Ala Thr Phe Ile Asn Ser Ile Ile Arg
            980                 985                 990

Asn Leu Ile Val Glu Asn Gly Thr Val Thr Leu Ile Asn Ser Lys Val
                995                1000                1005

Gln Asn Val Ser Leu Val Asn Ser Glu Ile Ile Lys Ile Asn Ser
    1010                1015                1020

Thr Val Gly Asn Asn Val Asn Tyr Ile Thr Thr Ile Gly Asn Asn
    1025                1030                1035

His Ala Lys Ser Ser Tyr Pro Ser Leu Asp Ser Gly Ser Ile Leu
    1040                1045                1050

Thr Ile Gly Ile Val Leu Asp Ile Ile Thr Ile Ile Ala Leu Ile
    1055                1060                1065

Leu Ile Lys Arg Arg Lys Lys Phe Ile
    1070                1075

<210> SEQ ID NO 32
<211> LENGTH: 141
<212> TYPE: PRT
<213> ORGANISM: Sulfolobus solfataricus

<400> SEQUENCE: 32

Met Lys Met Lys Lys Ser Asp Ile Ile Ile Leu Phe Ile Ala Leu
1               5                   10                  15

Ile Tyr Ile Leu Met Phe Ser Asn Ile Val Gln Ser Ala Ser Val Glu
            20                  25                  30

Gly Val Ser Met Tyr Pro Ile Phe Gln Asn Gly Ala Leu Thr Phe Tyr
        35                  40                  45
```

```
Val Lys Pro Ile Ser Ile Asn Glu Gly Asn Val Ile Ile Tyr Lys Ser
 50                  55                  60

Pro Tyr Phe Asn Asn Tyr Val Ile His Arg Val Ile Ala Thr Asp Asn
 65                  70                  75                  80

Gly Tyr Tyr Ile Thr Gln Gly Val Asp Lys Ile Thr Asn Pro Ile Pro
                     85                  90                  95

Asp Asn Arg Ile Gly Leu Glu Pro Ala Ser Gly Ile Pro Lys Asn Leu
                100                 105                 110

Val Val Gly Lys Ile Val Glu Phe Gly Asn Phe Thr Phe Ser Ile Pro
                115                 120                 125

Tyr Leu Gly Tyr Ile Ser Ile Leu Phe Ser Ser Ile Ile
130                 135                 140

<210> SEQ ID NO 33
<211> LENGTH: 1269
<212> TYPE: PRT
<213> ORGANISM: Sulfolobus solfataricus

<400> SEQUENCE: 33

Met Tyr Arg Tyr Ile Phe Leu Met Ser Met Leu Leu Ile Ser Ile Ile
  1               5                  10                  15

Pro Leu Val Phe Ala Ser Asn Pro Asn Met Tyr Gln Asn Pro Ile Thr
                 20                  25                  30

Leu Lys Glu Phe Arg Glu Ile Gly Thr Leu Asn Ala Asn Glu Glu Val
             35                  40                  45

Ile Val Thr Ile Phe Val Pro Leu Lys Asn Leu Asp Leu Leu Tyr Tyr
 50                  55                  60

Tyr Ala Ser Gly Ala Ser Asn Pro Ala Ser Pro Leu Tyr His Lys Phe
 65                  70                  75                  80

Leu Ser Pro His Glu Val Gln Gln Leu Phe Leu Pro Thr Glu Glu Tyr
                 85                  90                  95

Asn Gln Ile Leu Asn Tyr Val Lys Ser Ser Gly Phe Gln Val Ile Phe
                100                 105                 110

Thr Ala Ser Asn Ser Val Ile Val Ile Lys Gly Thr Val Gly Gln Val
                115                 120                 125

Glu Lys Tyr Leu Gly Thr Lys Tyr Ala Val Tyr Ser Asn Gly Ser Val
130                 135                 140

Thr Tyr Tyr Thr Asn Tyr Gly Tyr Pro Lys Ile Asn Ala Tyr Val Tyr
145                 150                 155                 160

Ser Ser Asn Ile Ser Ala Ile Phe Phe Ala His Pro Ser Thr Leu Ile
                165                 170                 175

Thr Glu Ser Thr Ile Lys Ser Phe Gln Gln Glu Ile Asn Gln Thr Phe
                180                 185                 190

Pro Leu Glu Gly Tyr Trp Pro Thr Val Leu Gln Lys Val Tyr Asn Val
                195                 200                 205

Thr Thr Glu Gly Glu Asn Thr Thr Ile Gly Ile Leu Asp Phe Tyr Gly
                210                 215                 220

Asp Pro Tyr Ile Val Gln Gln Leu Ala Tyr Phe Asp Lys Ile Thr Gly
225                 230                 235                 240

Leu Pro Asn Pro Pro Asn Phe Ser Val Val Pro Ile Gly Pro Tyr Asn
                245                 250                 255

Pro Asn Leu Gly Ile Val Thr Gly Trp Ala Gly Glu Ile Ser Leu Asp
                260                 265                 270

Val Glu Val Ala His Ala Ile Ala Pro Lys Ala Asn Ile Thr Leu Tyr
```

```
                275                 280                 285
Ile Ala Asn Pro Asn Ile Pro Leu Pro Ala Ile Ile Ala Tyr Ile Thr
290                 295                 300
Ser Gln Asn Lys Val Asp Thr Leu Ser Gln Ser Phe Ser Ile Pro Glu
305                 310                 315                 320
Ser Leu Phe Ser Ser Leu Phe Asn Gly Pro Leu Phe Tyr Ser Cys Ile
                325                 330                 335
Ile Leu Ser Asp Glu Tyr Tyr Ala Leu Gly Ser Ala Glu Gly Ile Thr
                340                 345                 350
Phe Leu Ala Ser Ser Gly Asp Ala Gly Gly Ser Gly Tyr Ser Asn Gly
                355                 360                 365
Pro Ile Gly Thr Val Gly Tyr Pro Ser Thr Ser Pro Phe Val Thr Ser
370                 375                 380
Val Gly Gly Thr Thr Val Tyr Val Gln Phe Pro Asn Gly Ser Tyr Tyr
385                 390                 395                 400
Gln Thr Ala Trp Ser Asn Tyr Gly Phe Val Pro Asn Val Asn Tyr
                405                 410                 415
Gly Gly Ser Thr Gly Gly Val Ser Ile Ile Glu Pro Lys Pro Trp Tyr
                420                 425                 430
Gln Trp Gly Leu Pro Thr Pro Ser Thr Tyr Pro Asn Gly Lys Leu Ile
                435                 440                 445
Pro Glu Ile Ser Ala Asn Ala Asn Val Tyr Pro Gly Ile Tyr Ile Val
450                 455                 460
Leu Pro Ser Asn Thr Thr Gly Ile Thr Gly Gly Thr Ser Glu Ala Ser
465                 470                 475                 480
Pro Leu Thr Ala Gly Val Leu Ala Thr Ile Glu Ser Tyr Thr His His
                485                 490                 495
Arg Ile Gly Leu Leu Asn Pro Ile Leu Thr Tyr Met Ala Glu Asn Tyr
                500                 505                 510
Tyr Gly Lys Val Ile Glu Pro Ile Thr Phe Gly Tyr Asn Ile Pro Trp
                515                 520                 525
Val Ala Thr Tyr Gly Tyr Asn Leu Val Thr Gly Tyr Gly Thr Ile Asn
530                 535                 540
Ala Gly Tyr Phe Glu Lys Ile Leu Pro Thr Leu Asn Leu Ser Lys Glu
545                 550                 555                 560
Leu Asn Val Ile Val Ser Val Tyr Asn Thr Ser Ile Pro Thr Val Ser
                565                 570                 575
Pro Gln Gln Phe Tyr Pro Gly Gln Arg Ile Leu Val Thr Ala Asn Ile
                580                 585                 590
Thr Tyr Pro Asn Gly Ser Pro Val Gln Thr Gly Glu Phe Lys Ala Leu
                595                 600                 605
Ile Glu Asn Tyr Leu Gly Leu Thr Thr Phe Asn Leu Thr Tyr Asn
                610                 615                 620
Ser Leu Thr Lys Leu Trp Thr Gly Ser Gly Val Leu Ser Asn Lys Ala
625                 630                 635                 640
Ser Gly Ile Leu Phe Val Tyr Val Tyr Gly Ser Ser Asp Gly Leu Arg
                645                 650                 655
Gly Ile Gly Tyr Tyr Glu Thr Phe Ser Gly Tyr Ile Thr Phe Asn
                660                 665                 670
Tyr Thr Thr Thr Phe Thr Pro Val Tyr Val Glu Leu Gly Asn Ala Glu
                675                 680                 685
Leu Gly Ile Thr Leu Ser Asn Ser Tyr Phe Gln Ala Pro Ile Gly Val
                690                 695                 700
```

```
Met Asn Ile Thr Leu Asn Ile Tyr Ser Tyr Asn Ile Thr Asn Ala
705                 710                 715                 720

Tyr Thr Phe Val Thr Thr Leu Ser Val Pro Ile Lys Asn Gly Val Gly
                725                 730                 735

Val Ile Asp Leu Pro Pro Asp Leu Ser Ile Gly Asp Leu Leu Ile Ile
            740                 745                 750

Ala Glu Gly Asn Ala Tyr Gly Phe Asp Ala Phe Thr Asn Gly Val Tyr
                755                 760                 765

Met Gln Thr Leu Phe Ile Leu Pro Gln Val Val Glu Pro Gly Ser
770                 775                 780

Val Ser Pro Gly Gln His Ile Thr Ile Glu Gly Ser Ile Ile Pro Pro
785                 790                 795                 800

Val Asn Leu Pro Ser Thr Thr Phe Gln Asp Ala Leu Gln Gly Thr Asn
                805                 810                 815

Ile Thr Ala Lys Leu Val Ser Ser Asn Gly Val Val Ile Asn Glu Ala
                820                 825                 830

Asn Ile Pro Leu Ser Pro Asn Gly Ile Tyr Phe Gly Tyr Leu Tyr Ile
                835                 840                 845

Pro Lys Asn Thr Pro Ser Gly Leu Tyr Asn Val Leu Leu Phe Ala Thr
                850                 855                 860

Tyr Tyr Ser Tyr Thr Leu Asn Thr Thr Ile Arg Gly Phe Tyr Tyr Gly
865                 870                 875                 880

Gln Ile Tyr Val Ser Asn Gln Ala Thr Ile Ser Val Lys Ser Val Asn
                885                 890                 895

Tyr Ala Phe Glu Gly Gln Thr Val Phe Ile Tyr Ala Asn Ile Thr Asn
                900                 905                 910

Gly Thr Asn Glu Ile Lys Phe Gly Met Phe Ser Ala Thr Val Tyr Pro
                915                 920                 925

Ser Ser Leu Ser Phe Asn Tyr Thr Thr Ile Ser Ile Ile Glu Ile
930                 935                 940

Pro Leu Trp Tyr Asn Pro Lys Ile Gly Glu Trp Glu Gly Asn Phe Thr
945                 950                 955                 960

Leu Pro Ser Ala Ile Ser Ala Gly Asn Leu Thr Tyr Leu Ala Gly Gln
                965                 970                 975

Gly Tyr Phe Gly Val Pro Phe Lys Val Leu Ile Thr Gly Ile Ser Ala
                980                 985                 990

Leu Gly Asn Pro Thr Thr Thr Asn  Ser Gly Asn Ala Tyr  Thr Ile Asn
                995                 1000                1005

Val Leu  Pro Tyr Thr Leu Phe  Thr Asn Gln Thr Leu  Asp Lys Thr
    1010                1015                1020

Leu Pro  Ser Tyr Ala Ser Leu  Val Asn Val Lys Ile  Leu Asn Val
    1025                1030                1035

Ser Gly  Asn Leu Leu Asn Asp  Phe Leu Thr Asn Val  Ile Ile Val
    1040                1045                1050

Asn Ser  Asn Val Lys Ile Leu  Asn Gly Asn Ile Ser  Asn Ile Val
    1055                1060                1065

Ile Arg  Asn Ser Thr Val Leu  Ile Met Gln Ser Asn  Ala Asn Asn
    1070                1075                1080

Ile Thr  Leu Tyr Asn Ser Thr  Leu Tyr Ala Ile Gly  Gly Ser Ile
    1085                1090                1095

Asn Gly  Leu Asn Val Val Asn  Ser Lys Val Val Pro  Ile Asn Ile
    1100                1105                1110
```

-continued

```
His Ile Gln Gly Leu Tyr Pro Glu Leu Pro Ser Ile Ser Ile Asn
    1115                1120                1125

Leu Pro Ser Lys Asn Val Thr Gly Thr Val Asn Val Thr Val Asn
    1130                1135                1140

Val Ile Gly Glu Asp Val Ser Arg Ile Asn Val Tyr Leu Asn Gly
    1145                1150                1155

Asn Leu Ile Asn Ser Phe Thr Thr Asn Gly Thr His Ile Val Thr
    1160                1165                1170

Ile Asn Thr Gln Asn Tyr Pro Asp Gly Gly Tyr Asn Leu Thr Val
    1175                1180                1185

Thr Ala Ile Gln Ser Asp Gly Leu Ser Ser Ser Asn Ser Ser Tyr
    1190                1195                1200

Leu Tyr Phe Glu Asn Gly Leu Thr Asn Leu Asn Thr Lys Val Asn
    1205                1210                1215

Val Ile Ser Asn Gln Leu Thr Asn Val Ser Asn Ser Leu Ser Ser
    1220                1225                1230

Ser Ile Ser Ser Leu Arg Thr Ala Ser Leu Glu Tyr Gln Ser Ile
    1235                1240                1245

Ser Leu Ala Ile Gly Ile Ile Ala Ile Val Leu Ala Ile Leu Ala
    1250                1255                1260

Leu Val Arg Arg Arg Arg
    1265

<210> SEQ ID NO 34
<211> LENGTH: 601
<212> TYPE: PRT
<213> ORGANISM: Sulfolobus solfataricus

<400> SEQUENCE: 34

Met Tyr Met Lys Ala Lys His Leu Ile Ser Leu Ile Val Ile Leu Thr
1               5                   10                  15

Pro Leu Val Thr Leu Leu Thr Ser Ala Val Tyr Thr Ser Gly Gly Ile
                20                  25                  30

Thr Phe Tyr Ser Pro Ala Tyr Asn Gly Glu Ser Tyr Tyr Thr Gly Gln
            35                  40                  45

Ser Ile Thr Ile Asp Ala Leu Leu Pro Gln Gln Phe Ala Thr Asp Ala
        50                  55                  60

Ala Thr Ile Asn Phe Phe Phe Pro Asn Ser Ser Leu Ala Val Thr Ile
65                  70                  75                  80

Pro Val Gln Ile Asn Gly Ser Gly Gly Ile Tyr Val Pro Asn Ala Tyr
                85                  90                  95

Ala Phe Pro Asn Val Pro Gly Thr Trp Gln Ile Thr Ile Glu Val Ala
            100                 105                 110

Gly Gly Val Ala Val Gly Thr Ile Asn Val Asn Val Ile Gln Arg Thr
        115                 120                 125

Pro Leu Val Thr Val His Leu Gly Tyr Gly Val Gly Gln Ala Leu
    130                 135                 140

Pro Gln Thr Pro Thr Ile Thr Leu Thr Phe Pro Asn Gly Thr Thr Ile
145                 150                 155                 160

Thr Val Pro Leu Gln Gly Thr Val Asn Val Pro Ser Gly Thr Ser Tyr
                165                 170                 175

Gln Val Glu Gln Ala Ile Thr Glu Asn Asn Ile Arg Trp Ala Thr Asn
            180                 185                 190

Tyr Thr Ser Gly Thr Ile Thr Pro Ala Thr Thr Ser Ile Thr Pro Thr
        195                 200                 205
```

Tyr Tyr Gln Gln Tyr Leu Val Thr Phe Asn Tyr Thr Val Gln Gly Gly
210                 215                 220

Thr Gly Tyr Ser Pro Pro Thr Val Tyr Arg Ser Leu Gly Met Asn
225                 230                 235                 240

Glu Thr Ala Lys Ala Pro Ala Ser Val Trp Val Asp Ala Asn Ser Ala
                245                 250                 255

Tyr Ile Tyr Ser Pro Glu Leu Gln Ser Asn Val Gln Gly Glu Arg Trp
            260                 265                 270

Ile Ala Val Asn Phe Thr Gly Ile Ile Lys Ala Pro Gly Glu Ile Asn
        275                 280                 285

Glu Tyr Tyr Ile Asn Gln Tyr Leu Val Thr Val Gln Ser Gln Ile Pro
290                 295                 300

Val Tyr Ala Ile Val Asn Gly Ala Asn Glu Thr Leu Asn Ser Thr Asn
305                 310                 315                 320

Trp Phe Thr Gln Gly Thr Thr Ile Lys Leu Glu Asn Ile Thr Lys Tyr
                325                 330                 335

Val Ser Ser Val Glu Arg Tyr Val Ile Ala Asn Phe Ser Pro Ser Glu
            340                 345                 350

Val Ile Thr Val Asn Gln Pro Thr Thr Ile Lys Val Asn Thr Val Thr
        355                 360                 365

Gln Tyr Phe Ile Asn Val Asn Ser Pro Val Gln Leu Lys Ala Leu Ile
370                 375                 380

Asn Gly Ala Asn Glu Ser Leu Thr Ala Gly Trp Tyr Asn Gln Gly Thr
385                 390                 395                 400

Ser Ile Lys Ile Glu Asn Leu Thr Tyr Tyr Val Gly Asn Gly Glu Arg
                405                 410                 415

Leu Ile Leu Gly Lys Val Leu Pro Ser Leu Glu Ile Ile Val Asn Gly
            420                 425                 430

Ser Tyr Thr Ile Ser Thr Thr Thr Ile Thr Gln Tyr Phe Val Asn Val
        435                 440                 445

Ser Ser Pro Ile Pro Val Gln Val Leu Ile Asn Gly Ser Lys Thr Ile
450                 455                 460

Leu Asn Ser Ser Trp Ile Asn Ala Gly Thr Ser Ile Leu Val Leu Asn
465                 470                 475                 480

Tyr Thr Tyr Asn Ile Ser Pro Gln Glu Arg Val Ile Ile Val Gly Ile
                485                 490                 495

Ser Pro Ser Gln Ser Phe Thr Val Asn Ser Pro Glu Thr Leu Lys Leu
            500                 505                 510

Leu Thr Val Thr Gln Tyr Leu Val Thr Ile Asn Gly Val Ser Lys Phe
        515                 520                 525

Tyr Asn Ser Gly Ser Lys Ile Val Leu Asn Ala Ser Val Pro Phe Tyr
530                 535                 540

Glu Thr Ala Thr Phe Lys Gly Thr Tyr Asn Val Ser Pro Gly Ala Thr
545                 550                 555                 560

Ile Thr Val Asn Gln Pro Ile Thr Glu Thr Leu Val Glu Ser Pro Asn
                565                 570                 575

Tyr Leu Ile Leu Gly Ala Ile Ala Ala Val Ile Ile Val Val Ala
            580                 585                 590

Val Val Val Ile Ile Leu Leu Arg Arg
        595                 600

<210> SEQ ID NO 35
<211> LENGTH: 340

```
<212> TYPE: PRT
<213> ORGANISM: Sulfolobus acidocaldarius

<400> SEQUENCE: 35

Met Asn Phe Lys Ser Ile Cys Leu Ile Ile Leu Leu Ser Ala Leu Ile
1               5                   10                  15

Ile Pro Tyr Ile Pro Gln Asn Ile Tyr Phe Phe Pro His Arg Asn Thr
                20                  25                  30

Thr Gly Ala Thr Ile Ser Ser Gly Leu Tyr Val Asn Pro Tyr Leu Tyr
            35                  40                  45

Tyr Thr Ser Pro Pro Ala Pro Ala Gly Ile Ala Ser Phe Gly Leu Tyr
        50                  55                  60

Asn Tyr Ser Gly Asn Val Thr Pro Tyr Val Ile Thr Thr Asn Glu Met
65                  70                  75                  80

Leu Gly Tyr Val Asn Ile Thr Ser Leu Leu Ala Tyr Asn Arg Glu Ala
                85                  90                  95

Leu Arg Tyr Gly Val Asp Pro Tyr Ser Ala Thr Leu Gln Phe Asn Ile
                100                 105                 110

Val Leu Ser Val Asn Thr Ser Asn Gly Val Tyr Ala Tyr Trp Leu Gln
            115                 120                 125

Asp Val Gly Gln Phe Gln Thr Asn Lys Asn Ser Leu Thr Phe Ile Asp
        130                 135                 140

Asn Val Trp Asn Leu Thr Gly Ser Leu Ser Thr Leu Ser Ser Ser Ala
145                 150                 155                 160

Ile Thr Gly Asn Gly Gln Val Ala Ser Ala Gly Gly Gly Gln Thr Phe
                165                 170                 175

Tyr Tyr Asp Val Gly Pro Ser Tyr Thr Tyr Ser Phe Pro Leu Ser Tyr
                180                 185                 190

Ile Tyr Ile Ile Asn Met Ser Tyr Thr Ser Asn Ala Val Tyr Val Trp
                195                 200                 205

Ile Gly Tyr Glu Ile Ile Gln Ile Gly Gln Thr Glu Tyr Gly Thr Val
            210                 215                 220

Asn Tyr Tyr Asp Lys Ile Thr Ile Tyr Gln Pro Asn Ile Ile Ser Ala
225                 230                 235                 240

Ser Leu Met Ile Asn Gly Asn Asn Tyr Thr Pro Asn Gly Leu Tyr Tyr
                245                 250                 255

Asp Ala Glu Leu Val Trp Gly Gly Gly Gly Asn Gly Ala Pro Thr Ser
            260                 265                 270

Phe Asn Ser Leu Asn Cys Thr Leu Gly Leu Tyr Tyr Ile Ser Asn Gly
                275                 280                 285

Ser Ile Thr Pro Val Pro Ser Leu Tyr Thr Phe Gly Ala Asp Thr Ala
        290                 295                 300

Glu Ala Ala Tyr Asn Val Tyr Thr Thr Met Asn Asn Gly Val Pro Ile
305                 310                 315                 320

Ala Tyr Asn Gly Ile Glu Asn Leu Thr Ile Leu Thr Asn Asn Phe Ser
                325                 330                 335

Val Ile Leu Ile
            340
```